US011773180B2

(12) United States Patent
Nakayama et al.

(10) Patent No.: US 11,773,180 B2
(45) Date of Patent: Oct. 3, 2023

(54) BISPECIFIC ANTIBODY WHICH BINDS TO CD40 AND EPCAM

(71) Applicant: Kyowa Kirin Co., Ltd., Tokyo (JP)

(72) Inventors: Makoto Nakayama, Tokyo (JP); Nobuaki Takahashi, Tokyo (JP); Sayaka Maeda, Tokyo (JP); Rinpei Niwa, Tokyo (JP)

(73) Assignee: KYOWA KIRIN CO., LTD., Tokyo (JP)

( * ) Notice: Subject to any disclaimer, the term of this patent is extended or adjusted under 35 U.S.C. 154(b) by 0 days.

(21) Appl. No.: 16/761,887

(22) PCT Filed: Nov. 6, 2018

(86) PCT No.: PCT/JP2018/041250
§ 371 (c)(1),
(2) Date: May 6, 2020

(87) PCT Pub. No.: WO2019/093342
PCT Pub. Date: May 16, 2019

(65) Prior Publication Data
US 2021/0380713 A1 Dec. 9, 2021

(30) Foreign Application Priority Data

Nov. 8, 2017 (JP) .............................. JP2017-215834

(51) Int. Cl.
C07K 16/00 (2006.01)
C07K 16/30 (2006.01)
C07K 16/28 (2006.01)
G01N 33/574 (2006.01)

(52) U.S. Cl.
CPC .......... C07K 16/30 (2013.01); C07K 16/2878 (2013.01); G01N 33/57492 (2013.01); C07K 2317/31 (2013.01); C07K 2317/35 (2013.01); C07K 2317/522 (2013.01); C07K 2317/524 (2013.01); C07K 2317/526 (2013.01); C07K 2317/53 (2013.01); C07K 2317/54 (2013.01); C07K 2317/55 (2013.01); C07K 2317/565 (2013.01); C07K 2317/75 (2013.01); C07K 2317/92 (2013.01)

(58) Field of Classification Search
CPC .............. C07K 16/30; C07K 16/2878; C07K 2317/31; C07K 2317/35; C07K 2317/522; C07K 2317/53; C07K 2317/54; C07K 2317/55; C07K 2317/565; C07K 2317/75; C07K 2317/92; G01N 33/57492
See application file for complete search history.

(56) References Cited

U.S. PATENT DOCUMENTS 10,233,258 B2    3/2019  Akamatsu et al.
2005/0266008 A1* 12/2005 Graziano ................ A61P 35/00
                                                424/155.1
2007/0238665 A1  10/2007 Lazar et al.
2008/0063635 A1   3/2008 Takahashi et al.
2011/0076722 A1   3/2011 Takahashi
2017/0022287 A1   1/2017 Igawa et al.
2017/0304437 A1* 10/2017 Ellmark .................... A61P 1/16
2017/0306038 A1* 10/2017 Brogdon ................ A61K 39/00
2017/0342169 A1  11/2017 Akamatsu et al.
2018/0194862 A1   7/2018 Akamatsu et al.

FOREIGN PATENT DOCUMENTS

WO    99/61057        12/1999
WO    2006/033386      3/2006
WO    2009/131239     10/2009
WO    2015/156268     10/2015
WO    2017/205738     11/2017

OTHER PUBLICATIONS

Ferrari et al (J Exp & Clin Cancer Res 34:123, 2015 (Year: 2015).*
Ye et al, J Immuno Therapy of Cancer V5, No. 87, abstract P370, published Nov. 7, 2017; IDS: Item CK, filed on Aug. 19, 2020. (Year: 2017).*
Seimetz et al, Cancer treatment Rev 36:458-467, 2010. (Year: 2010).*
Extended Search Report dated Jul. 9, 2021 in European Patent Application No. 18875043.4.
Ferrari, Francesca et al., "Solitomab, an EpCAM/CD3 bispecific antibody construct (BiTE®), is highly active against primary uterine and ovarian carcinosarcoma cell lines in vitro", J. Exp. Clin. Can. Res., 2015, vol. 34, No. 123, pp. 1-8.
Diehl et al., "CD40 activation in vivo overcomes peptide-induced peripheral cytotoxic T-lymphocyte tolerance and augments antitumor vaccine efficacy," Nature Medicine. Jul. 1999, vol. 5, No. 7, pp. 774-779.
Beatty et al., "Cancer immunotherapy: activating innate and adaptive immunity through CD40 agonists," Expert Review of Anticancer Therapy, Feb. 2017; vol. 17, No. 2, pp. 175-186.
Vonderheide et al., "Phase I study of the CD40 agonist antibody CP-870,893 combined with carboplatin and paclitaxel in patients with advanced solid tumors," Oncoimmunology, Jan. 2013, vol. 2, No. 1, pp. 1-10.
Bridges et al., "Selective in vivo antitumor effects of monoclonal anti-I-A antibody on B cell lymphoma," Journal of Immunology, 1987; vol. 139, pp. 4242-4249.
Brunekreeft et al., "Targeted delivery of CD40L promotes restricted activation of antigen-presenting cells and induction of cancer cell death," Molecular Cancer, 2014, vol. 13:85, pp. 1-13.

(Continued)

Primary Examiner — Lei Yao
(74) Attorney, Agent, or Firm — Wenderoth, Lind & Ponack, L.L.P.

(57) ABSTRACT

An object of the present invention is to provide a bispecific antibody comprising an antigen-binding domain that binds to CD40 and an antigen-binding domain that binds to an epithelial cell adhesion molecule (EpCAM). The present invention relates to a bispecific antibody comprising an antigen-binding domain that binds to CD40 and an antigen-binding domain that binds to EpCAM.

18 Claims, 15 Drawing Sheets
Specification includes a Sequence Listing.

(56) References Cited

OTHER PUBLICATIONS

Van der Gun et al., "Transcription factors and molecular epigenetic marks underlying EpCAM overexpression in ovarian cancer," British Journal of Cancer, 2011, vol. 105, pp. 312-319.
Chaudry et al., "EpCAM an immunotherapeutic target for gastrointestinal malignancy: current experience and future challenges," British Journal of Cancer, 2007, vol. 96, pp. 1013-1019.
Munz et al., "Side-by-side analysis of five clinically tested anti-EpCAM monoclonal antibodies," Cancer Cell International, 2010, vol. 10:44, pp. 1-12.
Linke et al., "Catumaxomab Clinical development and future directions," mAbs, 2010, vol. 2, Issue 2, pp. 129-136.
International Search Report dated Feb. 12, 2019 in International (PCT) Application No. PCT/JP2018/041250 with English-language translation.
Ye et al., "P370—Enhancement of tumor specific immunity by activation of CD40 through a biospecific molecule targeting CD40 and a tumor surface antigen," Journal of Immuno Therapy of Cancer, Nov. 2017, vol. 5 (Suppl 2), No. 87, p. 1.

\* cited by examiner (A)

(B)

(A)

(B)

(C)

BISPECIFIC ANTIBODY WHICH BINDS TO CD40 AND EPCAM

TECHNICAL FIELD

The present invention relates to a bispecific antibody comprising an antigen-binding domain that binds to CD40 and an antigen-binding domain that binds to an epithelial cell adhesion molecule (EpCAM), a bispecific antibody fragment thereof, a DNA encoding the bispecific antibody or the bispecific antibody fragment thereof, a vector comprising the DNA, a hybridoma and a transformant strain that produce the bispecific antibody or the bispecific antibody fragment thereof, a method for producing the bispecific antibody or the bispecific antibody fragment thereof, therapeutic and diagnostic agents comprising the bispecific antibody or the bispecific antibody fragment thereof, therapeutic and diagnostic methods using the bispecific antibody or the bispecific antibody fragment thereof, and a reagent for detection or measurement comprising the bispecific antibody or the bispecific antibody fragment thereof.

BACKGROUND ART

An antibody is a glycoprotein present in serum or tissue fluid of all mammals and recognizes a foreign antigen in the body. The antibody is involved in the body's defense by activating a complement system or activating effector functions such as phagocytic capacity, antibody-dependent cellular cytotoxicity capacity, mediator release capacity, and antigen presenting capability of FcR expressing cells through binding to a receptor (FcR) present on a cell surface.

One molecule of antibody is composed of two homologous light chains (L chains) and two homologous heavy chains (H chains) and comprises two antigen-binding sites. The classes and subclasses of the antibody are determined by the H chain, and each class and subclass have a different unique function. There are five different classes of human antibodies; IgG, IgA, IgM, IgD, and IgE. IgG is further classified into subclasses of IgG1, IgG2, IgG3, and IgG4, and IgA is further classified into subclasses of IgA1 and IgA2 (Charles A. J. et. al., Immunobiology, 1997, Current Biology Ltd/Garland Publishing Inc.).

A multivalent antibody is an antibody having a plurality of antigen-binding sites in one molecule. As an example of the multivalent antibody, first, it has been reported that a divalent antibody that monovalently binds to each of different two types of antigens was produced by expressing H chains and L chains derived from different two types of antibodies by one cell using a hybrid hybridoma (Non-Patent Document 1). However, in this method, there occur about 10 combinations of the H chains and the L chains of the antibodies. Therefore, the production amount of the multivalent antibody with a desired combination of the H chains and the L chains is low, and further, it is difficult to selectively isolate and purify such a multivalent antibody, and thus, the yield of a desired antibody decreases.

In order to overcome this problem, an attempt to produce an antibody with a desired combination by linking a plurality of antigen-binding sites and expressing them as a single polypeptide chain so as to reduce the variation of combinations between subunits has been reported.

As an example, an antibody comprising a single chain Fv (scFv) in which antigen-binding sites of an H chain and an L chain are linked with one polypeptide (Non-Patent Document 2) is known. Further, an antibody in which two antigen-binding sites are linked using a CH1 domain of an H chain constant region of IgG1 or a partial fragment of the domain, and an L chain constant region or a flexible linker (Gly-Gly-Gly-Gly-Ser), and the like have been reported (Non-Patent Document 4, Patent Document 1, and Patent Document 2).

These conventional multivalent antibodies had drawbacks that aggregation is likely to occur, and the stability and productivity are low. On the other hand, however, it has been found that a multivalent antibody, which comprises a plurality of antigen-binding sites in a single H chain polypeptide, and in which an antibody heavy chain variable region is bound through a linker having an amino acid sequence of an immunoglobulin domain or a fragment thereof has high stability and also has high productivity (Patent Document 3).

CD40 has been identified as an antigen expressed on the surface of a human B cell (Non-Patent Document 4) and is known as one member of the TNF receptor family. A TNF receptor family molecule is defined by the presence of a cysteine rich repeat in an extracellular domain. As the member of the TNF receptor family, other than CD40, for example, a low affinity NGF receptor, a TNF receptor, CD27, OX40, CD30, and the like are known.

A signal through the TNF receptor family is induced when the TNF family molecules of a homotrimer bind to three TNF receptor family members, however, a signal is transmitted intracellularly also by crosslinking antibodies specific to a TNF receptor family molecule, and therefore, it is considered that association of TNF receptor family molecules is required for signal transduction (Non-Patent Documents 5 and 6).

CD40 is a type I membrane-associated glycoprotein, and is known to be also expressed on various cell types such as B lymphocytes, dendritic cells, monocyte epithelial cells, and fibroblasts, or a certain type of tumor cells such as neoplastic human B cells. In a CD40-deficient mouse, it has been confirmed that thymus-dependent immunoglobulin class switching or germinal center formation is impaired, and an important role of CD40 in cellular and humoral immune responses has been demonstrated (Non-Patent Document 7).

A signal of CD40 is involved in immunoglobulin class switching or induction of CTL, and therefore, activation of tumor immunity or application to a pharmaceutical product as an adjuvant for a cancer vaccine is also expected (Non-Patent Document 8).

Examples of an antibody targeting existing CD40 include Chi-Lob 7/4, HCD-122, APX005M, SEA-CD40, CP870, 893 (21.4.1), and the like. (Non-Patent Document 9). Among them, CP870,893 has a strong CD40 signal inducing ability, and a clinical trial was conducted for solid tumors using systemic immune activation as a drug efficacy mechanism. However, effectiveness could not yet be demonstrated, and expression of toxicity derived from systemic immune activation such as cytokine syndrome, elevation of a thrombus marker, or elevation of a liver parameter has been reported (Non-Patent Document 10).

A physiological ligand of CD40 is CD40 Ligand (CD154, gp39). The CD40 ligand is expressed in activated T lymphocytes, and is responsible for an important regulatory mechanism such as differentiation or proliferation of B lymphocytes and escape from spontaneous apoptosis of B lymphocytes at germinal center through binding to CD40 on the surfaces of B lymphocytes (Non-Patent Document 11).

As the molecule having a CD40 signal inducing ability, a molecule in which an Fc region of an antibody is fused to the CD40 Ligand has been reported. Further, a fusion antibody of the CD40 Ligand and a single-chain antibody scFv against a cancer antigen was produced aiming at efficient CD40 signal induction in a tumor, and it has been reported that a CD40 signal is induced at a dose about 20 times lower than the CD40 Ligand. (Non-Patent Document 12).

As a bispecific antibody that recognizes CD40, an IgG-type anti-human GPC3/anti-mouse CD40 bispecific antibody having a heterodimerized heavy chain is known (Patent Document 4). In addition, a bispecific protein that binds to a cancer antigen such as nectin-4, PSMA, or EGFR and to CD40 and activates CD40 is known (Patent Document 5). Further, a method for activating a CD40-expressing cell in the vicinity of a cancer cell by a bispecific molecule such as a diabody having specificity for CD40 and a cancer cell surface antigen is known (Patent Document 6).

Epithelial cell adhesion molecules (EpCAM, CD326, GA733-2, HEA125, KS1/4, MK-1, MH99, MOC31, 323/A3, 17-1A, CO-17A, ESA, EGP-2, EGP34, EGP40, KSA, KS1/4, TROP-1, and TACST-1) are 40-kDa transmembrane-type membrane glycoproteins involved in cell adhesion, cell proliferation, and tumor progression, and function as homotypic cell adhesion factors.

EpCAM is known as a cancer antigen because it is highly expressed in many epithelium-derived cancer cells, and is expected as a target molecule for a cancer molecular target drug, a diagnostic marker, or a cancer vaccine target (Non-Patent Documents 13 and 14).

As an example of medicine targeting EpCAM, vaccine therapy using an anti-idiotypic antibody that binds to an EpCAM protein or an antigen recognition site of an anti-EpCAM antibody, and anti-EpCAM antibodies such as Adecatumumab (MT201), ING-1, and 3622W94 have been reported (Non-Patent Document 15).

Further, for the purpose of enhancing a cytotoxic activity by an anti-EpCAM antibody, Proxiniums Vivendiums (VB4-845) obtained by fusing an anti-EpCAM antibody to Pseudomonas exotoxin and EMD 273 066 (huKS-IL2) by fusing an anti-EpCAM antibody to IL-2 have been developed. A bispecific antibody Catumaxomab (Removab) that crosslinks a T cell to an EpCAM-positive tumor cell and damages the tumor cell because of its possession of an anti-CD3 antibody has been approved in Europe (Non-Patent Documents 14 and 16).

PRIOR ART DOCUMENTS

Patent Documents

Patent Document 1: US Patent Application Publication No. 2007/0071675
Patent Document 2: WO 2001/077342
Patent Document 3: WO 2009/131239
Patent Document 4: WO 2015/156268
Patent Document 5: WO 2017/205738
Patent Document 6: WO 99/61057

Non-Patent Documents

Non-Patent Document 1: Suresh et. al., Methods Enzymol. 121, 210-228, 1986
Non-Patent Document 2: Kranz et. al., J. Hematother. 5, 403-408, 1995
Non-Patent Document 3: Wu et. al., Nat. Biothech. 25, 1290-1297, 2007
Non-Patent Document 4: Clark et. al., PNAS USA 1986; 83: 4494-4498
Non-Patent Document 5: Chuntharapai A et. al., J. Immunol. 166(8), 4891, 2001
Non-Patent Document 6: Ashkenazi A et. al., Nat Rev Cancer 2, 420, 2002
Non-Patent Document 7: Kawabe et. al., Immunity 1994; 1:167-168
Non-Patent Document 8: Diehl L et. al. Nat Med. 1999 July; 5(7): 774-9
Non-Patent Document 9: Beatty G L et. al., Expert Rev Anticancer Ther. 2017 February; 17(2): 175-186
Non-Patent Document 10: Vonderheide R H et. al., Oncoimmunology. 2013 Jan. 1; 2(1): e23033
Non-Patent Document 11: Bridges et. al., J Immunol 1987; 139: 4242-4549
Non-Patent Document 12: 1541376565889_0 et. al., Mol Cancer. 2014 Apr. 17; 13: 85
Non-Patent Document 13: van der Gun B T et. al., Br J Cancer. 2011 Jul. 12; 105(2): 312-9
Non-Patent Document 14: Chaudry M A et. al., Br J Cancer. 2007 Apr. 10; 96(7): 1013-9
Non-Patent Document 15: Markus M et. al., Cancer Cell Int. 2010 Nov. 2; 10: 44
Non-Patent Document 16: Linke R et. al., MAbs. 2010, Vol. 2(2), pp. 129-136

SUMMARY OF INVENTION

Problems to be Solved by the Invention

A bispecific antibody against CD40 and EpCAM and its antitumor effect are not known. Therefore, an object of the present invention is to provide a bispecific antibody comprising an antigen-binding domain that binds to CD40 and an antigen-binding domain that binds to EpCAM, a bispecific antibody fragment thereof, a DNA encoding the bispecific antibody or the bispecific antibody fragment thereof, a vector comprising the DNA, a hybridoma and a transformant strain that produce the bispecific antibody or the bispecific antibody fragment thereof, a method for producing the bispecific antibody or the bispecific antibody fragment thereof, therapeutic and diagnostic agents comprising the bispecific antibody or the bispecific antibody fragment thereof, therapeutic and diagnostic methods using the bispecific antibody or the bispecific antibody fragment thereof, and a reagent for detection or measurement comprising the bispecific antibody or the bispecific antibody fragment thereof.

Means for Solving the Problems

As means for solving the above problems, the present invention provides a bispecific antibody comprising an antigen-binding domain that binds to CD40 and an antigen-binding domain that binds to EpCAM, or a bispecific antibody fragment thereof, and the like.

That is, the present invention relates to the following (1) to (35).

(1) A bispecific antibody, comprising an antigen-binding domain that binds to CD40 and an antigen-binding domain that binds to an epithelial cell adhesion molecule (EpCAM).
(2) The bispecific antibody according to (1), which divalently binds to each of CD40 and EpCAM.
(3) The bispecific antibody according to (1) or (2), wherein the antigen-binding domain that binds to CD40 comprises a heavy chain variable region (VH) and a light chain variable region (VL) of an antibody (anti-CD40 antibody) that specifically binds to CD40, and the antigen-binding domain that binds to EpCAM comprises VH and VL of an antibody (anti-EpCAM antibody) that specifically binds to EpCAM.

(4) The bispecific antibody according to any one of (1) to (3), which has two identical heavy chains comprising a polypeptide represented by a formula of VH1-X-VH2-Y in order from the N terminus {wherein VH1 represents VH of a first antibody, VH2 represents VH of a second antibody, X and Y each represents a polypeptide comprising CH1 of the antibody (wherein at least one of X and Y further comprises a hinge region of the antibody)} and four light chains comprising the same VL, and wherein one of the first antibody and the second antibody is the anti-CD40 antibody, and the other is the anti-EpCAM antibody.

(5) The bispecific antibody according to (4), wherein the light chain is a κ chain.

(6) The bispecific antibody according to (4) or (5) or a bispecific antibody fragment thereof, wherein X in the formula is a polypeptide composed of CH1 of human IgG, and Y is a polypeptide composed of CH1, a hinge region, CH2, and CH3 of human IgG.

(7) The bispecific antibody according to (4) or (5), wherein X in the formula is a polypeptide comprising the amino acid sequence represented by SEQ ID NO: 75, and Y is a polypeptide comprising the amino acid sequence represented by SEQ ID NO: 77.

(8) The bispecific antibody according to (4) or (5), wherein X in the formula is a polypeptide comprising CH1, a hinge region, CH2, and CH3 of human IgG, and Y is a polypeptide comprising CH1 of human IgG.

(9) The bispecific antibody according to (4) or (5), wherein X in the formula is a polypeptide comprising the amino acid sequence represented by SEQ ID NO: 77, and Y is a polypeptide comprising the amino acid sequence represented by SEQ ID NO: 75.

(10) The bispecific antibody according to any one of (3) to (9), wherein the VL is VL comprising complementarity determining regions (CDRs) 1 to 3 comprising the amino acid sequences represented by SEQ ID NOS: 23 to 25, respectively.

(11) The bispecific antibody according to any one of (3) to (10), wherein the VL is VL comprising the amino acid sequence represented by SEQ ID NO: 22.

(12) The bispecific antibody according to any one of (1) to (11), which has a CD40 agonistic activity.

(13) The bispecific antibody according to any one of (1) to (12), which does not exhibit a CD40 agonistic activity in the absence of a cell that expresses EpCAM, but exhibits the CD40 agonistic activity only in the presence of a cell that expresses EpCAM.

(14) The bispecific antibody according to any one of (3) to (13), wherein the anti-CD40 antibody is an anti-CD40 antibody that does not have an agonistic activity.

(15) The bispecific antibody according to any one of (4) to (14), wherein the first antibody is the anti-CD40 antibody, and the second antibody is the anti-EpCAM antibody.

(16) The bispecific antibody according to any one of (4) to (14), wherein the first antibody is the anti-EpCAM antibody, and the second antibody is the anti-CD40 antibody.

(17) The bispecific antibody according to any one of (3) to (16), wherein the anti-CD40 antibody is an anti-CD40 antibody comprising any one heavy chain variable region (VH) selected from the group consisting of the following (1a) to (1d):

(1a) VH comprising CDR1 to CDR3 comprising the amino acid sequences represented by SEQ ID NOS: 28 to 30, respectively;

(1b) VH comprising CDR1 to CDR3 comprising the amino acid sequences represented by SEQ ID NOS: 33 to 35, respectively;

(1c) VH comprising CDR1 to CDR3 comprising the amino acid sequences represented by SEQ ID NOS: 38 to 40, respectively; and (1d) VH comprising CDR1 to CDR3 comprising the amino acid sequences represented by SEQ ID NOS: 43 to 45, respectively.

(18) The bispecific antibody according to any one of (3) to (17), wherein the anti-CD40 antibody is an anti-CD40 antibody comprising VH comprising the amino acid sequence represented by any one of SEQ ID NOS: 27, 32, 37, and 42.

(19) The bispecific antibody according to any one of (3) to (18), wherein the anti-EpCAM antibody is an anti-EpCAM antibody comprising any one VH selected from the group consisting of the following (2a) to (2d):

(2a) VH comprising CDR1 to CDR3 comprising the amino acid sequences represented by SEQ ID NOS: 52 to 54, respectively;

(2b) VH comprising CDR1 to CDR3 comprising the amino acid sequences represented by SEQ ID NOS: 57 to 59, respectively;

(2c) VH comprising CDR1 to CDR3 comprising the amino acid sequences represented by SEQ ID NOS: 62 to 64, respectively; and (2d) VH comprising CDR1 to CDR3 comprising the amino acid sequences represented by SEQ ID NOS: 67 to 69, respectively.

(20) The bispecific antibody according to any one of (3) to (19), wherein the anti-EpCAM antibody is an anti-EpCAM antibody comprising VH comprising the amino acid sequence represented by any one of SEQ ID NOS: 51, 56, 61, and 66.

(21) A bispecific antibody fragment of the bispecific antibody according to any one of (1) to (20).

(22) The bispecific antibody fragment according to (21), which is a Fab-type bispecific antibody fragment or a F(ab')2-type bispecific antibody fragment.

(23) A DNA encoding the bispecific antibody according to any one of (1) to (20) or the bispecific antibody fragment according to (21) or (22).

(24) A recombinant vector, comprising the DNA according to (23).

(25) A transformant strain, obtained by introducing the recombinant vector according to (24) into a host cell.

(26) A method for producing the bispecific antibody according to any one of (1) to (20) or the bispecific antibody fragment according to (21) or (22), comprising culturing the transformant strain according to (25) in a culture medium, allowing the transformant strain to produce and accumulate the bispecific antibody according to any one of (1) to (20) or the bispecific antibody fragment according to (21) or (22) in a culture, and collecting the bispecific antibody or the bispecific antibody fragment from the culture.

(27) A therapeutic and/or diagnostic agent for a disease associated with at least one of human CD40 and human EpCAM, comprising the bispecific antibody according to any one of (1) to (20) or the bispecific antibody fragment according to (21) or (22) as an active ingredient.

(28) The agent according to (27), wherein the disease associated with at least one of human CD40 and human EpCAM is cancer.

(29) A therapeutic and/or diagnostic method for a disease associated with at least one of human CD40 and human EpCAM, using the bispecific antibody according to any one of (1) to (20) or the bispecific antibody fragment according to (21) or (22).

(30) The method according to (29), wherein the disease associated with at least one of human CD40 and human EpCAM is cancer.

(31) The bispecific antibody according to any one of (1) to (20) or the bispecific antibody fragment according to (21) or (22) for use in therapy and/or diagnosis for a disease associated with at least one of human CD40 and human EpCAM.

(32) The bispecific antibody according to (31) or the bispecific antibody fragment, wherein the disease associated with at least one of human CD40 and human EpCAM is cancer.

(33) Use of the bispecific antibody according to any one of (1) to (20) or the bispecific antibody fragment according to (21) or (22) for the manufacture of a therapeutic and/or diagnostic agent for a disease associated with at least one of human CD40 and human EpCAM.

(34) The use according to (33), wherein the disease associated with at least one of human CD40 and human EpCAM is cancer.

(35) A reagent for detecting or measuring at least one of EpCAM and CD40, comprising the bispecific antibody according to any one of (1) to (20) or the bispecific antibody fragment according to (21) or (22).

Effects of the Invention

According to the present invention, a bispecific antibody comprising an antigen-binding domain that binds to CD40 and an antigen-binding domain that binds to EpCAM, a bispecific antibody fragment thereof, a DNA encoding the bispecific antibody or the bispecific antibody fragment thereof, a vector comprising the DNA, a hybridoma and a transformant strain that produce the bispecific antibody or the bispecific antibody fragment thereof, a method for producing the bispecific antibody or the bispecific antibody fragment thereof, therapeutic and diagnostic agents comprising the bispecific antibody or the bispecific antibody fragment thereof, therapeutic and diagnostic methods using the bispecific antibody or the bispecific antibody fragment thereof, and a reagent for detection or measurement comprising the bispecific antibody or the bispecific antibody fragment thereof can be provided.

BRIEF DESCRIPTION OF DRAWINGS

FIG. 1(A) shows an N-terminal type bispecific antibody. FIG. 1(B) shows a C-terminal type bispecific antibody.

FIG. 10(A) shows the white blood cell count of the mice 24 hours after administration of an antibody. FIG. 10(B) shows the lymphocyte count of the mice 24 hours after administration of an antibody. FIG. 10(C) shows the monocyte count of the mice 24 hours after administration of an antibody. FIG. 10(D) shows the platelet count of the mice 24 hours after administration of an antibody. In each figure, the vertical axis of the graph represents each cell count ($1 \times 10^3$). R1090(N), R1090(C), and Epc112(C) denote R1090S55A-Ep203, Ct R1090S55A-Ep203, and Ct Epc112-R1066, respectively. An anti-DNP antibody was used as a negative control antibody, and 21.4.1 was used as an anti-CD40 agonistic antibody. 21.4.1 was administered at 1 mg/kg and the other antibodies were administered at 10 mg/kg.

EMBODIMENTS FOR CARRYING OUT THE INVENTION

Figure 1:
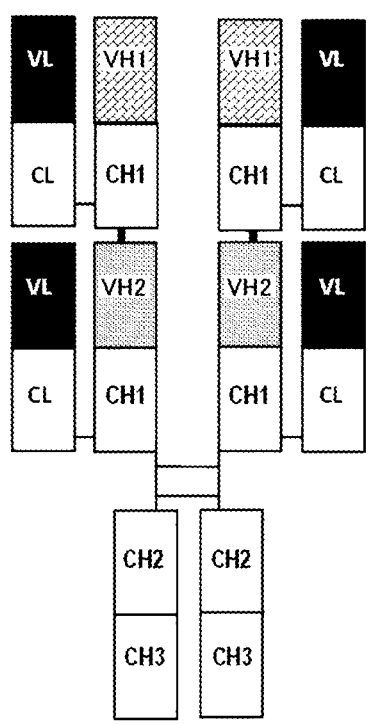
FIG. 1 shows an example of a structure of a bispecific antibody of the present invention.
Figure 1:
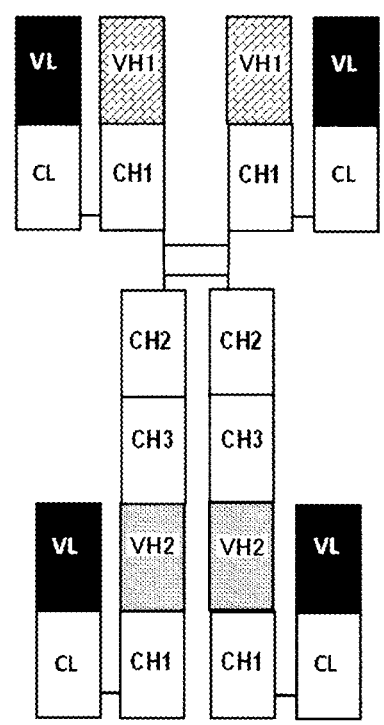

The present invention relates to a bispecific antibody comprising an antigen-binding domain that binds to CD40 and an antigen-binding domain that binds to EpCAM, or a bispecific antibody fragment thereof (hereinafter referred to as the bispecific antibody or the bispecific antibody fragment thereof of the present invention).

The CD40 in the present invention is used synonymously with TNF receptor superfamily member 5 (TNFRSF5), Bp50, CDW40, MGC9013, and p50. As the CD40, for example, human CD40 comprising an amino acid sequence represented by GenBank accession No. NP 001241 in NCBI (www.ncbi.nlm.nih.gov/) or SEQ ID NO: 6, monkey CD40 comprising an amino acid sequence represented by GenBank accession No. XP_005569274 or SEQ ID NO: 8, and the like are exemplified. Further, for example, a polypeptide that consists of an amino acid sequence in which one or more amino acids are deleted, substituted, or added in the amino acid sequence represented by SEQ ID NO: 6, GenBank accession No. NP 001241, or GenBank accession No. XP_005569274, and has the function of CD40 is exemplified.

A polypeptide comprising an amino acid sequence having generally 70% or more, preferably 80% or more, and more preferably 90% or more homology with the amino acid sequence represented by SEQ ID NO: 6, GenBank accession No. NP 001241, or GenBank accession No. XP_005569274, and most preferably, a polypeptide that consists of an amino acid sequence having 95%, 96%, 97%, 98%, and 99% or more homology and has the function of CD40 are also included in the CD40 of the present invention.

The polypeptide having an amino acid sequence in which one or more amino acid residues are deleted, substituted, or added in the amino acid sequence represented by SEQ ID NO: 6, GenBank accession No. NP 001241, or GenBank accession No. XP_005569274 can be obtained by, for example, introducing a site-specific mutation into a DNA encoding the amino acid sequence represented by SEQ ID NO: 6, GenBank accession No. NP 001241, or GenBank accession No. XP_005569274 using a site-specific mutagenesis method [Molecular Cloning, A Laboratory Manual, Second Edition, Cold Spring Harbor Laboratory Press (1989), Current Protocols in Molecular Biology, John Wiley & Sons (1987-1997), Nucleic Acids Research, 10, 6487 (1982), Proc. Natl. Acad. Sci. USA, 79, 6409 (1982), Gene, 34, 315 (1985), Nucleic Acids Research, 13, 4431 (1985), Proceeding of the National Academy of Sciences in USA, 82, 488 (1985)], or the like. The number of amino acids to be deleted, substituted, or added is not particularly limited, but is preferably one to several tens, for example, 1 to 20, and more preferably one to several, for example, 1 to 5 amino acids.

As a gene encoding CD40, for example, the nucleotide sequence of human CD40 represented by SEQ ID NO: 5 or GenBank accession No. NM 001250, the nucleotide sequence of monkey CD40 represented by SEQ ID NO: 7 or GenBank accession No. XM 011766922, and the like are exemplified. Further, a gene comprising a DNA that consists of a nucleotide sequence in which one or more bases are deleted, substituted, or added in the nucleotide sequence represented by SEQ ID NO: 5 or GenBank accession No. NM_001250, and encodes a polypeptide having the function of CD40, a gene comprising a DNA that consists of preferably a nucleotide sequence having 60% or more homology, more preferably a nucleotide sequence having 80% or more homology, and further more preferably a nucleotide sequence having 95% or more homology with the nucleotide sequence represented by SEQ ID NO: 5 or GenBank accession No. NM_001250, and encodes a polypeptide having the function of CD40, a gene comprising a DNA that consists of a DNA which hybridizes with a DNA consisting of the nucleotide sequence represented by SEQ ID NO: 5 or GenBank accession No. NM_001250 under stringent conditions, and that encodes a polypeptide having the function of CD40, and the like are also included in the gene encoding the CD40 of the present invention.

The DNA which hybridizes under stringent conditions means, for example, a hybridizable DNA that can be obtained by a colony hybridization method, a plaque hybridization method, a southern blot hybridization method, a DNA microarray method, or the like using a DNA having the nucleotide sequence represented by SEQ ID NO: 5 or GenBank accession No. NM_001250 as a probe. Specifically, a DNA that can be identified by washing a filter or a microscope slide under the condition of 65° C. using an SSC solution having a concentration of 0.1 to 2 times (a composition of the SSC solution having a concentration of 1 time is composed of 150 mmol/L sodium chloride and 15 mmol/L sodium citrate), after performing hybridization [Molecular Cloning, A Laboratory Manual, Second Edition, Cold Spring Harbor Laboratory Press (1989), Current Protocols in Molecular Biology, John Wiley & Sons (1987-1997), DNA Cloning 1: Core Techniques, A Practical Approach, Second Edition, Oxford University (1995)] at 65° C. in the presence of 0.7 to 1.0 mol/L sodium chloride using a filter or a microscope slide on which a DNA derived from a hybridized colony or plaque, or a PCR product or an oligo DNA having the sequence is immobilized can be exemplified. As the hybridizable DNA, for example, a DNA preferably having 60% or more homology, more preferably a DNA having 80% or more homology, and further more preferably a DNA having 95% or more homology with the nucleotide sequence represented by SEQ ID NO: 5 or GenBank accession No. NM_001250 can be exemplified.

A gene polymorphism is often recognized in a nucleotide sequence of a gene encoding a protein of a eukaryote. A gene in which a small-scale mutation has occurred in a nucleotide sequence due to such a polymorphism among genes used in the present invention is also included in the gene encoding the CD40 of the present invention.

The value of homology in the present invention may be a value calculated using a homology search program known to those skilled in the art unless otherwise particularly specified, however, with respect to a nucleotide sequence, a value calculated using a default parameter in BLAST [J. Mol. Biol., 215, 403 (1990)], and the like are exemplified, and with respect to an amino acid sequence, a value calculated using a default parameter in BLAST2 [Nucleic Acids Research, 25, 3389 (1997), Genome Research, 7, 649 (1997), www.ncbi.nlm.nih.gov/Education/BLASTinfo/information3.html], and the like are exemplified.

As for the default parameters, G (Cost to open gap) is 5 in the case of a nucleotide sequence and 11 in the case of an amino acid sequence, -E (Cost to extend gap) is 2 in the case of a nucleotide sequence and 1 in the case of an amino acid sequence, -q (Penalty for nucleotide mismatch) is -3, -r (reward for nucleotide match) is 1, -e (expect value) is 10, -W (wordsize) is 11 residues in the case of a nucleotide sequence and 3 residues in the case of an amino acid sequence, -y [Dropoff (X) for blast extensions in bits] is 20 in the case of blastn and 7 in the case of programs other than blastn, -X (X dropoff value for gapped alignment in bits) is 15, and -Z (final X dropoff value for gapped alignment in bits) is 50 in the case of blastn and 25 in the case of programs other than blastn (www.ncbi.nlm.nih.gov/blast/html/blastcgihelp.html).

A polypeptide composed of a partial sequence of the amino acid sequence of CD40 can be produced by a method known to those skilled in the art, and can be produced by, for example, deleting part of the DNA encoding the amino acid sequence represented by SEQ ID NO: 6, GenBank accession No. NP 001241, or GenBank accession No. XP_005569274 and culturing a transformant transfected with an expression vector comprising the resulting DNA. In addition, for example, a polypeptide having an amino acid sequence in which one or more amino acids are deleted, substituted, or added in the partial sequence of the amino acid sequence represented by SEQ ID NO: 6, GenBank accession No. NP 001241, or GenBank accession No. XP_005569274 can be obtained by the same method as described above based on the polypeptide or the DNA produced by the above method. Further, a polypeptide composed of the partial sequence of the amino acid sequence of CD40, or a polypeptide having an amino acid sequence in which one or more amino acids are deleted, substituted, or added in the partial sequence of the amino acid sequence of CD40 can also be produced using a chemical synthesis method such as a fluorenylmethyloxycarbonyl (Fmoc) method or a t-butyloxycarbonyl (tBoc) method.

As an extracellular domain of the CD40 in the present invention, for example, a region in which an amino acid sequence of human CD40 represented by GenBank accession No. NP 001241 is predicted using a known transmembrane region prediction program SOSUI (sosui.proteome-.bio.tuat.ac.jp/sosuiframe0.html), TMHMM ver. 2 (www.cbs.dtu.dk/services/TMHMM-2.0/), ExPASy Proteomics Server (Ca.expasy.org/), or the like can be exemplified. Specifically, the amino acid sequence shown at positions 21 to 194 of SEQ ID NO: 6 or GenBank accession No. NP 001241 is exemplified.

Examples of the function of CD40 include induction of a CD40 signal when a CD40 ligand or an agonist binds thereto to cause various actions. For example, when a CD40 signal is induced in a cancer cell, cell death or growth inhibition of the cancer cell, or the like is caused. When a CD40 signal is induced in a B lymphocyte, for example, activation of the B lymphocyte, promotion of expression of CD95, class switch recombination, somatic hypermutation, or the like is caused to induce production of an antibody with high antigen affinity or the like. When a CD40 signal is induced in a dendritic cell, for example, maturation of the dendritic cell or production of IL-12 is caused. When a CD40 signal is induced in a macrophage, for example, reduction in a surface marker of an M2 macrophage, induction of expression of a surface marker of an M1 macrophage, or proinflammatory cytokine production is caused.

The EpCAM in the present invention is used synonymously with CD326, GA733-2, HEA125, KS1/4, MK-1, MH99, MOC31, 323/A3, 17-1A, CO-17A, ESA, EGP-2, EGP34, EGP40, KSA, KS1/4, TROP-1, and TACST-1.

As the EpCAM, for example, human EpCAM comprising the amino acid sequence represented by GenBank Accession No. AAH14785 or SEQ ID NO: 16; monkey EpCAM comprising the amino acid sequence represented by GenBank Accession No. NP_001035118 or SEQ ID NO: 18; mouse EpCAM comprising the amino acid sequence represented by GenBank Accession No. NP_032558 or SEQ ID NO: 20; and the like are exemplified. Further, for example, a polypeptide that consists of an amino acid sequence in which one or more amino acids are deleted, substituted, or added in the amino acid sequence represented by SEQ ID NO: 16, AAH14785, GenBank accession No.

NP_001035118, or GenBank accession No. NP_032558, and has the function of EpCAM is exemplified.

A polypeptide comprising an amino acid sequence having preferably 70% or more, more preferably 80% or more, and further more preferably 90% or more homology with the amino acid sequence represented by SEQ ID NO: 16, AAH14785, GenBank accession No. NP_001035118, or GenBank accession No. NP_032558, and most preferably, a polypeptide that consists of an amino acid sequence having 95%, 96%, 97%, 98%, and 99% or more homology and has the function of EpCAM are also included in the EpCAM of the present invention.

The polypeptide having an amino acid sequence in which one or more amino acid residues are deleted, substituted, or added in the amino acid sequence represented by SEQ ID NO: 16, AAH14785, GenBank accession No. NP_001035118, or GenBank accession No. NP_032558 can be obtained by, for example, introducing a site-specific mutation into a DNA encoding the amino acid sequence represented by SEQ ID NO: 16, AAH14785, GenBank accession No. NP_001035118, or GenBank accession No. NP_032558 using the above-mentioned site-specific mutagenesis method, or the like. The number of amino acids to be deleted, substituted, or added is not particularly limited, but is preferably one to several tens, for example, 1 to 20, and more preferably one to several, for example, 1 to 5 amino acids.

As a gene encoding the EpCAM in the present invention, for example, a gene of human EpCAM comprising the nucleotide sequence represented by GenBank accession No. NM_002354 or SEQ ID NO: 15; a gene of monkey EpCAM comprising the nucleotide sequence represented by GenBank accession No. XM_015433685 or SEQ ID NO: 17; a gene of mouse EpCAM comprising the nucleotide sequence represented by GenBank accession No. NM_008532 or SEQ ID NO: 19; and the like are exemplified.

Further, for example, a gene comprising a DNA that consists of a nucleotide sequence in which one or more bases are deleted, substituted, or added in the nucleotide sequence represented by SEQ ID NO: 15, GenBank accession No. NM_002354, GenBank accession No. XM_015433685, or GenBank accession No. NM_008532, and encodes a polypeptide having the function of EpCAM, a gene comprising a DNA that consists of a nucleotide sequence having 60% or more homology, preferably a nucleotide sequence having 80% or more homology, and more preferably a nucleotide sequence having 95% or more homology with a nucleotide sequence represented by the nucleotide sequence represented by SEQ ID NO: 15, GenBank accession No. NM_002354, GenBank accession No. XM_015433685, or GenBank accession No. NM_008532, and encodes a polypeptide having the function of EpCAM, a gene comprising a DNA that consists of a DNA which hybridizes with a DNA comprising the nucleotide sequence represented by SEQ ID NO: 15, GenBank accession No. NM_002354, GenBank accession No. XM_015433685, or Gen accession No. NM_008532 under stringent conditions, and that encodes a polypeptide having the function of EpCAM, and the like are also included in the gene encoding the EpCAM of the present invention.

As an extracellular domain of the EpCAM in the present invention, for example, a region in which an amino acid sequence of human EpCAM represented by GenBank accession No. AAH14785 is predicted using a known transmembrane region prediction program SOSUI (sosui.proteome-.bio.tuat.ac.jp/sosuiframe0.html), TMHMM ver. 2 (www.cbs.dtu.dk/services/TMHMM-2.0/), ExPASy Proteomics Server (Ca.expasy.org/), or the like can be exemplified. Specifically, the amino acid sequence shown at positions 22 to 26 of SEQ ID NO: 10 or GenBank accession No. AAH14785 is exemplified.

Examples of the function of EpCAM include calcium-independent cell-cell adhesion, growth promotion through the upregulation of C-Myc, Cyclin A/E or the like in a cancer cell, and the like.

An antibody is a protein derived from a gene (referred to as "antibody gene") encoding all or part of a heavy chain variable region, a heavy chain constant region, a light chain variable region, and a light chain constant region constituting an immunoglobulin. The antibody of the present invention also includes an antibody or an antibody fragment having any immunoglobulin class and subclass.

The heavy chain (H chain) refers to a polypeptide having a higher molecular weight of the two types of polypeptides constituting an immunoglobulin molecule. The heavy chain determines the antibody class and subclass. IgA, IgD, IgE, IgG, and IgM comprise an α chain, a δ chain, an ε chain, a γ chain, and a μ chain as the heavy chain, respectively, and the heavy chain constant region is characterized by a different amino acid sequence. The light chain (L chain) refers to a polypeptide having a lower molecular weight of the two types of polypeptides constituting an immunoglobulin molecule. In the case of a human antibody, there exist two types, a κ chain and a λ chain, in the light chain.

The variable region (V region) generally refers to a region that is present in an amino acid sequence at the N-terminal side of an immunoglobulin and is rich in diversity. Because a part other than the variable region has a structure with less diversity, it is called a constant region (C region). The respective variable regions of the heavy chain and the light chain are associated to form an antigen-binding site and determine the binding property of the antibody to the antigen.

In the heavy chain of a human antibody, a variable region corresponds to an amino acid sequence at positions 1 to 117 numbered according to the EU index by Kabat et al. (Kabat et al., Sequences of proteins of immunological interest, 1991 Fifth edition), and a constant region corresponds to an amino acid sequence starting with position 118. In the light chain of a human antibody, an amino acid sequence at positions 1 to 107 numbered according to Kabat et al. (Kabat numbering) corresponds to a variable region, and an amino acid sequence starting with position 108 corresponds to a constant region. Hereinafter, the heavy chain variable region or the light chain variable region is abbreviated as VH or VL.

The antigen-binding site is a site that recognizes and binds to an antigen in an antibody, and refers to a site that forms a complementary conformation with an antigenic determinant (epitope). At the antigen-binding site, a strong intermolecular interaction between the antigenic determinants occurs. The antigen-binding site is constituted by VH and VL comprising at least three complementarity determining regions (CDRs). In the case of a human antibody, VH and VL each comprise three CDRs. These CDRs are referred to as CDR1, CDR2, and CDR3, respectively, in order from the N-terminal side.

In the constant region, the heavy chain constant region and the light chain constant region are referred to as CH and CL, respectively. The CH is classified into an α chain, a δ chain, an ε chain, a γ chain, and a μ chain which are subclasses of the heavy chain. The CH is constituted by a CH1 domain, a hinge domain, a CH2 domain, and a CH3 domain arranged in order from the N-terminal side, and the CH2 domain and the CH3 domain together are called an Fc region. On the other hand, the CL is classified into two subclasses called a Cλ chain and a Cκ chain.

In the present invention, the anti-CD40 antibody refers to a monoclonal antibody that specifically recognizes and binds to the extracellular domain of CD40. In addition, in the present invention, the anti-EpCAM antibody refers to a monoclonal antibody that specifically recognizes and binds to the extracellular domain of EpCAM. Further, in the present invention, the antibody also includes a polyclonal antibody and an oligoclonal antibody.

In the present invention, the binding of an antibody or an antibody fragment thereof to at least one of CD40 and EpCAM can be confirmed by a method in which the binding affinity of the antibody to a cell expressing at least one of CD40 and EpCAM is confirmed using, for example, a known immunological detection method, preferably a fluorescent cell staining method, or the like. Further, it is also possible to use known immunological detection methods [Monoclonal Antibodies—Principles and Practice, Third Edition, Academic Press (1996), Antibodies—A Laboratory Manual, Cold Spring Harbor Laboratory (1988), Monoclonal Antibody Experimental Manual, Kodansha scientific books (1987)], and the like in combination.

A monoclonal antibody is an antibody secreted by an antibody-producing cell maintaining monoclonality, and recognizes a single epitope (also referred to as an antigenic determinant). The monoclonal antibody molecules have the same amino acid sequence (primary structure) and have a single structure. The polyclonal antibody is a collection of antibody molecules secreted by antibody-producing cells of different clones. The oligoclonal antibody is a collection of antibody molecules in which a plurality of different monoclonal antibodies are mixed.

The epitope is a structural site of an antigen which an antibody recognizes and binds to. Examples of the epitope include a single amino acid sequence, a conformation composed of an amino acid sequence, an amino acid sequence to which a sugar chain is bound, a conformation composed of an amino acid sequence to which a sugar chain is bound, and the like, each of which a monoclonal antibody recognizes and binds to.

Examples of the monoclonal antibody in the present invention include an antibody produced by a hybridoma, and a genetically recombinant antibody produced by a transformant transformed with an expression vector comprising an antibody gene.

The hybridoma can be prepared by, for example, preparing an antigen, obtaining an antibody-producing cell having antigen specificity from an animal immunized with the antigen, and then fusing the antibody-producing cell with a myeloma cell. A desired monoclonal antibody can be obtained by culturing the hybridoma or by administering the hybridoma to an animal to convert the hybridoma into an ascites tumor, isolating the culture solution or the ascites, followed by purification. As the animal to be immunized with the antigen, any animal can be used as long as it can produce a hybridoma, however, a mouse, a rat, a hamster, a rabbit, or the like is preferably used. In addition, the hybridoma can also be produced by obtaining a cell having an antibody-producing ability from such an immunized animal, subjecting the cell to in vitro immunization, and then fusing the cell with a myeloma cell.

Examples of the genetically recombinant antibody in the present invention include antibodies produced using a gene recombinant technique such as a recombinant mouse antibody, a recombinant rat antibody, a recombinant hamster antibody, a recombinant rabbit antibody, a human chimeric antibody (also referred to as a chimeric antibody), a humanized antibody (also referred to as a CDR-grafted antibody), and a human antibody. In the genetically recombinant antibody, it is possible to determine which animal species the heavy chain and the light chain variable regions and constant regions derived from are applied according to the animal species to be used as a target and the purpose. For example, when the animal species to be used as a target is a human, as the variable region, one derived from a human or a non-human animal such as a mouse can be adopted, and as the constant region and the linker, those derived from a human can be adopted.

The chimeric antibody refers to an antibody composed of VH and VL of an antibody of an animal other than a human (non-human animal) and CH and CL of a human antibody. As the non-human animal, any animal such as a mouse, a rat, a hamster, or a rabbit can be used as long as it can produce a hybridoma. The chimeric antibody can be produced by obtaining cDNAs encoding VH and VL from a hybridoma derived from a non-human animal that produces a monoclonal antibody, inserting each of the cDNAs into an expression vector for an animal cell having DNAs encoding CH and CL of a human antibody, thereby constructing a chimeric antibody expression vector, and then introducing the vector into an animal cell to cause expression.

The humanized antibody refers to an antibody in which CDRs of VH and VL of a non-human animal antibody is grafted in the corresponding CDRs of VH and VL of a human antibody. A region other than the CDRs of VH and VL is referred to as a framework region (hereinafter referred to as FR). The humanized antibody can be produced by constructing a cDNA encoding the amino acid sequence of VH composed of the amino acid sequence of the CDRs of VH of a non-human animal antibody and the amino acid sequence of the FR of VH of an arbitrary human antibody, and a cDNA encoding the amino acid sequence of VL composed of the amino acid sequence of the CDRs of VL of a non-human animal antibody and the amino acid sequence of the FR of VL of an arbitrary human antibody, inserting each of the cDNAs into an expression vector for an animal cell having DNAs encoding CH and CL of a human antibody, thereby constructing a humanized antibody expression vector, and then introducing the vector into an animal cell to cause expression.

The human antibody originally refers to an antibody that is naturally present in the human body, but also includes antibodies that are obtained from a human antibody phage library and a human antibody-producing transgenic animal, each of which is produced by recent advancement of genetic engineering, cellular engineering, or developmental engineering technology, and the like.

The antibody that is naturally present in the human body can be obtained by, for example, infecting human peripheral blood lymphocytes with an EB virus or the like so as to immortalize the lymphocytes, followed by cloning to culture a lymphocyte that produces the antibody, and then purifying the antibody from the culture supernatant.

The human antibody phage library is a library in which an antibody fragment such as a Fab or an scFv is expressed on the surfaces of phages by inserting an antibody gene prepared from a human B cell into a phage gene. It is possible to collect a phage that expresses an antibody fragment having a desired antigen-binding activity from the library using a binding activity to a substrate onto which an antigen is immobilized as an index. The antibody fragment can further also be converted into a human antibody molecule composed of two complete H chains and two complete L chains using a genetic engineering technique.

The human antibody-producing transgenic animal means an animal in which a human antibody gene is incorporated into a cell. Specifically, for example, a human antibody-producing transgenic mouse can be produced by introducing a human antibody gene into a mouse ES cell, implanting the ES cell to an early embryo of a mouse and then allowing the embryo to develop into an individual. A human antibody derived from a human antibody-producing transgenic animal can be prepared by obtaining a hybridoma using a conventional hybridoma production method that is performed for a non-human animal, and culturing the hybridoma, thereby producing and accumulating the antibody in the culture supernatant.

The CH of the genetically recombinant antibody may be any CH as long as it belongs to a human immunoglobulin, but is preferably CH of the human immunoglobulin G (hIgG) class. Further, it is possible to use CH of any subclass such as hIgG1, hIgG2, hIgG3, and hIgG4 which belong to the hIgG class. In addition, the CL of the genetically recombinant antibody may be any CL as long as it belongs to a human immunoglobulin, and CL of the κ class or the λ class can be used.

In the present invention, the bispecific antibody refers to a protein that has two types of antigen-binding domains with different specificities and includes all or part of a heavy chain variable region, a heavy chain constant region, a light chain variable region, and a light chain constant region constituting an immunoglobulin. Each of the antigen-binding domains of the bispecific antibody may bind to different epitopes of a single antigen or may bind to different antigens.

In the present invention, an antigen-binding domain that binds to CD40 or EpCAM may be any as long as it specifically recognizes and binds to CD40 or EpCAM. For example, the domain may be in any form of a polypeptide that can be produced by a genetically recombination technique such as an antibody, a ligand, a receptor, or an interacting molecule present in nature, a protein molecule and a fragment thereof, a conjugate body with the a low-molecular weight molecule or a natural product of the protein molecule, or the like.

Further, the antigen-binding domain may be a binding protein recombined by utilizing a binding domain of a known binding molecule such as an antibody, a ligand, or a receptor, and specific examples include a recombinant protein comprising a CDR of an antibody that binds to each antigen, an antibody variable region comprising a CDR, a recombinant protein comprising an antibody variable region and a binding domain of a ligand that binds to each antigen, and the like. Among these, the antigen-binding domain is preferably an antibody variable region in the present invention.

The bispecific antibody or the bispecific antibody fragment thereof of the present invention may bind to CD40 and EpCAM expressed on the same cell, or may bind to CD40 and EpCAM expressed on different cells.

Examples of the cell that expresses CD40 include antigen-presenting cells such as B cells, dendritic cells (DC), macrophages, and monocytes, cancer cells such as Ramos cells, and the like.

Examples of the cell that expresses EpCAM include cancer cells of head and neck cancer, lung cancer, gastrointestinal cancer, breast cancer, urological cancer, and the like.

Examples of the bispecific antibody or the bispecific antibody fragment thereof of the present invention include a bispecific antibody or a bispecific antibody fragment thereof having a CD40 agonistic activity. As the bispecific antibody or the bispecific antibody fragment thereof of the present invention, a bispecific antibody or a bispecific antibody fragment thereof that does not exhibit a CD40 agonistic activity in the absence of an EpCAM molecule or a cell that expresses EpCAM, but exhibits a CD40 agonistic activity only in the presence of an EpCAM molecule or a cell that expresses EpCAM is preferred. Such a bispecific antibody or a bispecific antibody fragment thereof activates CD40 only in a lesion site such as cancer where a cell that expresses EpCAM is present, and therefore is preferred from the viewpoint that an adverse effect caused by systemic activation of CD40 does not occur.

The CD40 agonistic activity of the bispecific antibody or the bispecific antibody fragment thereof of the present invention refers to an activity of inducing activation of an antigen-presenting cell, an activity of inducing cell death of a tumor cell, or the like when the bispecific antibody or the bispecific antibody fragment thereof binds to CD40 on a cell to induce a signal through the CD40.

The CD40 agonistic activity can be confirmed by, for example, evaluation of an increase in the expression level of CD95 on a cell that expresses CD40 such as a Ramos cell.

That is, as the bispecific antibody or the bispecific antibody fragment thereof of the present invention, specifically, a bispecific antibody or a bispecific antibody fragment thereof that induces activation of an antigen-presenting cell that expresses CD40 and/or cell death of a tumor cell when it binds to EpCAM and CD40 in the presence of a cell that expresses EpCAM, and the like are exemplified.

In the present invention, the CD40 antagonistic activity refers to an activity of inhibiting activation of CD40 by a CD40 ligand or a CD40 agonist, or the like. For example, it refers to an activity of inhibiting signal induction when a CD40 ligand or a CD40 agonist binds to CD40, or the like.

The CD40 antagonistic activity of an antibody can be confirmed by inhibition of induction of the expression of CD95 by a CD40 ligand in a cell that expresses CD40 such as a Ramos cell by adding the antibody.

The number of binding domains to a certain antigen included in a single molecule of a bispecific antibody refers to a binding valence. For example, in the present invention, when a single molecule of a bispecific antibody has two antigen-binding domains that bind to CD40 and two antigen-binding domains that bind to EpCAM, the bispecific antibody divalently binds to each of CD40 and EpCAM.

In the present invention, one molecule of the bispecific antibody may bind to CD40 or EpCAM in whatever valence, but is preferably binds at least divalently to each of CD40 and EpCAM.

In addition, an antibody comprising a plurality of antigen-binding domains that are bound through an appropriate linker such as a linker comprising an immunoglobulin domain or a fragment thereof is also included in the bispecific antibody of the present invention.

In the bispecific antibody of the present invention, the positions of an antigen-binding domain that binds to CD40 and an antigen-binding domain that binds to EpCAM can be appropriately selected.

The bispecific antibody of the present invention can be produced using a known production technique ([Nature Protocols, 9, 2450-2463 (2014)], WO 1998/050431, WO 2001/7734, WO 2002/002773, and WO 2009/131239) or the like.

In the bispecific antibody of the present invention, the antigen-binding domain that binds to CD40 may be located closer to the N-terminal side or closer to the C-terminal side than the antigen-binding domain that binds to EpCAM.

As the bispecific antibody of the present invention, the V region of the antibody can be used as an antigen-binding domain, and examples thereof include an antibody comprising a heavy chain comprising a plurality of VHs for one heavy chain, an antibody comprising two heavy chains comprising one VH, and the like. Hereinafter, the first VH from the N terminus of an antibody comprising a heavy chain comprising a plurality of VHs for one heavy chain is represented by VH1, the second VH is represented by VH2, and the n-th VH is represented by VHn in some cases. In the case of an antibody comprising a heavy chain comprising two VHs for one heavy chain, VH located at the first place from the N-terminal side is represented by VH1, and VH located at the second place is represented by VH2.

As the bispecific antibody comprising a heavy chain comprising a plurality of VHs for one heavy chain, more specifically, an antibody comprising a heavy chain comprising two or more VHs bound through a linker comprising an immunoglobulin domain or a fragment thereof is exemplified.

When three or more VHs are bound, as the linker, different immunoglobulin domains or fragments thereof may be used, or the same immunoglobulin domains or a fragment thereof may be used. In addition, when two or more VHs are linked, it is possible to change the length or the type of an immunoglobulin domain or a fragment thereof so that each VH can specifically bind to an antigen.

Specifically, the bispecific antibody of the present invention has at least one of the features shown in the following (a) to (e):

(a) one heavy chain polypeptide comprises a plurality of (for example, 2 to 5) different VHs and the VHs are not close to each other;

(b) VHs are linked in tandem (in a vertical row) through a polypeptide linker comprising 10 or more amino acids. More specifically, VHs are linked using, for example, a linker comprising all or part of the amino acid sequence of an immunoglobulin domain;

(c) a light chain and a heavy chain are associated with each other to form an antigen-binding site;

(d) as illustrated in FIG. 1(A) or FIG. 1(B), it has a structure composed of two heavy chain polypeptides and at least four light chain polypeptides, and the two heavy chain polypeptides are linked to each other through a disulfide bond in a hinge region, and the light chain polypeptide and the heavy chain polypeptide are also linked to each other through a disulfide bond; and (e) a constant region of the heavy chain consists of, for example, all or part of a constant region of a natural antibody heavy chain (for example, a CH1 fragment, CH1, CH2, CH3, CH1-hinge, CH1-hinge-CH2, CH1-hinge-CH2-CH3, or the like).

In the present invention, it is possible to appropriately select the position of the VH of the anti-CD40 antibody (which means VH derived from the anti-CD40 antibody) and the position of the VH of the anti-EpCAM antibody (which means VH derived from the anti-EpCAM antibody) comprised in the bispecific antibody. For example, in the bispecific antibody having the structure illustrated in FIG. 1(A) or FIG. 1(B), the VH of the anti-CD40 antibody may be located closer to the N-terminal side or closer to the C-terminal side than the VH of the anti-EpCAM antibody, but is preferably located closer to the N-terminal side than the VH of the anti-EpCAM antibody.

In the present invention, the VLs comprised in the bispecific antibody may be the same VL or different VLs. The VH of the bispecific antibody that is a bispecific antibody comprising the same VL and that can bind to two different epitopes on two different antigens or the same antigen may be an optimized or altered VH so that each variable region can bind to a corresponding specific antigen or epitope, and for example, it is possible to select an appropriate VH using a method such as screening with amino acid alteration, or phage display.

The VL comprised in the bispecific antibody of the present invention may be any as long as it is the VL of the anti-CD40 antibody or the anti-EpCAM antibody, however, VL comprising CDR1, CDR2, and CDR3 comprising the amino acid sequences represented by SEQ ID NOS: 23, 24, and 25, respectively, and VL comprising the amino acid sequence represented by SEQ ID NO: 22 are preferred.

In the present invention, the linker refers to a chemical structure through which a plurality of antigen-binding domains are bound, and is preferably a polypeptide. Examples of the linker used for the bispecific antibody of the present invention include a linker comprising all or part of an amino acid sequence of an immunoglobulin domain, a linker comprising all or part of an amino acid sequence of a polypeptide composed of a plurality of immunoglobulin domains, and the like.

In the present invention, a C-terminal side polypeptide refers to a polypeptide chain that binds to the C terminus of an antigen-binding domain located closest to the C-terminal side among a plurality of antigen-binding domains. The bispecific antibody of the present invention may or may not have a C-terminal side polypeptide, but is preferably a bispecific antibody having a C-terminal side polypeptide. Examples of the C-terminal side polypeptide include a polypeptide comprising all or part of an amino acid sequence of an immunoglobulin domain, a polypeptide comprising all or part of an amino acid sequence of a polypeptide composed of a plurality of immunoglobulin domains, and the like.

As a linker or a C-terminal side polypeptide comprising part of an amino acid sequence of an immunoglobulin domain, the amino acid sequence selected from an immunoglobulin may be intermittent or consecutive, but is preferably a consecutive amino acid sequence. In addition, the amino acid sequence may comprise a hinge region.

In the present invention, the immunoglobulin domain comprises a peptide that has an amino acid sequence similar to an immunoglobulin and is composed of about 100 amino acid residues in which at least two cysteine residues are present as a smallest unit. In the present invention, the immunoglobulin domain also comprises a polypeptide that comprises a plurality of immunoglobulin domains as the smallest unit described above. Examples of the immunoglobulin domain include VH, CH1, CH2, and CH3 of an immunoglobulin heavy chain, and VL and CL of an immunoglobulin light chain, and the like.

The animal species of the immunoglobulin is not particularly limited, but is preferably a human. In addition, the subclass of the constant region of the immunoglobulin heavy chain may be any of IgD, IgM, IgG1, IgG2, IgG3, IgG4, IgA1, IgA2, and IgE, and preferably, IgG-derived and IgM-derived subclasses are preferred. In addition, the subclass of the constant region of the immunoglobulin light chain may be either of κ and λ.

Further, the immunoglobulin domain is also present in proteins other than the immunoglobulin, and for example, immunoglobulin domains comprised in proteins belonging to the immunoglobulin superfamily such as a major histocompatibility antigen (MHC), CD1, B7, and a T cell receptor (TCR) are exemplified. As the immunoglobulin domain used for the bispecific antibody of the present invention, any immunoglobulin domain can be applied.

In the case of a human antibody, the CH1 refers to a region having an amino acid sequence at positions 118 to 215 numbered according to the EU index. Similarly, the CH2 refers to a region having an amino acid sequence at positions 231 to 340 numbered according to the EU index of Kabat et al., and the CH3 refers to a region having an amino acid sequence at positions 341 to 446 numbered according to the EU index of Kabat et al. Between CH1 and CH2, an amino acid region rich in flexibility called a hinge region (hereinafter sometimes referred to as a hinge) is present. The hinge region refers to a region having an amino acid sequence at positions 216 to 230 numbered according to the EU index of Kabat et al.

The CL refers to a region having an amino acid sequence at positions 108 to 214 numbered according to Kabat numbering in the case of the κ chain of a human antibody, and refers to a region having an amino acid sequence at positions 108 to 215 in the case of the λ chain.

Examples of the linker and the C-terminal side polypeptide used for the bispecific antibody of the present invention include, but are not limited to, an immunoglobulin domain composed of CH1-hinge-CH2-CH3 arranged in order in the direction from the N terminus to the C terminus, an immunoglobulin domain composed of CH1-hinge-CH2, an immunoglobulin domain composed of CH1-hinge, an immunoglobulin domain composed of CH1, a fragment at the N-terminal side of CH1, a CH1 fragment composed of 14 amino acid residues in which the amino acid residue at position 14 is Cys, and a CH1 fragment composed of amino acid residues at positions 1 to 14 from the N terminus of CH1, and a fragment in which one or more amino acid residues are altered in the amino acid sequence of any of the immunoglobulin domain fragments.

In addition, in the present invention, as an example of the linker and the C-terminal side polypeptide, it is possible to appropriately combine and use all or part of fragments of an amino acid sequence composed of CH1, a hinge, CH2, and CH3 of an antibody. Further, it is also possible to partially delete such an amino acid sequence or change the order thereof and use the resultant. In addition, the subclass of the antibody to be used for the linker and the C-terminal side polypeptide is not particularly limited, but is preferably IgM or IgG4 or an IgG4 mutant obtained by substituting a Ser residue at position 228 in the heavy chain constant region of IgG4 with Pro, a Leu residue at position 235 therein with Asn, and an Arg residue at position 409 therein with Lys (hereinafter referred to as IgG4PE R409K), and is more preferably IgG4 and IgG4PE R409K.

In the present invention, examples of the linker and the C-terminal side polypeptide include a polypeptide composed of 14 amino acid residues at positions 1 to 14 at the N terminus of CH1 of IgG4 represented by SEQ ID NO: 75, a polypeptide composed of CH1 of IgG4 represented by SEQ ID NO: 75, a polypeptide composed of CH (CH1, a hinge, CH2, and CH3) of IgG4PE R409K represented by SEQ ID NO: 77, and the like, and a polypeptide composed of CH1 of IgG4 represented by SEQ ID NO: 75, and a polypeptide composed of CH of IgG4PE R409K represented by SEQ ID NO: 77 are more preferred.

As a combination of the linker and the C-terminal side peptide comprised in the bispecific antibody of the present invention, any combination may be adopted. As the bispecific antibody of the present invention, a bispecific antibody comprising a linker composed of CH1 of IgG4 comprising the amino acid sequence represented by SEQ ID NO: 75, and also comprising a C-terminal side peptide composed of CH (CH1, a hinge, CH2, and CH3) of IgG4PE R409K comprising an amino acid sequence represented by SEQ ID NO: 77, and a bispecific antibody comprising a linker composed of CH of IgG4PE R409K comprising the amino acid sequence represented by SEQ ID NO: 77, and also comprising a C-terminal side peptide composed of CH1 of IgG4 comprising the amino acid sequence represented by SEQ ID NO: 75 are preferred.

Among the bispecific antibodies of the present invention, an antibody composed of two heavy chains comprising the amino acid sequences of VH1, CH1, VH2, CH1, a hinge, CH2, and CH3 in order from the N-terminal side, and four light chains as shown in FIG. 1(A) is referred to as an N-terminal type bispecific antibody. Further, an antibody composed of two heavy chains comprising the amino acid sequences of VH1, CH1, a hinge, CH2, CH3, VH2, and CH1 in order from the N-terminal side, and four light chains as shown in FIG. 1(B) is referred to as a C-terminal type bispecific antibody.

A bispecific antibody or a bispecific antibody fragment thereof in which one or more of amino acid residues are deleted, added, substituted, or inserted in the amino acid sequence constituting the bispecific antibody or the bispecific antibody fragment thereof of the present invention, and which has the same activity as the above bispecific antibody or the bispecific antibody fragment thereof is also included in the bispecific antibody or the bispecific antibody fragment thereof of the present invention.

The number of amino acids to be deleted, substituted, inserted, and/or added is one or more, and is not particularly limited, and is a number such that deletion, substitution, insertion, or addition can be carried out using a well-known technique such as a site-specific mutagenesis method described in Molecular Cloning, The Second Edition, Cold Spring Harbor Laboratory Press (1989), Current Protocols in Molecular Biology, John Willy & Sons (1987-1997), Nucleic Acids Research, 10, 6487 (1982), Proc. Natl. Acad. Sci., USA, 79, 6409 (1982), Gene, 34, 315 (1985), Nucleic Acids Research, 13, 4431 (1985), Proc. Natl. Acad. Sci USA, 82, 488 (1985), or the like. For example, it is generally one to several tens, preferably 1 to 20, more preferably 1 to 10, and further more preferably 1 to 5.

The above description that one or more of amino acid residues in the amino acid sequence of the bispecific antibody of the present invention are deleted, substituted, inserted, or added indicates as follows. The description means that there is a deletion, substitution, insertion, or addition of one or a plurality of amino acid residues in arbitrary one amino acid sequence or a plurality of amino acid sequences in the same sequence. Further, such a deletion, substitution, insertion, or addition may sometimes occur simultaneously, and the amino acid residues to be substituted, inserted, or added may be either a natural type or an unnatural type.

Examples of the natural amino acid residue include L-alanine, L-asparagine, L-aspartic acid, L-glutamine, L-glutamic acid, glycine, L-histidine, L-isoleucine, L-leucine, L-lysine, L-arginine, L-methionine, L-phenylalanine, L-proline, L-serine, L-threonine, L-tryptophan, L-tyrosine, L-valine, L-cysteine, and the like.

Hereinafter preferred examples of mutually substitutable amino acid residues are shown. Amino acid residues included in the same group can be mutually substituted.

group A: leucine, isoleucine, norleucine, valine, norvaline, alanine, 2-aminobutanoic acid, methionine, O-methylserine, t-butyl glycine, t-butyl alanine, and cyclohexylalanine group B: aspartic acid, glutamic acid, isoaspartic acid, isoglutamic acid, 2-aminoadipic acid, and 2-aminosuberic acid group C: asparagine and glutamine group D: lysine, arginine, ornithine, 2,4-diaminobutanoic acid, and 2,3-diaminopropionic acid group E: proline, 3-hydroxyproline, and 4-hydroxyproline group F: serine, threonine, and homoserine group G: phenylalanine and tyrosine The bispecific antibody or the bispecific antibody fragment thereof of the present invention also includes an antibody comprising any amino acid residue subjected to post-translational modification. Examples of the post-translational modification include deletion of a lysine residue at the C terminus of the H chain (lysine clipping), substitution of a glutamine residue at the N terminus of a polypeptide with pyroglutamate (pyroGlu), and the like [Beck et al, Analytical Chemistry, 85, 715-736 (2013)].

Specific examples of the bispecific antibody of the present invention include any one bispecific antibody selected from the group consisting of the following (1) to (3), and the like:

(1) a bispecific antibody comprising a V region of the anti-CD40 antibody (which means a V region derived from the anti-CD40 antibody) and a V region of the anti-EpCAM antibody (which means a V region derived from the anti-EpCAM antibody), (2) a bispecific antibody comprising CDR1 to CDR3 of VH and CDR1 to CDR3 of VL of the anti-CD40 antibody, and CDR1 to CDR3 of VH and CDR1 to CDR3 of VL of the anti-EpCAM antibody, and (3) a bispecific antibody comprising VH and VL of the anti-CD40 antibody, and VH and VL of the anti-EpCAM antibody.

In the bispecific antibody described in the above (2), the CDR1 to CDR3 of VL of the anti-CD40 antibody and the CDR1 to CDR3 of VL of the anti-EpCAM antibody may be the same or different, respectively, but are preferably the same.

In addition, in the bispecific antibody described in the above (3), the VL of the anti-CD40 antibody and the VL of the anti-EpCAM antibody may be the same or different, but are preferably the same.

The anti-CD40 antibody of the present invention may or may not have a CD40 agonistic activity, but is preferably an anti-CD40 antibody that does not have a CD40 agonistic activity. Further, the anti-CD40 antibody of the present invention may or may not have a CD40 antagonistic activity, but is preferably an anti-CD40 antibody that does not have a CD40 antagonistic activity.

Examples of the anti-CD40 antibody of the present invention include an anti-CD40 antibody comprising VL comprising CDR1, CDR2, and CDR3 comprising the amino acid sequences represented by SEQ ID NOS: 23, 24, and 25, respectively, and any one VH selected from the following (1a) to (1d):

(1a) VH comprising CDR1, CDR2, and CDR3 comprising the amino acid sequences represented by SEQ ID NOS: 28, 29, and 30, respectively, (1b) VH comprising CDR1, CDR2, and CDR3 comprising the amino acid sequences represented by SEQ ID NOS: 33, 34, and 35, respectively, (1c) VH comprising CDR1, CDR2, and CDR3 comprising the amino acid sequences represented by SEQ ID NOS: 38, 39, and 40, respectively, and (1d) VH comprising CDR1, CDR2, and CDR3 comprising the amino acid sequences represented by SEQ ID NOS: 43, 44, and 45, respectively.

The anti-CD40 antibody of the present invention also includes an anti-CD40 antibody comprising amino acid sequences of CDR1 to CDR3 of VH and VL having at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, or at least 99% homology with the amino acid sequences of CDR1 to CDR3 of VH specified in any one of the above (1a) to (1d) and the amino acid sequences of CDR1 to CDR3 of VL represented by SEQ ID NOS: 23 to 25, respectively.

The anti-CD40 antibody of the present invention also includes an antibody described in the following (i) or (ii).

(i) An antibody that binds to CD40 competitively with the anti-CD40 antibody comprising VL comprising CDR1, CDR2, and CDR3 comprising the amino acid sequences represented by SEQ ID NOS: 23, 24, and 25, respectively, and VH specified in any one of the above (1a) to (1d)

(ii) An antibody that binds to the same epitope as the anti-CD40 antibody comprising VL comprising CDR1, CDR2, and CDR3 comprising the amino acid sequences represented by SEQ ID NOS: 23, 24, and 25, respectively, and VH specified in any one of the above (1a) to (1d)

As another example of the anti-CD40 antibody of the present invention, an anti-CD40 antibody comprising VL comprising the amino acid sequence represented by SEQ ID NO: 22 and VH comprising the amino acid sequence represented by SEQ ID NO: 27, 32, 37, or 42 is exemplified.

Examples of the anti-EpCAM antibody of the present invention include an anti-EpCAM antibody comprising VL comprising CDR1, CDR2, and CDR3 comprising the amino acid sequences represented by SEQ ID NOS: 23, 24, and 25, respectively, and any one VH selected from the following (2a) to (2d):

(2a) VH comprising CDR1, CDR2, and CDR3 comprising the amino acid sequences represented by SEQ ID NOS: 52, 53, and 54, respectively, (2b) VH comprising CDR1, CDR2, and CDR3 comprising the amino acid sequences represented by SEQ ID NOS: 57, 58, and 59, respectively, (2c) VH comprising CDR1, CDR2, and CDR3 comprising the amino acid sequences represented by SEQ ID NOS: 62, 63, and 64, respectively, and (2d) VH comprising CDR1, CDR2, and CDR3 comprising the amino acid sequences represented by SEQ ID NOS: 67, 68, and 69, respectively.

The anti-EpCAM antibody of the present invention also includes an anti-EpCAM antibody comprising amino acid sequences of CDR1 to CDR3 of VH and VL having at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, or at least 99% homology with the amino acid sequences of CDR1 to CDR3 of VH specified in any one of the above (2a) to (2d) and the amino acid sequences of CDR1 to CDR3 of VL represented by SEQ ID NOS: 23 to 25, respectively.

The anti-EpCAM antibody of the present invention also includes an antibody described in the following (i) or (ii).

(i) An antibody that binds to EpCAM competitively with the anti-EpCAM antibody comprising VL comprising CDR1, CDR2, and CDR3 comprising the amino acid sequences represented by SEQ ID NOS: 23, 24, and 25, respectively, and VH specified in any one of the above (2a) to (2d)

(ii) An antibody that binds to the same epitope as the anti-EpCAM antibody comprising VL comprising CDR1, CDR2, and CDR3 comprising the amino acid sequences represented by SEQ ID NOS: 23, 24, and 25, respectively, and VH specified in any one of the above (2a) to (2d)

As another example of the anti-EpCAM antibody of the present invention, a bispecific antibody comprising VL comprising an amino acid sequence represented by SEQ ID NO: 22 and VH comprising the amino acid sequence represented by SEQ ID NO: 51, 56, 61, or 66 is exemplified.

More specific examples of the bispecific antibody of the present invention include a bispecific antibody comprising VL comprising CDR1, CDR2, and CDR3 comprising the amino acid sequences represented by SEQ ID NOS: 23, 24, and 25, respectively, and VH1 and VH2 specified in the following (i) to (ii).

(i) VH1 that comprises CDR1, CDR2, and CDR3 comprising the amino acid sequences represented by SEQ ID NOS: 28, 29, and 30; SEQ ID NOS: 33, 34, and 35; SEQ ID NOS: 38, 39, and 40; or SEQ ID NOS: 43, 44, and 45, respectively, and binds to CD40, and VH2 that comprises CDR1, CDR2, and CDR3 comprising the amino acid sequences represented by SEQ ID NOS: 52, 53, and 54; SEQ ID NOS: 57, 58, and 59; SEQ ID NOS: 62, 63, and 64; or SEQ ID NOS: 67, 68, and 69, respectively, and binds to EpCAM (ii) VH1 that comprises CDR1, CDR2, and CDR3 comprising the amino acid sequences represented by SEQ ID NOS: 52, 53, and 54; SEQ ID NOS: 57, 58, and 59; SEQ ID NOS: 62, 63, and 64; or SEQ ID NOS: 67, 68, and 69, respectively, and binds to EpCAM, and VH2 that comprises CDR1, CDR2, and CDR3 comprising the amino acid sequences represented by SEQ ID NOS: 28, 29, and 30; SEQ ID NOS: 33, 34, and 35; SEQ ID NOS: 38, 39, and 40; or SEQ ID NOS: 43, 44, and 45, respectively, and binds to CD40

As another specific example of the bispecific antibody of the present invention, a bispecific antibody comprising VL comprising the amino acid sequence represented by SEQ ID NO: 22 and VH1 and VH2 specified in the following (i) to (ii) is exemplified.

(i) VH1 that comprises the amino acid sequence represented by SEQ ID NO: 27, 32, 37, or 42, and binds to CD40, and VH2 that comprises the amino acid sequence represented by SEQ ID NO: 51, 56, 61, or 66, and binds to EpCAM (ii) VH1 that comprises the amino acid sequence represented by SEQ ID NO: 51, 56, 61, or 66, and binds to EpCAM, and VH2 that comprises the amino acid sequence represented by SEQ ID NO: 27, 32, 37, or 42, and binds to CD40

As one aspect of the present invention, a bispecific antibody that comprises a heavy chain composed of a polypeptide represented by a formula of VH1-X-VH2-Y in order from the N terminus {in the formula, VH1 represents VH of a first antibody (which means VH derived from a first antibody), VH2 represents VH of a second antibody (which means VH derived from a second antibody), and X and Y each represent a polypeptide (here, at least one of X and Y further comprises a hinge region of the antibody); hereinafter referred to as the formula (I)}, wherein either one of the first antibody and the second antibody is the anti-CD40 antibody, and the other is the anti-EpCAM antibody.

As each of X and Y in the above formula (I), for example, a polypeptide comprising any one of CH1, CH2, CH3, and a hinge of the antibody (here, at least one of X and Y further comprises a hinge region of the antibody) is exemplified.

As one aspect of the present invention, an aspect in which either one of X and Y in the above formula (I) is CH1, and the other is a polypeptide comprising CH1, CH2, CH3, and a hinge is exemplified. Specifically, for example, aspects in which X is a polypeptide comprising CH1, a hinge, CH2, and CH3 of human IgG4 or human IgG1, and Y is a polypeptide comprising CH1 of human IgG4 or human IgG1; X is a polypeptide comprising a constant region comprising Pro at position 228, Glu at position 235, and Lys at position 409 in the constant region of human IgG4, and Y is a polypeptide comprising CH1 of human IgG4 or human IgG1; X is a polypeptide comprising CH1 of human IgG4 or human IgG1, and Y is a polypeptide comprising CH1, a hinge, CH2, and CH3 of human IgG4 or human IgG1; X is a polypeptide comprising CH1 of human IgG4 or human IgG1, and Y is a polypeptide comprising a constant region comprising Pro at position 228, Glu at position 235, and Lys at position 409 in the constant region of human IgG4; X is a polypeptide comprising the amino acid sequence represented by SEQ ID NO: 75, and Y is a polypeptide comprising the amino acid sequence represented by SEQ ID NO: 77; and X is a polypeptide comprising the amino acid sequence represented by SEQ ID NO: 77, and Y is a polypeptide comprising the amino acid sequence represented by SEQ ID NO: 75 are exemplified.

As one aspect of the present invention, a bispecific antibody comprising two identical heavy chains composed of a polypeptide represented by the formula (I) is more preferred, a bispecific antibody comprising two identical heavy chains composed of a polypeptide represented by the formula (I) and four identical light chains or two each of two types of light chains is further more preferred, and a bispecific antibody comprising two identical heavy chains composed of a polypeptide represented by the formula (I) and four identical light chains is still further more preferred.

In the above preferred aspect, it is preferred that the two identical heavy chains are bound to each other through a disulfide bond via the cysteine residues in the hinge regions to form a polymer. In addition, it is preferred that one heavy chain is bound to the cysteine residue of the constant region of the light chain through a disulfide bond via the cysteine residue of CH1 to form a polymer. Therefore, it is preferred that the bispecific antibody of the present invention has a heterohexamer structure in which two heavy chains and four light chains are polymerized.

As a preferred aspect of the present invention, a bispecific antibody that comprises two heavy chains composed of a polypeptide represented by the formula (I) {the formula of VH1-X-VH2-Y in order from the N terminus {in the formula, VH1 represents the VH of a first antibody, VH2 represents the VH of a second antibody, X represents a polypeptide comprising the amino acid sequence represented by SEQ ID NO: 75, and Y represents a polypeptide comprising the amino acid sequence represented by SEQ ID NO: 77}, and four light chains comprising VL comprising CDR1, CDR2, and CDR3 comprising the amino acid sequences represented by SEQ ID NOS: 23, 24, and 25, respectively, wherein the VH1 and the VH2 are VH specified in the following (i) or (ii) is exemplified.

(i) VH1 is the VH of the anti-human CD40 antibody that comprises CDR1, CDR2, and CDR3 comprising the amino acid sequences represented by SEQ ID NOS: 28, 29, and 30; SEQ ID NOS: 33, 34, and 35; SEQ ID NOS: 38, 39, and 40; or SEQ ID NOS: 43, 44, and 45, respectively, and VH2 is the VH of the anti-human EpCAM antibody that comprises CDR1, CDR2, and CDR3 comprising the amino acid sequences represented by SEQ ID NOS: 52, 53, and 54; SEQ ID NOS: 57, 58, and 59; SEQ ID NOS: 62, 63, and 64; or SEQ ID NOS: 67, 68, and 69, respectively (ii) VH1 is the VH of the anti-human EpCAM antibody that comprises CDR1, CDR2, and CDR3 comprising the amino acid sequences represented by SEQ ID NOS: 52, 53, and 54; SEQ ID NOS: 57, 58, and 59; SEQ ID NOS: 62, 63, and 64; or SEQ ID NOS: 67, 68, and 69, respectively, and VH2 is the VH of the anti-human CD40 antibody that comprises CDR1, CDR2, and CDR3 comprising the amino acid sequences represented by SEQ ID NOS: 28, 29, and 30; SEQ ID NOS: 33, 34, and 35; SEQ ID NOS: 38, 39, and 40; or SEQ ID NOS: 43, 44, and 45, respectively Here, the light chain may be a λ chain or a κ chain, but is preferably a κ chain.

Further, here, as one example of the bispecific antibody in which VH1 is the VH of the anti-human CD40 antibody that comprises CDR1, CDR2, and CDR3 comprising the amino acid sequences represented by SEQ ID NOS: 33, 34, and 35, respectively, and VH2 is the VH of the anti-human EpCAM antibody that comprises CDR1, CDR2, and CDR3 comprising the amino acid sequences represented by SEQ ID NOS: 57, 58, and 59, respectively, R1090S55A-Ep203 is exemplified.

As a more preferred aspect of the present invention, a bispecific antibody that comprises two heavy chains composed of a polypeptide represented by the formula (I) {the formula of VH1-X-VH2-Y in order from the N terminus {in the formula, VH1 represents the VH of a first antibody, VH2 represents the VH of a second antibody, X represents a polypeptide comprising the amino acid sequence represented by SEQ ID NO: 75, and Y represents a polypeptide comprising the amino acid sequence represented by SEQ ID NO: 77}, and four light chains comprising VL comprising the amino acid sequence represented by SEQ ID NO: 22, wherein the VH1 and the VH2 are VH specified in the following (i) or (ii) is exemplified.

(i) VH1 is the VH of the anti-human CD40 antibody comprising the amino acid sequence represented by SEQ ID NO: 27, 32, 37, or 42, and VH2 is the VH of the anti-human EpCAM antibody comprising the amino acid sequence represented by SEQ ID NO: 51, 56, 61, or 66

(ii) VH1 is the VH of the anti-human EpCAM antibody comprising the amino acid sequence represented by SEQ ID NO: 51, 56, 61, or 66, and VH2 is the VH of the anti-human CD40 antibody comprising the amino acid sequence represented by SEQ ID NO: 27, 32, 37, or 42

Here, the light chain may be a λ chain or a κ chain, but is preferably a κ chain.

Further, here, as one example of the bispecific antibody in which VH1 is the VH of the anti-human CD40 antibody comprising the amino acid sequence represented by SEQ ID NO: 32, and VH2 is the VH of the anti-human EpCAM antibody comprising the amino acid sequence represented by SEQ ID NO: 56, R1090S55A-Ep203 is exemplified.

As a preferred aspect of the present invention, a bispecific antibody that comprises two heavy chains composed of a polypeptide represented by the formula (I) {the formula of VH1-X-VH2-Y in order from the N terminus {in the formula, VH1 represents the VH of a first antibody, VH2 represents the VH of a second antibody, X represents a polypeptide comprising the amino acid sequence represented by SEQ ID NO: 77, and Y represents a polypeptide comprising the amino acid sequence represented by SEQ ID NO: 75}, and four light chains comprising VL comprising CDR1, CDR2, and CDR3 comprising the amino acid sequences represented by SEQ ID NOS: 23, 24, and 25, respectively, wherein the VH1 and the VH2 are VH specified in the following (i) or (ii) is exemplified.

(i) VH1 is the VH of the anti-human CD40 antibody that comprises CDR1, CDR2, and CDR3 comprising the amino acid sequences represented by SEQ ID NOS: 28, 29, and 30; SEQ ID NOS: 33, 34, and 35; SEQ ID NOS: 38, 39, and 40; or SEQ ID NOS: 43, 44, and 45, respectively, and VH2 is the VH of the anti-human EpCAM antibody that comprises CDR1, CDR2, and CDR3 comprising the amino acid sequences represented by SEQ ID NOS: 52, 53, and 54; SEQ ID NOS: 57, 58, and 59; SEQ ID NOS: 62, 63, and 64; or SEQ ID NOS: 67, 68, and 69, respectively (ii) VH1 is the VH of the anti-human EpCAM antibody that comprises CDR1, CDR2, and CDR3 comprising the amino acid sequences represented by SEQ ID NOS: 52, 53, and 54; SEQ ID NOS: 57, 58, and 59; SEQ ID NOS: 62, 63, and 64; or SEQ ID NOS: 67, 68, and 69, respectively, and VH2 is the VH of the anti-human CD40 antibody that comprises CDR1, CDR2, and CDR3 comprising the amino acid sequences represented by SEQ ID NOS: 28, 29, and 30; SEQ ID NOS: 33, 34, and 35; SEQ ID NOS: 38, 39, and 40; or SEQ ID NOS: 43, 44, and 45, respectively Here, the light chain may be a λ chain or a κ chain, but is preferably a κ chain.

Further, here, as one example of the bispecific antibody in which VH1 is the VH of the anti-human CD40 antibody that comprises CDR1, CDR2, and CDR3 comprising the amino acid sequences represented by SEQ ID NOS: 33, 34, and 35, respectively, and VH2 is the VH of the anti-human EpCAM antibody that comprises CDR1, CDR2, and CDR3 comprising the amino acid sequences represented by SEQ ID NOS: 57, 58, and 59, respectively, Ct R1090S55A-Ep203 is exemplified.

Further, as one example of the bispecific antibody in which VH1 is the VH of the anti-human EpCAM antibody that comprises CDR1, CDR2, and CDR3 comprising the amino acid sequences represented by SEQ ID NOS: 67, 68, and 69, respectively, and VH2 is the VH of the anti-human CD40 antibody that comprises CDR1, CDR2, and CDR3 comprising the amino acid sequences represented by SEQ ID NOS: 28, 29, and 30, respectively, Ct Epc112-R1066 is exemplified.

As a more preferred aspect of the present invention, a bispecific antibody that comprises two heavy chains composed of a polypeptide represented by the formula (I) {the formula of VH1-X-VH2-Y in order from the N terminus {in the formula, VH1 represents the VH of a first antibody, VH2 represents the VH of a second antibody, X represents a polypeptide comprising the amino acid sequence represented by SEQ ID NO: 77, and Y represents a polypeptide comprising an amino acid sequence represented by SEQ ID NO: 75}, and four light chains comprising VL comprising the amino acid sequence represented by SEQ ID NO: 22, wherein the VH1 and the VH2 are VH specified in the following (i) or (ii) is exemplified.

(i) VH1 is the VH of the anti-human CD40 antibody that comprises the amino acid sequence represented by SEQ ID NO: 27, 32, 37, or 42, and VH2 is the VH of the anti-human EpCAM antibody that comprises the amino acid sequence represented by SEQ ID NO: 51, 56, 61, or 66

(ii) VH1 is the VH of the anti-human EpCAM antibody that comprises the amino acid sequence represented by SEQ ID NO: 51, 56, 61, or 66, and VH2 is the VH of the anti-human CD40 antibody that comprises the amino acid sequence represented by SEQ ID NO: 27, 32, 37, or 42

Here, the light chain may be a λ chain or a κ chain, but is preferably a κ chain.

Further, here, as one example of the bispecific antibody in which VH1 is the VH of the anti-human CD40 antibody comprising the amino acid sequence represented by SEQ ID NO: 32, and VH2 is the VH of the anti-human EpCAM antibody comprising the amino acid sequence represented by SEQ ID NO: 56, Ct R1090S55A-Ep203 is exemplified.

Further, as one example of the bispecific antibody in which VH1 is the VH of the anti-human EpCAM antibody comprising the amino acid sequence represented by SEQ ID NO: 66, and VH2 is the VH of the anti-human CD40 antibody comprising the amino acid sequence represented by SEQ ID NO: 27, Ct Epc112-R1066 is exemplified.

The bispecific antibody or the bispecific antibody fragment thereof of the present invention also comprises an antibody or a bispecific antibody fragment thereof having an effector activity.

The effector activity refers to an antibody-dependent cellular cytotoxicity activity that is caused via the Fc region of the antibody, and examples thereof include an antibody-dependent cellular cytotoxicity activity (ADCC activity), a complement-dependent cytotoxicity activity (CDC activity), an antibody-dependent cellular phagocytosis activity (ADCP activity) that is caused by phagocytes such as macrophages and dendritic cells, an opsonin effect, and the like.

The ADCC activity and the CDC activity in the present invention can be measured using a known measurement method [Cancer Immunol. Immunother., 36, 373 (1993)].

The ADCC activity refers to an activity in which an antibody binding to an antigen on a target cell binds to an Fc receptor of an immune cell via the Fc region of the antibody so as to activate the immune cell (a natural killer cell or the like) and damage the target cell.

The Fc receptor (FcR) is a receptor that binds to the Fc region of the antibody, and the binding of the antibody induces various effector activities. Each FcR corresponds to the subclass of an antibody, and IgG, IgE, IgA, and IgM bind specifically to FcγR, FcεR, FcαR, and FcμR, respectively. Further, in the FcγR, there are subtypes of FcγRI (CD64), FcγRII (CD32), and FcγRIII (CD16), and the subtypes have isoforms of FcγRIA, FcγRIB, FcγRIC, FcγRIIA, FcγRIIB, FcγRIIC, FcγRIIIA, and FcγRIIIB, respectively. The different types of FcγRs are present on different cells [Annu. Rev. Immunol. 9: 457-492 (1991)]. In humans, FcγRIIIB is expressed specifically in neutrophils, and FcγRIIIA is expressed in monocytes, natural killer cells (NK cells), macrophages, and some T cells. An NK cell-dependent ADCC activity is induced through the binding of the antibody to FcγRIIIA The CDC activity refers to an activity in which an antibody binding to an antigen on a target cell activates a series of cascades (complement activation pathways) composed of complement-related protein groups in the blood, and damages the target cell. In addition, a protein fragment generated by the activation of the complement induces the migration and activation of an immune cell. The cascade of CDC activity starts when C1q first binds to the Fc region, and subsequently binds to C1r and C1s that are two serine proteases, whereby a C1 complex is formed.

The CDC activity or the ADCC activity of the bispecific antibody or the bispecific antibody fragment thereof of the present invention against an antigen-expressing cell can be evaluated by a known measurement method [Cancer Immunol. Immunother., 36, 373 (1993)].

As a method for controlling the effector activity of the bispecific antibody of the present invention, a method for controlling the amount of fucose (also referred to as core fucose) that is α-1,6-linked to N-acetylglucosamine (GlcNAc) present at the reducing end of an N-linked complex sugar chain to be bound to asparagine (Asn) at position 297 of the Fc region (a constant region composed of CH2 and CH3 domains) of the antibody (WO 2005/035586, WO 2002/31140, and WO 00/61739), a method for controlling the effector activity by altering an amino acid residue of the Fc region of the antibody (WO 00/42072), and the like are known.

The ADCC activity of the antibody can be increased or decreased by controlling the amount of fucose to be added to the bispecific antibody. For example, as a method for decreasing the content of fucose to be bound to the N-linked complex sugar chain bound to Fc of the antibody, by expressing the bispecific antibody using an α1,6-fucosyltransferase gene-deficient host cell, the bispecific antibody having a high ADCC activity can be obtained. On the other hand, as a method for increasing the content of fucose to be bound to the N-linked complex sugar chain bound to Fc of the bispecific antibody, by expressing the antibody using a host cell transfected with an α1,6-fucosyltransferase gene, the bispecific antibody having a low ADCC activity can be obtained.

In addition, the ADCC activity or the CDC activity can be increased or decreased by altering an amino acid residue in the Fc region of the bispecific antibody. For example, by using the amino acid sequence of the Fc region described in US Patent Application Publication No. 2007/0148165, the CDC activity of the bispecific antibody can be increased. Further, by performing an amino acid alteration described in U.S. Pat. Nos. 6,737,056, 7,297,775, 7,317,091, or the like, the ADCC activity or the CDC activity can be increased or decreased.

Further, a bispecific antibody in which the effector activity is controlled may be obtained by combining the above-mentioned methods.

The stability of the bispecific antibody of the present invention can be evaluated by measuring the amount of an aggregate (oligomer) formed in a sample stored during a purification process or under certain conditions. That is, a case where the aggregate amount is decreased under the same conditions is evaluated that the stability of the antibody is improved. The aggregate amount can be measured by separating an aggregated antibody and a non-aggregated antibody using appropriate chromatography including gel filtration chromatography.

The productivity of the bispecific antibody of the present invention can be evaluated by measuring the amount of an antibody produced from an antibody-producing cell in a culture solution. More specifically, the productivity can be evaluated by measuring the amount of an antibody contained in a culture supernatant obtained by removing the producing cell from the culture solution using an appropriate method such as an HPLC method or an ELISA method.

In the present invention, the antibody fragment is a protein that comprises an antigen-binding domain and has a binding activity to the antigen. Examples of the antibody fragment in the present invention include a Fab, a Fab', a F(ab')$_2$, an scFv, a diabody, a dsFv, a peptide comprising a CDR, and the like.

The Fab is an antibody fragment, which has a molecular weight of about 50,000 and has an antigen-binding activity, and in which about a half of an H chain at the N-terminal side and the entire L chain are bound through a disulfide bond (S—S bond) among the fragments obtained by treating an IgG antibody with a protease papain (cleaved at an amino acid residue at position 224 in the H chain).

The F(ab')$_2$ is an antibody fragment, which has a molecular weight of about 100,000 and has an antigen-binding activity, and is slightly larger than a molecule obtained by binding Fabs through an S—S bond in the hinge region among the fragments obtained by treating IgG with a protease pepsin (cleaved at an amino acid residue at position 234 in the H chain).

The Fab' is an antibody fragment, which has a molecular weight of about 50,000 and has an antigen-binding activity, and in which an S—S bond in the hinge region of the above F(ab')2 is cleaved.

The scFv is a VH-P-VL or VL-P-VH polypeptide in which one VH and one VL are linked using an appropriate peptide linker (P) of 12 or more residues, and is an antibody fragment having an antigen-binding activity.

The diabody is an antibody fragment in which scFvs having the same or different antigen-binding specificities form a dimer, and is an antibody fragment having a divalent antigen-binding activity to the same antigen or antigen-binding activities each specific for different antigens.

The dsFv refers to a molecule obtained by binding polypeptides in which one amino acid residue in each of VH and VL is substituted with a cysteine residue through an S—S bond between the cysteine residues.

The peptide comprising a CDR is configured to comprise at least one region of CDRs of VH or VL. A peptide comprising a plurality of CDRs can be produced by binding CDRs directly or through an appropriate peptide linker. The peptide comprising a CDR can also be produced by constructing DNAs encoding CDRs of VH and VL of the bispecific antibody of the present invention, inserting the DNAs into an expression vector for a prokaryote or an expression vector for a eukaryote, and then introducing the expression vector into a prokaryote or a eukaryote and expressing the peptide. In addition, the peptide comprising a CDR can also be produced by a chemical synthesis method such as an Fmoc method or a tBoc method.

The bispecific antibody fragment of the present invention is essentially composed of a portion of the structure of a bispecific antibody, and is a protein that comprises two types of antigen-binding domains having different antigen-binding site specificities of the bispecific antibody, and has a binding activity to both of the two types of antigens.

Figure 12:
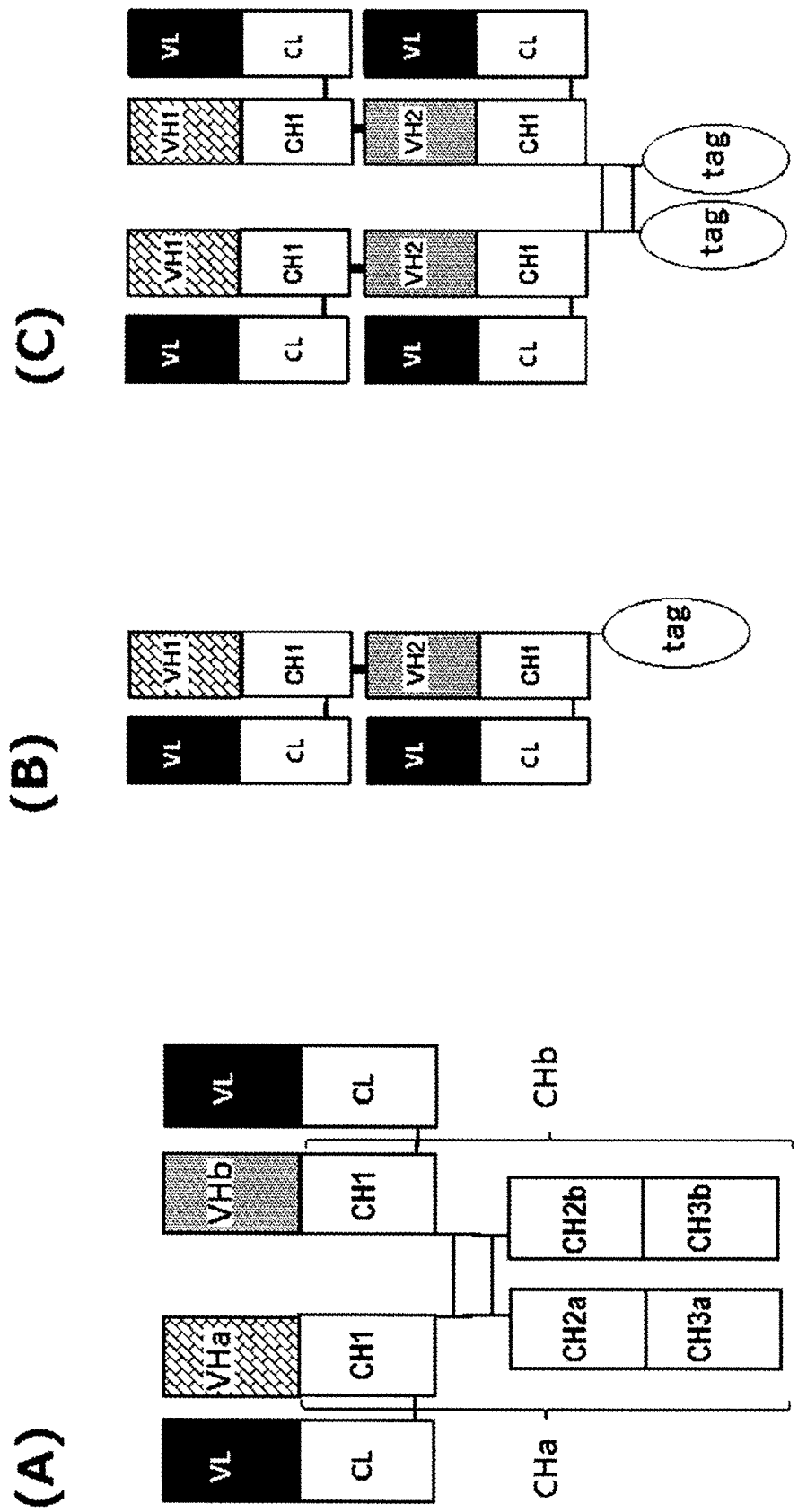
FIG. 12(A) shows a structure of a hetero-IgG type bispecific antibody.
FIG. 12(B) shows a structure of a Fab-type bispecific antibody fragment.
FIG. 12(C) shows a F(ab')2-type bispecific antibody.

Examples of the bispecific antibody fragment of the present invention include a Fab-type bispecific antibody fragment shown in FIG. 12(B) and a F(ab')$_2$-type bispecific antibody fragment shown in FIG. 12(C).

An Fc region that comprises an amino acid residue alteration aiming at enhancing or eliminating the effector activity of the antibody, stabilizing the antibody, and controlling the blood half-life can also be used for the bispecific antibody of the present invention.

As the bispecific antibody or the bispecific antibody fragment of the present invention, a derivative of the antibody in which a radioisotope, a low-molecular weight drug, a high-molecular weight drug, a protein, an antibody drug, or the like is bound to the bispecific antibody or the bispecific antibody fragment thereof of the present invention in a chemical or genetic engineering manner is included.

The derivative of the antibody in the present invention can be produced by binding a radioisotope, a low-molecular weight drug, a high-molecular weight drug, an immunostimulant, a protein, an antibody drug, or the like to the N-terminal side or the C-terminal side of an H chain or an L chain of the bispecific antibody or the bispecific antibody fragment thereof of the present invention, an appropriate substituent or a side chain in the bispecific antibody or the bispecific antibody fragment thereof, further, a sugar chain or the like in the bispecific antibody or the bispecific antibody fragment thereof using a chemical method [Introduction to Antibody Engineering, Chijin Shokan Co. Ltd. (1994)].

Further, the derivative of the antibody in the present invention can be produced by a genetic engineering technique in which a DNA encoding the bispecific antibody or the bispecific antibody fragment of the present invention is ligated to a DNA encoding a desired protein or antibody drug, the resultant is inserted into an expression vector, and the expression vector is introduced into an appropriate host cell to cause expression.

Examples of the radioisotope include $^{111}$In, $^{131}$I, $^{125}$I, $^{90}$Y $^{64}$Cu, $^{99}$Tc, $^{77}$Lu, $^{211}$At, and the like. The radioisotope can be directly bound to the antibody by a chloramine T method or the like. In addition, a substance that chelates the radioisotope may be bound to the antibody. Examples of the chelating agent include 1-isothiocyanatobenzyl-3-methyldiethylenetriaminepentaacetic acid (MX-DTPA) and the like.

Examples of the low-molecular weight drug include anticancer agents such as an alkylating agent, a nitrosourea agent, an antimetabolite, an antibiotic, a plant alkaloid, a topoisomerase inhibitor, a hormonal therapy agent, a hormone antagonist, an aromatase inhibitor, a P-glycoprotein inhibitor, a platinum complex derivative, an M-phase inhibitor, or a kinase inhibitor [Clinical oncology, Japanese Journal of Cancer and Chemotherapy (1996)], anti-inflammatory agents such as a steroidal agent such as hydrocortisone or prednisone, a nonsteroidal agent such as aspirin or indomethacin, an immunomodulatory agent such as gold thiomalate or penicillamine, an immunosuppressive agent such as cyclophosphamide or azathioprine, an antihistamine agent such as chlorpheniramine maleate or clemastine [Inflammation and anti-inflammatory therapy, Ishiyaku Publishers, Inc. (1982)], and the like.

Examples of the anticancer agent include amifostine (Ethyol), cisplatin, dacarbazine (DTIC), dactinomycin, mechlorethamine (nitrogen mustard), streptozocin, cyclophosphamide, ifosfamide, carmustine (BCNU), lomustine (CCNU), doxorubicin (Adriamycin), epirubicin, gemcitabine (Gemzar), daunorubicin, procarbazine, mitomycin, cytarabine, etoposide, 5-fluorouracil, fluorouracil, vinblastine, vincristine, bleomycin, daunomycin, peplomycin, estramustine, paclitaxel (Taxol), docetaxel (Taxotere), aldesleukin, asparaginase, busulfan, carboplatin, oxaliplatin, nedaplatin, cladribine, camptothecin, 10-hydroxy-7-ethyl-camptothecin (SN38), floxuridine, fludarabine, hydroxyurea, idarubicin, mesna, irinotecan (CPT-11), nogitecan, mitoxantrone, topotecan, leuprolide, megestrol, melphalan, mercaptopurine, hydroxycarbamide, plicamycin, mitotane, pegaspargase, pentostatin, pipobroman, tamoxifen, goserelin, leuprorelin, flutamide, teniposide, testolactone, thioguanine, thiotepa, uracil mustard, vinorelbine, chlorambucil, hydrocortisone, prednisolone, methylprednisolone, vindesine, nimustine, semustine, capecitabine, Tomudex, azacitidine, UFT, oxaloplatin, gefitinib (Iressa), imatinib (STI571), erlotinib, an FMS-like tyrosine kinase 3 (Flt3) inhibitor, a vascular endothelial growth facotr receptor (VEGFR) inhibitor, a fibroblast growth factor receptor (FGFR) inhibitor, an epidermal growth factor receptor (EGFR) inhibitor such as Tarceva, radicicol, 17-allylamino-17-demethoxygeldanamycin, rapamycin, amsacrine, all-trans retinoic acid, thalidomide, lenalidomide, anastrozole, fadrozole, letrozole, exemestane, bucillamine, mizoribine, cyclosporine, hydrocortisone, bexarotene (Targretin), dexamethasone, a progestin, an estrogen, anastrozole (Arimidex), Leuplin, aspirin, indomethacin, celecoxib, azathioprine, penicillamine, gold thiomalate, chlorpheniramine maleate, chlorpheniramine, clemastine, tretinoin, bexarotene, arsenic, bortezomib, allopurinol, calicheamicin, ibritumomab tiuxetan, targretin, ozogamine, clarithromycin, leucovorin, ketoconazole, aminoglutethimide, suramin, methotrexate or maytansinoid or a derivative thereof, and the like.

Examples of a method for binding a low-molecular weight drug to the bispecific antibody of the present invention include a method for binding the drug to an amino group of the antibody through glutaraldehyde, a method for binding an amino group of the drug to a carboxyl group of the antibody through water-soluble carbodiimide, and the like.

Examples of the high-molecular weight drug include polyethylene glycol (PEG), albumin, dextran, polyoxyethylene, a styrene-maleic acid copolymer, polyvinylpyrrolidone, a pyran copolymer, hydroxypropyl methacrylamide, and the like. By binding such a high-molecular weight compound to the bispecific antibody or the bispecific antibody fragment of the present invention, an effect such as (1) improvement of the stability against various chemical, physical or biological factors, (2) significant extension of the blood half-life, or (3) elimination of immunogenicity or suppression of antibody production is expected [Bioconjugate pharmaceutical product, Hirokawa-Shoten Ltd. (1993)].

Examples of a method for binding PEG to the bispecific antibody of the present invention include a method for reacting with a PEGylation reagent, and the like [Bioconjugate pharmaceutical product, Hirokawa-Shoten Ltd. (1993)]. Examples of the PEGylation reagent include a modifying agent to an $\eta_L$-amino group of lysine (JP-A-S61-178926), a modifying agent to a carboxyl group of aspartic acid and glutamic acid (JP-A-S56-23587), a modifying agent to a guanidino group of arginine (JP-A-H2-117920), and the like.

The immunostimulant may be a natural product known as an immunologic adjuvant, and specific examples thereof include a drug that enhances immunity such as a $\beta(1 \rightarrow 3)$ glucan (for example, lentinan or schizophyllan) or $\alpha$-galactosylceramide (KRN7000), and the like.

Examples of the protein include a cytokine or a growth factor that activates immunocompetent cells such as NK cells, macrophages, or neutrophils, or a toxic protein, and the like.

Examples of the cytokine or the growth factor include interferon (hereinafter referred to as IFN)-$\alpha$, IFN-$\beta$, and IFN-$\gamma$, interleukin (hereinafter referred to as IL)-2, IL-12, IL-15, IL-18, IL-21, and IL-23, a granulocyte colony stimulating factor (G-CSF), a granulocyte-macrophage colony stimulating factor (GM-CSF), a macrophage colony stimulating factor (M-CSF), and the like.

Examples of the toxic protein include ricin, diphtheria toxin, ONTAK, and the like, and also include a protein toxin in which a mutation has been introduced into the protein for regulating toxicity.

A fusion antibody with a protein or an antibody drug can be produced by ligating a cDNA encoding the protein to a cDNA encoding the bispecific antibody or the bispecific antibody fragment of the present invention to construct a DNA encoding the fusion antibody, inserting the DNA into an expression vector for a prokaryote or a eukaryote, and then introducing the expression vector into a prokaryote or a eukaryote to cause expression.

When the derivative of the antibody is used for a detection method or a quantification method, as a reagent for detection, a reagent for quantification or a diagnostic agent, examples of the drug that binds to the bispecific antibody or the bispecific antibody fragment thereof of the present invention include a labeling substance to be used for a general immunological detection or measurement method. Examples of the labeling substance include an enzyme such as alkaline phosphatase, peroxidase, or luciferase, a luminescent substance such as acridinium ester or lophine, or a fluorescent substance such as fluorescein isothiocyanate (FITC) or tetramethylrhodamine isothiocyanate (RITC), Alexa (registered trademark) Fluor 488, or R-phycoerythrin (R-PE), and the like.

In the present invention, the bispecific antibody and the bispecific antibody fragment thereof having a cytotoxic activity such as a CDC activity or an ADCC activity are included. The CDC activity or the ADCC activity of the bispecific antibody or the bispecific antibody fragment thereof of the present invention against an antigen-expressing cell can be evaluated by a known measurement method [Cancer Immunol. Immunother., 36, 373 (1993)].

Further, the present invention relates to a composition comprising a bispecific antibody or a bispecific antibody fragment thereof that specifically recognizes and binds to CD40 and EpCAM or a therapeutic agent for a disease associated with at least one of CD40 and EpCAM, preferably a disease involved in a CD40 and EpCAM-expressing cell, comprising the bispecific antibody or the bispecific antibody fragment thereof as an active ingredient.

The disease associated with at least one of CD40 and EpCAM may be, for example, any as long as it is a disease associated with at least one of CD40 and EpCAM, and for example, a malignant tumor, cancer, and the like are exemplified.

Examples of the malignant tumor and cancer in the present invention include, large intestine cancer, colorectal cancer, lung cancer, breast cancer, glioma, malignant melanoma (melanoma), thyroid cancer, renal cell carcinoma, leukemia, lymphoma, T cell lymphoma, stomach cancer, pancreatic cancer, cervical cancer, endometrial cancer, ovarian cancer, bile duct cancer, esophageal cancer, liver cancer, head and neck cancer, skin cancer, urinary tract cancer, bladder cancer, prostate cancer, choriocarcinoma, pharyngeal cancer, laryngeal cancer, mesothelioma, pleural tumor, arrhenoblastoma, endometrial hyperplasia, endometriosis, embryoma, fibrosarcoma, Kaposi's sarcoma, angioma, cavernous hemangioma, angioblastoma, retinoblastoma, astrocytoma, neurofibroma, oligodendroglioma, medulloblastoma, neuroblastoma, glioma, rhabdomyosarcoma, glioblastoma, osteogenic sarcoma, leiomyosarcoma, Wilm's tumor, and the like.

The therapeutic agent comprising the bispecific antibody or the bispecific antibody fragment thereof of the present invention, or a derivative thereof may comprise only the antibody or the bispecific antibody fragment thereof, or a derivative thereof as an active ingredient, however, in general, it is preferably provided as a pharmaceutical preparation produced by mixing it together with one or more pharmacologically acceptable carriers using an arbitrary method known in the technical field of pharmaceutics.

As the route of administration, it is preferred to use the most effective route for the treatment, and examples thereof include oral administration or parenteral administration such as intraoral, intra-airway, intrarectal, subcutaneous, intramuscular, and intravenous administration. Above all, intravenous administration is preferred.

Examples of a dosage form include a spray, a capsule, a tablet, a powder, a granule, a syrup, an emulsion, a suppository, an injection, an ointment, a tape, and the like.

A dose or administration frequency varies depending on a desired therapeutic effect, an administration method, a treatment duration, an age, a body weight, or the like, but is generally 10 µg/kg to 10 mg/kg per day for an adult.

Further, the present invention relates to a reagent for immunological detection or measurement of at least one of CD40 and EpCAM, which comprises the bispecific antibody or the bispecific antibody fragment thereof of the present invention, or a diagnostic agent for a disease associated with at least one of CD40 and EpCAM, preferably a disease involved in a CD40 and EpCAM-expressing cell. In addition, the present invention relates to a method for immunological detection or measurement of at least one of CD40 and EpCAM using the bispecific antibody or the bispecific antibody fragment thereof of the present invention, a therapeutic method for a disease associated with at least one of CD40 and EpCAM, preferably a disease involved in a CD40 and EpCAM-expressing cell, or a diagnostic method for a disease associated with at least one of CD40 and EpCAM, preferably a disease involved in a CD40 and EpCAM-expressing cell.

Examples of a method for detecting or measuring the amount of at least one of CD40 and EpCAM in the present invention include known arbitrary methods. For example, an immunological detection or measurement method and the like are exemplified.

The immunological detection or measurement method is a method for detecting or measuring the amount of an antibody or the amount of an antigen using a labeled antigen or antibody. Examples of the immunological detection or measurement method include a radioimmunoassay method (MA), an enzyme immunoassay method (EIA or ELISA), a fluorescence immunoassay method (FIA), a luminescent immunoassay method, a Western blotting method, a physicochemical method, and the like.

By detecting or measuring a cell expressing at least one of CD40 and EpCAM using the bispecific antibody or the bispecific antibody fragment thereof of the present invention, it is possible to diagnose a disease associated with at least one of CD40 and EpCAM, preferably a disease involved in a CD40 and EpCAM-expressing cell.

It is possible to use a known immunological detection method for detecting a cell expressing at least one of CD40 and EpCAM, however, for example, an immunoprecipitation method, an immunocytochemical staining method, an immunohistochemical staining method, or a fluorescent antibody staining method, and the like are exemplified. In addition, for example, a fluorescent antibody staining method such as an FMAT 8100 HTS system (manufactured by Applied Biosystems, Inc.), and the like are also exemplified.

Examples of a biological sample to be subjected to detection or measurement of at least one of CD40 and EpCAM in the present invention include a tissue cell, blood, plasma, serum, pancreatic juice, urine, feces, a tissue fluid, a culture solution, and the like, and there is no particular limitation as long as the sample may contain a cell expressing at least one of CD40 and EpCAM.

The diagnostic agent comprising the bispecific antibody or the bispecific antibody fragment thereof of the present invention, or a derivative thereof, may comprise a reagent for performing an antigen-antibody reaction or a reagent for detecting the reaction in accordance with a desired diagnostic method. Examples of the reagent for performing an antigen-antibody reaction include a buffer, a salt, and the like.

Examples of the reagent for detection include a reagent, which is used for a general immunological detection or measurement method, such as a labeled secondary antibody that binds to the bispecific antibody or the bispecific antibody fragment thereof, or a derivative thereof, or a substrate corresponding to a label.

Hereinafter, a method for producing the bispecific antibody of the present invention, a method for evaluating the activity of the bispecific antibody or the bispecific antibody fragment thereof, and a therapeutic method and a diagnostic method for a disease using the bispecific antibody or the bispecific antibody fragment thereof will be specifically described.

1. Method for Producing Monoclonal Antibody

A method for producing a monoclonal antibody of the present invention comprises the following operation steps. That is, (1) at least one of the purification of an antigen to be used as an immunogen and the production of a cell in which the antigen is overexpressed on the cell surface, (2) a step of preparing an antibody-producing cell by immunizing an animal with the antigen, followed by collecting the blood, examining an antibody titer thereof to determine when to resect the spleen or the like, (3) preparing a myeloma cell (myeloma), (4) fusing the antibody-producing cell with the myeloma, (5) screening a hybridoma group that produces a target antibody, (6) separating (cloning) a monoclonal cell from the hybridoma group, (7) in some cases, culturing the hybridoma for producing a monoclonal antibody in a large amount, or breeding an animal implanted with the hybridoma, (8) investigating the bioactivity of the monoclonal antibody produced in this manner, and the antigen-binding specificity thereof, or examining the characteristics as a labeling reagent, and the like.

Hereinafter, a method for producing a monoclonal antibody that binds to CD40 and a monoclonal antibody that binds to EpCAM, which are used for producing the bispecific antibody that binds to CD40 and EpCAM of the present invention, will be described in detail according to the above-mentioned steps. The method for producing the antibody is not particularly limited thereto, and for example, an antibody-producing cell other than a spleen cell, and a myeloma can also be used.

(1) Purification of Antigen

A cell allowed to express at least one of CD40 and EpCAM can be obtained by introducing an expression vector comprising a cDNA encoding the full length of at least one of CD40 and EpCAM or a partial length thereof into *E. coli*, yeast, an insect cell, an animal cell, or the like. In addition, at least one of CD40 and EpCAM is purified from various human cultured tumor cells or human tissues or the like in which at least one of CD40 and EpCAM is expressed in a large amount and can be used as an antigen.

In addition, the cultured tumor cell or the tissue or the like can also be used as an antigen as it is. Further, a synthetic peptide having a partial sequence of at least one of CD40 and EpCAM is prepared by a chemical synthesis method such as an Fmoc method or a tBoc method and can also be used as an antigen.

At least one of CD40 and EpCAM used in the present invention can be produced using a method described in Molecular Cloning, A Laboratory Manual, Second Edition, Cold Spring Harbor Laboratory Press (1989), or Current Protocols In Molecular Biology, John Wiley & Sons (1987-1997), or the like, for example, by expressing a DNA encoding at least one of CD40 and EpCAM in a host cell using the following method.

A recombinant vector is produced by inserting a full-length cDNA comprising a region encoding at least one of CD40 and EpCAM downstream of a promoter in an appropriate expression vector. A DNA fragment that has been prepared based on the full-length cDNA and has an appropriate length and comprises a region encoding a polypeptide may be used in place of the full-length cDNA. Subsequently, by introducing the obtained recombinant vector into a host cell suitable for the expression vector, a transformant that produces at least one of CD40 and EpCAM can be obtained.

As the expression vector, any vector can be used as long as it can be integrated into an autonomous replicating element or a chromosome in a host cell to be used, and comprises an appropriate promoter at a position capable of transcribing a DNA encoding at least one of CD40 and EpCAM.

As the host cell, any cell, for example, a microorganism belonging to the genus *Escherichia* such as *E. coli*, yeast, an insect cell, an animal cell, or the like, can be used as long as it can express a target gene.

When a prokaryote such as *E. coli* is used as the host cell, the recombinant vector is preferably a vector that can replicate autonomously in the prokaryote, and also comprises a promoter, a ribosomal binding sequence, a DNA comprising a region encoding at least one of CD40 and EpCAM, and a transcription termination sequence. In addition, the transcription termination sequence is not necessarily needed for the recombinant vector, however, it is preferred that the transcription termination sequence is located immediately downstream of a structural gene. Further, the recombinant vector may comprise a gene that controls the promoter.

As the recombinant vector, it is preferred to use a plasmid in which a distance between a Shine-Dalgarno sequence that is a ribosomal binding sequence, and a start codon is appropriately adjusted (for example, 6 to 18 bases).

In addition, in the nucleotide sequence of the DNA encoding at least one of CD40 and EpCAM, it is possible to substitute a base so that a codon becomes optimum for expression in a host, and as a result, the production rate of at least one of the target CD40 and EpCAM can be improved.

As the expression vector, any vector can be used as long as it can exhibit its function in a host cell to be used, and examples thereof include pBTrp2, pBTac1, pBTac2 (manufactured by Roche Diagnostics K.K.), pKK233-2 (manufactured by Pharmacia Corporation), pSE280 (manufactured by Invitrogen, Inc.), pGEMEX-1 (manufactured by Promega Corporation), pQE-8 (manufactured by QIAGEN, Inc.), pKYP10 (JP-A-S58-110600), pKYP200 [Agricultural Biological Chemistry, 48, 669 (1984)], pLSA1 [Agric. Biol. Chem., 53, 277 (1989)], pGEL1 [Proc. Natl. Acad. Sci. USA, 82, 4306 (1985)], pBluescript II SK(−) (manufactured by Stratagene Corporation), pTrs30 [prepared from *E. coli* JM109/pTrS30 (FERM BP-5407)], pTrs32 [prepared from *E. coli* JM109/pTrS32 (FERM BP-5408)], pGHA2 [prepared from *E. coli* IGHA2 (FERM BP-400), JP-A-S60-221091], pGKA2 [prepared from *E. coli* IGKA2 (FERM BP-6798), JP-A-S60-221091], pTerm2 (U.S. Pat. Nos. 4,686,191, 4,939,094, or U.S. Pat. No. 5,160,735), pSupex, pUB110, pTP5, pC194, pEG400 [J. Bacteriol., 172, 2392 (1990)], pGEX (manufactured by Pharmacia Corporation), pET System (manufactured by Novagen, Inc.), pME18SFL3 (manufactured by Toyobo Co., Ltd.), and the like.

As the promoter, any promoter may be used as long as it functions in a host cell to be used. Examples thereof include promoters derived from *E. coli*, a phage, or the like such as a trp promoter (Ptrp), a lac promoter, a PL promoter, a PR promoter, or a T7 promoter. In addition, examples thereof also include artificially designed and altered promoters such as a tandem promoter in which two Ptrp promoters are linked in tandem, a tac promoter, a lacT7 promoter, or a let I promoter.

Examples of the host cell include *E. coli* XL1-Blue, *E. coli* XL2-Blue, *E. coli* DH1, *E. coli* MC1000, *E. coli* KY3276, *E. coli* W1485, *E. coli* JM109, *E. coli* HB101, *E. coli* No. 49, *E. coli* W3110, *E. coli* NY49, *E. coli* DH5α, and the like.

As a method for introducing a recombinant vector into a host cell, any method can be used as long as it is a method for introducing a DNA into a host cell to be used, and examples thereof include a method using calcium ions [Proc. Natl. Acad. Sci. USA, 69, 2110 (1972), Gene, 17, 107 (1982), Molecular & General Genetics, 168, 111 (1979)].

When an animal cell is used as a host, as the expression vector, any vector can be used as long as it functions in an animal cell, and examples thereof include pcDNAI (manufactured by Invitrogen, Inc.), pcDM8 (manufactured by Funakoshi Co., Ltd.), pAGE107 [JP-A-H3-22979; Cytotechnology, 3, 133 (1990)], pAS3-3 (JP-A-H2-227075), pCDM8 [Nature, 329, 840 (1987)], pcDNAI/Amp (manufactured by Invitrogen, Inc.), pcDNA3.1 (manufactured by Invitrogen, Inc.), pREP4 (manufactured by Invitrogen, Inc.), pAGE103 [J. Biochemistry, 101, 1307 (1987)], pAGE210, pME18SFL3, pKANTEX93 (WO 97/10354), and the like.

As the promoter, any promoter can be used as long as it can exhibit its functions in an animal cell, and examples thereof include a cytomegalovirus (CMV) immediate early (IE) gene promoter, an SV40 early promoter, a retrovirus promoter, a metallothionein promoter, a heat-shock promoter, an SRα promoter, or a Moloney murine leukemia virus promoter or enhancer. In addition, a human CMV IE gene enhancer may be used together with the promoter.

Examples of the host cell include a human Burkitt's lymphoma cell Namalwa, an African Green Monkey kidney-derived cell COS, a Chinese hamster ovary-derived cell CHO, a human leukemia cell HBT5637 (JP-A-S63-000299), and the like.

As a method for introducing a recombinant vector into a host cell, any method can be used as long as it is a method for introducing a DNA into an animal cell, and examples thereof include an electroporation method [Cytotechnology, 3, 133 (1990)], a calcium phosphate method (JP-A-H2-227075), a lipofection method [Proc. Natl. Acad. Sci. USA, 84, 7413 (1987)], and the like.

At least one of CD40 and EpCAM can be produced by culturing a microorganism having a recombinant vector incorporating a DNA encoding at least one of CD40 and EpCAM, or a transformant derived from an animal cell or the like obtained as described above in a culture medium, producing and accumulating at least one of the CD40 and the EpCAM in the culture, and then collecting it from the culture. A method for culturing the transformant in a culture medium can be carried out according to a usual method used for culturing a host.

In the case of being expressed in a cell derived from a eukaryote, it is possible to obtain at least one of CD40 and EpCAM to which a sugar or a sugar chain is added.

When culturing a microorganism transformed with a recombinant vector using an inducible promoter, an inducer may be added to a culture medium as needed. For example, when a microorganism transformed with a recombinant vector using a lac promoter is cultured, isopropyl-β-D-thiogalactopyranoside or the like may be added to a culture medium, and when a microorganism transformed with a recombinant vector using a trp promoter is cultured, indoleacrylic acid or the like may be added to a culture medium.

Examples of the culture medium in which the transformant obtained using an animal cell as a host is cultured include RPMI 1640 medium [The Journal of the American Medical Association, 199, 519 (1967)], Eagle's MEM medium [Science, 122, 501 (1952)], Dulbecco's modified MEM medium [Virology, 8, 396 (1959)], Medium 199 [Proc. Soc. Exp. Biol. Med., 73, 1 (1950)], Iscove's modified Dulbecco's medium (IMDM), which are generally used, or a culture medium in which fetal bovine serum (FBS) or the like is added to any of these culture media, and the like. The culture is usually carried out under the conditions of pH 6 to 8 and 30 to 40° C. in the presence of 5% $CO_2$ for 1 to 7 days. In addition, during the culture, an antibiotic such as kanamycin or penicillin may be added to the culture medium as needed.

As a method for expressing a gene encoding at least one of CD40 and EpCAM, a method of secretory production, fused protein expression, or the like [Molecular Cloning, A Laboratory Manual, Second Edition, Cold Spring Harbor Laboratory Press (1989)] can be used in addition to direct expression. Examples of a method for producing at least one of CD40 and EpCAM include a method for producing it in a host cell, a method for secreting it out of a host cell, and a method for producing it on an outer membrane of a host cell, and an appropriate method can be selected by changing a host cell to be used or the structure of at least one of CD40 and EpCAM to be produced.

For example, an antigen-fusion protein can be produced by preparing a DNA in which a DNA encoding an Fc region of an antibody, a DNA encoding glutathione S-transferase (GST), a DNA encoding a FLAG tag or a DNA encoding a Histidine tag, or the like is ligated to a DNA encoding an amino acid sequence of an extracellular domain, followed by expression and purification. Specific examples thereof include an Fc-fusion protein in which an extracellular domain of at least one of CD40 and EpCAM is bound to an Fc region of human IgG, and a fusion protein in which an extracellular domain of at least one of CD40 and EpCAM is fused with glutathione S-transferase (GST).

When at least one of CD40 and EpCAM is produced in a host cell or on an outer membrane of a host cell, at least one of CD40 and EpCAM can be actively secreted outside the host cell using the method of Paulson et al. [J. Biol. Chem., 264, 17619 (1989)], the method of Lowe et al. [Proc. Natl. Acad. Sci., USA, 86, 8227 (1989), Genes Develop., 4, 1288 (1990)], or a method described in JP-A-H05-336963, WO 94/23021, or the like. In addition, the production amount of at least one of CD40 and EpCAM can also be increased utilizing a gene amplification system using a dihydrofolate reductase gene or the like (JP-A-H2-227075).

At least one of the produced CD40 and EpCAM can be isolated and purified, for example, as follows.

When at least one of CD40 and EpCAM is expressed in cells in a dissolved state, the cells are collected by centrifugation after completion of the culture, suspended in an aqueous buffer solution, followed by homogenization of the cells using an ultrasonic homogenizer, a French press, a Manton Gaulin homogenizer, a Dyno mill, or the like, whereby a cell-free extract solution is obtained. It is possible to obtain a purified protein from a supernatant obtained by centrifugation of the cell-free extract solution using methods such as general protein isolation and purification methods, that is, a solvent extraction method, a salting-out method using ammonium sulfate or the like, a desalting method, a precipitation method using an organic solvent, anion exchange chromatography using a resin such as diethylaminoethyl (DEAE)-Sepharose or DIAION HPA-75 (manufactured by Mitsubishi Chemical Corporation), cation exchange chromatography using a resin such as S-Sepharose FF (manufactured by Pharmacia Corporation), hydrophobic chromatography using a resin such as Butyl Sepharose or Phenyl Sepharose, a gel filtration method using a molecular sieve, affinity chromatography, a chromatofocusing method, electrophoresis such isoelectric focusing electrophoresis, and the like alone or in combination.

When at least one of CD40 and EpCAM is expressed in cells by forming an insoluble body, the cells are collected and then homogenized in the same manner as described above, followed by centrifugation, whereby the insoluble body of at least one of the CD40 and the EpCAM is collected as a precipitated fraction. The collected insoluble body of at least one of the CD40 and the EpCAM is solubilized with a protein denaturing agent. At least one of the CD40 and the EpCAM is returned to a normal conformation by diluting or dialyzing the solubilized solution, and thereafter, a purified protein of a polypeptide can be obtained by the same isolation and purification methods as described above.

When at least one of CD40 and EpCAM, or a derivative thereof such as a sugar-modified body thereof is extracellularly secreted, at least one of the CD40 and the EpCAM, or the derivative thereof such as a sugar-modified body thereof can be collected in a culture supernatant. The culture supernatant is subjected to a treatment using a method such as centrifugation in the same manner as described above, thereby obtaining a soluble fraction, and then by using the same isolation and purification methods as described above, a purified protein can be obtained from the soluble fraction.

In addition, at least one of CD40 and EpCAM used in the present invention can also be produced using a chemical synthesis method such an Fmoc method or a tBoc method. Specifically, for example, chemical synthesis can be carried out using a peptide synthesizer manufactured by Advanced Chemtech, Inc., PerkinElmer, Inc., Pharmacia Corporation, Protein Technology Instrument, Inc., Synthecell-Vega Biomolecules Corporation, Perceptive, Inc., Shimadzu Corporation, or the like.

(2) Step of Preparing Antibody-Producing Cell

By immunizing an animal such as a mouse, a rat, or a hamster at the age of 3 to 20 weeks with the antigen obtained in (1), and an antibody-producing cell in the spleen, the lymph node, or the peripheral blood of the animal is collected. In addition, as the animal, for example, a transgenic mouse that produces a human-derived antibody described in the document of Tomizuka. et al. [Tomizuka. et al., Proc Natl Acad Sci USA., 97, 722 (2000)], a conditional knockout mouse of CD40 or EpCAM for enhancing immunogenicity, or the like is exemplified as an immunized animal.

The immunization is carried out by administering an antigen together with an appropriate adjuvant such as a Freund's complete adjuvant, an aluminum hydroxide gel, Bordetella pertussis vaccine, or the like. As a method for administration of an immunogen when immunizing a mouse, any method of subcutaneous injection, intraperitoneal injection, intravenous injection, intradermal injection, intramuscular injection, footpad injection, and the like may be used, but intraperitoneal injection, footpad injection, or intravenous injection is preferred. When the antigen is a partial peptide, a conjugate of the antigen with a carrier protein such as BSA (bovine serum albumin) or KLH (Keyhole Limpet hemocyanin) is produced and used as an immunogen.

The administration of the antigen is carried out 5 to 10 times every 1 to 2 weeks after the first administration. On day 3 to 7 after each administration, the blood is collected from a venous plexus of the fundus, and the antibody titer of the serum thereof is measured using an enzyme immunoassay method [Antibodies—A Laboratory Manual, Cold Spring Harbor Laboratory (1988)] or the like. If an animal whose serum shows a sufficient antibody titer against the antigen used for the immunization is used as a supply source for the antibody-producing cell for fusion, the effect of the subsequent procedure can be enhanced.

On day 3 to 7 after the final administration of the antigen, a tissue including the antibody-producing cell such as the spleen is extracted from the immunized animal, and the antibody-producing cell is collected. The antibody-producing cell is a lymphocyte that is a plasma cell and a progenitor cell thereof. The cell may be obtained from any site of an individual and can be generally obtained from the spleen, the lymph node, the bone marrow, the tonsil, the peripheral blood, or an appropriate combination thereof, or the like, but spleen cells are most generally used. When spleen cells are used, the spleen is shredded and loosened, followed by centrifugation, and then red blood cells are removed, whereby the antibody-producing cells for fusion are obtained.

(3) Step of Preparing Myeloma

As a myeloma, a cell that is derived from a mammal such as a mouse, a rat, a guinea pig, a hamster, a rabbit, or a human, and that has no ability of autoantibody production can be used, however, generally, an established cell line obtained from a mouse, for example, a 8-azaguanine resistant mouse (BALB/c derived) myeloma cell line P3-X63Ag8-U1 (P3-U1) [Current Topics in Microbiology and Immunology, 18, 1 (1978)], P3-NS1/1-Ag41 (NS-1) [European J. Immunology, 6, 511 (1976)], SP2/0-Ag14 (SP-2) [Nature, 276, 269 (1978)], P3-X63-Ag8653 (653) [J. Immunology, 123, 1548 (1979)], P3-X63-Ag8 (X63) [Nature, 256, 495 (1975)], or the like is used. The cell line is subcultured in a suitable culture medium, for example, an 8-azaguanine medium [RPMl-1640 medium supplemented with glutamine, 2-mercaptoethanol, gentamicin, FCS, and 8-azaguanine], Iscove's modified Dulbecco's medium (hereinafter referred to as "IMDM"), or Dulbecco's modified Eagle medium (hereinafter referred to as "DMEM"). The above cell line is subcultured in a normal culture medium (for example, DMEM medium containing 10% FCS) 3 to 4 days before cell fusion, and $2\times10^7$ or more cells are ensured on the day of performing the fusion.

(4) Cell Fusion

The antibody-producing cells for fusion obtained in (2) and the myeloma cells obtained in (3) are well washed with Minimum Essential Medium (MEM) or PBS (1.83 g of disodium phosphate, 0.21 g of monopotassium phosphate, 7.65 g of sodium chloride, 1 L of distilled water, pH 7.2), and mixed to give the antibody-producing cells for fusion: the myeloma cells=5:1 to 10:1, followed by centrifugation, and then the supernatant is removed. After the precipitated cell clusters are well loosened, a mixed solution of polyethylene glycol 1000 (PEG-1000), MEM medium, and dimethylsulfoxide is added thereto while stirring at 37° C. Further, 1 to 2 mL of MEM medium is added thereto every 1 to 2 minutes for several times, and then MEM medium is added so that the total amount becomes 50 mL. After centrifugation, the supernatant is removed, the precipitated cell clusters are gently loosened, and then the cells are gently suspended in HAT medium [a normal culture medium supplemented with hypoxanthine, thymidine, and aminopterin]. The resulting suspension is cultured in a 5% $CO_2$ incubator at 37° C. for 7 to 14 days.

In addition, the cell fusion can also be carried out by the following method. The spleen cells and the myeloma cells are well washed with a serum-free medium (for example, DMEM), or phosphate buffered saline (hereinafter referred to as "phosphate buffer solution"), and mixed so that the ratio of the spleen cells to the myeloma cells becomes about 5:1 to 10:1, followed by centrifugation. The supernatant is removed, and after the precipitated cell clusters are well loosened, 1 mL of a serum-free medium containing 50% (w/v) polyethylene glycol (molecular weight 1000 to 4000) is dropped thereto while stirring. Thereafter, 10 mL of the serum-free medium is slowly added thereto, followed by centrifugation. The supernatant is removed again, the precipitated cells are suspended in a normal culture medium containing an appropriate amount of a hypoxanthine-aminopterin-thymidine (HAT) solution and human interleukin 2 (IL-2) (hereinafter referred to as "HAT medium"), and the suspension is dispensed in each well of a culture plate (hereinafter referred to as "plate"), and then the cells are cultured in the presence of 5% carbon dioxide gas at 37° C. for about 2 weeks. During the culture, the HAT medium is supplemented as appropriate.

(5) Selection of Hybridoma Group

When the myeloma cells used for the fusion are an 8-azaguanine resistant strain, that is, a hypoxanthine-guanine-phosphoribosyltransferase (HGPRT)-deficient strain, the unfused myeloma cells and the fused cells between the myeloma cells cannot survive in the HAT medium. On the other hand, the fused cells between the antibody-producing cells, and the hybridomas of the antibody-producing cell and the myeloma cell can survive in the HAT medium, however, the life span of the fused cells between the antibody-producing cells is reached shortly. Therefore, by continuing the culture in the HAT medium, only the hybridomas of the antibody-producing cell and the myeloma cell survive, and as a result, the hybridomas can be obtained.

For a hybridoma grown in a colonial form, medium replacement with a culture medium obtained by removing aminopterin from the HAT medium (hereinafter referred to as HT medium) is carried out. Thereafter, a portion of the culture supernatant is collected, and a hybridoma that produces an antibody can be selected using the below-mentioned antibody titer measurement method. Examples of the antibody titer measurement method include various known techniques such as a radioisotopic immunoassay method (RIA method), a solid-phase enzyme immunoassay method (ELISA method), a fluorescent antibody method, and a passive hemagglutination reaction method, but an RIA method or an ELISA method is preferred from the viewpoint of detection sensitivity, rapidity, accuracy, a possibility of automation of an operation, and the like.

The hybridoma determined to produce a desired antibody by measuring the antibody titer is transferred to another plate, and cloning is carried out. Examples of the cloning method include a limiting dilution method in which culture is carried out by dilution so that one cell is contained in one well of a plate, a soft agar method in which culture is carried out in a soft agar medium to collect colonies, a method in which one cell is isolated using a micromanipulator, a method in which one cell is isolated using a cell sorter, and the like.

For a well in which the antibody titer is observed, cloning is repeated 2 to 4 times using, for example, a limiting dilution method, and the cell in which the antibody titer is stably observed is select as a hybridoma strain that produces a monoclonal antibody against human CD40 or EpCAM.

(6) Preparation of Monoclonal Antibody

The monoclonal antibody-producing hybridoma obtained in (5) is intraperitoneally injected into a mouse or a nude mouse at the age of 8 to 10 weeks having been subjected to a pristane treatment [0.5 mL of 2,6,10,14-tetramethylpentadecane (Pristane) is intraperitoneally administered, followed by rearing the mouse for 2 weeks]. In 10 to 21 days, the hybridoma is converted into an ascites tumor. The ascites is collected from this mouse, followed by centrifugation, removing solids, and then salting out with 40% to 50% ammonium sulfate. Thereafter, purification is carried out by a caprylic acid precipitation method, a DEAE-Sepharose column, a protein A column, or a gel filtration column, and then an IgG or IgM fraction is collected and a purified monoclonal antibody is prepared. In addition, by growing the hybridoma in the peritoneal cavity of a mouse of the same strain (for example, BALB/c) or a Nu/Nu mouse, a rat, a guinea pig, a hamster, a rabbit, or the like, ascites containing a large amount of a monoclonal antibody that binds to CD40 or EpCAM can be obtained.

After culturing the monoclonal antibody-producing hybridoma obtained in (5) in RPMI 1640 medium supplemented with 10% FBS, or the like, the supernatant is removed by centrifugation, and the residue is suspended in GIT medium, Hybridoma SFM medium supplemented with 5% Daigo's GF21, or the like, and then cultured for 3 to 7 days by flask culture, spinner culture, bag culture, or the like. The obtained cell suspension is centrifuged, and purification from the obtained supernatant is carried out by a protein A column or a protein G column, and then an IgG fraction is collected, whereby a purified monoclonal antibody can also be obtained. As a simple method for the purification, it is also possible to use a commercially available monoclonal antibody purification kit (for example, MabTrap GII kit manufactured by Amersham Pharmacia Biotech, Inc.), and the like.

The determination of the subclass of the antibody is carried out by an enzyme immunoassay method using a subclass typing kit. The quantitative determination of a protein content can be carried out by to Lowry method or a method of calculation from the absorbance at 280 nm [1.4 ($OD_{280}$)=1 mg/mL immunoglobulin].

(7) Binding Assay of Monoclonal Antibody to CD40 or EpCAM

The binding activity of the monoclonal antibody to CD40 or EpCAM can be measured by a binding assay system such as an Ouchterlony method, an ELISA method, an RIA method, a flow cytometry method (FCM), or a surface plasmon resonance method (SPR).

An Ouchterlony method is a simple method, but a concentration operation is needed when the concentration of the antibody is low. On the other hand, when an ELISA method or an RIA method is used, by allowing a culture supernatant to directly react with an antigen-adsorbed solid phase and further by using antibodies corresponding to various immunoglobulin isotypes and subclasses as secondary antibodies, it is possible to identify the isotype and subclass of the antibody and also to measure the binding activity of the antibody.

As a specific example of the procedure, at least one of the purified or partially purified recombinant CD40 and EpCAM is adsorbed to a solid phase surface of a 96-well plate for ELISA or the like, and then the solid phase surface to which the antigen is not adsorbed is blocked with a protein unrelated to the antigen, for example, bovine serum albumin (BSA). After an ELISA plate is washed with phosphate buffer saline (PBS) and PBS containing 0.05% Tween 20 (Tween-PBS), or the like, a serially diluted first antibody (for example, mouse serum, a culture supernatant, or the like) is reacted therewith, and then the antibody is bound to the antigen immobilized on the plate. Subsequently, as a second antibody, an anti-immunoglobulin antibody labeled with biotin, an enzyme (horse radish peroxidase (HRP), alkaline phosphatase (ALP), or the like), a chemiluminescent substance or a radioactive compound, or the like, is dispensed to allow the second antibody to react with the first antibody bound to the plate. After well washing with Tween-PBS, a reaction according to the labeling substance of the second antibody is carried out, and then a monoclonal antibody that specifically reacts with the target antigen is selected.

In an FCM method, the binding activity of an antibody to an antigen-expressing cell can be measured [Cancer Immunol. Immunother., 36, 373 (1993)]. Binding of an antibody to a membrane protein antigen expressed on a cell membrane means that the antibody recognizes the conformation of an antigen present in nature and binds thereto.

Examples of an SPR method include a kinetics analysis by Biacore. For example, by using Biacore T100, the kinetics in binding of an antigen and a test substance are measured, and the result is analyzed with an analysis software attached to an instrument. As a specific example of the procedure, after fixing an anti-mouse IgG antibody to a sensor chip CMS by an amine coupling method, a test substance such as a hybridoma culture supernatant or a purified monoclonal antibody is allowed to flow to bind an appropriate amount, further the antigen at a plurality of known concentrations is allowed to flow, and then binding and dissociation are measured. Subsequently, a kinetics analysis by a 1:1 binding model is carried out with respect to the obtained data using the software attached to the instrument to acquire various parameters. Alternatively, after fixing at least one of CD40 and EpCAM onto the sensor chip by, for example, an amine coupling method, a purified monoclonal antibody at a plurality of known concentrations is allowed to flow, and then binding and dissociation are measured. A kinetics analysis by a bivalent binding model is carried out with respect to the obtained data using the software attached to the instrument to acquire various parameters.

In addition, in the present invention, it is possible to select an antibody that binds to CD40 or EpCAM competitively with the antibody against CD40 or EpCAM by allowing a test antibody to coexist in the above binding assay system to cause a reaction. That is, by screening an antibody whose binding to an antigen is inhibited when a test antibody is added, it is possible to obtain an antibody that competes with the antibody obtained above, for binding to CD40 or EpCAM.

(8) Identification of Epitope of Monoclonal Antibody Against CD40 or EpCAM

In the present invention, the identification of an epitope which the antibody recognizes and binds to can be carried out as follows.

For example, a partially deficient variant of an antigen, a mutant of an antigen in which an amino acid residue different among species is altered, or a mutant of an antigen in which a specific domain is altered is produced, and if the reactivity of the antibody against the deficient variant or the mutant is lowered, it becomes clear that the deficient site or the amino acid-altered site is an epitope of the antibody. Such a partially deficient variant or a mutant of an antigen may be obtained as a secretory protein using a suitable host cell, for example, E. coli, yeast, a plant cell, a mammalian cell, or the like, or may be prepared as an antigen-expressing cell by expressing it on a cell membrane of a host cell. In the case of a membrane-associated antigen, in order to express it while maintaining the conformation of the antigen, it is preferred to express it on the membrane of a host cell. In addition, it is also possible to confirm the reactivity of the antibody by producing a synthetic peptide mimicking the primary structure or the conformation of the antigen. As for a synthetic peptide, a method for producing various partial peptides of the molecule thereof using a known peptide synthesis technique, and the like are exemplified.

For example, with respect to the extracellular domain of human and mouse CD40 or EpCAM, it is possible to identify an epitope of an antibody by producing a chimeric protein in which domains constituting the respective regions are appropriately combined, and then confirming the reactivity of the antibody with the protein. Thereafter, it is possible to further identify the epitope in detail by variously synthesizing an oligopeptide of the corresponding region or a mutant or the like of the peptide using an oligopeptide synthesis technique well known to those skilled in the art, and then confirming the reactivity of the antibody with the peptide. As a simple method for obtaining various types of oligopeptides, a commercially available kit [for example, SPOTs Kit (manufactured by Genosys Biotechnologies, Inc.), a series of multipin peptide synthesis kit (manufactured by Chiron Corporation) using a multipin synthesis method, or the like] can also be used.

An antibody that binds to the same epitope as an epitope to which an antibody that binds to CD40 or EpCAM binds can be obtained by identifying an epitope of an antibody obtained in the above-mentioned binding assay system, producing a partial synthetic peptide of the epitope, a synthetic peptide mimicking the conformation of the epitope, a recombinant of the epitope, or the like, and then performing immunization therewith.

For example, if the epitope is a membrane protein, an antibody specific to the epitope can be more efficiently produced by producing a recombinant fusion protein in which the entire extracellular domain or a part of the extracellular domain is linked to an appropriate tag, for example, a FLAG tag, a Histidine tag, a GST protein or an antibody Fc region, or the like, and performing immunization with the recombinant protein.

2. Production of Genetically Recombinant Antibody

As production examples of genetically recombinant antibodies, methods for producing a chimeric antibody, a humanized antibody, and a human antibody will be described below, although the methods are schematically described in P. J. Delves., ANTIBODY PRODUCTION ESSENTIAL TECHNIQUES., 1997 WILEY, P. Shepherd and C. Dean. Monoclonal Antibodies., 2000 OXFORD UNIVERSITY PRESS, and J. W. Goding., Monoclonal Antibodies: principles and practice., 1993 ACADEMIC PRESS, and the like. In addition, genetically recombinant mouse, rat, hamster, and rabbit antibodies can also be produced using the same method.

(1) Acquisition of cDNA Encoding V Region of Monoclonal Antibody from Hybridoma

Acquisition of cDNAs encoding VH and VL of a monoclonal antibody can be carried out, for example, as follows.

First, mRNA is extracted from a hybridoma that produces a monoclonal antibody, and cDNAs are synthesized. Subsequently, the synthesized cDNAs are each cloned into a vector such as a phage or a plasmid, thereby producing a cDNA library. A recombinant phage or a recombinant plasmid comprising a cDNA encoding VH or VL is isolated from the library using a DNA encoding a C region part or a V region part of the antibody as a probe, respectively. The entire nucleotide sequence of VH or VL in the isolated recombinant phage or recombinant plasmid is determined, and then the entire amino acid sequence of VH or VL is deduced from the nucleotide sequence.

As a non-human animal used for producing a hybridoma, a mouse, a rat, a hamster, a rabbit, or the like is used, but any animal can be used as long as a hybridoma can be produced.

For the preparation of the total RNA from a hybridoma, a guanidine thiocyanate-cesium trifluoroacetate method [Methods in Enzymol., 154, 3 (1987)], or a kit such as RNA easy Kit (manufactured by QIAGEN, Inc.), or the like is used.

In the preparation of mRNA from the total RNA, an oligo (dT)-immobilized cellulose column method [Molecular Cloning, A Laboratory Manual, Second Edition, Cold Spring Harbor Laboratory Press (1989)], or a kit such as Oligo-dT30<Super> mRNA Purification Kit (manufactured by Takara Bio Inc.), or the like is used. Further, it is also possible to prepare mRNA using a kit such as Fast Track mRNA Isolation Kit (manufactured by Invitrogen, Inc.), or QuickPrep mRNA Purification Kit (manufactured by Pharmacia Corporation).

In the synthesis of cDNAs and the production of a cDNA library, a known method [Molecular Cloning, A Laboratory Manual, Second Edition, Cold Spring Harbor Laboratory Press (1989), Current Protocols in Molecular Biology, Supplement 1, John Wiley & Sons (1987-1997)], or a kit such as SuperScript Plasmid System for cDNA Synthesis and Plasmid Cloning (manufactured by Invitrogen, Inc.) or ZAP-cDNA Synthesis Kit (manufactured by Stratagene Corporation), or the like is used.

When the cDNA library is produced, as the vector into which a cDNA synthesized using mRNA extracted from a hybridoma as a template is incorporated, any vector can be used as long as it can incorporate the cDNA.

For example, ZAP Express [Strategies, 5, 58 (1992)], pBluescript II SK(+) [Nucleic Acids Research, 17, 9494 (1989)], λZAPII (manufactured by Stratagene Corporation), λgt 10, λgt 11 [DNA Cloning: A Practical Approach, I, 49 (1985)], Lambda BlueMid (manufactured by Clontech Laboratories, Inc.), λExCell, pT7T3-18U (manufactured by Pharmacia Corporation), pcD2 [Mol. Cell. Biol., 3, 280 (1983)], pUC18 [Gene, 33, 103 (1985)], or the like is used.

As E. coli into which a cDNA library constructed by a phage or a plasmid vector is introduced, any E. coli can be used as long as it can introduce, express, and maintain the cDNA library. For example, XL1-Blue MRF' [Strategies, 5, 81 (1992)], C600 [Genetics, 39, 440 (1954)], Y1088, Y1090 [Science, 222, 778 (1983)], NM522 [J. Mol. Biol., 166, 1 (1983)], K802 [J. Mol. Biol., 16, 118 (1966)], JM105 [Gene, 38, 275 (1985)], or the like is used.

In the selection of a cDNA clone encoding VH or VL of a non-human antibody from the cDNA library, a colony hybridization method using an isotope or a fluorescently labeled probe, or a plaque hybridization method [Molecular Cloning, A Laboratory Manual, Second Edition, Cold Spring Harbor Laboratory Press (1989)], or the like is used.

In addition, it is possible to prepare a cDNA encoding VH or VL by preparing a primer and performing a polymerase chain reaction method [hereinafter referred to as a PCR method, Molecular Cloning, A Laboratory Manual, Second Edition, Cold Spring Harbor Laboratory Press (1989), Current Protocols in Molecular Biology, Supplement 1, John Wiley & Sons (1987-1997)] using a cDNA synthesized from mRNA or a cDNA library as a template.

The selected cDNA is cleaved with an appropriate restriction enzyme or the like, and then cloned into a plasmid such as pBluescript SK(−) (manufactured by Stratagene Corporation), and the nucleotide sequence of the cDNA is determined by a commonly used nucleotide sequence analysis method or the like. For example, after performing a reaction such as a dideoxy method [Proc. Natl. Acad. Sci. USA, 74, 5463 (1977)], an analysis is carried out using an automatic nucleotide sequence analyzer such as A.L.F. DNA sequencer (manufactured by Pharmacia Corporation).

By deducing the entire amino acid sequence of each of VH and VL from the determined entire nucleotide sequence and comparing it with the entire amino acid sequence of each of VH and VL of a known antibody [Sequences of Proteins of Immunological Interest, US Dept. Health and Human Services (1991)], it is confirmed whether the obtained cDNA encodes the complete amino acid sequence of each of VH and VL of the antibody comprising a secretion signal sequence.

With respect to the complete amino acid sequence of each of VH and VL of the antibody comprising a secretion signal sequence, by comparison with the entire amino acid sequence of each of VH and VL of a known antibody [Sequences of Proteins of Immunological Interest, US Dept. Health and Human Services (1991)], the length of the secretion signal sequence and the N-terminal amino acid sequence can be deduced, and further the subgroup to which these belong can be identified.

In addition, the amino acid sequence of each CDR of VH and VL can be deduced by comparison with the amino acid sequence of each of VH and VL of a known antibody [Sequences of Proteins of Immunological Interest, US Dept. Health and Human Services (1991)].

Further, with respect to the obtained complete amino acid sequence of each of VH and VL, it is possible to confirm whether the complete amino acid sequence of each of VH and VL is new by, for example, carrying out a homology search by a BLAST method [J. Mol. Biol., 215, 403 (1990)] or the like using an arbitrary database such as SWISS-PROT or PIR-Protein.

(2) Construction of Expression Vector for Genetically Recombinant Antibody

An expression vector for a genetically recombinant antibody can be constructed by cloning a DNA encoding at least one of CH and CL of a human antibody into an expression vector for an animal cell.

As a C region of a human antibody, CH and CL of an arbitrary human antibody can be used, and for example, CH of γ1 subclass and CL of κ class of a human antibody, or the like can be used. As a DNA encoding CH or CL of a human antibody, a cDNA is used, but it is also possible to use a chromosomal DNA composed of an exon and an intron.

As the expression vector for an animal cell, any vector can be used as long as it can incorporate a gene encoding a C region of a human antibody and express the gene, and for example, pAGE107 [Cytotechnol., 3, 133 (1990)], pAGE103 [J. Biochem., 101, 1307 (1987)], pHSG274 [Gene, 27, 223 (1984)], pKCR [Proc. Natl. Acad. Sci. USA, 78, 1527 (1981)], pSG1bd2-4 [Cytotechnol., 4, 173 (1990)], pSE1UK1Sed1-3 [Cytotechnol., 13, 79 (1993)], INPEP4 (manufactured by Biogen-IDEC, Inc.), N5KG1val (U.S. Pat. No. 6,001,358), N5KG4PE R409K (described in WO 2006/033386), an N5KG2 vector (described in WO 2003/033538), a transposon vector (WO 2010/143698), or the like can be used.

As a promoter and an enhancer of the expression vector for an animal cell, an SV40 early promoter [J. Biochem., 101, 1307 (1987)], Moloney murine leukemia virus LTR [Biochem. Biophys. Res. Commun., 149, 960 (1987), a CMV promoter (U.S. Pat. No. 5,168,062), or a promoter [Cell, 41, 479 (1985)] and an enhancer [Cell, 33, 717 (1983)] of an immunoglobulin H chain, or the like can be used.

In the expression of a genetically recombinant antibody, a vector carrying both genes of the antibody H chain and L chain (tandem-type vector) [J. Immunol. Methods, 167, 271 (1994)] is used from the viewpoints of ease of construction of the vector, ease of introduction into an animal cell, balance of the expression levels of the antibody H chain and L chain in the cell, and the like, however, a plurality of vectors separately carrying each of the genes of the antibody H chain and L chain (separation-type vectors) can also be used in combination.

As the tandem-type expression vector for a genetically recombinant antibody, pKANTEX93 (WO 97/10354), pEE18 [Hybridoma, 17, 559 (1998)], N5KG1val (U.S. Pat. No. 6,001,358), N5KG4PE R409K (described in WO 2006/033386), an N5KG2 vector (described in WO 2003/033538), a Tol2 transposon vector (WO 2010/143698), or the like is used.

(3) Construction of Chimeric Antibody Expression Vector

By cloning the cDNA encoding VH or VL of a non-human antibody obtained in (1) upstream of each gene encoding CH or CL of a human antibody in the expression vector for a genetically recombinant antibody obtained in (2), a chimeric antibody expression vector can be constructed.

First, in order to ligate the cDNA encoding VH or VL of a non-human antibody at the 3'-terminal side with CH or CL of a human antibody at the 5'-terminal side, cDNAs of VH and VL designed so that the nucleotide sequence of a ligation region encodes an appropriate amino acid and to become an appropriate restriction enzyme recognition sequence are produced. Subsequently, the produced cDNAs of VH and VL are each cloned upstream of each gene encoding CH or CL of a human antibody in the expression vector for a genetically recombinant antibody obtained in (2) so that they are expressed in an appropriate form, whereby a chimeric antibody expression vector is constructed.

In addition, each cDNA encoding VH or VL of a non-human antibody is amplified by a PCR method using a synthetic DNA comprising an appropriate restriction enzyme recognition sequence at both ends, and is cloned into the expression vector for a genetically recombinant antibody obtained in (2), whereby a chimeric antibody expression vector can also be constructed.

(4) Production of cDNA Encoding V Region of Humanized Antibody

A cDNA encoding VH or VL of a humanized antibody can be produced as follows. First, each amino acid sequence of a framework region (hereinafter referred to as FR) of VH or VL of a human antibody, to which the amino acid sequence of a CDR of VH or VL of a non-human antibody obtained in (1) is to be grafted is selected.

As the amino acid sequence of FR to be selected, any amino acid sequence can be used as long as it is derived from a human antibody. For example, an amino acid sequence of FR of a human antibody registered in a database such as Protein Data Bank, or a common amino acid sequence in each subgroup of FR of a human antibody [Sequences of Proteins of Immunological Interest, US Dept. Health and Human Services (1991)], or the like is used. In order to suppress a decrease in the binding activity of an antibody, an amino acid sequence of human FR having a homology as high as possible (60% or more) with the amino acid sequence of FR of VH or VL of the original non-human antibody is selected.

Subsequently, each of the amino acid sequences of the CDRs of the original non-human antibody is grafted to the selected amino acid sequence of the FR of VH or VL of a human antibody, and each amino acid sequence of VH or VL of a humanized antibody is designed. By converting the designed amino acid sequence into a DNA sequence in consideration of the usage frequency of codons found in the nucleotide sequence of the antibody gene [Sequences of Proteins of Immunological Interest, US Dept. Health and Human Services (1991)], each cDNA sequence of VH or VL of a humanized antibody is designed.

Based on the designed cDNA sequence, several synthetic DNAs having a length of around 100 to 150 bases are synthesized and a PCR reaction is carried out using them. In this case, from the viewpoint of the reaction efficiency in the PCR reaction and the length of a synthesizable DNA, preferably 4 to 6 synthetic DNAs are designed for each of the H chain and the L chain. In addition, it is also possible to synthesize and use a synthetic DNA having a full-length variable region.

Further, by introducing an appropriate restriction enzyme recognition sequence at the 5' terminus of the synthetic DNA located at both ends, a cDNA encoding VH or VL of a humanized antibody can be easily cloned into the expression vector for a genetically recombinant antibody obtained in (2). After the PCR reaction, each amplified product is cloned into a plasmid such as pBluescript SK(−) (manufactured by Stratagene Corporation), the nucleotide sequence is determined by the same method as described in (1), and thus a plasmid comprising a DNA sequence encoding the amino acid sequence of VH or VL of a desired humanized antibody is obtained.

(5) Alteration of Amino Acid Sequence of V Region of Humanized Antibody

The antigen-binding activity of a humanized antibody prepared merely by grafting only CDRs of VH and VL of a non-human antibody to FRs of VH and VL of a human antibody is decreased as compared with that of the original non-human animal antibody [BIO/TECHNOLOGY, 9, 266 (1991)]. For this reason, the lowered antigen-binding activity of a humanized antibody can be increased by identifying amino acid residues directly involved in the binding to an antigen, amino acid residues interacting with the amino acid residues of CDRs, and amino acid residues maintaining the conformation of the antibody and indirectly involved in the binding to an antigen, and substituting the amino acid residues with amino acid residues of the original non-human antibody.

In order to identify the amino acid residues of FR involved in the antigen-binding activity, it is possible to construct and analyze the conformation of the antibody using X-ray crystallography [J. Mol. Biol., 112, 535 (1977)], or computer modeling [Protein Engineering, 7, 1501 (1994)], or the like. Further, it is possible to obtain an altered humanized antibody having a necessary antigen-binding activity by producing several types of variants for each antibody, and repeatedly examining the correlation with each antigen-binding activity through trial and error.

The amino acid residues of FRs of VH and VL of a human antibody can be altered by carrying out a PCR reaction described in (4) using a synthetic DNA for alteration. With respect to the amplification product after the PCR reaction, the nucleotide sequence is determined to confirm that the desired alteration has been carried out by the method described in (1).

(6) Construction of Expression Vector for Humanized Antibody

An expression vector for a humanized antibody can be constructed by cloning each cDNA encoding VH or VL of the constructed humanized antibody upstream of each gene encoding CH or CL of a human antibody of the expression vector for a genetically recombinant antibody obtained in (2).

For example, the cloning is carried out upstream of each gene encoding CH or CL of a human antibody in the expression vector for a genetically recombinant antibody obtained in (2) by introducing an appropriate restriction enzyme recognition sequence at the 5' terminus of the synthetic DNA located at both ends among the synthetic DNAs used when constructing VH or VL of the humanized antibody obtained in (4) and (5) so that they are expressed in an appropriate form.

(7) Construction of Expression Vector for Human Antibody

When a hybridoma that produces a monoclonal antibody is established using an animal that produces a human antibody as an immunized animal, the amino acid sequences and the cDNA sequences of VH and VL of a human antibody can be obtained in (1). Therefore, by cloning each gene encoding VH or VL of a human antibody obtained in (1) upstream of each gene encoding CH or CL of a human antibody of the expression vector for a genetically recombinant antibody obtained in (2), an expression vector for a human antibody can be constructed.

(8) Transient Expression of Genetically Recombinant Antibody

By transiently expressing a genetically recombinant antibody using the expression vector for a genetically recombinant antibody obtained in (3), (6) and (7), or an expression vector obtained by alteration thereof, the antigen-binding activities of many types of genetically recombinant antibodies obtained can be efficiently evaluated.

As a host cell into which the expression vector is introduced, any cell can be used as long as it is a host cell capable of expressing a genetically recombinant antibody. For example, a COS-7 cell [American Type Culture Collection (ATCC) number: CRL1651] is used. In the introduction of the expression vector into a COS-7 cell, a DEAE-dextran method [Methods in Nucleic Acids Res., CRC press (1991)], a lipofection method [Proc. Natl. Acad. Sci. USA, 84, 7413 (1987)], or the like is used.

After the introduction of the expression vector, the expression level and the antigen-binding activity of the genetically recombinant antibody in a culture supernatant are measured using an enzyme immunoassay method [Monoclonal Antibodies-Principles and practice, Third Edition, Academic Press (1996), Antibodies-A Laboratory Manual, Cold Spring Harbor Laboratory (1988), Monoclonal Antibody Experimental Manual, Kodansha scientific books (1987)], or the like.

(9) Acquisition of Stable Expression Cell Line of Genetically Recombinant Antibody and Preparation of Genetically Recombinant Antibody A transformant strain that stably expresses a genetically recombinant antibody can be obtained by introducing the expression vector for a genetically recombinant antibody obtained in (3), (6), and (7) into an appropriate host cell.

As the introduction of the expression vector into a host cell, for example, an electroporation method [JP-A-H2-257891, Cytotechnology, 3, 133 (1990)], a calcium ion method, an electroporation method, a spheroplast method, a lithium acetate method, a calcium phosphate method, a lipofection method, and the like are exemplified. In addition, as a method for introducing a gene into an animal described below, for example, a microinjection method, a method for introducing a gene into an ES cell using an electroporation or lipofection method, a nuclear transfer method, and the like are exemplified.

As a host cell into which the expression vector for a genetically recombinant antibody is introduced, any cell can be used as long as it is a host cell capable of expressing a genetically recombinant antibody. For example, mouse SP2/0-Ag14 cells (ATCC CRL 1581), mouse P3X63-Ag8.653 cells (ATCC CRL 1580), Chinese hamster CHO-K1 cells (ATCC CCL-61), DUKXB11 (ATCC CCL-9096), Pro-5 cells (ATCC CCL-1781), CHO-S cells (Life Technologies, Cat No. 11619), dihydrofolate reductase gene (dhfr)-deficient CHO cells (CHO/DG44 cells) [Proc. Natl. Acad. Sci. USA, 77, 4216 (1980)], Lec13 cells having acquired lectin resistance [Somatic Cell and Molecular Genetics, 12, 55 (1986)], α1,6-fucosyltransferase gene-deficient CHO cells (WO 2005/035586 and WO 02/31140), Rat YB2/3HL.P2.G11.16Ag.20 cells (ATCC No.: CRL 1662), and the like are used.

In addition, it is also possible to use a host cell in which the activity of a protein such as an enzyme involved in the intracellular synthesis of sugar nucleotide GDP-fucose, a protein such as an enzyme involved in sugar chain modification such that the 1-position of fucose is α-linked to the 6-position of N-acetylglucosamine at the reducing end of an N-glycoside-linked complex sugar chain, a protein involved in the intracellular transport of sugar nucleotide GDP-fucose to the Golgi body, or the like is decreased or lost, for example, α1,6-fucosyltransferase gene-deficient CHO cells (WO 2005/035586 and WO 02/31140), or the like.

After introduction of the expression vector, a transformant strain that stably expresses a genetically recombinant antibody is selected by culturing the transformant strain in a medium for animal cell culture containing a drug such as G418 sulfate (hereinafter referred to as G418) (JP-A-H2-257891).

As the medium for animal cell culture, RPMI 1640 medium (manufactured by Invitrogen, Inc.), GIT medium (manufactured by Nippon Pharmaceutical Co., Ltd.), EX-CELL 301 medium (manufactured by JRH Biosciences, Inc.), EX-CELL 302 medium (manufactured by JRH Bioscience, Inc.), EX-CELL 325 medium (manufactured by JRH Bioscience., Inc.), IMDM medium (manufactured by Invitrogen, Inc.) or Hybridoma-SFM medium (manufactured by Invitrogen, Inc.), or a medium in which any of various additives such as FBS to is added to any of these media, or the like is used. By culturing the obtained transformant strain in the medium, a genetically recombinant antibody is expressed and accumulated in the culture supernatant. The expression level and the antigen-binding activity of the genetically recombinant antibody in the culture supernatant can be measured by an ELISA method or the like. In addition, the expression level of the genetically recombinant antibody produced by the transformant strain can be increased using a DHFR amplification system (JP-A-H2-257891) or the like.

The genetically recombinant antibody can be purified using a protein A column from the culture supernatant of the transformant strain [Monoclonal Antibodies—Principles and Practice, Third Edition, Academic Press (1996), Antibodies—A Laboratory Manual, Cold Spring Harbor Laboratory (1988)]. In addition, the purification can also be carried out by combining methods used for purifying a protein such as gel filtration, ion exchange chromatography, and ultrafiltration.

The molecular weights of an H chain, an L chain, or the entire antibody molecule of a purified genetically recombinant antibody can be measured using polyacrylamide gel electrophoresis [Nature, 227, 680 (1970)], or a Western blotting method [Monoclonal Antibodies—Principles and Practice, Third Edition, Academic Press (1996), Antibodies—A Laboratory Manual, Cold Spring Harbor Laboratory (1988)], or the like.

3. Production of Bispecific Antibody of Bispecific Antibody Fragment Thereof

The bispecific antibody of the present invention can be produced by, for example, first, obtaining a plurality of monoclonal antibodies that bind to different epitopes using the method described in the above 1., subsequently determining the cDNA sequences of VH and VL of each antibody using the method described in the above 2., and then designing a bispecific antibody to which the antigen-binding site of each antibody is linked or a bispecific antibody fragment thereof.

Specifically, the production can be carried out by synthesizing a DNA in which the antigen-binding site of each antibody is appropriately combined with a linker, integrating the DNA into the expression vector for a genetically recombinant antibody described in the above 2. (2), and then expressing the bispecific antibody or the bispecific antibody fragment thereof. More specifically, the production can be carried out by synthesizing a DNA encoding a polypeptide in which the VH of each antibody is linked through a linker, and also synthesizing a DNA encoding VL of each antibody, integrating the DNAs into the expression vector for a genetically recombinant antibody described in the above 2. (2), and then expressing the bispecific antibody or the bispecific antibody fragment thereof. It is also possible to produce a bispecific antibody having an arbitrary polypeptide chain at the C-terminal side (C-terminal side polypeptide) of an antigen-binding domain closest to the C terminus or a bispecific antibody fragment thereof using an expression vector for an animal cell into which a gene encoding an arbitrary polypeptide chain is introduced in place of the gene encoding CH or CL in 2. (2). The gene encoding an arbitrary polypeptide chain may be integrated into an expression vector for an animal cell after it is bound to a DNA encoding a polypeptide in which the VH of each antibody is linked through a linker, or may be integrated into an expression vector for an animal cell separately from a DNA encoding a polypeptide in which the VH of each antibody is linked through a linker.

The antigen-binding site can be isolated and obtained by a technique such as a phage display method or a yeast display method other than the method using a hybridoma described in the above 1. [Emmanuelle Laffy et. Al., Human Antibodies 14, 33-55, (2005)].

As the linker and the C-terminal side polypeptide, for example, a polypeptide chain is exemplified. Specifically, it refers to, for example, a polypeptide obtained by binding a plurality of antigen-binding domains. For example, an immunoglobulin domain composed of CH1-hinge-CH2-CH3 arranged in this order in the direction from the N terminus to the C terminus, an immunoglobulin domain composed of CH1-hinge-CH2, an immunoglobulin domain composed of CH1-hinge, an immunoglobulin domain composed of CH1, a fragment at the N-terminal side of CH1, a CH1 fragment composed of 14 amino acid residues in which an amino acid residue at position 14 is Cys and a CH1 fragment composed of amino acid residues at positions 1 to 14 from the N terminus of CH1, and a fragment in which one or more amino acid residues are altered in the amino acid sequence of any of the immunoglobulin domain fragments can be exemplified.

As the linker and the C-terminal side polypeptide, more specifically, for example, a polypeptide composed of 14 amino acid residues at positions 1 to 14 at the N terminus of CH1 of IgG4 represented by SEQ ID NO: 75, a polypeptide composed of CH1 of IgG4 represented by SEQ ID NO: 75, a polypeptide composed of CH (CH1, a hinge, CH2, and CH3) of IgG4PE R409K represented by SEQ ID NO: 77, and the like are exemplified.

In addition, in the case of producing a bispecific antibody composed of a plurality of VHs and a single VL or the bispecific antibody fragment thereof, a screening using a phage display method or the like is carried out and each VH most suitable for the single VL is selected so that each antigen-binding site comprised in the bispecific antibody reacts with each specific antigen.

Specifically, first, an animal is immunized with a first antigen using the method described in the above 1. to produce a hybridoma from its spleen, and a DNA sequence encoding a first antigen-binding site is cloned. Subsequently, an animal is immunized with a second antigen, a cDNA library is prepared from its spleen, and a DNA encoding the amino acid sequence of VH is obtained from the library by PCR.

Subsequently, a phage library expressing an scFv in which VH obtained by immunization with the second antigen and VL of the first antigen-binding site are linked is produced, and a phage displaying an scFv that specifically binds to the second antigen is selected by panning using the phage library. From the selected phage, a DNA sequence encoding the amino acid sequence of the VH of a second antigen-binding site is cloned.

Further, a DNA sequence encoding the amino acid sequence of a polypeptide in which the VH of the first antigen-binding site and the VH of the second antigen-binding site are linked through the above-mentioned linker is designed, and the DNA sequence and a DNA sequence encoding the amino acid sequence of the single VL are inserted into, for example, the expression vector for a genetically recombinant antibody described in the above 2. (2), whereby the expression vector for the bispecific antibody or the bispecific antibody fragment thereof of the present invention can be constructed. In addition, by using an expression vector for an animal cell transfected with a gene encoding an arbitrary polypeptide chain in place of the gene encoding CH in 2. (2), a bispecific antibody having an arbitrary polypeptide chain (C-terminal side polypeptide) at a C-terminal side of the VH of the second antigen-binding site or a bispecific antibody fragment thereof can be produced.

4. Evaluation of Activity of Bispecific Antibody or Bispecific Antibody Fragment Thereof of the Present Invention The evaluation of the activity of the purified bispecific antibody or bispecific antibody fragment thereof can be carried out as follows.

The binding activity of the bispecific antibody or the bispecific antibody fragment thereof of the present invention to a cell line expressing at least one of CD40 and EpCAM can be measured using the binding assay system described in the above 1. (7).

The CDC activity or the ADCC activity against a cell expressing at least one of CD40 and EpCAM can be measured by a known measurement method [Cancer Immunol. Immunother., 36, 373 (1993)].

The cell death-inducing activity of the bispecific antibody or the bispecific antibody fragment thereof of the present invention can be measured by the following method. For example, cells are seeded in a 96-well plate, and after adding an antibody and culturing the cells for a certain period of time, WST-8 reagent (manufactured by Dojindo Molecular Technologies, Inc.) is allowed to react, and then an absorbance at 450 nm is measured with a plate reader to measure a cell survival rate.

5. Therapeutic Method for Disease Using Bispecific Antibody or Bispecific Antibody Fragment Thereof of the Present Invention The bispecific antibody or the bispecific antibody fragment thereof of the present invention can be used for a treatment of a disease associated with at least one of CD40 and EpCAM, preferably a disease involved in a CD40 and EpCAM-expressing cell. As the disease associated with at least one of CD40 and EpCAM, for example, a malignant tumor, cancer, and the like are exemplified.

Examples of the malignant tumor and cancer include, large intestine cancer, colorectal cancer, lung cancer, breast cancer, glioma, malignant melanoma (melanoma), thyroid cancer, renal cell carcinoma, leukemia, lymphoma, T cell lymphoma, stomach cancer, pancreatic cancer, cervical cancer, endometrial cancer, ovarian cancer, bile duct cancer, esophageal cancer, liver cancer, head and neck squamous cell cancer, skin cancer, urinary tract cancer, bladder cancer, prostate cancer, choriocarcinoma, pharyngeal cancer, laryngeal cancer, pleural tumor, arrhenoblastoma, endometrial hyperplasia, endometriosis, embryoma, fibrosarcoma, Kaposi's sarcoma, angioma, cavernous hemangioma, angioblastoma, retinoblastoma, astrocytoma, neurofibroma, oligodendroglioma, medulloblastoma, neuroblastoma, glioma, rhabdomyosarcoma, glioblastoma, osteogenic sarcoma, leiomyosarcoma, Wilm's tumor, and the like.

A therapeutic agent comprising the bispecific antibody or the bispecific antibody fragment thereof of the present invention, or a derivative thereof may comprise only the antibody or the bispecific antibody fragment thereof, or a derivative thereof as an active ingredient, however, in general, it is preferably provided as a pharmaceutical preparation produced by mixing it together with one or more pharmacologically acceptable carriers using a method known in the technical field of pharmaceutics.

Examples of a route of administration include oral administration or parenteral administration such as intraoral, intra-airway, intrarectal, subcutaneous, intramuscular, and intravenous administration. Examples of a dosage form include a spray, a capsule, a tablet, a powder, a granule, a syrup, an emulsion, a suppository, an injection, an ointment, a tape, and the like. Various pharmaceutical preparations can be produced by a conventional method using an excipient, a filler, a binder, a wetting agent, a disintegrating agent, a surfactant, a lubricant, a dispersant, a buffer, a preservative, a solubilizing agent, an antiseptic, a coloring agent, a flavoring agent, a stabilizer, and the like that are generally used.

Examples of the excipient include lactose, fructose, glucose, corn starch, sorbit, crystalline cellulose, sterile water, ethanol, glycerol, a saline solution, a buffer solution, and the like. Examples of the disintegrating agent include starch, sodium alginate, gelatin, calcium carbonate, calcium citrate, dextrin, magnesium carbonate, synthetic magnesium silicate, and the like.

Examples of the binder include methyl cellulose or a salt thereof, ethyl cellulose, gum arabic, gelatin, hydroxypropyl cellulose, polyvinyl pyrrolidone, and the like. Examples of the lubricant include talc, magnesium stearate, polyethylene glycol, hydrogenated vegetable oil, and the like.

Examples of the stabilizer include amino acids such as arginine, histidine, lysine and methionine, human serum albumin, gelatin, dextran 40, methyl cellulose, sodium sulfite, sodium metasulfite, and the like.

Examples of other additives include syrup, vaseline, glycerin, ethanol, propylene glycol, citric acid, sodium chloride, sodium nitrite, sodium phosphate and the like.

Examples of the pharmaceutical preparation suitable for oral administration include an emulsion, a syrup, a capsule, a tablet, a powder, a granule, and the like.

A liquid preparation such as an emulsion or a syrup is produced using water, a sugar such as sucrose, sorbitol, or fructose, a glycol such as polyethylene glycol or propylene glycol, an oil such as sesame oil, olive oil, or soybean oil, a preservative such as p-hydroxybenzoic acid ester, a flavor such as strawberry flavor or peppermint, or the like, as an additive.

A capsule, a tablet, a powder, a granule, or the like can be produced using an excipient such as lactose, glucose, sucrose, or mannitol, a disintegrating agent such as starch or sodium alginate, a lubricant such as magnesium stearate or talc, a binder such as polyvinyl alcohol, hydroxypropyl cellulose, or gelatin, a surfactant such as a fatty acid ester, a plasticizer such as glycerin, or the like as an additive.

Examples of the pharmaceutical preparation suitable for parenteral administration include an injection, a suppository, a spray, and the like. An injection is produced using a carrier composed of a salt solution, a glucose solution, or a mixture of both, or the like.

A suppository is produced using a carrier such as cacao butter, a hydrogenated fat, or carboxylic acid. A spray is produced using a carrier which does not stimulate the buccal or airway mucous membrane of a recipient and disperses the bispecific antibody or the bispecific antibody fragment thereof of the present invention as fine particles so as to facilitate absorption thereof, or the like. Examples of the carrier include lactose, glycerin, and the like. In addition, it can also be produced as an aerosol or a dry powder. Further, a component exemplified as the additive for the pharmaceutical preparation suitable for oral administration can also be added to the above-mentioned parenteral preparation.

An effective amount to be administered as a combination of an effective amount of the bispecific antibody of the present invention and a suitable diluent and a pharmacologically usable carrier is 0.0001 mg to 100 mg per kg of the body weight at one time, and is administered at intervals of 2 days to 8 weeks.

6. Diagnostic Method for Disease Using Bispecific Antibody or Bispecific Antibody Fragment Thereof of the Present Invention By detecting or measuring a cell in which at least one of CD40 and EpCAM is expressed using the bispecific antibody or the bispecific antibody fragment thereof of the present invention, it is possible to diagnose a disease associated with at least one of CD40 and EpCAM, preferably a disease involved in a CD40 and EpCAM-expressing cell.

The diagnosis of a malignant tumor or cancer that is a disease associated with at least one of CD40 and EpCAM can be carried out by, for example, detecting or measuring at least one of CD40 and EpCAM as follows.

First, with respect to biological samples collected from the bodies of a plurality of healthy subjects, at least one of CD40 and EpCAM is detected or measured by the following immunological method using the bispecific antibody or the bispecific antibody fragment of the present invention, or a derivative thereof, and then the abundance of at least one of CD40 and EpCAM in the biological samples of the healthy subjects is examined.

Subsequently, also the abundance of at least one of CD40 and EpCAM in a biological sample of a test subject is examined in the same manner, and then the abundance is compared with the abundance of the healthy subjects. When the abundance of at least one of CD40 and EpCAM of the test subject increases as compared with that of the healthy subjects, the test subject is diagnosed as having cancer. With respect also to the diagnosis of the other diseases associated with at least one of CD40 and EpCAM, the diagnosis can be carried out by the same method.

The immunological method is a method in which a labeled antigen or antibody is used, and the amount of the antibody or the amount of the antigen is detected or measured. Examples thereof include a radioactive material labeled immune antibody method, an enzyme immunoassay method, a fluorescence immunoassay method, a luminescence immunoassay method, a Western blotting method, a physicochemical method, and the like.

Examples of the radioactive material labeled immune antibody method include a method in which the bispecific antibody or the bispecific antibody fragment thereof of the present invention is reacted with an antigen or a cell expressing an antigen, or the like, and further reacted with an anti-immunoglobulin antibody or a binding fragment subjected to radiolabeling, followed by measurement with a scintillation counter or the like.

Examples of the enzyme immunoassay method include a method in which the bispecific antibody or the bispecific antibody fragment thereof of the present invention is reacted with an antigen or a cell expressing an antigen, or the like, and further reacted with an anti-immunoglobulin antibody or a binding fragment subjected to labeling, followed by measurement of a coloring dye with an absorptiometer. For example, a sandwich ELISA method and the like are exemplified.

As a labeling substance used in the enzyme immunoassay method, a known enzyme label [enzyme immunoassay method, IGAKU-SHOIN Ltd. (1987)] can be used. For example, an alkaline phosphatase label, a peroxidase label, a luciferase label, a biotin label, or the like is used.

The sandwich ELISA method is a method in which after binding an antibody to a solid phase, an antigen that is a detection or measurement target is trapped, and then a second antibody is reacted with the trapped antigen. In the ELISA method, two types of antibodies that are antibodies or antibody fragments binding to an antigen desired to be detected or measured and have different antigen-binding sites are prepared, and among them, a first antibody or antibody fragment is adsorbed to a plate (for example, a 96-well plate) in advance, and subsequently, a second antibody or antibody fragment is labeled with a fluorescent substance such as FITC, an enzyme such as peroxidase, biotin, or the like beforehand. Cells separated from the inside of the living body or a homogenate liquid thereof, tissues or a homogenate liquid thereof, a cell culture supernatant, serum, pleural effusion, ascites, intraocular fluid, or the like is allowed to react with the plate to which the antibody is adsorbed, and thereafter to react with the labeled antibody or antibody fragment, and then, a detection reaction is carried out according to the labeled material. From a calibration curve prepared by serially diluting an antigen at known concentrations, the antigen concentration in the test sample is calculated.

As the antibody used in the sandwich ELISA method, either a polyclonal antibody or a monoclonal antibody may be used, and an antibody fragment such as a Fab, a Fab', or a F(ab)$_2$ may be used. The combination of the two types antibodies used in the sandwich ELISA method may be a combination of monoclonal antibodies or antibody fragments thereof which bind to different epitopes, or may be a combination of a polyclonal antibody and a monoclonal antibody or an antibody fragment thereof.

As the fluorescence immunoassay method, measurement is carried out by, for example, a method described in the document [Monoclonal Antibodies-Principles and Practice, Third Edition, Academic Press (1996), Monoclonal Antibody Experimental Manual, Kodansha scientific books (1987)], or the like. As a labeling substance used in the fluorescence immunoassay method, a known fluorescent label [Fluorescent Antibody Method, Soft Science, Inc. (1983)] can be used. For example, FITC, RITC, or the like is used.

As the luminescence immunoassay method, measurement is carried out by, for example, a method described in the document [Bioluminescence and Chemiluminescence Clinical Test 42, Hirokawa-Shoten Ltd. (1998)], or the like. As a labeling substance used in the luminescence immunoassay method, a known luminescent label is exemplified, and for example, an acridinium ester, lophine, or the like is used.

As the Western blotting method, measurement is carried out by fractionating an antigen or a cell expressing an antigen or the like by SDS (sodium dodecyl sulfate)—PAGE [Antibodies—A Laboratory Manual Cold Spring Harbor Laboratory (1988)], thereafter blotting the gel on a polyvinylidene fluoride (PVDF) membrane or a nitrocellulose membrane, reacting an antibody or an antibody fragment that binds to the antigen with the membrane, and then further reacting it with an anti-IgG antibody or an antibody fragment thereof labeled with a fluorescent substance such as FITC, labeled with an enzyme such as peroxidase, or labeled with biotin, or the like, followed by visualizing the label. An example is shown below.

First, cells or tissues expressing a polypeptide having a desired amino acid sequence are lysed, and 0.1 to 30 μg in terms of protein amount per lane is electrophoresed by an SDS-PAGE method under reducing conditions. Subsequently, the electrophoresed protein is transferred to a PVDF membrane and is reacted with PBS containing 1 to 10% BSA (hereinafter referred to as BSA-PBS) for 30 minutes at room temperature to perform a blocking operation. Then, the bispecific antibody of the present invention is reacted therewith, and the membrane is washed with PBS containing 0.05 to 0.1% Tween 20 (Tween-PBS), and then a goat anti-mouse IgG labeled with peroxidase is reacted therewith for 2 hours at room temperature. By washing with Tween-PBS, and detecting a band to which the antibody is bound using ECL Western Blotting Detection Reagents (manufactured by Amersham, Inc.) or the like, an antigen is detected. As the antibody used for detection by Western blotting, an antibody capable of binding to a polypeptide that does not retain a natural conformation is used.

As the physicochemical method, for example, by binding at least one of CD40 and EpCAM which are antigens and the bispecific antibody or the bispecific antibody fragment thereof of the present invention, an aggregate is formed, and the aggregate is detected. As another physicochemical method, a capillary tube method, a one-dimensional immunodiffusion method, an immunoturbidimetric method, a latex immunoturbidimetric method [Outline of Clinical Examination Method, KANEHARA & Co., LTD. (1998)], or the like can also be used.

In the latex immunoturbidimetric method, when a carrier such as a polystyrene latex having a particle diameter of about 0.1 to 1 μm sensitized with an antibody or an antigen is used to cause an antigen-antibody reaction with a corresponding antigen or antibody, the scattered light is increased in a reaction solution and the transmitted light is decreased. The antigen concentration or the like in a test sample is measured by detecting this change as an absorbance or an integrating sphere turbidity.

On the other hand, for the detection or measurement of a cell that expresses at least one of CD40 and EpCAM, a known immunological detection method can be used, but it is preferred to use an immunoprecipitation method, an immunocytochemical staining method, an immunohistochemical staining method, a fluorescent antibody staining method, or the like.

As the immunoprecipitation method, a cell expressing at least one of CD40 and EpCAM or the like is reacted with the bispecific antibody or the bispecific antibody fragment thereof of the present invention, and then a carrier having a specific binding ability to an immunoglobulin such as Protein G Sepharose is added thereto, thereby precipitating an antigen-antibody complex.

Alternatively, it can also be carried out by the following method. First, the bispecific antibody or the bispecific antibody fragment thereof of the present invention is immobilized on a 96-well plate for ELISA, followed by blocking with BSA-PBS. Subsequently, BSA-PBS is discarded, and the plate is well washed with PBS, and then a lysate solution of cells or tissues expressing at least one of CD40 and EpCAM is reacted therewith. From the plate after being well washed, an immunoprecipitated material is extracted with a sample buffer for SDS-PAGE, and then detected by the above-mentioned Western blotting.

The immunocytostaining method or the immunohistochemical staining method is a method in which a cell or a tissue expressing an antigen or the like is treated with a surfactant or methanol, or the like for enhancing the permeability of the antibody in some cases, and then reacted with the bispecific antibody of the present invention, and further reacted with an anti-immunoglobulin antibody or a binding fragment thereof fluorescently labeled with FITC or the like, labeled with an enzyme such as peroxidase, or labeled with biotin, or the like, and thereafter the label is visualized, and then observed with a microscope. In addition, detection can be carried out by a fluorescent antibody staining method in which a fluorescently labeled antibody is reacted with a cell and analyzed with a flow cytometer [Monoclonal Antibodies—Principles and Practice, Third edition, Academic Press (1996), Monoclonal Antibody Experimental Manual, Kodansha scientific books (1987)]. In particular, the bispecific antibody or the bispecific antibody fragment thereof of the present invention enables detection of at least one of CD40 and EpCAM expressed on a cell membrane by a fluorescent antibody staining method.

In addition, when the FMAT 8100 HTS system (manufactured by Applied Biosystems, Inc.) or the like is used among the fluorescent antibody staining methods, it is possible to measure the amount of an antigen or the amount of an antibody without separating the formed antibody-antigen complex from a free antibody or antigen not involved in the formation of the antibody-antigen complex.

EXAMPLES

Hereinafter, the present invention will be more specifically described by way of Examples, however, the present invention is not limited to the following Examples.

Example 1

Preparation of Soluble Human and Monkey CD40 Antigens and Soluble Human and Monkey EpCAM Antigens 1. Preparation of Soluble Antigens of Human CD40 and Monkey CD40

Each of the extracellular domain proteins of human and monkey CD40 in which FLAG-Fc was added to the C-terminal end was produced by a method described below. The nucleotide sequence encoding the extracellular domain of human CD40 is represented by SEQ ID NO: 1, the amino acid sequence deduced from the nucleotide sequence is represented by SEQ ID NO: 2, the nucleotide sequence encoding the extracellular domain of monkey CD40 is represented by SEQ ID NO: 3, and the amino acid sequence deduced from the nucleotide sequence is represented by SEQ ID NO: 4.

(1) Production of Human and Monkey CD40-FLAG-Fc Vectors

A gene fragment of the extracellular domain of human CD40 consisting the nucleotide sequence represented by SEQ ID NO: 1 was produced based on a human CD40 gene sequence (Genbank Accession Number: NM_001250, SEQ ID NO: 5, an amino acid sequence encoded by the gene is represented by SEQ ID NO: 6).

An INPEP4 vector (manufactured by Biogen-IDEC GmbH) comprising a FLAG-tag and an Fc region of human IgG was digested with restriction enzymes KpnI and XbaI, and a gene fragment of the extracellular domain to which a human CD40 signal sequence coding region consisting a nucleotide sequence at positions 1 to 60 of the nucleotide sequence represented by SEQ ID NO: 1 was added was inserted at an appropriate site, whereby a human CD40-FLAG-Fc expression vector was produced.

In the same manner, a monkey CD40-FLAG-Fc expression vector comprising a gene fragment of the extracellular domain of monkey CD40 consisting of the nucleotide sequence represented by SEQ ID NO: 3 was produced based on a monkey CD40 gene sequence (SEQ ID NO: 7, an amino acid sequence encoded by the gene is represented by SEQ ID NO: 8) cloned from a monkey peripheral blood mononuclear cell (PBMC).

(2) Production of Human and Monkey CD40-FLAG-Fc Proteins

The human CD40-FLAG-Fc expression vector produced in 1-(1) was introduced into HEK 293 cells using FreeStyle (trademark) 293 Expression System (manufactured by Thermo Fisher, Inc.) and the cells were cultured to express a protein in a transient expression system. The culture supernatant was collected 5 days after introduction of the vector, and filtered through a membrane filter (manufactured by Millipore Corporation) having a pore diameter of 0.22

The culture supernatant was subjected to affinity purification using a Protein A resin (MabSelect, manufactured by GE Healthcare, Inc.). The antibody adsorbed to the Protein A was washed with Dulbecco's phosphate buffered saline [D-PBS(−) without Ca and Mg, liquid; hereinafter referred to as D-PBS(−), manufactured by Nacalai Tesque, Inc.], eluted with a 20 mM sodium citrate and 50 mM NaCl buffer solution (pH 3.4) and collected in a tube containing a 1 M sodium phosphate buffer solution (pH 7.0).

Subsequently, the buffer solution was replaced with D-PBS(−) by ultrafiltration using VIVASPIN (manufactured by Sartrius stealin), followed by filter sterilization with a membrane filter Millex-Gv (manufactured by Millipore Corporation) having a pore diameter of 0.22 whereby a human CD40-FLAG-Fc protein was produced. In the same manner, a monkey CD40-FLAG-Fc protein was produced using the monkey CD40-FLAG-Fc expression vector produced in 1-(1). The concentration of the obtained protein was determined by measuring an absorbance at a wavelength of 280 nm and calculating it using an extinction coefficient estimated from the amino acid sequence of each protein.

(3) Production of Human and Monkey CD40-GST Vectors

An N5 vector (manufactured by Biogen-IDEC GmbH) comprising a GST region was digested with restriction enzymes BglII and KpnI, and a gene fragment of the extracellular domain of human CD40 consisting of the nucleotide sequence represented by SEQ ID NO: 1 described in 1-(1) was inserted at an appropriate site, whereby a human CD40-GST expression vector was produced. In the same manner, a monkey CD40-GST expression vector comprising a gene fragment of the extracellular domain consisting of the nucleotide sequence represented by SEQ ID NO: 3 was produced.

(4) Production of Human and Monkey CD40-GST Proteins

The human CD40-GST vector produced in 1-(3) was introduced into HEK 293 cells in the same manner as in 1-(2), and the cells were cultured, and then, the culture supernatant was filtered through a membrane filter. The culture supernatant was reacted with Glutathione Sepharose 4B (manufactured by GE Healthcare), and washed with D-PBS(−), and then subjected to affinity purification using 10 mM Glutathione in 50 mM Tris-HCl (pH 8.0) as an elution buffer solution.

The eluted fusion protein solution was subjected to ultrafiltration and filter sterilization with a membrane filter in the same manner as in 1-(2), whereby a human CD40-GST protein was obtained. Further, by using the monkey CD40-GST vector, a monkey CD40-GST protein was obtained in the same manner. The concentration of the obtained protein was determined by measuring an absorbance at a wavelength of 280 nm and calculating it using an extinction coefficient estimated from the amino acid sequence of each protein.

2. Preparation of Soluble Antigens of Human, Monkey, and Mouse EpCAM

Each of the extracellular domain proteins of human, monkey, and mouse EpCAM in which FLAG-Fc or GST was added to the C terminus was produced by a method described below. The nucleotide sequence encoding the extracellular domain of human EpCAM is represented by SEQ ID NO: 9, the amino acid sequence deduced from the nucleotide sequence is represented by SEQ ID NO: 10, the nucleotide sequence encoding the extracellular domain of monkey EpCAM is represented by SEQ ID NO: 11, the amino acid sequence deduced from the nucleotide sequence is represented by SEQ ID NO: 12, the nucleotide sequence encoding the extracellular domain of mouse EpCAM is represented by SEQ ID NO: 13, and the amino acid sequence deduced from the nucleotide sequence is represented by SEQ ID NO: 14.

Human, monkey, and mouse EpCAM-FLAG-Fc proteins were obtained in the same manner as described in 1-(1) and (2) based on a human EpCAM gene represented by SEQ ID NO: 15 (Genbank Accession Number: NM_002354, the amino acid sequence encoded by the gene is represented by SEQ ID NO: 16), a monkey EpCAM gene represented by SEQ ID NO: 17 (Genbank Accession Number: XM_015433685, the amino acid sequence encoded by the gene is represented by SEQ ID NO: 18), and a mouse EpCAM gene represented by SEQ ID NO: 19 (Genbank Accession Number: NM_008532, the amino acid sequence encoded by the gene is represented by SEQ ID NO: 20), respectively.

Note that in an EpCAM-FLAG-Fc expression vector, as a signal sequence coding region, a nucleotide sequence at positions 1 to 63 of the nucleotide sequence represented by SEQ ID NO: 15 was integrated. Further, human, monkey, and mouse EpCAM-GST proteins were obtained in the same manner as described in 1-(3) and (4), respectively. The concentration of each of the obtained proteins was determined by measuring an absorbance at a wavelength of 280 nm and calculating it using an extinction coefficient estimated from the amino acid sequence of each protein.

Example 2

Production of Human EpCAM-Expressing HEK 293 Cells for Membrane Expression

By using pEF6/V5-His TOPO TA Expression Kit (manufactured by Invitrogen, Inc.), the human EpCAM gene represented by SEQ ID NO: 15 was TOPO-cloned, and by selecting a clone in which the human EpCAM gene was inserted in the forward direction, a human EpCAM expression vector for membrane expression, pEF6-human EpCAM full was obtained.

The obtained expression vector pEF6-human EpCAM full was introduced into HEK 293 cells using FreeStyle (trademark) 293 Expression System (manufactured by Thermo Fisher, Inc.) and the cells were cultured to express a protein in a transient expression system. After the introduction of the gene, the cells were subjected to shaking culture for 24 hours, followed by centrifugation, whereby human EpCAM/HEK 293 cells were obtained.

Example 3

Acquisition of Anti-CD40 Antibody
1. Production of CD40-Immunized Human Antibody M13 Phage Library As an immunogen, the human CD40-FLAG-Fc produced in Example 1 was intraperitoneally administered to a human antibody-producing mouse [Ishida & Lonberg, IBC's 11th Antibody Engineering, Abstract 2000; Ishida, I. et al., Cloning & Stem Cells 4, 85-96 (2002) and Isamu Ishida (2002) Experimental medicine 20, 6, 846-851] a total of 4 times. Only at the first immunization, Alum gel (2 mg/mouse) and pertussis vaccine ($1\times10^9$ vaccines/mouse) were added as adjuvants.

The second immunization was carried out two weeks after the first immunization, the third immunization was carried out 1 week thereafter, the final immunization was carried out 10 days after the third immunization, and dissection was carried out 4 days after the final immunization and the spleen was surgically excised out. The excised spleen was placed on a cell strainer (manufactured by Falcon, Inc.) and cells were transferred to a tube while gently smashing with a silicon rod, and centrifuged to precipitate the cells, then the cells were reacted with a red blood cell depletion reagent (manufactured by Sigma-Aldrich Co. LL) in ice for 3 minutes, followed by further centrifugation.

RNA was extracted from the obtained spleen cells using RNeasy Mini kit (manufactured by QIAGEN, Inc.), cDNAs were amplified using a SMARTer RACE cDNA amplification kit (manufactured by Clontech Laboratories, Inc.), and a VH gene fragment was further amplified by PCR. The VH gene fragment and a VL gene fragment that is a human antibody germ-line sequence and comprises an L6 sequence consisting of the nucleotide sequence represented by SEQ ID NO: 21 were inserted into a phagemid pCANTAB 5E (manufactured by Amersham Pharmacia, Inc.) so as to transform E. coli TG1 (manufactured by Lucigen Corporation), whereby plasmids were obtained.

Note that the L6 sequence encodes a light chain variable region (VL) of a human antibody consisting of the amino acid sequence represented by SEQ ID NO: 22, and the amino acid sequences of CDR1, CDR2, and CDR3 of the VL (also represented by LCDR1, LCDR2, and LCDR3, respectively) are represented by SEQ ID NOS: 23, 24, and 25, respectively.

By infecting VCSM13 Interference Resistant Helper Phage (manufactured by Agilent Technologies, Inc.) with the obtained plasmids, a CD40-immunized human antibody M13 phage library that has a VL gene composed of the L6 sequence and comprises a library of VH genes was obtained.

2. Acquisition of Anti-CD40 Monoclonal Antibody

By using the CD40-immunized human antibody M13 phage library, an anti-CD40 monoclonal antibody comprising the VL encoded by L6 was obtained by the following phage display method. MAXISORP STARTUBE (manufactured by NUNC, Inc.) in which the human CD40-GST obtained in Example 1 was immobilized and a portion to which the human CD40-GST is not bound was blocked using SuperBlock Blockig Buffer (manufactured by Thermo Fisher, Inc.), and the human antibody M13 phage library were allowed to react at room temperature for 1 to 2 hours, and washing was carried out 3 times each with D-PBS(−) and PBS containing 0.1% Tween 20 (hereinafter referred to as PBS-T, manufactured by Wako Pure Chemical Industries, Ltd.), and thereafter, the phage was eluted with 0.1 M Gly-HCl (pH 2.2).

The eluted phage was used to infect TG1 competent cells to amply the phage, which was reacted again with human CD40-GST immobilized on MAXISORP STARTUBE, followed by washing 5 times each with D-PBS(−) and PBS-T, and thereafter, the phage was eluted with 0.1 M Gly-HCl (pH 2.2).

This operation was repeated twice or three times to concentrate the phage displaying an scFv that specifically binds to human CD40. The concentrated phage was used to infect TG1, which was then inoculated in a SOBAG plate (2.0% tryptone, 0.5% Yeast extract, 0.05% NaCl, 2.0% glucose, 10 mM MgCl$_2$, 100 μg/mL ampicillin, and 1.5% agar) to form a colony.

The colony was inoculated and cultured, and then infected with VCSM13 Interference Resistant Helper Phage, and cultured again, whereby a monoclonal phage was obtained. By using the obtained monoclonal phage, a clone that binds to both human and monkey CD40-GST was selected by ELISA.

In the ELISA, MAXISORP (manufactured by NUNC, Inc.) in which the human or monkey CD40-GST in Example 1 was immobilized on each well and a portion to which the human or monkey CD40-GST is not bound was blocked using SuperBlock Blockig Buffer (manufactured by Thermo Fisher, Inc.) was used. To each well, each phage clone was added and reacted at room temperature for 30 minutes, and thereafter, each well was washed 3 times with PBS-T.

Subsequently, an anti-M13 antibody (manufactured by GE Healthcare, Inc.) labeled with horseradish peroxidase was diluted by 5000 times with PBS-T containing 10% Block Ace (manufactured by Dainippon Pharmaceutical Co., Ltd.), and the resultant was added in an amount of 50 μL to each well, and incubated at room temperature for 30 minutes. After the microplate was washed four times with PBS-T, a TMB chromogenic substrate solution (manufactured by DAKO, Inc.) was added in an amount of 50 μL to each well and incubated at room temperature for 10 minutes. The coloring reaction was stopped by adding a 2 N HCl solution (50 μL/well) to each well, and an absorbance at a wavelength of 450 nm (reference wavelength: 570 nm) was measured using a plate reader (Emax, Molecular Devices, Inc.).

A sequence analysis was carried out for clones bound to both human and monkey CD40, whereby anti-CD40 antibodies having the VL encoded by L6, R1066, R1090S55A, R2089, and R2178 were obtained. In Table 1, the entire nucleotide sequence encoding the VH of each of the obtained CD40 antibodies and the amino acid sequence deduced from the nucleotide sequence, and the amino acid sequences of CDR1 to CDR3 of VH (hereinafter sometimes referred to as HCDR1 to HCDR3) are shown.

TABLE 1

| Sequence Information of VH of Anti-Human CD40 Antibody | | | | |
|---|---|---|---|---|
| Clone name | R1066 | R1090SS55A | R2089 | R2178 |
| Nucleotide sequence encoding VH | SEQ ID NO: 26 | SEQ ID NO: 31 | SEQ ID NO: 36 | SEQ ID NO: 41 |
| Amino acid sequence of VH | SEQ ID NO: 27 | SEQ ID NO: 32 | SEQ ID NO: 37 | SEQ ID NO: 42 |
| Amino acid sequence of HCDR1 | SEQ ID NO: 28 | SEQ ID NO: 33 | SEQ ID NO: 38 | SEQ ID NO: 43 |
| Amino acid sequence of HCDR2 | SEQ ID NO: 29 | SEQ ID NO: 34 | SEQ ID NO: 39 | SEQ ID NO: 44 |
| Amino acid sequence of HCDR3 | SEQ ID NO: 30 | SEQ ID NO: 35 | SEQ ID NO: 40 | SEQ ID NO: 45 |

Soluble IgG expression vectors into which genes of the obtained anti-CD40 antibodies, R1066, R1090S55A, R2089, and R2178 were integrated, respectively, were produced. First, the L6 gene encoding the common VL of R1066, R1090S55A, R2089, and R2178 was subcloned into the BglII-BsiWI site of N5KG4PE R409K (described in WO 2006/033386).

Thereafter, each of the VH genes of R1066, R1090S55A, R2089, and R2178 was subcloned into the SalI-NheI site of N5KG4PE R409K, whereby N5KG4PE R409K_R1066, N5KG4PE R409K_R1090S55A, N5KG4PE R409K_R2089, and N5KG4PE R409K_R2178 that are expression vectors for the anti-CD40 monoclonal antibodies, R1066, R1090S55A, R2089, and R2178, each having the constant region of human IgG4PE R409K, were obtained, respectively.

Further, in order to produce the anti-CD40 monoclonal antibody 21.4.1 described in WO 2003/040170 as a positive control antibody of the anti-CD40 antibody, an expression vector was produced. The nucleotide sequence of the VH of 21.4.1 is represented by SEQ ID NO: 46 and the amino acid sequence of the VH deduced from the sequence is represented by SEQ ID NO: 47. Further, the nucleotide sequence of the VL of 21.4.1 is represented by SEQ ID NO: 48 and the amino acid sequence of the VL deduced from the sequence is represented by SEQ ID NO: 49.

The genes encoding the VH and the VL of 21.4.1 were synthesized and subcloned into the SalI-NheI and BglII-BsiWI sites of an N5KG2 vector (described in WO 2003/033538), respectively, whereby an expression vector N5KG2_21.4.1 for the anti-CD40 monoclonal antibody 21.4.1 having a constant region of human IgG2 was obtained.

Example 4

Acquisition of Anti-EpCAM Antibody
1. Production of EpCAM-Immunized Human Antibody M13 Phage Library By using the human EpCAM-Fc in Example 1, an EpCAM-immunized human antibody M13 phage library that has a VL gene composed of the L6 sequence and comprises a library of VH genes was obtained in the same manner as in Example 3, 1.

2. Acquisition of Anti-EpCAM Antibody

By using MAXISORP STARTUBE (manufactured by NUNC, Inc.) in which the mouse EpCAM-GST obtained in Example 1 was immobilized and a portion to which the mouse EpCAM-GST is not bound was blocked using SuperBlock Blockig Buffer (manufactured by Thermo Fisher, Inc.), and the EpCAM-immunized human antibody M13 phage library, a phage displaying an scFv that specifically binds to mouse EpCAM was monocloned in the same manner as in Example 3, 2.

Note that in some experimental lots, the concentration of the phage that specifically binds to human EpCAM was carried out by an operation in which the eluted phage is added to cells obtained by subjecting the human EpCAM/HEK 293 in Example 2 to CFSE staining and EpCAM-negative HEK 293 cells and reacted in ice for 1 hour, followed by washing, and then, CFSE-positive cells are sorted using FACS Aria III (manufactured by BD, Inc.), and a phage is eluted with 0.1 M Gly-HCl (pH 2.2) in place of the second and subsequent biopanning operations using the mouse EpCAM-GST. From the monocloned phage, a clone having binding affinity to human, monkey, and mouse EpCAM-GST was selected by ELISA.

The ELISA was carried out in the same manner as in Example 3, 2 using MAXISORP (manufactured by NUNC, Inc.) in which the human, monkey, or mouse EpCAM-GST in Example 1 was immobilized and a portion to which the human, monkey, or mouse EpCAM-GST is not bound was blocked using SuperBlock Blockig Buffer (manufactured by Thermo Fisher, Inc.).

A sequence analysis was carried out for clones bound to all the human, monkey, and mouse EpCAM-GST, whereby anti-EpCAM antibodies having the VL encoded by L6, Ep59, Ep203, Epc051, and Epc112 were obtained. In the same display manner as in Table 1, the sequence information of the VH of each of the EpCAM antibodies are shown in Table 2.

TABLE 2

Sequence Information of VH of Anti-EpCAM Antibody

| Clone name | Ep59 | Ep203 | Epc051 | Epc112 |
|---|---|---|---|---|
| Nucleotide sequence encoding VH | SEQ ID NO: 50 | SEQ ID NO: 55 | SEQ ID NO: 60 | SEQ ID NO: 65 |
| Amino acid sequence of VH | SEQ ID NO: 51 | SEQ ID NO: 56 | SEQ ID NO: 61 | SEQ ID NO: 66 |
| Amino acid sequence of HCDR1 | SEQ ID NO: 52 | SEQ ID NO: 57 | SEQ ID NO: 62 | SEQ ID NO: 67 |
| Amino acid sequence of HCDR2 | SEQ ID NO: 53 | SEQ ID NO: 58 | SEQ ID NO: 63 | SEQ ID NO: 68 |
| Amino acid sequence of HCDR3 | SEQ ID NO: 54 | SEQ ID NO: 59 | SEQ ID NO: 64 | SEQ ID NO: 69 |

In addition, as a positive control antibody of the anti-EpCAM antibody, an antibody having a variable region of an anti-EpCAM monoclonal antibody 3622W94 described in WO 2003/040725 was produced. The nucleotide sequence of the VH of 3622W94 is represented by SEQ ID NO: 70 and the amino acid sequence of the VH deduced from the sequence is represented by SEQ ID NO: 71. The nucleotide sequence of the VL of 3622W94 is represented by SEQ ID NO: 72 and the amino acid sequence of the VL deduced from the sequence is represented by SEQ ID NO: 73.

The genes encoding the VH and the VL of 3622W94 were synthesized, and the VL was subcloned into the restriction enzyme site BglII-BsiWI of a Tol2 transposon expression vector pKTABEX-TC26 described in WO 2010/143698, and the VH was subcloned into the restriction enzyme site SalI-NheI thereof, whereby an expression vector pKTA-BEX-TC26 3622W94 for the anti-EpCAM monoclonal antibody 3622W94 having a constant region of human IgG1 was obtained.

Example 5

Construction of Expression Vector for Bispecific Antibody that Binds to CD40 and EpCAM Bispecific antibodies that have a structure shown in FIG. 1(A) and FIG. 1(B) and bind to at least one of human and monkey CD40 and at least one of human, monkey, and mouse EpCAM were produced by the following method. As the form of the bispecific antibody, the form described in WO 2009/131239 was adopted.

Among the bispecific antibodies, an antibody composed of two heavy chains comprising the amino acid sequences of VH1, CH1, VH2, CH1, a hinge, CH2, and CH3 in order from the N-terminal side, and four light chains is referred to as an N-terminal type bispecific antibody. Further, an antibody composed of two heavy chains comprising the amino acid sequences of VH1, CH1, a hinge, CH2, CH3, VH2, and CH1 in order from the N-terminal side, and four light chains is referred to as a C-terminal type bispecific antibody. VH1 and VH2 are either the VH of the anti-CD40 antibody or the VH of the anti-EpCAM antibody, and one is the VH of the anti-CD40 antibody and the other is the VH of the anti-EpCAM antibody.

In the following description, a polypeptide that connects VH1 to VH2 is referred to as a linker, and a gene that encodes the amino acid sequence of the linker is referred to as a linker gene. In addition, a polypeptide that binds to VH2 at the C-terminal side is referred to as a C-terminal side polypeptide, and a gene that encodes the C-terminal side polypeptide is referred to as a C-terminal side sequence gene.

The N-terminal type bispecific antibody produced by the following steps has CH1 (the nucleotide sequence is represented by SEQ ID NO: 74 and the amino acid sequence is represented by SEQ ID NO: 75) of IgG4 as the linker. In addition, it has a polypeptide (the nucleotide sequence is represented by SEQ ID NO: 76 and the amino acid sequence is represented by SEQ ID NO: 77) composed of CH (CH1, a hinge, CH2, and CH3) of IgG4 PE R409K described in WO 2006/033386 as the C-terminal side polypeptide of VH2.

The C-terminal type bispecific antibody has a polypeptide (the nucleotide sequence is represented by SEQ ID NO: 76 and the amino acid sequence is represented by SEQ ID NO: 77) composed of CH of IgG4 PE R409K as the linker. In addition, it has CH1 (the nucleotide sequence is represented by SEQ ID NO: 74 and the amino acid sequence is represented by SEQ ID NO: 75) of IgG4 as the C-terminal side polypeptide. Further, the bispecific antibody produced by the following steps has a light chain comprising the VL encoded by L6.

The name of the bispecific antibody, the structure of the bispecific antibody, the clone of the anti-CD40 antibody and the clone of the anti-EpCAM antibody used for the production of the bispecific antibody are shown in Table 3. Note that in the following, Nt may sometimes be added to the name of the N-terminal type bispecific antibody.

TABLE 3

| Name of bispecific antibody | Structure of bispecific antibody | Clone of VH1 antibody | Clone of VH2 antibody |
|---|---|---|---|
| R1066-Ep59 | N-terminal type | R1066 | Ep59 |
| R1066-Ep203 | N-terminal type | R1066 | Ep203 |
| R1066-Epc051 | N-terminal type | R1066 | Epc051 |
| R1066-Epc112 | N-terminal type | R1066 | Epc112 |
| R1090S55A-Ep59 | N-terminal type | R1090S55A | Ep59 |
| R1090S55A-Ep203 | N-terminal type | R1090S55A | Ep203 |
| R1090S55A-Epc051 | N-terminal type | R1090S55A | Epc051 |
| R1090S55A-Epc112 | N-terminal type | R1090S55A | Epc112 |
| R2089-Ep59 | N-terminal type | R2089 | Ep59 |
| R2089-Ep203 | N-terminal type | R2089 | Ep203 |
| R2089-Epc051 | N-terminal type | R2089 | Epc051 |
| R2089-Epc112 | N-terminal type | R2089 | Epc112 |
| R2178-Ep59 | N-terminal type | R2178 | Ep59 |
| R2178-Ep203 | N-terminal type | R2178 | Ep203 |
| R2178-Epc051 | N-terminal type | R2178 | Epc051 |
| R2178-Epc112 | N-terminal type | R2178 | Epc112 |
| Ep59-R1066 | N-terminal type | Ep59 | R1066 |
| Ep59-R1090S55A | N-terminal type | Ep59 | R1090S55A |
| Ep59-R2089 | N-terminal type | Ep59 | R2089 |
| Ep59-R2178 | N-terminal type | Ep59 | R2178 |
| Ep203-R1066 | N-terminal type | Ep203 | R1066 |
| Ep203-R1090S55A | N-terminal type | Ep203 | R1090S55A |
| Ep203-R2089 | N-terminal type | Ep203 | R2089 |
| Ep203-R2178 | N-terminal type | Ep203 | R2178 |
| Ct R1066-Ep59 | C-terminal type | R1066 | Ep59 |
| Ct R1066-Ep203 | C-terminal type | R1066 | Ep203 |
| Ct R1090S55A-Ep59 | C-terminal type | R1090S55A | Ep59 |
| Ct R1090S55A-Ep203 | C-terminal type | R1090S55A | Ep203 |

TABLE 3-continued

| Name of bispecific antibody | Structure of bispecific antibody | Clone of VH1 antibody | Clone of VH2 antibody |
|---|---|---|---|
| Ct Ep59-R1066 | C-terminal type | Ep59 | R1066 |
| Ct Ep59-R1090S55A | C-terminal type | Ep59 | R1090S55A |
| Ct Ep203-R1066 | C-terminal type | Ep203 | R1066 |
| Ct Ep203-R1090S55A | C-terminal type | Ep203 | R1090S55A |
| Ct R1066-Epc051 | C-terminal type | R1066 | Epc051 |
| Ct R1066-Epc112 | C-terminal type | R1066 | Epc112 |
| Ct Epc112-R1066 | C-terminal type | Epc112 | R1066 |

1. Production of Expression Vector for N-Terminal Type Bispecific Antibody

As for the N-terminal type bispecific antibodies among the bispecific antibodies shown in Table 3, an expression vector was produced by a method described below.

The L6 gene (SEQ ID NO: 21) encoding the common VL of R1066, R1090S55A, R2089, and R2178 obtained in Example 3 and Ep59, Ep203, Epc051, and Epc112 obtained in Example 4 was subcloned into the BglII-BsiWI site of N5KG4PE R409K (described in WO 2006/033386).

Thereafter, a linker gene (SEQ ID NO: 74), which encodes the same amino acid sequence as CH1 of human IgG4 that is the linker, and in which the used codon was changed was synthesized. By using this linker gene and the VH gene of the anti-CD40 antibody obtained in Example 3 or the anti-EpCAM antibody obtained in Example 4 as the templates, a gene fragment of the linker gene and a VH2 portion was amplified by PCR using KOD FX Neo DNA Polymerase (manufactured by Toyobo Co., Ltd.). By ligating the amplified gene fragment to N5KG4PE R409K cleaved with NheI, an expression plasmid vector for the N-terminal type bispecific antibodies was obtained.

2. Production of Expression Vector for C-Terminal Type Bispecific Antibody

As for the C-terminal type bispecific antibodies among the bispecific antibodies shown in Table 3, an expression vector was produced by a method described below.

The L6 gene (SEQ ID NO: 21) encoding the common VL of the anti-CD40 antibodies, R1066, R1090S55A, R2089, and R2178 obtained in Example 3 and the anti-EpCAM antibodies, Ep59, Ep203, Epc051, and Epc112 obtained in Example 4 was subcloned into the BglII-BsiWI site of N5KG4PE R409K (described in WO 2006/033386).

Thereafter, a C-terminal side sequence gene (SEQ ID NO: 78), which encodes the same amino acid sequence as CH1 of human IgG4 that is the C-terminal side polypeptide, and in which the used codon was changed and a stop codon is included, was synthesized. By using the VH gene of the anti-CD40 antibody obtained in Example 3 or the anti-EpCAM antibody obtained in Example 4 and the synthesized C-terminal side sequence gene as the templates, a gene fragment of VH2 and the C-terminal side sequence was amplified by PCR using KOD FX Neo (manufactured by Toyobo Co., Ltd.).

Further, by using N5KG4PE R409K as the template, a linker gene fragment was amplified by PCR using KOD FX Neo (manufactured by Toyobo Co., Ltd.). By ligating the amplified gene fragment to N5KG4PE R409K cleaved with NheI and BamHI, an expression plasmid vector for the C-terminal type bispecific antibodies shown in Table 3 was obtained.

Example 6

Preparation of Monoclonal Antibody that Binds to CD40, Monoclonal Antibody that Binds to EpCAM, and Bispecific Antibody that Binds to CD40 and EpCAM Each of the anti-CD40 monoclonal antibody, the anti-EpCAM monoclonal antibody, and the bispecific antibody having each of the binding sites for CD40 and EpCAM (CD40-EpCAM bispecific antibody) subcloned into either of the antibody expression plasmid vectors N5KG4PE R409K and N5KG2 in Example 3 to Example 5 was expressed and purified.

1. Production of Anti-CD40 Monoclonal Antibody and CD40-EpCAM Bispecific Antibody The expression vector for the anti-CD40 monoclonal antibody was co-transfected into Expi293 cells by Expi293 (trademark) Expression System (manufactured by Thermo Fisher, Inc.), and Transfection Enhancer was added thereto after 16 hours, whereby the antibody was expressed in a transient expression system.

The culture supernatant was collected 4 days after introduction of the vector, and filtered through a membrane filter (manufactured by Millipore Corporation) having a pore diameter of 0.22 and thereafter, the antibody was subjected to affinity purification using a Protein A resin (MabSelect, manufactured by GE Healthcare, Inc.). As the washing solution, D-PBS(−) was used. The antibody adsorbed to the Protein A was eluted with a 20 mM sodium citrate and 50 mM NaCl buffer solution (pH 3.0) and collected in a tube containing a 200 mM sodium phosphate buffer solution (pH 7.0).

Subsequently, the solution was concentrated using VIVASPIN (manufactured by Sartrius stealin), and the buffer solution was replaced with D-PBS(−) using a Nap Column (manufactured by GE Healthcare, Inc.). Further, a monomer fraction was fractionated from the antibody solution using AKTA FPLC (manufactured by GE Healthcare, Inc.) and Superdex High-performance Columns (manufactured by GE Healthcare, Inc.). By performing filter sterilization with a membrane filter (Millex-Gv, manufactured by Millipore Corporation) having a pore diameter of 0.22 μm, a purified antibody was obtained.

An absorbance at a wavelength of 280 nm of the antibody solution was measured, and the concentration of the purified antibody was calculated using an extinction coefficient estimated from the amino acid sequence of each antibody. The CD40-EpCAM bispecific antibody was also produced in the same manner.

2. Preparation of Anti-EpCAM Monoclonal Antibody

The expression vector pKTABEX-TC26 3622W94 for the anti-EpCAM monoclonal antibody 3622W94 produced in Example 4 was transfected into CHO-K1 cells by an electroporation method together with a Tol2 transposase expression vector. A resistant strain was selected in a culture medium supplemented with 3 μg/mL cycloheximide (manufactured by Sigma-Aldrich Co. LL). After 14 to 21 days, an antibody-producing well was selected by soluble IgG Fc sandwich ELISA.

The well in which the production amount of the antibody was large was subjected to extended culture, and further, the amount of the antibody was measured again, and a strain having a high expression level was established as a 3622W94 expression strain. The established 3622W94 expression strain was cultured in EXCEL 302 medium (manufactured by Sigma-Aldrich Co. LL), the supernatant was collected and filtered through a membrane filter (manufactured by Millipore Corporation) having a pore diameter of 0.22 μm, and thereafter, the antibody was subjected to affinity purification using a Protein A resin (Mab Select, manufactured by GE Healthcare, Inc.). As the washing solution, D-PBS(−) was used.

The antibody adsorbed to the Protein A was eluted with a 20 mM sodium citrate and 50 mM NaCl buffer solution (pH 3.0) and collected in a tube containing a 200 mM sodium phosphate buffer solution (pH 7.0). Subsequently, the solution was concentrated using VIVASPIN (manufactured by Sartrius stealin), and the buffer solution was replaced with D-PBS(−) using a Nap Column (manufactured by GE Healthcare, Inc.).

Further, a monomer fraction was fractionated from the antibody solution using AKTA FPLC (manufactured by GE Healthcare, Inc.) and Superdex High-performance Columns (manufactured by GE Healthcare, Inc.). By performing filter sterilization with a membrane filter (Millex-GV, manufactured by Millipore Corporation) having a pore diameter of 0.22 µm, a purified antibody was obtained. An absorbance at a wavelength of 280 nm of the antibody solution was measured, and the concentration of the purified antibody was calculated using an extinction coefficient estimated from the amino acid sequence of each antibody.

Example 7

Evaluation of Expression of CD40 and EpCAM in Cell Line by Flow Cytometer

The expression of CD40 and EpCAM on cell surfaces of Burkitt's lymphoma cells, Ramos cells (ATCC No. CCL-1596), human colon cancer cells, Colo 205 cells (ATCC No. CCL-222), human embryonic kidney cells, HEK 293 cells (ATCC No. CRL-1573), and the human EpCAM/HEK 293 cells obtained in Example 2 was evaluated by a fluorescence activated cell sorting (FACS) method according to the following procedure. In the evaluation, the anti-CD40 antibody 21.4.1 and the anti-EpCAM antibody 3622W94 obtained in Example 6 were used.

Ramos cells were suspended in Staining Buffer (SB) that is D-PBS(−) containing 0.1% $NaN_3$ and 1% FBS at a cell density of $1\times10^6$ cells/mL, and the suspension was dispensed in a 96-well round bottom plate (manufactured by Falcon, Inc.) at 100 µL/well. After centrifugation (2000 rpm, 4° C., 2 minutes), the supernatant was removed, and to the resulting pellet, 10 µg/mL of the anti-CD40 antibody 21.4.1 and the anti-EpCAM antibody 3622W94 obtained in Example 6 were added at 50 µL/well to suspend the pellet, and the resulting suspension was left to stand for 30 minutes at ice temperature.

After further centrifugation (2000 rpm, 4° C., 2 minutes), the supernatant was removed, the resulting pellet was washed three times with 200 µL/well of SB, and thereafter, 1 µg/mL of Goat F(ab')2 Anti-Human IgG (γ chain specific) R-phycoerythrin (R-PE) Conjugate (manufactured by Southern Biotech, Inc.) was added at 50 µL/well, and the resultant was incubated for 30 minutes at ice temperature. After washing twice with SB, the cells were suspended in 200 µL/well of SB, and the fluorescence intensity of each cell was measured using a flow cytometer FACSCANTO II (manufactured by Becton, Dickinson and Company).

Similarly, Colo 205 cells, HEK 293 cells, and human EpCAM/HEK 293 cells were evaluated, respectively. As the negative control, IgG4 antibodies 5228P, L235E, and R409K mutants (hereinafter referred to as anti-DNP antibodies) produced according to the method described in Example 5 of WO 2006/033386 using a vector encoding VL and VH (GenBank accession No. VL U16688, VH U116687) of the 2,4-dinitrophenol (DNP) antibody described in Mol Immunol. 1996 June; 33 (9): 759-68 were used.

Figure 2:
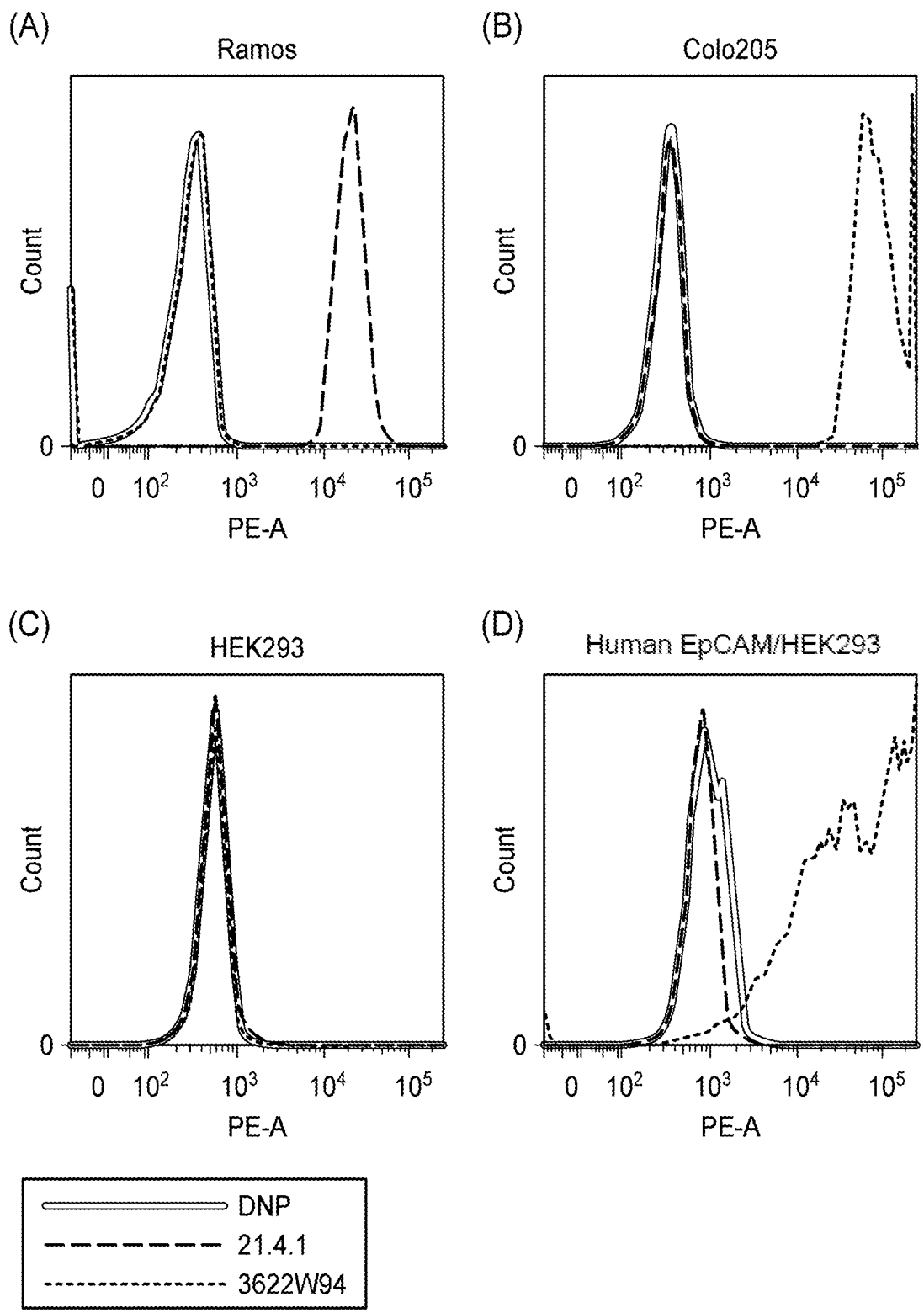
FIG. 2(A), FIG. 2(B), FIG. 2(C), and FIG. 2(D) show the results of evaluating the expression of CD40 and EpCAM in cells using a flow cytometer with respect to Ramos cells, Colo 205 cells, HEK 293 cells, and human EpCAM/HEK 293 cells, respectively. The vertical axis represents a cell count, and the horizontal axis represents a fluorescence intensity. A broken line indicates the binding affinity of an anti-CD40 antibody 21.4.1, a dotted line indicates the binding affinity of an anti-EpCAM antibody 3622W94, and an outlined line indicates the binding affinity of an anti-DNP antibody as a control antibody.

The results measured for the Ramos cells are shown in FIG. 2(A), for the Colo 205 cells in FIG. 2(B), for the HEK 293 cells in FIG. 2(C), and for the human EpCAM/HEK 293 cells in FIG. 2(D).

As shown in FIG. 2(A), to the Ramos cells, 21.4.1 that is the anti-CD40 antibody exhibited a binding activity and 3622W94 that is the anti-EpCAM antibody did not exhibit a binding activity. On the other hand, as shown in FIG. 2(B) and FIG. 2(D), to the Colo 205 cells and the human EpCAM/HEK 293 cells, 21.4.1 did not exhibit a binding activity and 3622W94 exhibited a binding activity. Further, as shown in FIG. 2(C), to the HEK 293 cells, both 21.4.1 and 3622W94 did not exhibit a binding activity.

Accordingly, it could be confirmed that the Ramos cells are positive for CD40 and negative for EpCAM, the Colo 205 cells and the human EpCAM/HEK 293 cells are negative for CD40 and positive for EpCAM, and the HEK 293 cells are negative for both CD40 and EpCAM.

Example 8

Evaluation of CD40 Signal Inducing Activity of CD40 Monoclonal Antibody by Analysis of Expression Level of CD95 Using Flow Cytometry The CD40 signal inducing ability of the CD40 monoclonal antibodies obtained in Example 6 was evaluated by an FCM method as follows using an increase in the expression level of CD95 on Ramos cells as an index.

Ramos cells ($2\times10^6$ cells/mL) were seeded in a U-bottom 96-well plate (manufactured by Falcon, Inc.) at 50 µL/well, and a test antibody diluted to 0.2, 2, or 20 µg/mL (final concentration of 0.1, 1, or 10 µg/mL) with RPMI 1640 medium (manufactured by Sigma-Aldrich Co. LL) containing 10% FBS was added thereto at 50 µg/mL, and the cells were cultured at 37° C. under 5.0% carbon dioxide gas for 16 hours.

After centrifugation (2000 rpm, 4° C., 2 minutes), the supernatant was removed, and the pellet was washed 3 times with 200 µL/well of SB. After centrifugation (2000 rpm, 4° C., 2 minutes), the supernatant was removed, and a PE mouse anti-human CD95 (manufactured by Becton, Dickinson and Company) antibody was added to the pellet to suspend the pellet, and then, the resulting suspension was left to stand for 30 minutes at ice temperature.

After further centrifugation (2000 rpm, 4° C., 2 minutes), the supernatant was removed, and the pellet was washed 3 times with 200 µL/well of SB. Thereafter, 7-aminoactinomycin (7AAD) (manufactured by Becton, Dickinson and Company) diluted by 100 times was suspended in 200 µL/well of SB, and the fluorescence intensity of CD95 on Ramos cells was measured with a flow cytometer FACSCANTO II (manufactured by Becton, Dickinson and Company). As the negative control, the anti-DNP antibody was used.

Figure 3:
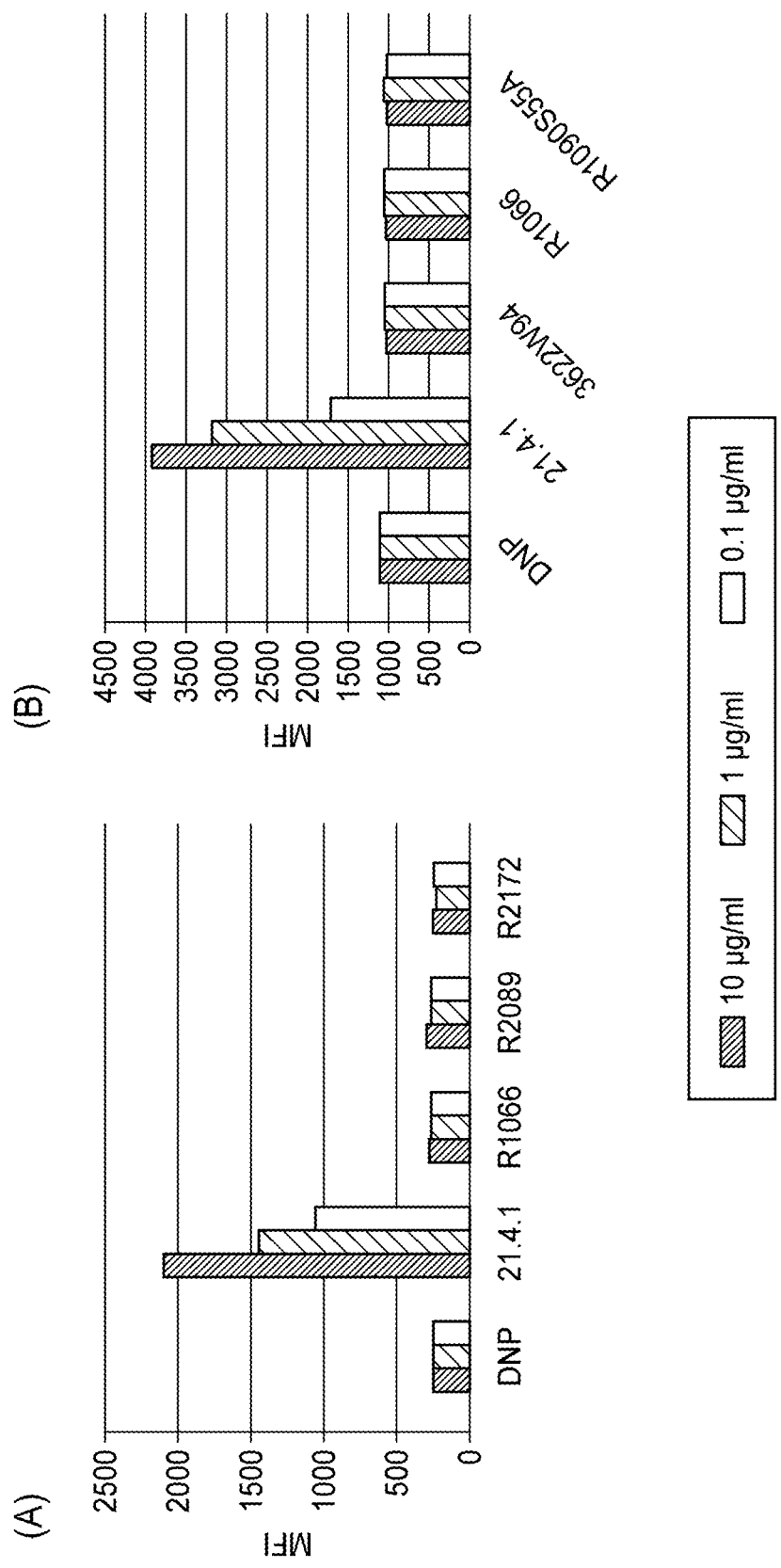
FIG. 3(A) and FIG. 3(B) show the results of evaluating the CD40 signal inducing activity of an anti-CD40 antibody monoclonal antibody using the induction of expression of CD95 on Ramos cells as an index. The vertical axis represents a fluorescence intensity, and shows the binding affinity of an anti-CD95 antibody to Ramos cells when each antibody was added at 10, 1, or 0.1 μg/mL. For comparison, an anti-DNP antibody was used as a negative control antibody, and 21.4.1 was used as an anti-CD40 agonistic antibody.

FIG. 3(A) shows the results of evaluating the anti-CD40 antibodies 21.4.1, R1066, R2089, and R2178, and FIG. 3(B) shows the results of evaluating the anti-CD40 antibodies 21.4.1, R1066, and R1090S55A and the anti-EpCAM antibody 3622W94.

From these evaluation results, it was found that the expression of CD95 on the Ramos cells is increased only when the anti-CD40 agonistic antibody 21.4.1 was added among the test antibodies 21.4.1, R1066, R2089, R2178, R1090S55A, and 3622W94.

That is, it was demonstrated that only 21.4.1 is an agonistic antibody that induces a signal of CD40, and the anti-CD40 monoclonal antibodies R1066, R2089, R2178, and R1090S55A obtained in Example 3 are non-agonistic antibodies that do not induce a signal to CD40. Further, when a similar test was carried out in the presence of a CD40 ligand, all of the anti-CD40 monoclonal antibodies R1066, R2089, R2178, and R1090S55A did not inhibit the expression of CD95 on the Ramos cells by the CD40 ligand (data not shown). That is, it was demonstrated that the anti-CD40 monoclonal antibodies R1066, R2089, R2178, and R1090S55A are all non-antagonistic antibodies that do not inhibit the signal induction to CD40 by the CD40 ligand.

Example 9

Evaluation of Binding Affinity of CD40-EpCAM Bispecific Antibody to EpCAM by Biacore For the purpose of confirming the binding activity and the species cross-reactivity of the CD40-EpCAM bispecific antibodies obtained in Example 6 to each of human, monkey, and mouse EpCAM, by using the human, monkey, and mouse EpCAM-GST produced in Example 1, a binding affinity test by a surface plasmon resonance method (SPR method) was carried out. As a measurement device, Biacore T100 (manufactured by GE Healthcare, Inc.) was used.

An anti-human IgG antibody was immobilized on a CM5 sensor chip (manufactured by GE Healthcare, Inc.) using Human Antibody Capture Kit (manufactured by GE Healthcare, Inc.) according to the package insert. A test antibody prepared at 1 to 3 µg/mL was added to a flow cell for 10 seconds at a flow rate of 10 µL/min.

Subsequently, each of human, monkey, and mouse EpCAM-GST protein solutions (diluted with HBS-EP+ (manufactured by GE Healthcare, Inc.) containing 0.1% BSA) diluted by 2-fold in 5 steps from 10 or 100 nM as an analyte was added at a flow rate of 30 µL/min, and a binding reaction of each antibody and the analyte was measured for 2 minutes and a dissociation reaction was measured for 10 minutes.

The measurement was carried out by a single cycle kinetics method. The obtained sensorgram was analyzed using Bia Evaluation Software (manufactured by GE Healthcare, Inc.), and the kinetic constant of each antibody was calculated.

A calculated dissociation constant [kd/ka=$K_D$] of each of the bispecific antibodies for human, monkey, and mouse EpCAM, and a value obtained by dividing the dissociation constant for human EpCAM by the dissociation constant for monkey EpCAM or mouse EpCM are shown in Table 4.

TABLE 4

| $K_D$ value | Human EpCAM [nM] | Monkey EpCAM [nM] | Human EpCAM [nM]/ Monkey EpCAM [nM] | Mouse EpCAM [nM] | Human EpCAM [nM]/ Mouse EpCAM [nM] |
|---|---|---|---|---|---|
| R1066-Ep59 | 9.60 | 73.73 | 0.13 | 15.26 | 0.63 |
| R1066-Ep203 | 12.82 | 22.22 | 0.58 | 15.82 | 0.81 |
| R1066-Epc051 | 11.27 | 75.35 | 0.15 | 21.87 | 0.52 |
| R1066-Epc112 | 8.31 | 14.76 | 0.56 | 16.46 | 0.51 |
| R1090S55A-Ep59 | 11.40 | 14.13 | 0.81 | 28.68 | 0.40 |
| R1090S55A-Ep203 | 9.51 | 16.47 | 0.58 | 16.72 | 0.57 |
| R1090S55A-Epc051 | 7.43 | 50.05 | 0.15 | 20.00 | 0.37 |
| R1090S55A-Epc112 | 7.90 | 13.09 | 0.60 | 19.64 | 0.40 |
| R2087-Ep59 | 8.88 | 10.39 | 0.85 | 17.80 | 0.50 |
| R2087-Ep203 | 9.62 | 9.02 | 1.07 | 17.67 | 0.54 |
| R2089-Epc051 | 7.60 | 5.48 | 1.39 | 24.21 | 0.31 |
| R2089-Epc112 | 7.83 | 4.13 | 1.90 | 21.13 | 0.37 |
| R2178-Ep59 | 9.99 | 4.29 | 2.33 | 203.70 | 0.05 |

TABLE 4-continued

| $K_D$ value | Human EpCAM [nM] | Monkey EpCAM [nM] | Human EpCAM [nM]/ Monkey EpCAM [nM] | Mouse EpCAM [nM] | Human EpCAM [nM]/ Mouse EpCAM [nM] |
|---|---|---|---|---|---|
| R2178-Ep203 | 8.67 | 2.12 | 4.08 | 241.80 | 0.04 |
| R2178-Epc051 | 7.66 | 1.78 | 4.31 | 16.56 | 0.46 |
| R2178-Epc112 | 7.15 | 9.11 | 0.78 | 14.84 | 0.48 |
| Ep59-R1066 | 5.00 | 5.09 | 0.98 | 6.18 | 0.81 |
| Ep59-R1090S55A | 3.11 | 3.37 | 0.92 | 3.86 | 0.80 |
| Ep59-R2089 | 4.69 | 4.48 | 1.05 | 5.47 | 0.86 |
| Ep59-R2178 | 5.23 | 6.54 | 0.80 | 6.55 | 0.80 |
| Ep203-R1066 | 6.49 | 6.54 | 0.99 | 13.25 | 0.49 |
| Ep203-R1090S55A | 4.98 | 6.90 | 0.72 | 11.77 | 0.42 |
| Ep203-R2089 | 5.80 | 5.87 | 0.99 | 11.52 | 0.50 |
| Ep203-R2178 | 4.15 | 5.11 | 0.81 | 11.68 | 0.36 |
| Ct R1066-Ep59 | 10.19 | 8.96 | 1.14 | 51.98 | 0.20 |
| Ct R1066-Ep203 | 25.74 | 14.01 | 1.84 | 24.30 | 1.06 |
| Ct R1090S55A-Ep59 | 11.94 | 10.84 | 1.10 | 18.10 | 0.66 |
| Ct R1090S55A-Ep203 | 14.54 | 13.31 | 1.09 | 24.23 | 0.60 |
| Ct Ep59-R1066 | 6.63 | 5.93 | 1.12 | 13.36 | 0.50 |
| Ct Ep59-R1090S55A | 5.78 | 5.25 | 1.10 | 13.78 | 0.42 |
| Ct Ep203-R1066 | 6.11 | 5.98 | 1.02 | 18.69 | 0.33 |
| Ct Ep203-R1090S55A | 4.47 | 4.29 | 1.04 | 17.28 | 0.26 |

As shown in Table 4, the $K_D$ values of the CD40-EpCAM bispecific antibodies for human, monkey, and mouse EpCAM were in the $10^{-8}$M order or less, and strong binding was shown except for the binding of R2178-Ep59 and R2178-Ep203 to mouse EpCAM.

The $K_D$ values of the CD40-EpCAM bispecific antibodies other than R1066-Ep59, R1066-Epc051, and R1090S55A-Epc051 for monkey EpCAM are between 1/5 and 5 times the $K_D$ values for human EpCAM, and therefore, it was demonstrated that the antibodies have high species cross-reactivity between human-monkey EpCAM.

Further, the $K_D$ values of the CD40-EpCAM bispecific antibodies other than R2178-Ep59 and R2178-Ep203 for mouse EpCAM are between 1/5 and 5 times the $K_D$ values for human EpCAM, and therefore, it was demonstrated that the antibodies have high species cross-reactivity between human-mouse EpCAM.

Example 10

Evaluation of Binding Affinity of CD40-EpCAM Bispecific Antibody to CD40 by Biacore For the purpose of confirming the binding activity and the species cross-reactivity of the CD40-EpCAM bispecific antibodies obtained in Example 6 to each of human and monkey CD40, by using the human and monkey CD40-GST produced in Example 1, a binding affinity test by a surface plasmon resonance method (SPR method) was carried out. As a measurement device, Biacore T100 (manufactured by GE Healthcare, Inc.) was used.

An anti-human IgG antibody was immobilized on a CM5 sensor chip (manufactured by GE Healthcare, Inc.) using Human Antibody Capture Kit (manufactured by GE Healthcare, Inc.) according to the package insert. A test antibody prepared at 1 to 3 µg/mL was added to a flow cell for 10 seconds at a flow rate of 10 µL/min.

Subsequently, each of human and monkey CD40-GST protein solutions (diluted with HBS-EP+ containing 0.1% BSA) diluted by 2-fold in 5 steps from 1.25 nM as an analyte was added at a flow rate of 30 µL/min, and a binding reaction of each antibody and the analyte was measured for 2 minutes and a dissociation reaction was measured for 10 minutes. The measurement was carried out by a single cycle kinetics method.

The obtained sensorgram was analyzed using Bia Evaluation Software (manufactured by GE Healthcare, Inc.), and the kinetic constant of each antibody was calculated. A calculated dissociation constant [kd/ka=$K_D$] of each of the bispecific antibodies for human and monkey CD40, and a value obtained by dividing the dissociation constant for human CD40 by the dissociation constant for monkey CD40 are shown in Table 5.

TABLE 5

| $K_D$ value | Human CD40 [nM] | Monkey CD40 [nM] | Human CD40 [nM]/Monkey CD40 [nM] |
|---|---|---|---|
| R1066-Ep59 | 2.23 | 1.19 | 1.87 |
| R1066-Ep203 | 2.97 | 1.04 | 2.87 |
| R1066-Epc051 | 4.03 | 0.29 | 13.92 |
| R1066-Epc112 | 2.57 | 1.18 | 2.18 |
| R1090S55A-Ep59 | 1.31 | 0.77 | 1.70 |
| R1090S55A-Ep203 | 1.30 | 0.80 | 1.62 |
| R1090S55A-Epc051 | 1.21 | 0.71 | 1.70 |
| R1090S55A-Epc112 | 1.30 | 0.81 | 1.60 |
| R2089-Ep59 | 1.48 | 1.71 | 0.86 |
| R2089-Ep203 | 1.60 | 2.22 | 0.72 |
| R2089-Epc051 | 1.05 | 1.71 | 0.61 |
| R2089-Epc112 | 0.52 | 2.12 | 0.25 |
| R2178-Ep59 | 21.70 | 1.46 | 14.85 |
| R2178-Ep203 | 0.16 | 1.46 | 0.11 |
| R2178-Epc051 | 2.30 | 1.78 | 1.29 |
| R2178-Epc112 | 2.59 | 2.71 | 0.95 |
| Ep59-R1066 | NC | NC | — |
| Ep59-R1090S55A | NC | NC | — |
| Ep59-R2089 | 1.29 | 1.65 | 0.78 |
| Ep59-R2178 | 0.34 | 0.61 | 0.56 |
| Ep203-R1066 | NC | NC | — |
| Ep203-R1090S55A | NC | NC | — |
| Ep203-R2089 | 0.29 | 3.35 | 0.09 |
| Ep203-R2178 | NC | NC | — |
| Ct R1066-Ep59 | 0.40 | 1.10 | 0.36 |
| Ct R1066-Ep203 | 7.43 | 2.71 | 2.74 |
| Ct R1090S55A-Ep59 | 0.98 | 1.54 | 0.64 |
| Ct R1090S55A-Ep203 | 1.17 | 1.67 | 0.70 |
| Ct Ep59-R1066 | NC | NC | — |
| Ct Ep59-R1090S55A | NC | NC | — |
| Ct Ep203-R1066 | NC | NC | — |
| Ct Ep203-R1090S55A | NC | NC | — |

NC: Not Calculated

As shown in Table 5, the $K_D$ values of the respective CD40-EpCAM bispecific antibodies R1066-Ep59, R1066-Ep203, R1066-Epc051, R1066-Epc112, R1090S55A-Ep59, R1090S55A-Ep203, R1090S55A-Epc051, R1090S55A-Epc112, R2089-Ep59, R2089-Ep203, R2089-Epc051, R2089-Epc112, R2178-Ep203, R2178-Epc051, R2178-Epc112, Ep59-R2089, Ep59-R2178, Ep203-R2089, Ct R1066-Ep59, Ct R1066-Ep203, Ct R1090S55A-Ep59, and Ct R1090S55A-Ep203 for human CD40 and monkey CD40 were all in the $10^{-9}$ M order or less and strong binding was shown.

In addition, the $K_D$ values of the CD40-EpCAM bispecific antibodies R1066-Ep59, R1066-Ep203, R1066-Epc112, R1090S55A-Ep59, R1090S55A-Ep203, R1090S55A-Epc051, R1090S55A-Epc112, R2089-Ep59, R2089-Ep203, R2089-Epc051, R2089-Epc112, R2178-Epc051, R2178-Epc112, Ep59-R2089, Ep59-R2178, Ct R1066-Ep59, Ct R1066-Ep203, Ct R1090S55A-Ep59, and Ct R1090S55A-Ep203 for monkey CD40 are between 1/5 and 5 times the $K_D$ values for human CD40, and therefore, it was demonstrated that the antibodies have high species cross-reactivity between human-monkey CD40.

Example 11

Evaluation of CD40 Signal Inducing Activity of CD40-EpCAM Bispecific Antibody by Analysis of Expression Level of CD95 Using Flow Cytometry The CD40 signal inducing activity of the CD40-EpCAM bispecific antibodies obtained in Example 6 against Ramos cells in the coexistence with EpCAM-positive or negative cells was evaluated by an FCM method as follows using an increase in the expression level of CD95 on the Ramos cells as an index.

Ramos cells ($4 \times 10^6$ cells/mL) were seeded in a U-bottom 96-well plate (manufactured by Falcon, Inc.) at 25 µL/well, and a test antibody diluted to 0.2, 2, or 20 µg/mL (final concentration of 0.1, 1, or 10 µg/mL) with RPMI 1640 medium (manufactured by Sigma-Aldrich Co. LL) containing 10% FBS was added thereto at 50 µg/mL, and further, Expi293 cells, human EpCAM-expressing HEK 293 cells, or Colo 205 cells ($4 \times 10^6$ cells/mL) were added thereto at 25 µL/well, and the cells were cultured at 37° C. under 5.0% carbon dioxide gas for 16 hours.

After centrifugation (2000 rpm, 4° C., 2 minutes), the supernatant was removed, and the pellet was washed 3 times with 200 µL/well of SB. After centrifugation (2000 rpm, 4° C., 2 minutes), the supernatant was removed, and a PE mouse anti-human CD95 antibody (manufactured by Becton, Dickinson and Company) and FITC mouse anti-human CD20 were added to the pellet to suspend the pellet, and then, the resulting suspension was left to stand for 30 minutes at ice temperature.

After further centrifugation (2000 rpm, 4° C., 2 minutes), the supernatant was removed, and the pellet was washed 3 times with 200 µL/well of SB. Thereafter, 7AAD (manufactured by Becton, Dickinson and Company) diluted by 100 times was suspended in 200 µL/well of SB, and the fluorescence intensity of CD95 on Ramos cells present in a CD20-positive fraction was measured with a flow cytometer FACSCANTO II (manufactured by Becton, Dickinson and Company). As the negative control, the anti-DNP antibody was used.

Figure 4:
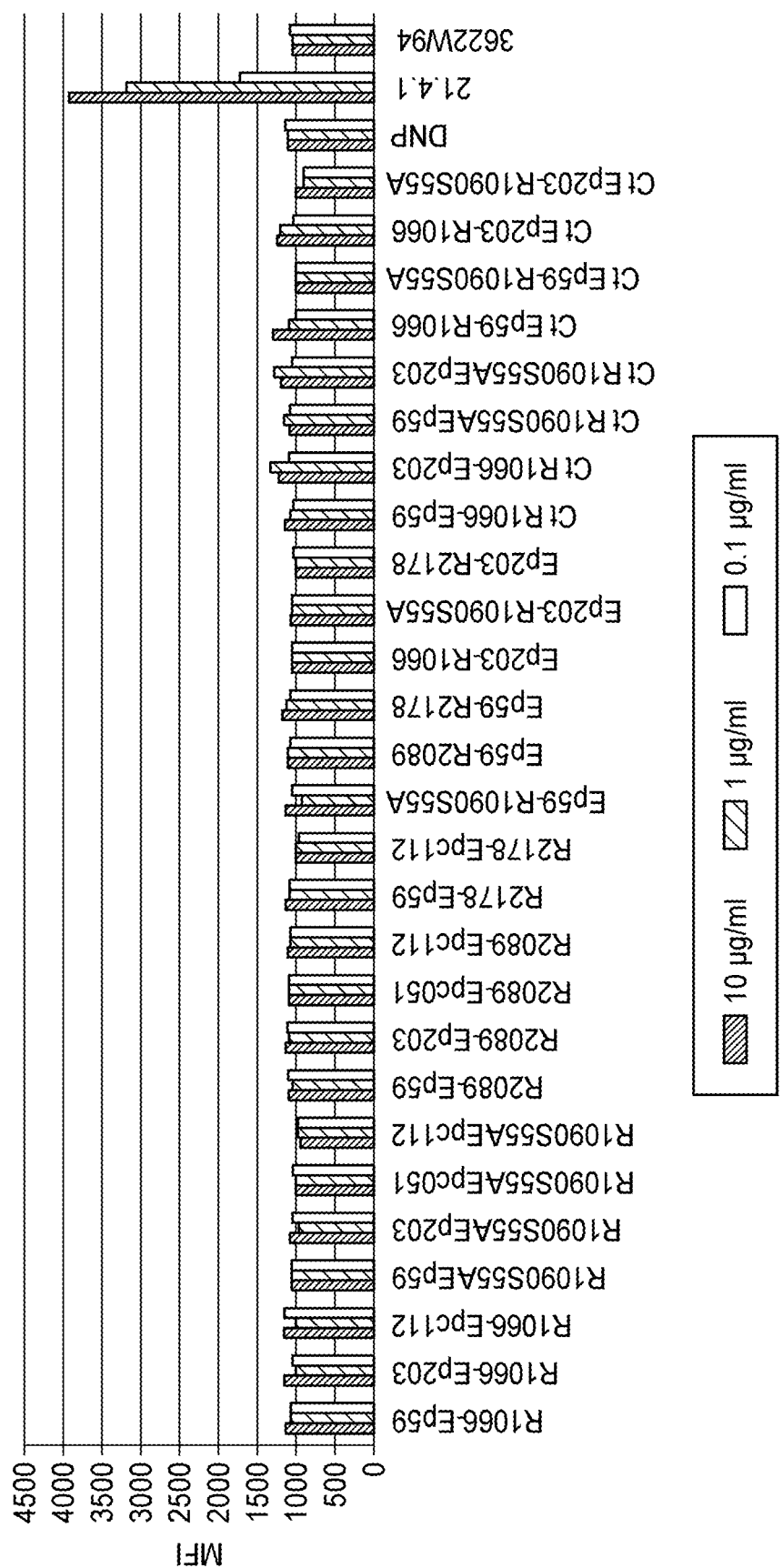
FIG. 4 shows the CD40 signal inducing activity of a CD40-EpCAM bispecific antibody against Ramos cells cocultured with HEK 293 cells. The vertical axis represents a fluorescence intensity, and shows the binding affinity of an anti-CD95 antibody to Ramos cells when each antibody was added at 10, 1, or 0.1 μg/mL. For comparison, an anti-DNP antibody was used as a negative control antibody, 21.4.1 was used as an anti-CD40 agonistic antibody, and 3622W94 was used as an anti-EpCAM antibody.
Figure 5:
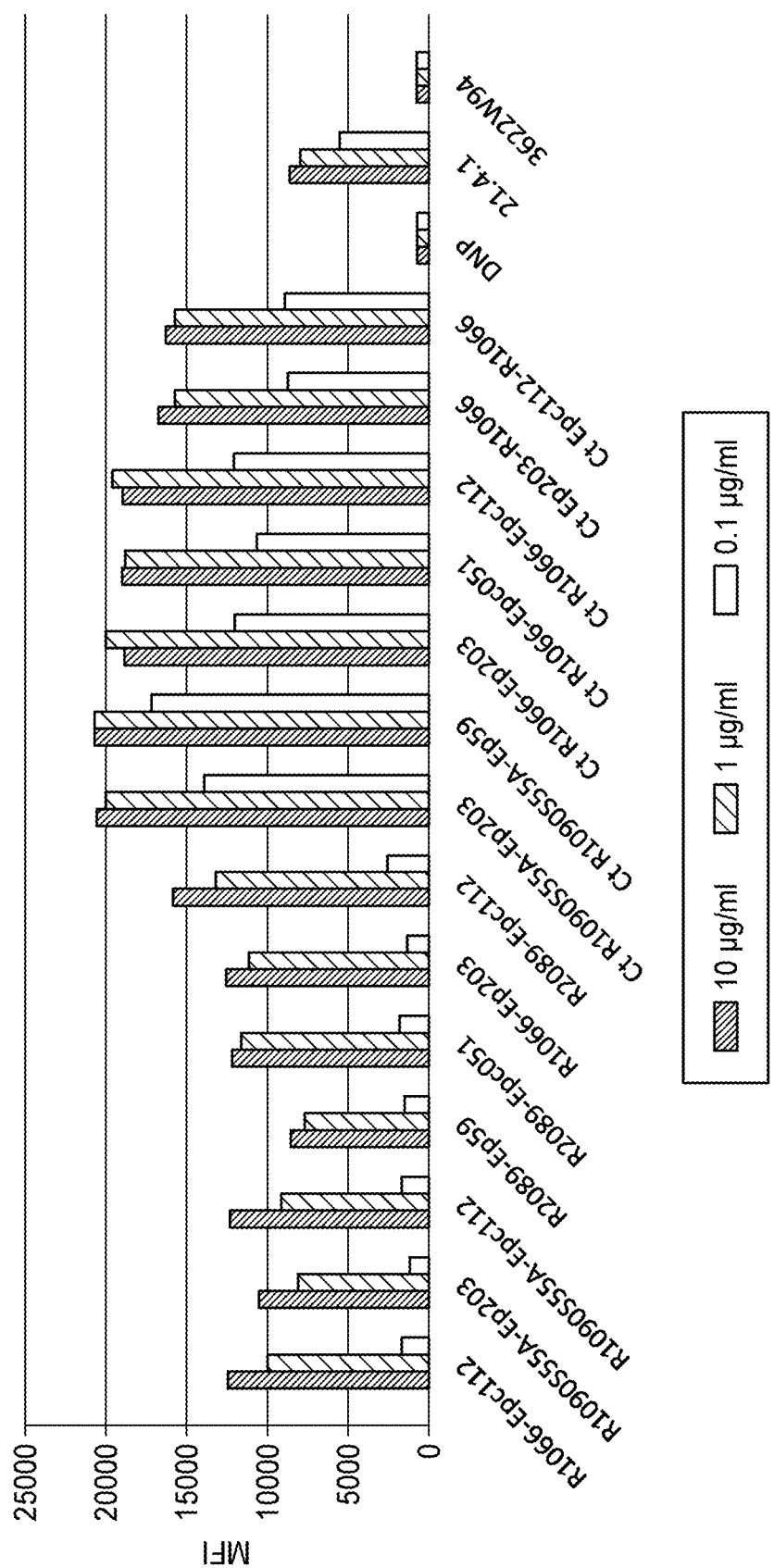
FIG. 5 shows the CD40 signal inducing activity of a CD40-EpCAM bispecific antibody against Ramos cells cocultured with human EpCAM/HEK 293 cells. The vertical axis represents a fluorescence intensity, and shows the binding affinity of an anti-CD95 antibody to Ramos cells when each antibody was added at 10, 1, or 0.1 μg/mL. For comparison, an anti-DNP antibody was used as a negative control antibody, 21.4.1 was used as an anti-CD40 agonistic antibody, and 3622W94 was used as an anti-EpCAM antibody.
Figure 6:
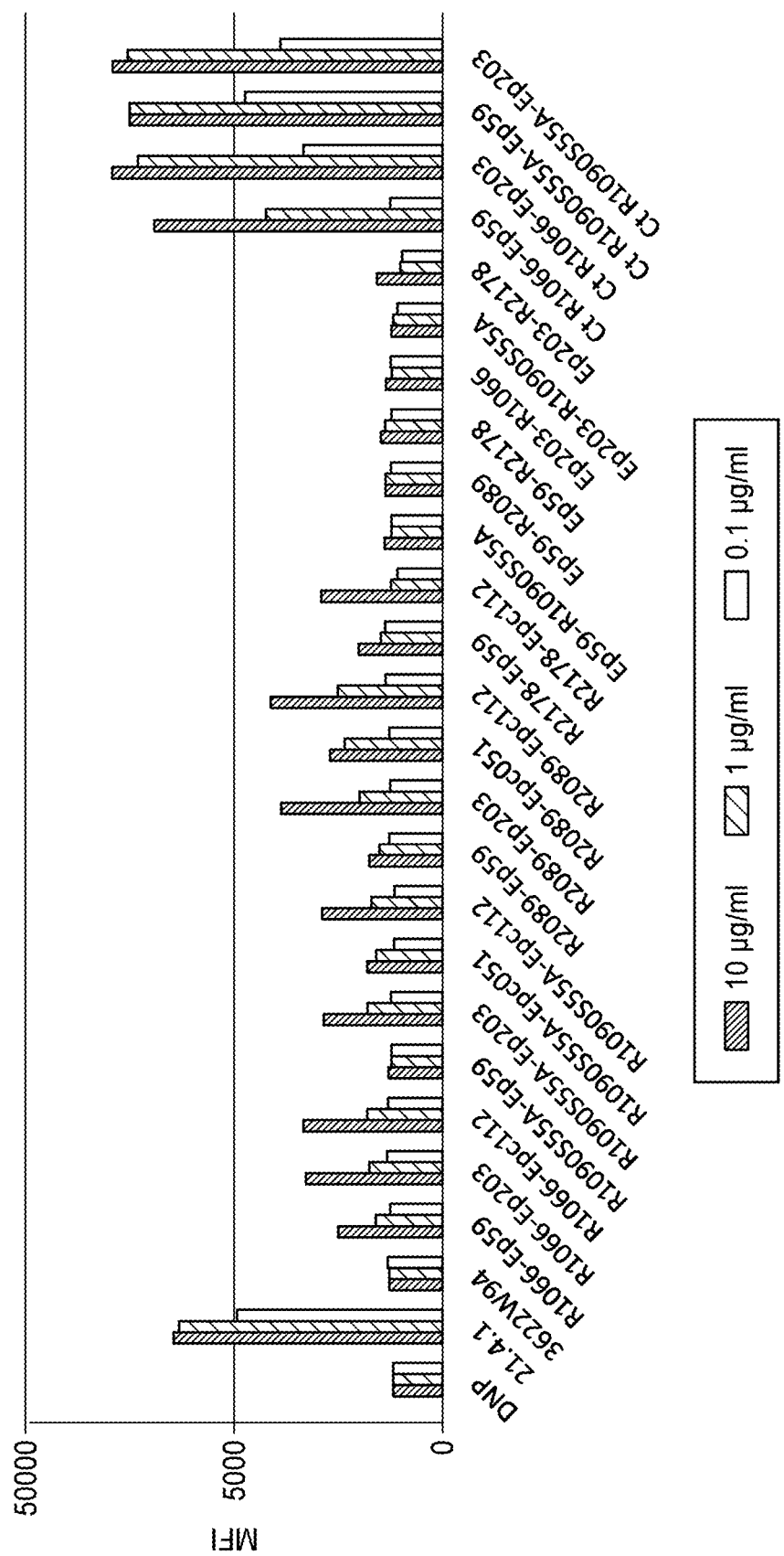
FIG. 6 shows the CD40 signal inducing activity of a CD40-EpCAM bispecific antibody against Ramos cells cocultured with Colo 205 cells. The vertical axis represents a fluorescence intensity, and shows the binding affinity of an anti-CD95 antibody to Ramos cells when each antibody was added at 10, 1, or 0.1 μg/mL. For comparison, an anti-DNP antibody was used as a negative control antibody, 21.4.1 was used as an anti-CD40 agonistic antibody, and 3622W94 was used as an anti-EpCAM antibody.

The results of the Ramos cells cocultured with the HEK 293 cells are shown in FIG. 4, the results of the Ramos cells cocultured with the human EpCAM/HEK 293 cells are shown in FIG. 5, and the results of the Ramos cells cocultured with the Colo 205 cells are shown in FIG. 6.

As shown in FIG. 4, it was found that when the Ramos cells were cocultured with any of the HEK 293 cells, the human EpCAM/HEK 293 cells, and the Colo 205 cells in the presence of the anti-CD40 antibody 21.4.1 produced in Example 3, the expression level of CD95 on the Ramos cells was increased and a signal of CD40 was induced.

Further, as shown in FIGS. 4 to 6, it was shown that when the human EpCAM/HEK 293 cells or the Colo 205 cells and the Ramos cells were cocultured in the presence of the anti-EpCAM antibody 3622W94 produced in Example 4, the expression level of CD95 on the Ramos cells was equivalent to that of the negative control, and a CD40 signal was not induced.

On the other hand, as shown in FIG. 4, when the HEK 293 cells that are negative for EpCAM and the Ramos cells were cocultured, any of the CD40-EpCAM bispecific antibody clones did not induce a signal of CD40, however, as shown in FIGS. 5 and 6, when the human EpCAM/HEK 293 cells or the Colo 205 cells that are positive for EpCAM and the Ramos cells were cocultured, it was shown that the CD40-EpCAM bispecific antibody increased the expression level of CD95 on the Ramos cells and induced a signal of CD40.

Figure 7:
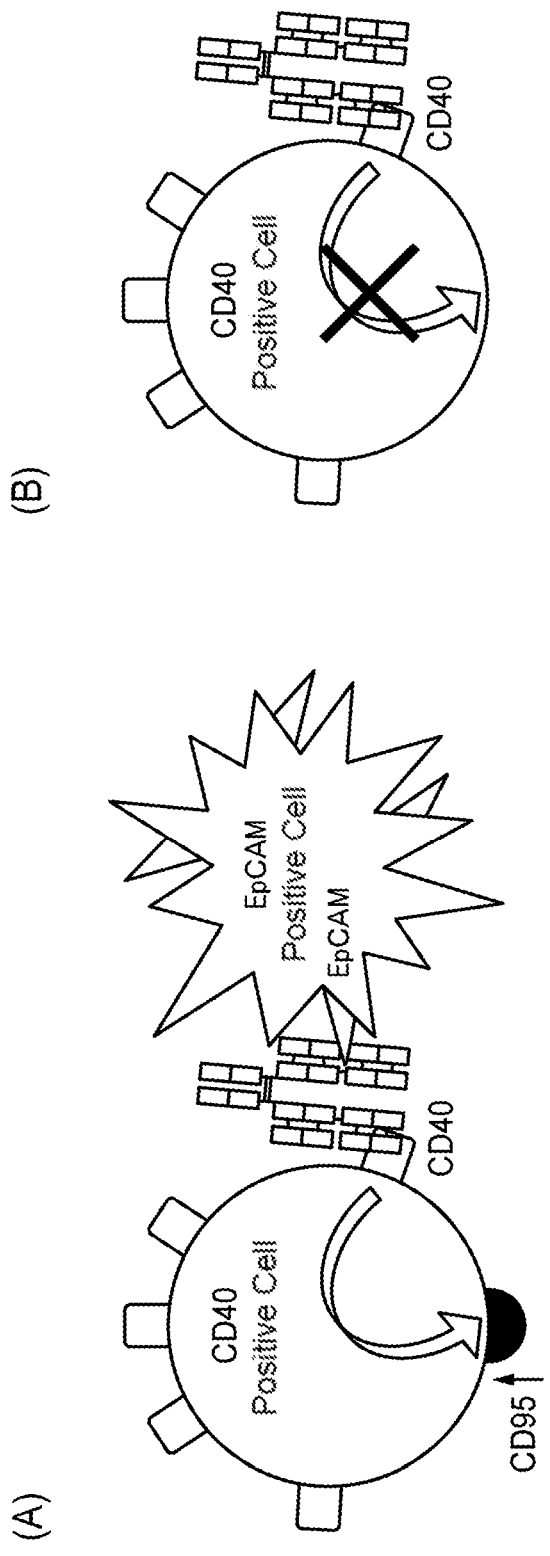
FIG. 7(A) is a schematic view of the action of a CD40-EpCAM bispecific antibody on a CD40-positive cell in the presence of an EpCAM-positive cell. When the CD40-EpCAM bispecific antibody binds to both the EpCAM-positive cell and the CD40-positive cell, a CD40 signal is induced in the CD40-positive cell. As a result, the expression of CD95 is induced on the CD40-positive cell.
FIG. 7(B) is a schematic view of the action of the CD40-EpCAM bispecific antibody on the CD40-positive cell in the absence of the EpCAM-positive cell. When the CD40-EpCAM bispecific antibody binds only to the CD40-positive cell, a CD40 signal is not induced.

These results suggest that as shown in FIG. 7(B), when the CD40-EpCAM bispecific antibody binds to CD40 on the Ramos cell alone, a CD40 signal is not induced, and as shown in FIG. 7(A), only when EpCAM-positive cells coexist, a CD40 signal is induced.

It has been confirmed that neither of the anti-CD40 antibody nor the anti-EpCAM antibody that are parent antibodies induces a CD40 signal in Ramos cells in the coexistence with EpCAM-positive cells [shown in FIGS. 3(A) and 3(B) for the anti-CD40 antibody, but the data for the anti-EpCAM antibody are omitted], however, it was found that the CD40-EpCAM bispecific antibody has a CD40 signal inducing activity which is not possessed by the parent antibodies.

This suggests that the CD40-EpCAM bispecific antibody of the present invention specifically induces a signal in CD40-positive cells such as immune cells and tumor cells specifically to a lesion site where cells that express EpCAM are present such as a tumor.

Further, as shown in FIG. 5, the CD40 signal inducing activity of the CD40-EpCAM bispecific antibody when the hEpCAM/HEK cells and the Ramos cells were cocultured was higher in the order of a C-terminal type bispecific antibody in which VH1 consists of the VH of the anti-CD40 antibody and VH2 consists of the VH of the anti-EpCAM antibody, a C-terminal type bispecific antibody in which VH1 consists of the VH of the anti-EpCAM antibody and VH2 consists of the VH of the anti-CD40 antibody, and an N-terminal type bispecific antibody in which VH1 consists of the VH of the anti-CD40 antibody and VH2 consists of the VH of the anti-EpCAM antibody.

As shown in FIG. 6, also when the Colo 205 cells and the Ramos cells were cocultured, almost the same tendency was confirmed. On the other hand, it was shown that an N-terminal type bispecific antibody in which VH1 consists of the VH of the anti-EpCAM antibody and VH2 consists of the VH of the anti-CD40 antibody does not have a CD40 signal inducing activity.

That is, the strength of the CD40 agonistic activity of the CD40-EpCAM bispecific antibody depending on the presence of EpCAM-positive cells depends on the form of the CD40-EpCAM bispecific antibody and the arrangement of the VH of the anti-CD40 antibody and the VH of the anti-EpCAM antibody, and the activity of the C-terminal type bispecific antibody was higher than that of the N-terminal type bispecific antibody. That is, it was demonstrated that the activity of the bispecific antibody in which VH1 consists of the VH of the anti-CD40 antibody and VH2 consists of the VH of the anti-EpCAM antibody is stronger than that of the bispecific antibody in which VH1 consists of the VH of the anti-EpCAM antibody and VH2 consists of the VH of the anti-CD40 antibody.

Example 12

Production of Fluorescently Labeled Antibody

In order to analyze the localization of the CD40-EpCAM bispecific antibody on the cell surface by an immunofluorescence staining method, fluorescence labeling of the CD40-EpCAM bispecific antibody and a cell surface marker antibody was carried out.

By using Alexa Fluor 488 Microscale Protein Labeling Kit (manufactured by Molecular Probes, Inc.), a fluorescently labeled antibody in which the CD40-EpCAM bispecific antibody Ct R1090S55A-Ep203 was labeled with Alexa 488 was produced according to the method described in the package insert.

In addition, HER2 was selected as a surface marker that is not expressed in Ramos cells but expressed in Colo 205 cells, and by using Alexa Fluor 647 Microscale Protein Labeling Kit (manufactured by Molecular Probes, Inc.), an antibody in which a known anti-HER2 antibody (described in WO 1992/022653) was labeled with Alexa 647 was produced according to the method described in the package insert.

Example 13

Confirmation of Accumulation of EpCAM-Positive Cells and CD40-Positive Cells at Crosslinked Site by CD40-EpCAM Bispecific Antibody In order to confirm a state where the CD40-EpCAM bispecific antibody binds to Ramos cells and EpCAM-positive cells, evaluation by an immunofluorescence staining method was carried out using Ct R1090S55A-Ep203-Alexa 488.

Ramos cells ($1 \times 10^6$ cells/mL) were seeded in a flat-bottom 96-well plate (manufactured by Greiner Bio-one, Inc.) at 50 µL/well, and Ct R1090S55A-Ep203-Alexa 488 prepared in Example 13 and HER2 Ab-Alexa 647 were diluted with phenol red-free RPMI-1640 medium (manufactured by Gibco, Inc.), and added thereto at 2 µg/mL (final concentration of 1 µg/mL) and 100 µg/mL, respectively.

Further, Colo 205 cells ($1 \times 10^6$ cells/mL) were added thereto at 50 µL/well, and cultured at 37° C. under 5.0% carbon dioxide gas for 14 hours, and observed using InCell Analyzer 6000 (manufactured by GE Healthcare, Inc.).

Figure 8:
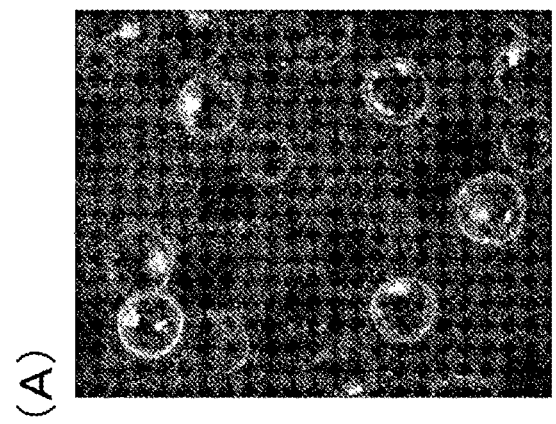
FIG. 8(A) shows the result of immunofluorescence staining of Ramos cells and Colo 205 cells with an HER2 antibody fluorescently labeled with Alexa 647.
FIG. 8(B) shows the result of immunofluorescence staining of Ramos cells and Colo 205 cells with Ct R1090S55A-Ep203 fluorescently labeled with Alexa 488.
FIG. 8(C) shows the superposition of the results. The arrows indicate spots where strong fluorescence was observed.
Figure 8:
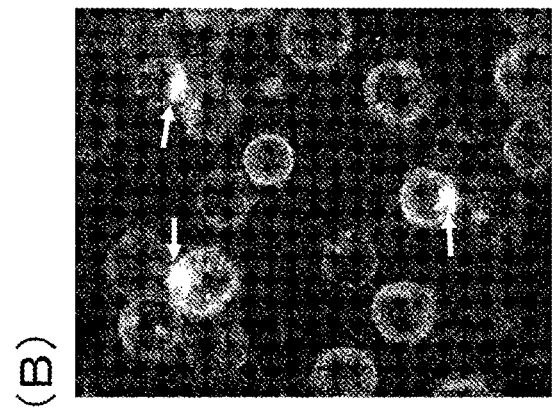
Figure 8:
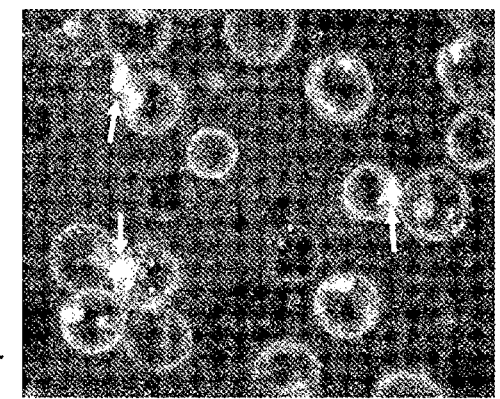
Figure 9:
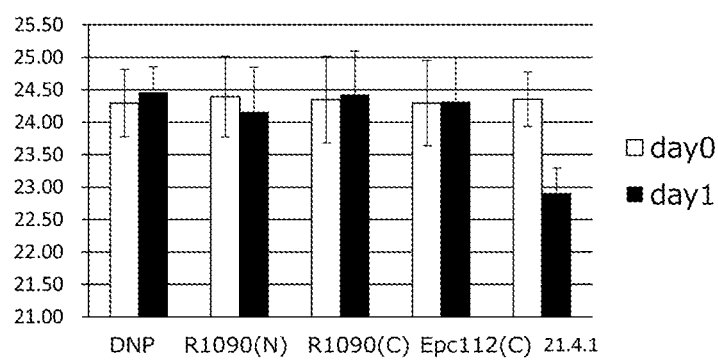
FIGS. 9(A) to 9(C) show the results of a toxicity test using mice. The vertical axis in FIG. 9(A) represents the body weight (g) of the mice. The vertical axis in FIG. 9(B) represents AST (Unit/L) in the peripheral blood of the mice. The vertical axis in FIG. 9(C) represents ALT (Unit/L) in the peripheral blood of the mice. In each figure, the gray bar graph shows the measured value before administration, and the black bar graph shows the measured value 24 hours after administration. R1090(N), R1090(C), and Epc112(C) denote R1090S55A-Ep203, Ct R1090S55A-Ep203, and Ct Epc112-R1066, respectively. An anti-DNP antibody was used as a negative control antibody, and 21.4.1 was used as an anti-CD40 agonistic antibody. 21.4.1 was administered at 1 mg/kg and the other antibodies were administered at 10 mg/kg.
Figure 9:
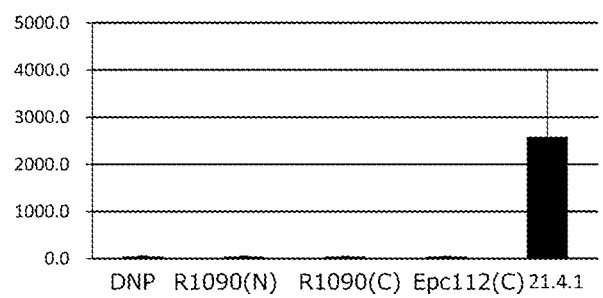
Figure 9:
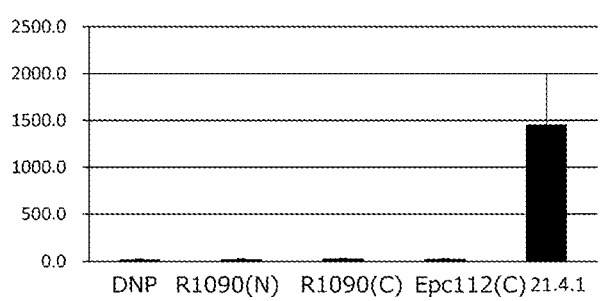
Figure 10:
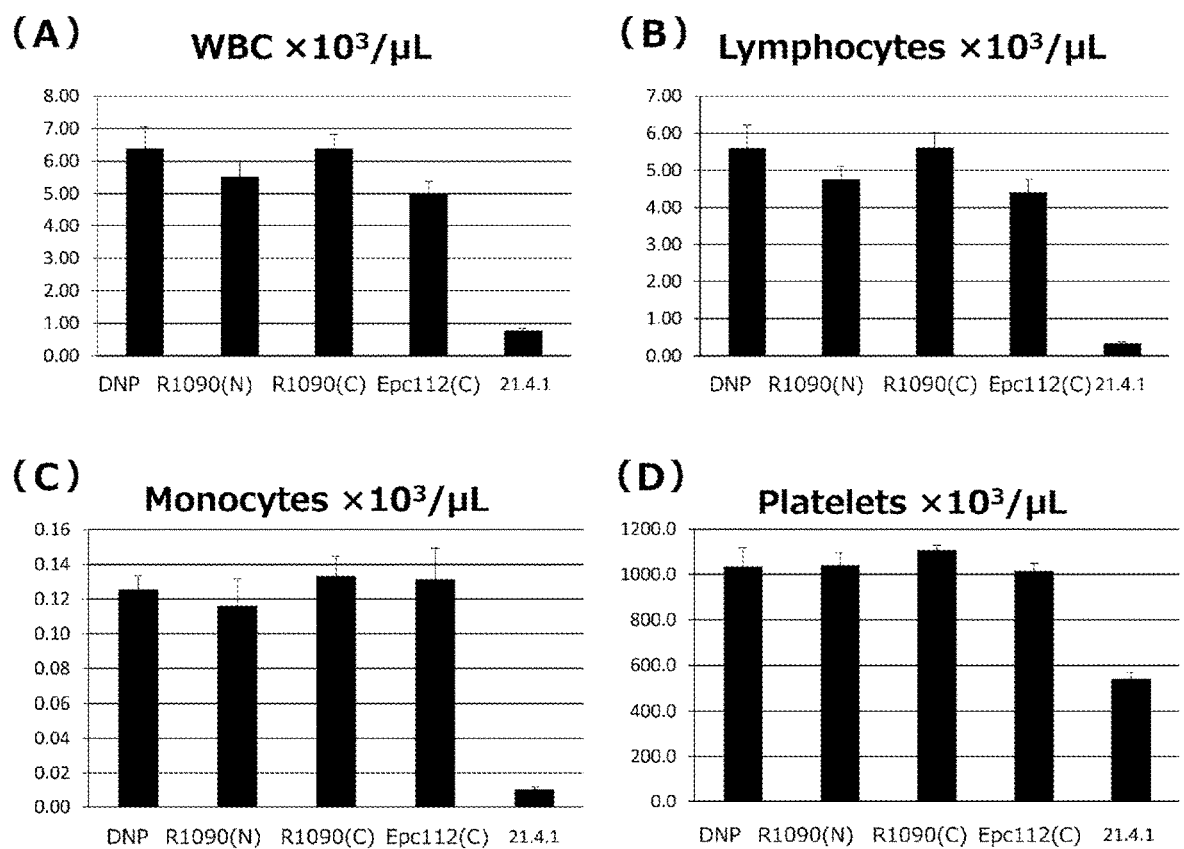
FIGS. 10(A) to 10(D) show the results of a toxicity test using mice.

In FIG. 8(A), the result of detecting the Colo 205 cells by Alexa 647 with which the HER2 antibody was labeled is shown, in FIG. 8(B), the result of detecting Alexa 488 with which Ct R1090S55A-Ep203 was labeled is shown, and the superposition of the results is shown in FIG. 8(C).

Since HER2 is not expressed in the Ramos cells but is expressed in the Colo 205 cells, fluorescence is observed only from the Colo 205 cells in FIG. 8(A). Therefore, the cells observed in FIG. 8(A) are the Colo 205 cells, and the cells observed in FIG. 8(B) but not observed in FIG. 8(A) are the Ramos cells.

In FIG. 8(B), as for Ct R1090S55A-Ep203-Alexa 488, fluorescence is observed from both the Ramos cell and the Colo 205 cell. Accordingly, it could be confirmed that Ct R1090S55A-Ep203 binds to CD40 and EpCAM also on the cell surface.

As shown in FIG. 8(B) and FIG. 8(C), a state where Ct R1090S55A-Ep203-Alexa 488 was accumulated on a contact face of the Colo 205 cell and the Ramos cell, and strong fluorescence is emitted was observed (portions indicated by arrows). From this result, it was demonstrated that the CD40-positive cells and the EpCAM-positive cells were crosslinked, and the CD40-EpCAM bispecific antibody was accumulated on the contact face thereof.

It is known that TNFRSF comprising CD40 induces a signal when it forms a trimer or higher-order assembly, and it is considered that by accumulating the CD40-EpCAM bispecific antibody on a contact face of cells, CD40 to which the CD40-EpCAM bispecific antibody binds is also accumulated, and therefore, a signal of CD40 is induced.

In addition, it has also been observed that the CD40-EpCAM bispecific antibody accumulated on a contact face of cells is internalized into cells, and this suggests that by the induction of a CD40 signal, the internalization of CD40 is promoted.

Example 14

Toxicity Test of Antibody in Mice

The CD40-EpCAM bispecific antibodies Ct R1090S55A-Ep203, Ct Epc112-R1066, and R1090S55A-Ep203 and the anti-CD40 agonistic antibody 21.4.1 all do not have cross-reactivity with mouse CD40, and therefore, in the examination using a mouse model, a human CD40 BAC Tg mouse (hereinafter referred to as hCD40Tg mouse) in which a BAC vector comprising human CD40 was introduced into a C17BL/6J Jcl mouse was used.

The hCD40Tg mouse was produced by introducing a BAC clone (CTD-2532119) (Invitrogen, Inc.) into a fertilized egg after purification. The produced hCD40Tg mouse was mated with a C17BL/6J Jcl mouse and subjected to a test after confirming that it had the human CD40 gene by a PCR method.

Each of the CD40-EpCAM bispecific antibodies Ct R1090S55A-Ep203, Ct Epc112-R1066, and R1090S55A-Ep203, the anti-CD40 agonistic antibody 21.4.1, and the anti-DNP antibody that is a control antibody was administered to five hCD40Tg mice in each group through the tail vein, and the body weight before the administration and 24 hours after the administration, the peripheral blood cell count, the plasma asparagine aminotransferase (AST) level, and the plasma alanine aminotransferase (ALT) level 24 hours after the administration were measured. The dose of the antibody was set to 10 mg/kg except for 21.4.1, and the dose of 21.4.1 was set to 1 mg/kg since it is difficult to administer 21.4.1 at a dose of 10 mg/kg because of its toxicity.

As a result, as shown in FIGS. 9(A) to 9(C) and FIGS. 10(A) to 10(D), in the group to which 21.4.1 was administered, a decrease in the body weight after the administration, an increase in AST and ALT, each of which is a liver deviation enzyme, and a decrease in leukocytes, lymphocytes, monocytes, and platelets in the peripheral blood were observed, however, in the group to which Ct R1090S55A-Ep203, Ct Epc112-R1066, and R1090S55A-Ep203 were administered, no change was observed in the same manner as in the group to which the DNP antibody that is the negative control was administered.

From the above results, it was demonstrated that the CD40-EpCAM bispecific antibody of the present invention significantly reduces its systemic toxicity as compared with the prior antibody.

Example 15

Antitumor Effect of Antibody on Mouse Syngeneic Model

In order to examine the antitumor effect of the CD40-EpCAM bispecific antibodies Ct R1090S55A-Ep203, Ct Epc112-R1066, and R1090S55A-Ep203, and the anti-CD40 agonistic antibody 21.4.1 on mice, examination was carried out using a mouse syngeneic model.

1. Preparation of Tumor Cell mEpCAM/B16F10

As tumor cells to be grafted, a mouse melanoma cell line B16-F10 (ATCC CRL-6475) in which mouse EpCAM is not expressed, and mEpCAM/B16F10 that is B16-F10 made to express mouse EpCAM were produced by the following method.

By using the mouse EpCAM gene represented by SEQ ID NO: 19, mEpCAM (945 bp) was cut out with BamHI/NotI from a mouse EpCAM expression vector for membrane expression, pEF6-mouse EpCAM full produced in the same manner as in Example 2, and ligated to pcDNA3.1(+) that was treated with BamHI/NotI similarly, whereby pcDNA3-mouse EpCAM full was obtained.

The obtained expression vector pcDNA3.1-mouse EpCAM full was introduced into B16F10 cells using lipofectamine 3000 (manufactured by Thermo Fisher Scientific, Inc.) and cultured, and selection was carried out using 3 mg/mL G418 from the following day. Sorting of a high expression fraction was repeated three times by a cell sorter, whereby B16F10 cells highly expressing mouse EpCAM were obtained.

2. Antitumor Test Using Mouse Syngeneic Model

B16-F10 or mEpCAM/B16F10 ($1 \times 10^6$ cells) was subcutaneously grafted to hCD40Tg mice (Day −8). On Days 0, 3 and 7, each antibody was administered to 5 animals in each group through the tail vein. The dose of the antibody was set to 10 mg/kg except for 21.4.1, and the dose of 21.4.1 was set to 1 mg/kg since it is difficult to administer 21.4.1 at a dose of 10 mg/kg because of its toxicity. The major axis and the minor axis of a tumor were measured using calipers, and a tumor volume was calculated according to the formula: minor axis x minor axis x major axis/2. The results are shown in FIG. 11(A) and FIG. 11(B).

Figure 11:
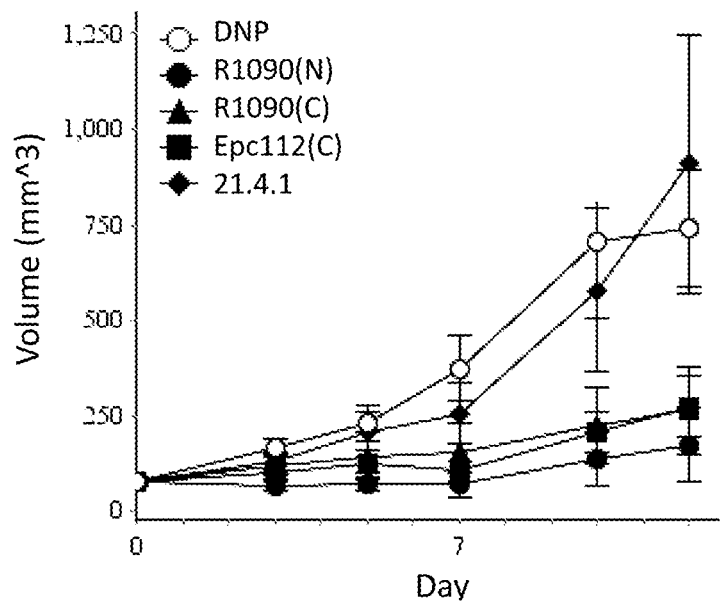
FIG. 11(A) shows the results of evaluation of the antitumor effect of a CD40-EpCAM bispecific antibody in mice implanted with mEpCAM/B16F10.
FIG. 11(B) shows the results of evaluation of the antitumor effect of the CD40-EpCAM bispecific antibody in mice implanted with B16F10. In each figure, the vertical axis represents a tumor volume ($mm^3$), and the horizontal axis represents the day when the administration day is regarded as day 0. An anti-DNP antibody was used as a negative control antibody, and 21.4.1 was used as an anti-CD40 agonistic antibody. 21.4.1 was administered at 1 mg/kg and the other antibodies were administered at 10 mg/kg.
Figure 11:
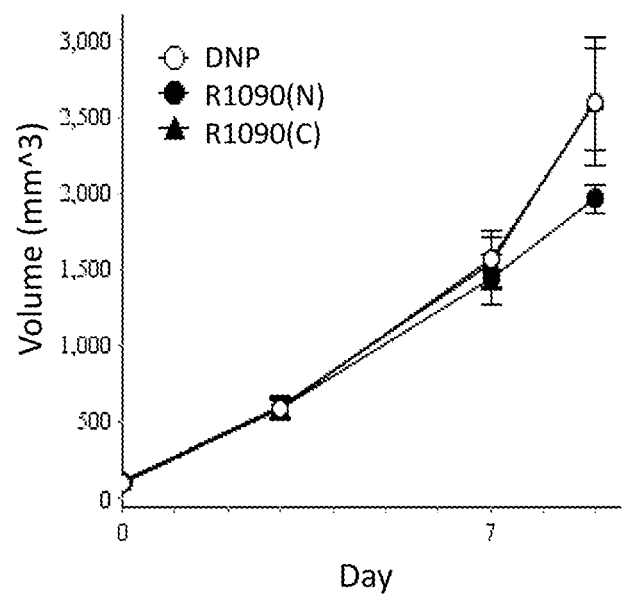

As shown in FIG. 11(A), the CD40-EpCAM bispecific antibodies Ct R1090S55A-Ep203, Ct Epc112-R1066, and R1090S55A-Ep203 all exhibited remarkable drug efficacy against mEpCAM/B16F10. On the other hand, as shown in FIG. 11(B), no drug efficacy was exhibited against B16-F10 that does not express EpCAM. From the above results, it was demonstrated that the produced CD40-EpCAM bispecific antibodies have EpCAM-dependent drug efficacy.

Example 16

Construction of Expression Vector for Bispecific Antibody or Antibody Fragment that Binds to CD40 and EpCAM 1. Designing of Bispecific Antibody or Antibody Fragment (1) Designing of Hetero-IgG Type Bispecific Antibody As a bispecific antibody that monovalently binds to each of CD40 and EpCAM, a bispecific antibody having a structure shown in FIG. 12(A) (hereinafter referred to as a hetero-IgG type bispecific antibody) was designed. As the Fc region of the hetero-IgG type bispecific antibody, an Fc region described in WO 2016/071004 was adopted.

The hetero-IgG type bispecific antibody has two different heavy chain constant regions (CHs), and hereinafter these are referred to as CHa and CHb, respectively. The nucleotide sequence and the amino acid sequence of CHa are represented by SEQ ID NOS: 79 and 80. Further, the nucleotide sequence and the amino acid sequence of CHb are represented by SEQ ID NOS: 81 and 82. A heavy chain variable region of the antibody binds to the N-terminal side of each of CHa and CHb to form a heavy chain. Hereinafter, the heavy chain variable regions that bind to CHa and CHb are referred to as VHa and VHb, respectively. The hetero-IgG type bispecific antibody is composed of one heavy chain formed by linking VHa and CHa from the N-terminal side, one heavy chain formed by linking VHb and CHb from the N-terminal side, and two identical light chains.

(2) Designing of Fab-Type Bispecific Antibody Fragment

As a bispecific antibody fragment that monovalently binds to each of CD40 and EpCAM, an antibody fragment having a structure shown in FIG. 12(B) (hereinafter referred to as a Fab-type bispecific antibody fragment) was designed. As the structure of the Fab-type bispecific antibody fragment, a structure from the N terminus to the middle of the hinge of an antibody described in WO 2009/131239 was adopted, and FLAG-Tag was linked to the C terminal side of the heavy chain. That is, the Fab-type bispecific antibody fragment is composed of one heavy chain formed by linking VH1, CH1, VH2, CH1, part of a hinge, and FLAG-Tag in order from the N-terminal side, and two light chains. The gene sequence from CH1 bound to the C-terminal side of VH2 to FLAG-Tag of the Fab-type bispecific antibody fragment is described in SEQ ID NO: 83, and the amino acid sequence is described in SEQ ID NO: 84.

(3) Designing of F(ab')2-Type Bispecific Antibody Fragment

As a bispecific antibody fragment that divalently binds to each of CD40 and EpCAM, an antibody fragment having a structure shown in FIG. 12(C) (hereinafter referred to as a F(ab')2-type bispecific antibody fragment) was designed. As the structure of the F(ab')2-type bispecific antibody fragment, a structure from the N terminus to the hinge of an antibody described in WO 2009/131239 was adopted, and FLAG-Tag was linked to the C terminal side of the heavy chain. That is, the F(ab')2-type bispecific antibody fragment is composed of two heavy chains formed by linking VH1, CH1, VH2, CH1, a hinge, and FLAG-Tag in order from the N-terminal side, and four light chains. The gene sequence from CH1 that binds to the C-terminal side of VH2 to FLAG-Tag of the F(ab')2-type bispecific antibody fragment is described in SEQ ID NO: 85, and the amino acid sequence is described in SEQ ID NO: 86.

The VHa of the hetero-IgG type bispecific antibody produced by the following steps is the VH of the anti-CD40 antibody, and the VHb is the VH of the anti-EpCAM antibody. Further, the VH1 of the Fab-type and F(ab')2-type bispecific antibody fragments is the VH of the anti-CD40 antibody, and the VH2 is the VH of the anti-EpCAM antibody.

The Fab-type and F(ab')$_2$-type bispecific antibodies produced by the following steps have CH1 of IgG4 (the nucleotide sequence is represented by SEQ ID NO: 74 and the amino acid sequence is represented by SEQ ID NO: 75) as a linker between VH1 and VH2.

In addition, the hetero-IgG type bispecific antibody, the Fab-type bispecific antibody fragment, and the F(ab')$_2$-type bispecific antibody fragment produced by the following steps have a light chain comprising the VL encoded by L6.

The name of the bispecific antibody/the antibody fragment, the structure of the bispecific antibody/the antibody fragment, the clone of the anti-CD40 antibody and the clone of the anti-EpCAM antibody used for the production of the antibody/the antibody fragment are shown in Table 4.

TABLE 6

| Name of antibody/ antibody fragment | Structure of antibody/ antibody fragment | VHa/ VH1 | VHb/ VH2 |
|---|---|---|---|
| hetero-IgG R1090S55A-Ep203 | hetero-IgG type | R1090S55A | Ep203 |
| hetero-IgG R1090S55A-Ep59 | hetero-IgG type | R1090S55A | Ep59 |
| hetero-IgG R1066-Ep203 | hetero-IgG type | R1066 | Ep203 |
| hetero-IgG R1066-Epc112 | hetero-IgG type | R1066 | Epc112 |
| hetero-IgG R1066-Ep59 | hetero-IgG type | R1066 | Ep59 |
| hetero-IgG R2089-Epc112 | hetero-IgG type | R2089 | Epc112 |
| R1090S55A-Ep203 Fab | Fab type | R1090S55A | Ep203 |
| R1066-Ep203 Fab | Fab type | R1066 | Ep203 |
| R1090S55A-Ep203 F(ab')2 | F(ab')2 type | R1090S55A | Ep203 |
| R1066-Ep203 F(ab')2 | F(ab')2 type | R1066 | Ep203 |

2. Production of Expression Vector for Bispecific Antibody or Antibody Fragment (1) Production of Expression Vector for Hetero-IgG Type Bispecific Antibody As for the hetero-IgG type bispecific antibodies shown in Table 4, an expression vector was produced by a method described below.

A gene in which the nucleotide sequence encoding CHa represented by SEQ ID NO: 79 was ligated to the nucleotide sequence encoding the VH of R1066, R1090S55A, or R2089 obtained in Example 3 was synthesized and ligated to the BglII-BamHI site of pCI-Hygro2.01 (synthesized based on a pCI vector manufactured by Promega, Inc.).

Further, a VH gene of each of Ep59, Ep203, and Epc112 obtained in Example 4 was subcloned into the SalI-NheI site of N5KG4PE R409K_R1066 obtained in Example 3. Thereafter, a gene fragment from the L6 gene (SEQ ID NO: 21) encoding VL to the region of VH was amplified by a PCR reaction using PrimeSTAR Max DNA Polymerase (manufactured by Takara Bio, Inc.), and a synthesized nucleotide sequence encoding CHb represented by SEQ ID NO: 81 was ligated to the XbaI-NheI site of the plasmid subcloned into the NheI-BamHI site of pCI-Hygro2.01, whereby an expression plasmid vector for the hetero-IgG type bispecific antibodies shown in Table 4 was obtained.

(2) Production of Expression Vector for Fab-Type Bispecific Antibody Fragment

As for the Fab-type bispecific antibody fragments shown in Table 4, an expression vector was produced by a method described below.

By using the expression vector for the N-terminal type bispecific antibodies R1066-Ep203 and R1090S55A-Ep203 produced in Example 5-1 as the template, a gene fragment in which FLAG-Tag was added to a sequence from VL to four residues at the N-terminal side of the hinge region was amplified by a PCR reaction using PrimeSTAR Max DNA Polymerase (manufactured by Takara Bio, Inc.), and ligated to the XbaI-BamHI site of pCI-Hygro2.01, whereby an expression plasmid vector for the Fab-type bispecific antibody fragments shown in Table 4 was obtained. The gene sequence from CH1 that binds to the C-terminal side of VH2 to FLAG-Tag of the Fab-type bispecific antibody fragment is described in SEQ ID NO: 83, and the amino acid sequence is described in SEQ ID NO: 84.

(3) Production of Expression Vector for F(ab')2-Type Bispecific Antibody Fragment As for the F(ab')2-type bispecific antibody fragments shown in Table 4, an expression vector was produced by a method described below.

By using the expression vector for the N-terminal type bispecific antibodies R1066-Ep203 and R1090S55A-Ep203 produced in Example 5-1 as the template, a gene fragment in which FLAG-Tag was added to a sequence from VL to the hinge was amplified by a PCR reaction using PrimeSTAR Max DNA Polymerase (manufactured by Takara Bio, Inc.), and ligated to the XbaI-BamHI site of pCI-Hygro2.01, whereby an expression plasmid vector for the F(ab')$_2$-type bispecific antibody fragments shown in Table 4 was obtained. The gene sequence from CH1 that binds to the N-terminal side of VH2 to FLAG-Tag of the F(ab)$_2$-type bispecific antibody fragment is described in SEQ ID NO: 85, and the amino acid sequence is described in SEQ ID NO: 86.

Example 17

Preparation of Bispecific Antibody that Binds to CD40 and EpCAM

A bispecific antibody or an antibody fragment having each of the binding sites for CD40 and EpCAM subcloned into the antibody expression plasmid vector pCI-Hygro2.01 produced in Example 16 was expressed and purified by the following method, respectively.

1. Production of Hetero-IgG Type Bispecific Antibody

The expression vector encoding a heavy chain composed of VHa and CHa and the expression vector encoding a heavy chain composed of VHb and CHb produced in Example 16-2(1) were co-transfected into Expi293 cells by Expi293 (trademark) Expression System (manufactured by Thermo Fisher, Inc.), and Transfection Enhancer was added thereto after 16 hours, whereby the antibody was expressed in a transient expression system.

The culture supernatant was collected 4 days after introduction of the vectors, and filtered through a membrane filter (manufactured by Millipore Corporation) having a pore diameter of 0.22 μm, and thereafter, the antibody was subjected to affinity purification using a Protein A resin (Mab Select, manufactured by GE Healthcare, Inc.). As the washing solution, D-PBS(-) was used. The antibody adsorbed to the Protein A was eluted with a 100 mM sodium citrate and 50 mM NaCl buffer solution (pH 3.5) and collected in a tube containing a 1 M Tris-HCl buffer solution (pH 9.0).

Subsequently, the solution was concentrated using VIVASPIN (manufactured by Sartrius stealin), and the buffer solution was replaced with D-PBS(-) using a Nap Column (manufactured by GE Healthcare, Inc.). Further, a monomer fraction was fractionated from the antibody solution using AKTA FPLC (manufactured by GE Healthcare, Inc.) and Superdex High-performance Columns (manufactured by GE Healthcare, Inc.). By performing filter sterilization with a membrane filter (Millex-Gv, manufactured by Millipore Corporation) having a pore diameter of 0.22 μm, a purified antibody was obtained.

An absorbance at a wavelength of 280 nm of the antibody solution was measured, and the concentration of the purified antibody was calculated using an extinction coefficient estimated from the amino acid sequence of each antibody. In addition, after a sugar chain of the prepared hetero-IgG type bispecific antibody was enzymatically digested, a mass analysis was carried out using Synapt G2 (manufactured by Waters Corporation) so as to confirm that the antibody is a hetero-IgG type bispecific antibody having one heavy chain composed of VHa and CHa and one heavy chain composed of VHb and CHb.

2. Production of Fab-Type Bispecific Antibody Fragment and F(ab')2-Type Bispecific Antibody Fragment The expression vector for the Fab-type bispecific antibody fragment produced in Example 16-2(2) was transfected into Expi293 cells by Expi293 (trademark) Expression System (manufactured by Thermo Fisher, Inc.), and Transfection Enhancer was added thereto after 16 hours, whereby an antibody fragment was expressed in a transient expression system.

The culture supernatant was collected 4 days after introduction of the vector, and filtered through a membrane filter (manufactured by Millipore Corporation) having a pore diameter of 0.22 μm, and thereafter, the antibody fragment was subjected to affinity purification using a Protein L resin (manufactured by ProteinExpress Co., Ltd.). As the washing solution, D-PBS(-) was used. The antibody fragment adsorbed to the Protein L was eluted with a 100 mM glycine buffer solution (pH 2.5) and collected in a tube containing a 1 M Tris-HCl buffer solution (pH 8.0).

Subsequently, the solution was concentrated using VIVASPIN (manufactured by Sartrius stealin), and the buffer solution was replaced with D-PBS(-) using a Nap Column (manufactured by GE Healthcare, Inc.). Further, a fraction in which a fragment having a molecular weight equivalent to that of each of the Fab-type bispecific antibody fragments is eluted was fractionated from the antibody fragment solution using AKTA FPLC (manufactured by GE Healthcare, Inc.) and Superdex High-performance Columns (manufactured by GE Healthcare, Inc.). By performing filter sterilization with a membrane filter (Millex-Gv, manufactured by Millipore Corporation) having a pore diameter of 0.22 μm, a purified antibody fragment was obtained.

Further, by using the expression vector for the F(ab')2-type bispecific antibody fragment produced in Example 16-2(3), a F(ab')2-type bispecific antibody fragment was obtained in the same manner as described above. The purified F(ab')2-type bispecific antibody fragment was evaluated by SDS-PAGE so as to confirm that the content of the Fab' molecule in which the disulfide bond between the heavy chains was reduced is low.

An absorbance at a wavelength of 280 nm of the antibody fragment solution was measured, and the concentration of the purified antibody fragment was calculated using an extinction coefficient estimated from the amino acid sequence of each antibody fragment.

Example 18

Production of Human EpCAM-Expressing Expi293 Cells

The human EpCAM expression vector for membrane expression, pEF6-human EpCAM full obtained in Example 2 was transfected into Expi293 cells by Expi293 (trademark) Expression System (manufactured by Thermo Fisher, Inc.), and the cells were cultured, whereby a protein was expressed in a transient expression system. After the transfection, shaking culture was carried out for 24 hours, followed by centrifugation, whereby Expi293 cells expressing human EpCAM on a cell membrane (hereinafter referred to as human EpCAM/Expi293 cells) were obtained.

Example 19

Evaluation of CD40 Signal Inducing Activity of Hetero-Bispecific Antibody by Analysis of Expression Level of CD95 Using Flow Cytometry The CD40 signal inducing activity of the hetero-IgG type bispecific antibody obtained in Example 17-1 against Ramos cells in the coexistence with EpCAM-positive or negative cells was evaluated by an FCM method as follows using an increase in the expression level of CD95 on the Ramos cells as an index.

The evaluation was carried out in the same manner as in Example 11 except that the concentration of a test antibody to be added was set to 2 μg/mL (final concentration: 1 μg/mL), and further, a cell line to be cocultured with the Ramos cells was changed to Expi293 cells or human EpCAM/Expi293 cells obtained in Example 18.

Figure 13:
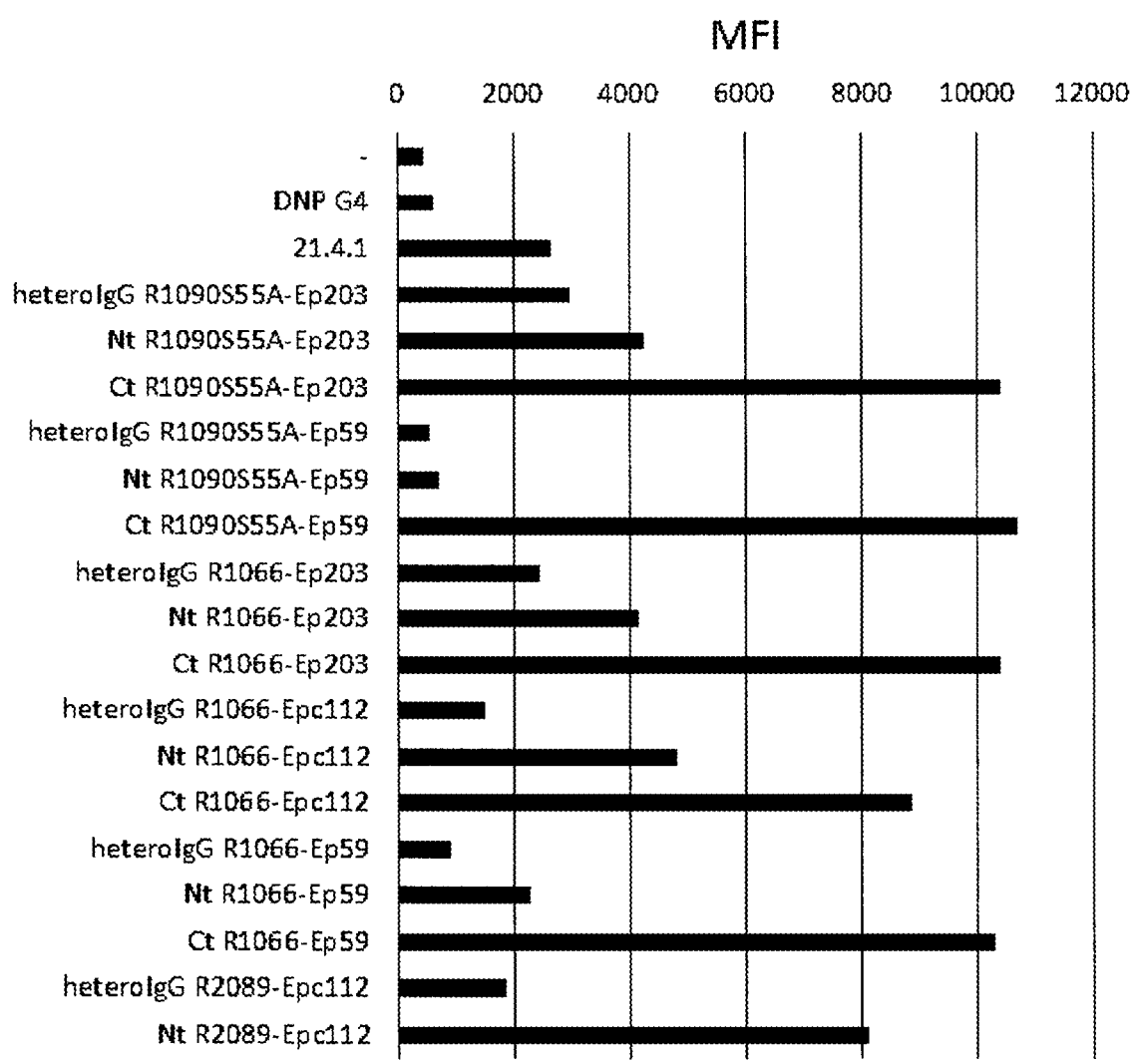
FIG. 13 shows the CD40 signal inducing activity of a CD40-EpCAM bispecific antibody against Ramos cells cocultured with human EpCAM/Expi293 cells. The horizontal axis represents a fluorescence intensity, and shows the binding affinity of an anti-CD95 antibody to the Ramos cells when each antibody was added at 1 μg/mL. For comparison, an anti-DNP antibody was used as a negative control antibody, and 21.4.1 was used as an anti-CD40 agonistic antibody.
Figure 14:
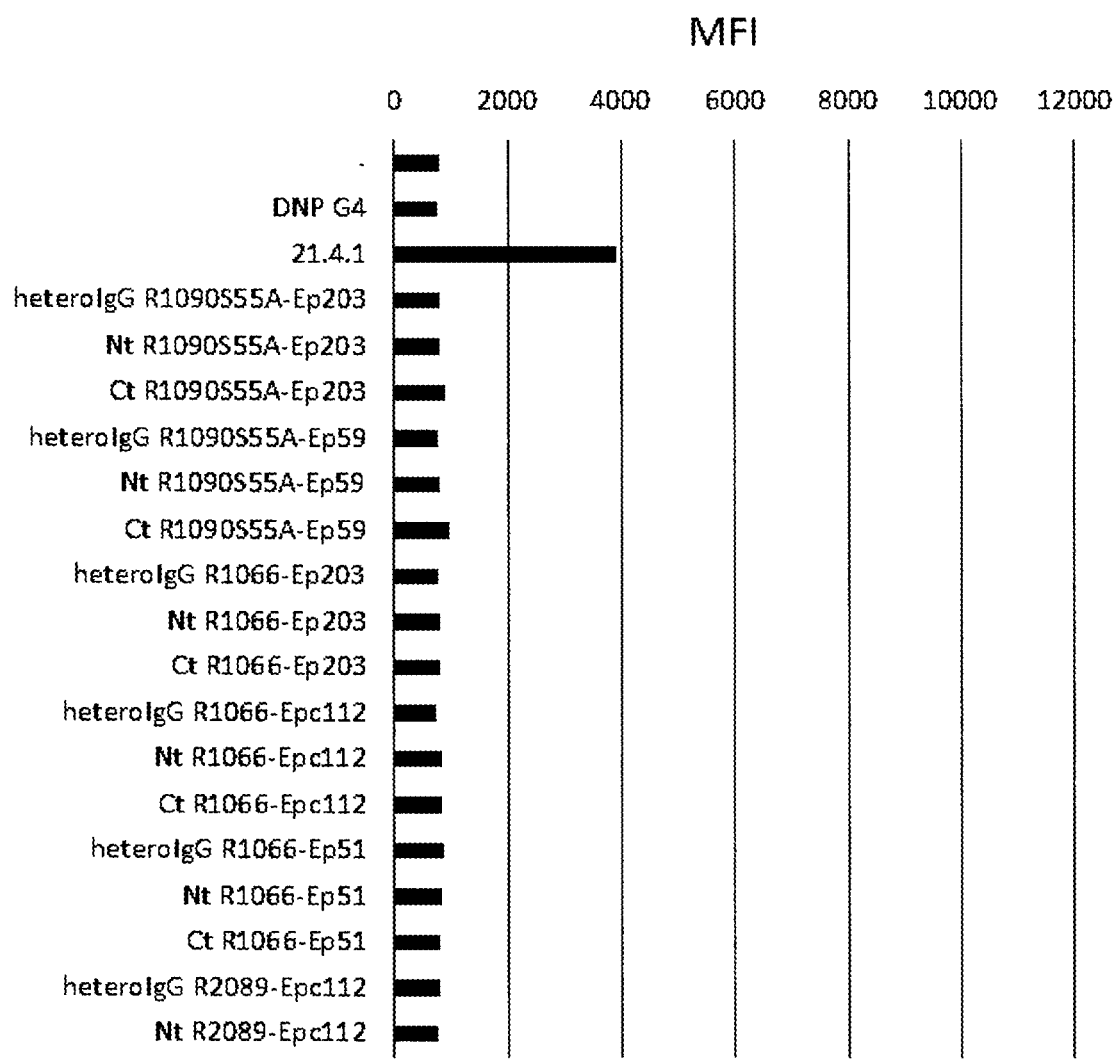
FIG. 14 shows the CD40 signal inducing activity of a CD40-EpCAM bispecific antibody against Ramos cells cocultured with Expi293 cells. The horizontal axis represents a fluorescence intensity, and shows the binding affinity of an anti-CD95 antibody to the Ramos cells when each antibody was added at 1 μg/mL. For comparison, an anti-DNP antibody was used as a negative control antibody, and 21.4.1 was used as an anti-CD40 agonistic antibody.

The results of the Ramos cells cocultured with the human EpCAM/Expi293 cells are shown in FIG. 13, and the results of the Ramos cells cocultured with the Expi293 cells are shown in FIG. 14.

As shown in FIG. 13 and FIG. 14, it was confirmed that when the Ramos cells and either of the Expi293 cells and the human EpCAM/Expi293 cells were cocultured in the presence of the anti-CD40 antibody 21.4.1 produced in Example 3, the expression level of CD95 on the Ramos cells was increased, and a signal of CD40 was induced.

As shown in FIG. 14, when the Expi293 cells that are negative for EpCAM and the Ramos cells were cocultured, any clone of the hetero-IgG type, N-terminal type, and C-terminal type CD40-EpCAM bispecific antibodies did not induce a signal of CD40.

On the other hand, as shown in FIG. 13, it was demonstrated that when the human EpCAM/Expi293 cells that are positive for EpCAM and the Ramos cells were cocultured, the expression level of CD95 on the Ramos cells was increased, and a signal of CD40 was induced by almost all the CD40-EpCAM bispecific antibodies. The strength of the signal inducing activity varies depending on the combination of the VH of the anti-CD40 antibody and the VH of the anti-EpCAM antibody, however, among the bispecific antibodies comprising the same combination of the VH of the anti-CD40 antibody and the VH of the anti-EpCAM antibody, the strength of the activity was higher in the order of the C-terminal type CD40-EpCAM bispecific antibody, the N-terminal type CD40-EpCAM bispecific antibody, and the hetero-IgG type CD40-EpCAM bispecific antibody.

Accordingly, it was demonstrated that the C-terminal type and N-terminal type CD40-EpCAM bispecific antibodies that divalently bind to each of CD40 and EpCAM have an EpCAM-dependent CD40 signal inducing activity stronger than the hetero-IgG type bispecific antibody that monovalently binds to each of CD40 and EpCAM.

Example 20

Comparison of CD40 Signal Inducing Activity of Fab-Type and F(ab)$_2$-Type Bispecific Antibody Fragments by Analysis of Expression Level of CD95 Using Flow Cytometry The CD40 signal inducing activity of the Fab-type and F(ab')2-type bispecific antibody fragments obtained in Example 17-2 against Ramos cells in the coexistence with EpCAM-positive or negative cells was evaluated by an FCM method as follows using an increase in the expression level of CD95 on the Ramos cells as an index.

The evaluation was carried out in the same manner as in Example 19 except that data were obtained at 6-point concentrations of a test antibody to be added in a 3-fold dilution series from 133.3 nM (final concentration: 66.7 nM). The results of the Ramos cells cocultured with the human EpCAM/Expi293 cells are shown in FIG. 15(A), and the results of the Ramos cells cocultured with the Expi293 cells are shown in FIG. 15(B).

Figure 15:
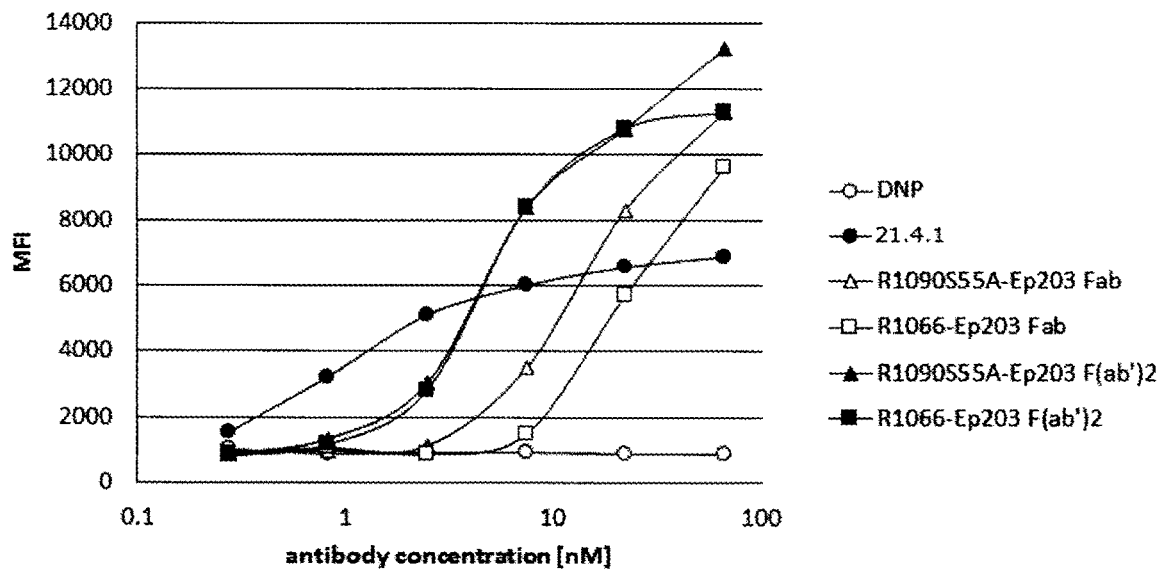
FIG. 15(A) shows the CD40 signal inducing activity of a CD40-EpCAM bispecific antibody fragment against Ramos cells cocultured with human EpCAM/Expi293 cells.
FIG. 15(B) shows the CD40 signal inducing activity of a CD40-EpCAM bispecific antibody fragment against Ramos cells cocultured with Expi293 cells. In each figure, the horizontal axis represents an antibody concentration. Further, the vertical axis represents a fluorescence intensity, and shows the binding affinity of an anti-CD95 antibody to the Ramos cells when each antibody was added. For comparison, an anti-DNP antibody was used as a negative control antibody, and 21.4.1 was used as an anti-CD40 agonistic antibody.
Figure 15:
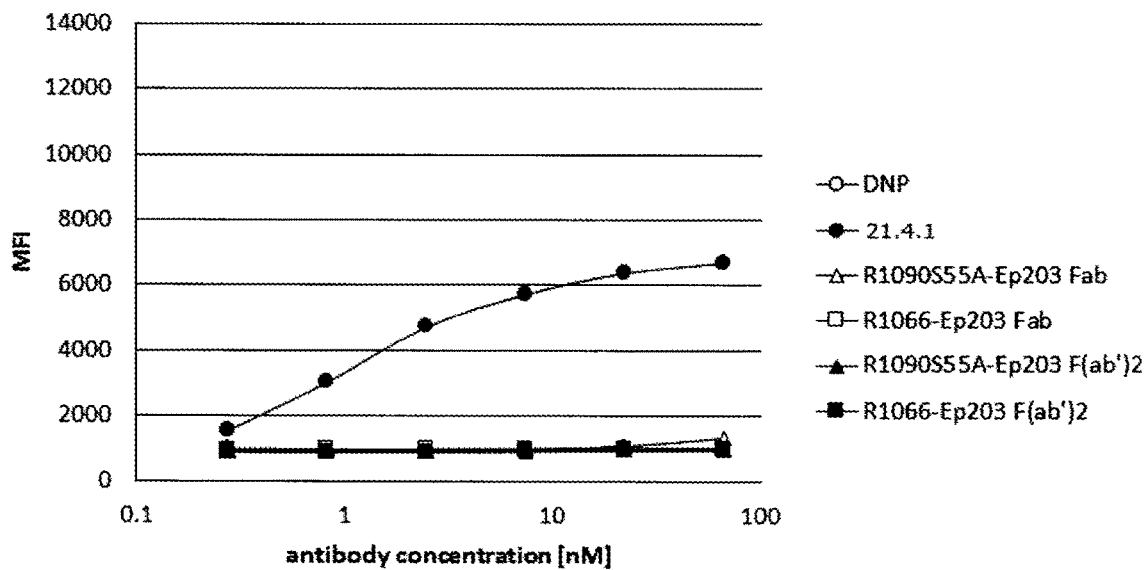

As shown in FIG. 15(A) and FIG. 15(B), it was confirmed that when the Ramos cells and either of the Expi293 cells and the human EpCAM/Expi293 cells were cocultured in the presence of the anti-CD40 antibody 21.4.1 produced in Example 3, the expression level of CD95 on the Ramos cells was increased, and a signal of CD40 was induced.

As shown in FIG. 15(B), when the Expi293 cells that are negative for EpCAM and the Ramos cells were cocultured in the presence of the Fab-type and F(ab)$_2$-type CD40-EpCAM bispecific antibody fragments, any clone did not induce a signal of CD40. On the other hand, as shown in FIG. 15(A), it was demonstrated that when the human EpCAM/Expi293 cells that are positive for EpCAM and the Ramos cells were cocultured, the expression level of CD95 on the Ramos cells was increased, and a signal of CD40 was induced by either of the Fab-type and F(ab)$_2$-type CD40-EpCAM bispecific antibody fragments. The signal inducing activity varies depending on the combination of the VH of the anti-CD40 antibody and the VH of the anti-EpCAM antibody, however, the signal inducing activity of the F(ab')$_2$-type CD40-EpCAM bispecific antibody fragment was stronger than that of the Fab-type CD40-EpCAM bispecific antibody fragment.

The F(ab)$_2$-type bispecific antibody fragment has a form similar to the structure formed by dimerization of the Fab-type bispecific antibody fragment through a disulfide bond by cysteine comprised in the hinge region. When the combination of VH1 and VH2 is the same, the amino acid sequences of the Fab-type and F(ab')2-type bispecific antibody fragments are the same except for the hinge. The F(ab')2-type bispecific antibody has a longer hinge, however, the hinge region does not have a function such as direct binding to an antigen or the like other than dimerization. Therefore, when the combination of VH1 and VH2 is the same, the difference in the EpCAM-dependent CD40 signal inducing activity between the Fab-type and F(ab')2-type bispecific antibodies is considered to be due to the difference in binding valence.

When the EpCAM-dependent CD40 signal inducing activities of the Fab-type and F(ab')2-type CD40-EpCAM bispecific antibodies were compared, the activity of the F(ab')2-type CD40-EpCAM bispecific antibody was stronger, and therefore, it is suggested that as for the EpCAM-dependent CD40 signal inducing activity, an antibody fragment that divalently binds to each of CD40 and EpCAM has a stronger activity than an antibody fragment that monovalently binds to each of CD40 and EpCAM.

While the present invention has been described in detail and with reference to specific embodiments thereof, it will be apparent to one skill in the art that various changes and modifications can be made therein without departing from the spirit and scope thereof. This application is based on Japanese Patent Application (Japanese Patent Application No. 2017-215834) filed on Nov. 8, 2017, the entire contents of which are incorporated hereinto by reference.

SEQUENCE LISTING FREE TEXT

SEQ ID NO: 23-Description of artificial sequence: amino acid sequence of LCDR1 of L6

SEQ ID NO: 24-Description of artificial sequence: amino acid sequence of LCDR2 of L6

SEQ ID NO: 25-Description of artificial sequence: amino acid sequence of LCDR3 of L6

SEQ ID NO: 28-Description of artificial sequence: amino acid sequence of HCDR1 of R1066

SEQ ID NO: 29-Description of artificial sequence: amino acid sequence of HCDR2 of R1066 SEQ ID NO: 30-Description of artificial sequence: amino acid sequence of HCDR3 of R1066

SEQ ID NO: 33-Description of artificial sequence: amino acid sequence of HCDR1 of R1090S55A SEQ ID NO: 34-Description of artificial sequence: amino acid sequence of HCDR2 of R1090S55A SEQ ID NO: 35-Description of artificial sequence: amino acid sequence of HCDR3 of R1090S55A SEQ ID NO: 38-Description of artificial sequence: amino acid sequence of HCDR1 of R2089

SEQ ID NO: 39-Description of artificial sequence: amino acid sequence of HCDR2 of R2089

SEQ ID NO: 40-Description of artificial sequence: amino acid sequence of HCDR3 of R2089

SEQ ID NO: 43-Description of artificial sequence: amino acid sequence of HCDR1 of R2178

SEQ ID NO: 44-Description of artificial sequence: amino acid sequence of HCDR2 of R2178

SEQ ID NO: 45-Description of artificial sequence: amino acid sequence of HCDR3 of R2178

SEQ ID NO: 52-Description of artificial sequence: amino acid sequence of HCDR1 of Ep59

SEQ ID NO: 53-Description of artificial sequence: amino acid sequence of HCDR2 of Ep59

SEQ ID NO: 54-Description of artificial sequence: amino acid sequence of HCDR3 of Ep59

SEQ ID NO: 70-Description of artificial sequence: nucleotide sequence of VH of 3622W94

SEQ ID NO: 71-Description of artificial sequence: amino acid sequence of synthetic construct SEQ ID NO: 72-Description of artificial sequence: nucleotide sequence of VL of 3622W94

SEQ ID NO: 73-Description of artificial sequence: amino acid sequence of synthetic construct SEQ ID NO: 74-Description of artificial sequence: nucleotide sequence of CH1 of IgG4

SEQ ID NO: 75-Description of artificial sequence: amino acid sequence of synthetic construct SEQ ID NO: 76-Description of artificial sequence: nucleotide sequence of CH of IgG4PE R409K SEQ ID NO: 77-Description of artificial sequence: amino acid sequence of synthetic construct SEQ ID NO: 78-Description of artificial sequence: nucleotide sequence of CH1 of IgG4 comprising stop codon SEQ ID NO: 79-Description of artificial sequence: nucleotide sequence of CHa of hetero-IgG type bispecific antibody SEQ ID NO: 80-Description of artificial sequence: amino acid sequence of synthetic construct SEQ ID NO: 81-Description of artificial sequence: nucleotide sequence of CHb of hetero-IgG type bispecific antibody SEQ ID NO: 82-Description of artificial sequence: amino acid sequence of synthetic construct SEQ ID NO: 83-Description of artificial sequence: nucleotide sequence of CH1-tag of Fab-type bispecific antibody SEQ ID NO: 84-Description of artificial sequence: amino acid sequence of synthetic construct SEQ ID NO: 85-Description of artificial sequence: nucleotide sequence of CH1-tag of F(ab')2-type bispecific antibody SEQ ID NO: 86-Description of artificial sequence: amino acid sequence of synthetic construct

The invention claimed is:

1. A bispecific antibody, comprising an antigen-binding domain that binds to CD40 and an antigen-binding domain that binds to an epithelial cell adhesion molecule (EpCAM), wherein the antigen-binding domain that binds to CD40 comprises a heavy chain variable region (VH) and a light chain variable region (VL) of an antibody (anti-CD40 antibody) that specifically binds to CD40, wherein the VL comprises complementarity determining regions (CDRS) 1 to 3 comprising the amino acid sequences represented by SEQ ID NOS: 23 to 25, respectively, and wherein the VH comprises CDRS 1 to 3 comprising the amino acid sequences represented by SEQ ID NOS: 33 to 35, respectively, and wherein the antigen-binding domain that binds to EpCAM comprises VH and VL of an antibody (anti- EpCAM antibody) that specifically binds to EpCAM, wherein the VL comprises CDRS 1 to 3 comprising the amino acid sequences represented by SEQ ID NOS: 23 to 25, respectively, and wherein the VH comprises CDRS 1 to 3 comprising the amino acid sequenceS represented by SEQ ID NOS: 57 to 59, respectively.

2. The bispecific antibody according to claim 1, which bivalently binds to each of CD40 and EpCAM.

3. The bispecific antibody according to claim 1, wherein the VL is VL comprising the amino acid sequence represented by SEQ ID NO: 22.

4. The bispecific antibody according to claim 1, wherein the anti-CD40 antibody is an anti-CD40 antibody comprising VH comprising the amino acid sequence represented by SEQ ID NO: 32.

5. The bispecific antibody according to claim 1, wherein the anti-EpCAM antibody is an anti-EpCAM antibody comprising VH comprising the amino acid sequence represented by SEQ ID NO: 56.

6. The bispecific antibody according to claim 1, wherein the antibody is an antibody fragment selected from the group consisting of a Fab-type bispecific antibody fragment and a F(ab')2-type bispecific antibody fragment.

7. The bispecific antibody according to claim 1, which has a CD40 agonistic activity.

8. The bispecific antibody according to claim 1, which does not exhibit a CD40 agonistic activity in the absence of a cell that expresses EpCAM, but exhibits the CD40 agonistic activity only in the presence of a cell that expresses EpCAM.

9. The bispecific antibody according to claim 1,
which has two identical heavy chains comprising a polypeptide represented by a formula of VH1-X-VH2-Y in order from the N terminus
{wherein VH1 represents VH of a first antibody,
VH2 represents VH of a second antibody,
X and Y each represents a polypeptide comprising CH1 of the antibody (wherein at least one of X and Y further comprises a hinge region of the antibody)} and
four light chains comprising the same VL, and
wherein one of the first antibody and the second antibody is the anti-CD40 antibody, and the other is the anti-EpCAM antibody.

10. The bispecific antibody according to claim 9, wherein the light chain is a κ chain.

11. The bispecific antibody according to claim 9, wherein X in the formula is a polypeptide composed of CH1 of human IgG, and Y is a polypeptide composed of CH1, a hinge region, CH2, and CH3 of human IgG.

12. The bispecific antibody according to claim 9, wherein X in the formula is a polypeptide comprising the amino acid sequence represented by SEQ ID NO: 75, and Y is a polypeptide comprising the amino acid sequence represented by SEQ ID NO: 77.

13. The bispecific antibody according to claim 9, wherein X in the formula is a polypeptide comprising CH1, a hinge region, CH2, and CH3 of human IgG, and Y is a polypeptide comprising CH1 of human IgG.

14. The bispecific antibody according to claim 9, wherein X in the formula is a polypeptide comprising the amino acid sequence represented by SEQ ID NO: 77, and Y is a polypeptide comprising the amino acid sequence represented by SEQ ID NO: 75.

15. The bispecific antibody according to claim 9, wherein the first antibody is the anti-CD40 antibody, and the second antibody is the anti-EpCAM antibody.

16. The bispecific antibody according to claim 9, wherein the first antibody is the anti-EpCAM antibody, and the second antibody is the anti-CD40 antibody.

17. The bispecific antibody according to claim 9, which bivalently binds to each of CD40 and EpCAM, wherein X in the formula is a polypeptide comprising the amino acid sequence represented by SEQ ID NO: 77, and Y is a polypeptide comprising the amino acid sequence represented by SEQ ID NO: 75, wherein the first antibody is the anti-CD40 antibody, and the second antibody is the anti-EpCAM antibody, wherein the VL is VL comprising the amino acid sequence represented by SEQ ID NO: 22, wherein the anti-CD40 antibody is an anti-CD40 antibody comprising VH comprising the amino acid sequence represented by SEQ ID NO: 32, wherein the anti-EpCAM antibody is an anti-EpCAM antibody comprising VH comprising the amino acid sequence represented by SEQ ID NO: 56.

18. The bispecific antibody according to claim 9, which bivalently binds to each of CD40 and EpCAM, wherein X in the formula is a polypeptide comprising CH1, a hinge region, CH2, and CH3 of human IgG, and Y is a polypeptide comprising CH1 of human IgG, wherein the first antibody is the anti-CD40 antibody, and the second antibody is the anti-EpCAM antibody, wherein the VL is VL comprising the amino acid sequence represented by SEQ ID NO: 22, wherein the anti-CD40 antibody is an anti-CD40 antibody comprising VH comprising the amino acid sequence represented by SEQ ID NO: 32, wherein the anti-EpCAM antibody is an anti-EpCAM antibody comprising VH comprising the amino acid sequence represented by SEQ ID NO: 56.

* * * * *

SEQUENCE LISTING

```
<160> NUMBER OF SEQ ID NOS: 86

<210> SEQ ID NO 1
<211> LENGTH: 522
<212> TYPE: DNA
<213> ORGANISM: Homo sapiens
<220> FEATURE:
<221> NAME/KEY: CDS
<222> LOCATION: (1)..(522)

<400> SEQUENCE: 1 gaa cca ccc act gca tgc aga gaa aaa cag tac cta ata aac agt cag     48
Glu Pro Pro Thr Ala Cys Arg Glu Lys Gln Tyr Leu Ile Asn Ser Gln
1               5                   10                  15 tgc tgt tct ttg tgc cag cca gga cag aaa ctg gtg agt gac tgc aca     96
Cys Cys Ser Leu Cys Gln Pro Gly Gln Lys Leu Val Ser Asp Cys Thr
            20                  25                  30 gag ttc act gaa acg gaa tgc ctt cct tgc ggt gaa agc gaa ttc cta    144
Glu Phe Thr Glu Thr Glu Cys Leu Pro Cys Gly Glu Ser Glu Phe Leu
        35                  40                  45 gac acc tgg aac aga gag aca cac tgc cac cag cac aaa tac tgc gac    192
Asp Thr Trp Asn Arg Glu Thr His Cys His Gln His Lys Tyr Cys Asp
    50                  55                  60 ccc aac cta ggg ctt cgg gtc cag cag aag ggc acc tca gaa aca gac    240
Pro Asn Leu Gly Leu Arg Val Gln Gln Lys Gly Thr Ser Glu Thr Asp
65                  70                  75                  80 acc atc tgc acc tgt gaa gaa ggc tgg cac tgt acg agt gag gcc tgt    288
Thr Ile Cys Thr Cys Glu Glu Gly Trp His Cys Thr Ser Glu Ala Cys
                85                  90                  95 gag agc tgt gtc ctg cac cgc tca tgc tcg ccc ggc ttt ggg gtc aag    336
Glu Ser Cys Val Leu His Arg Ser Cys Ser Pro Gly Phe Gly Val Lys
            100                 105                 110 cag att gct aca ggg gtt tct gat acc atc tgc gag ccc tgc cca gtc    384
Gln Ile Ala Thr Gly Val Ser Asp Thr Ile Cys Glu Pro Cys Pro Val
        115                 120                 125 ggc ttc ttc tcc aat gtg tca tct gct ttc gaa aaa tgt cac cct tgg    432
Gly Phe Phe Ser Asn Val Ser Ser Ala Phe Glu Lys Cys His Pro Trp
    130                 135                 140
```

| | |
|---|---|
| aca agc tgt gag acc aaa gac ctg gtt gtg caa cag gca ggc aca aac<br>Thr Ser Cys Glu Thr Lys Asp Leu Val Val Gln Gln Ala Gly Thr Asn<br>145                  150                      155                  160 | 480 |
| aag act gat gtt gtc tgt ggt ccc cag gat cgg ctg aga gcc<br>Lys Thr Asp Val Val Cys Gly Pro Gln Asp Arg Leu Arg Ala<br>                  165                      170 | 522 |

<210> SEQ ID NO 2
<211> LENGTH: 174
<212> TYPE: PRT
<213> ORGANISM: Homo sapiens

<400> SEQUENCE: 2

Glu Pro Pro Thr Ala Cys Arg Glu Lys Gln Tyr Leu Ile Asn Ser Gln
1                  5                      10                  15

Cys Cys Ser Leu Cys Gln Pro Gly Gln Lys Leu Val Ser Asp Cys Thr
                  20                      25                      30

Glu Phe Thr Glu Thr Glu Cys Leu Pro Cys Gly Glu Ser Glu Phe Leu
                  35                      40                      45

Asp Thr Trp Asn Arg Glu Thr His Cys His Gln His Lys Tyr Cys Asp
    50                      55                      60

Pro Asn Leu Gly Leu Arg Val Gln Gln Lys Gly Thr Ser Glu Thr Asp
65                  70                      75                  80

Thr Ile Cys Thr Cys Glu Glu Gly Trp His Cys Thr Ser Glu Ala Cys
                  85                      90                      95

Glu Ser Cys Val Leu His Arg Ser Cys Ser Pro Gly Phe Gly Val Lys
                  100                    105                    110

Gln Ile Ala Thr Gly Val Ser Asp Thr Ile Cys Glu Pro Cys Pro Val
            115                    120                    125

Gly Phe Phe Ser Asn Val Ser Ser Ala Phe Glu Lys Cys His Pro Trp
        130                    135                    140

Thr Ser Cys Glu Thr Lys Asp Leu Val Val Gln Gln Ala Gly Thr Asn
145                  150                      155                  160

Lys Thr Asp Val Val Cys Gly Pro Gln Asp Arg Leu Arg Ala
                  165                    170

<210> SEQ ID NO 3
<211> LENGTH: 522
<212> TYPE: DNA
<213> ORGANISM: Macaca fascicularis
<220> FEATURE:
<221> NAME/KEY: CDS
<222> LOCATION: (1)..(522)

<400> SEQUENCE: 3

| | |
|---|---|
| gaa cca ccc act gca tgc aga gaa aaa cag tac cta ata aac agt cag<br>Glu Pro Pro Thr Ala Cys Arg Glu Lys Gln Tyr Leu Ile Asn Ser Gln<br>1                  5                      10                  15 | 48 |
| tgc tgt tct ttg tgc cag cca gga cag aaa ctg gtg agt gac tgc aca<br>Cys Cys Ser Leu Cys Gln Pro Gly Gln Lys Leu Val Ser Asp Cys Thr<br>                  20                      25                      30 | 96 |
| gag ttc acc gaa aca gaa tgc ctt cct tgc ggt gaa agc gaa ttc cta<br>Glu Phe Thr Glu Thr Glu Cys Leu Pro Cys Gly Glu Ser Glu Phe Leu<br>                  35                      40                      45 | 144 |
| gac acc tgg aat aga gag aca cgc tgc cac cag cac aaa tac tgc gac<br>Asp Thr Trp Asn Arg Glu Thr Arg Cys His Gln His Lys Tyr Cys Asp<br>    50                      55                      60 | 192 |
| ccc aac cta ggg ctt cgg gtc cag cag aag ggc acc tca gaa aca gac<br>Pro Asn Leu Gly Leu Arg Val Gln Gln Lys Gly Thr Ser Glu Thr Asp | 240 |

```
              65                  70                  75                  80
acc atc tgc acc tgt gaa gaa ggc ctg cac tgt acg agt gag tcc tgt        288
Thr Ile Cys Thr Cys Glu Glu Gly Leu His Cys Thr Ser Glu Ser Cys
                85                  90                  95 gag agc tgt gtc ccg cac cgc tca tgc ttg cct ggc ttt ggg gtc aag        336
Glu Ser Cys Val Pro His Arg Ser Cys Leu Pro Gly Phe Gly Val Lys
            100                 105                 110 cag att gct aca ggg gtt tct gat acc atc tgt gag ccc tgc ccg gtc        384
Gln Ile Ala Thr Gly Val Ser Asp Thr Ile Cys Glu Pro Cys Pro Val
        115                 120                 125 ggc ttc ttc tcc aat gtg tca tct gct ttt gaa aag tgt cgc cct tgg        432
Gly Phe Phe Ser Asn Val Ser Ser Ala Phe Glu Lys Cys Arg Pro Trp
    130                 135                 140 aca agc tgt gag acc aaa gac ctg gtt gtg caa cag gca ggc aca aac        480
Thr Ser Cys Glu Thr Lys Asp Leu Val Val Gln Gln Ala Gly Thr Asn
145                 150                 155                 160 aag act gat gtt gtc tgt ggt ccc cag gat cgg cag aga gcc                522
Lys Thr Asp Val Val Cys Gly Pro Gln Asp Arg Gln Arg Ala
                165                 170

<210> SEQ ID NO 4
<211> LENGTH: 174
<212> TYPE: PRT
<213> ORGANISM: Macaca fascicularis

<400> SEQUENCE: 4

Glu Pro Pro Thr Ala Cys Arg Glu Lys Gln Tyr Leu Ile Asn Ser Gln
1               5                   10                  15

Cys Cys Ser Leu Cys Gln Pro Gly Gln Lys Leu Val Ser Asp Cys Thr
            20                  25                  30

Glu Phe Thr Glu Thr Glu Cys Leu Pro Cys Gly Glu Ser Glu Phe Leu
        35                  40                  45

Asp Thr Trp Asn Arg Glu Thr Arg Cys His Gln His Lys Tyr Cys Asp
    50                  55                  60

Pro Asn Leu Gly Leu Arg Val Gln Gln Lys Gly Thr Ser Glu Thr Asp
65                  70                  75                  80

Thr Ile Cys Thr Cys Glu Glu Gly Leu His Cys Thr Ser Glu Ser Cys
                85                  90                  95

Glu Ser Cys Val Pro His Arg Ser Cys Leu Pro Gly Phe Gly Val Lys
            100                 105                 110

Gln Ile Ala Thr Gly Val Ser Asp Thr Ile Cys Glu Pro Cys Pro Val
        115                 120                 125

Gly Phe Phe Ser Asn Val Ser Ser Ala Phe Glu Lys Cys Arg Pro Trp
    130                 135                 140

Thr Ser Cys Glu Thr Lys Asp Leu Val Val Gln Gln Ala Gly Thr Asn
145                 150                 155                 160

Lys Thr Asp Val Val Cys Gly Pro Gln Asp Arg Gln Arg Ala
                165                 170

<210> SEQ ID NO 5
<211> LENGTH: 834
<212> TYPE: DNA
<213> ORGANISM: Homo sapiens
<220> FEATURE:
<221> NAME/KEY: CDS
<222> LOCATION: (1)..(834)

<400> SEQUENCE: 5 atg gtt cgt ctg cct ctg cag tgc gtc ctc tgg ggc tgc ttg ctg acc         48
```

```
                Met Val Arg Leu Pro Leu Gln Cys Val Leu Trp Gly Cys Leu Leu Thr
                1               5                   10                  15 gct gtc cat cca gaa cca ccc act gca tgc aga gaa aaa cag tac cta            96
Ala Val His Pro Glu Pro Pro Thr Ala Cys Arg Glu Lys Gln Tyr Leu
            20                  25                  30 ata aac agt cag tgc tgt tct ttg tgc cag cca gga cag aaa ctg gtg           144
Ile Asn Ser Gln Cys Cys Ser Leu Cys Gln Pro Gly Gln Lys Leu Val
        35                  40                  45 agt gac tgc aca gag ttc act gaa acg gaa tgc ctt cct tgc ggt gaa           192
Ser Asp Cys Thr Glu Phe Thr Glu Thr Glu Cys Leu Pro Cys Gly Glu
    50                  55                  60 agc gaa ttc cta gac acc tgg aac aga gag aca cac tgc cac cag cac           240
Ser Glu Phe Leu Asp Thr Trp Asn Arg Glu Thr His Cys His Gln His
65                  70                  75                  80 aaa tac tgc gac ccc aac cta ggg ctt cgg gtc cag cag aag ggc acc           288
Lys Tyr Cys Asp Pro Asn Leu Gly Leu Arg Val Gln Gln Lys Gly Thr
                85                  90                  95 tca gaa aca gac acc atc tgc acc tgt gaa gaa ggc tgg cac tgt acg           336
Ser Glu Thr Asp Thr Ile Cys Thr Cys Glu Glu Gly Trp His Cys Thr
            100                 105                 110 agt gag gcc tgt gag agc tgt gtc ctg cac cgc tca tgc tcg ccc ggc           384
Ser Glu Ala Cys Glu Ser Cys Val Leu His Arg Ser Cys Ser Pro Gly
        115                 120                 125 ttt ggg gtc aag cag att gct aca ggg gtt tct gat acc atc tgc gag           432
Phe Gly Val Lys Gln Ile Ala Thr Gly Val Ser Asp Thr Ile Cys Glu
    130                 135                 140 ccc tgc cca gtc ggc ttc ttc tcc aat gtg tca tct gct ttc gaa aaa           480
Pro Cys Pro Val Gly Phe Phe Ser Asn Val Ser Ser Ala Phe Glu Lys
145                 150                 155                 160 tgt cac cct tgg aca agc tgt gag acc aaa gac ctg gtt gtg caa cag           528
Cys His Pro Trp Thr Ser Cys Glu Thr Lys Asp Leu Val Val Gln Gln
                165                 170                 175 gca ggc aca aac aag act gat gtt gtc tgt ggt ccc cag gat cgg ctg           576
Ala Gly Thr Asn Lys Thr Asp Val Val Cys Gly Pro Gln Asp Arg Leu
            180                 185                 190 aga gcc ctg gtg gtg atc ccc atc atc ttc ggg atc ctg ttt gcc atc           624
Arg Ala Leu Val Val Ile Pro Ile Ile Phe Gly Ile Leu Phe Ala Ile
        195                 200                 205 ctc ttg gtg ctg gtc ttt atc aaa aag gtg gcc aag aag cca acc aat           672
Leu Leu Val Leu Val Phe Ile Lys Lys Val Ala Lys Lys Pro Thr Asn
    210                 215                 220 aag gcc ccc cac ccc aag cag gaa ccc cag gag atc aat ttt ccc gac           720
Lys Ala Pro His Pro Lys Gln Glu Pro Gln Glu Ile Asn Phe Pro Asp
225                 230                 235                 240 gat ctt cct ggc tcc aac act gct gct cca gtg cag gag act tta cat           768
Asp Leu Pro Gly Ser Asn Thr Ala Ala Pro Val Gln Glu Thr Leu His
                245                 250                 255 gga tgc caa ccg gtc acc cag gag gat ggc aaa gag agt cgc atc tca           816
Gly Cys Gln Pro Val Thr Gln Glu Asp Gly Lys Glu Ser Arg Ile Ser
            260                 265                 270 gtg cag gag aga cag tga                                                   834
Val Gln Glu Arg Gln
        275
```

<210> SEQ ID NO 6
<211> LENGTH: 277
<212> TYPE: PRT
<213> ORGANISM: Homo sapiens

<400> SEQUENCE: 6

```
Met Val Arg Leu Pro Leu Gln Cys Val Leu Trp Gly Cys Leu Leu Thr
1               5                   10                  15

Ala Val His Pro Glu Pro Pro Thr Ala Cys Arg Glu Lys Gln Tyr Leu
            20                  25                  30

Ile Asn Ser Gln Cys Cys Ser Leu Cys Gln Pro Gly Gln Lys Leu Val
            35                  40                  45

Ser Asp Cys Thr Glu Phe Thr Glu Thr Glu Cys Leu Pro Cys Gly Glu
50                  55                  60

Ser Glu Phe Leu Asp Thr Trp Asn Arg Glu Thr His Cys His Gln His
65                  70                  75                  80

Lys Tyr Cys Asp Pro Asn Leu Gly Leu Arg Val Gln Gln Lys Gly Thr
                85                  90                  95

Ser Glu Thr Asp Thr Ile Cys Thr Cys Glu Glu Gly Trp His Cys Thr
            100                 105                 110

Ser Glu Ala Cys Glu Ser Cys Val Leu His Arg Ser Cys Ser Pro Gly
            115                 120                 125

Phe Gly Val Lys Gln Ile Ala Thr Gly Val Ser Asp Thr Ile Cys Glu
130                 135                 140

Pro Cys Pro Val Gly Phe Phe Ser Asn Val Ser Ser Ala Phe Glu Lys
145                 150                 155                 160

Cys His Pro Trp Thr Ser Cys Glu Thr Lys Asp Leu Val Val Gln Gln
                165                 170                 175

Ala Gly Thr Asn Lys Thr Asp Val Val Cys Gly Pro Gln Asp Arg Leu
            180                 185                 190

Arg Ala Leu Val Val Ile Pro Ile Ile Phe Gly Ile Leu Phe Ala Ile
            195                 200                 205

Leu Leu Val Leu Val Phe Ile Lys Lys Val Ala Lys Lys Pro Thr Asn
            210                 215                 220

Lys Ala Pro His Pro Lys Gln Glu Pro Gln Glu Ile Asn Phe Pro Asp
225                 230                 235                 240

Asp Leu Pro Gly Ser Asn Thr Ala Ala Pro Val Gln Glu Thr Leu His
                245                 250                 255

Gly Cys Gln Pro Val Thr Gln Glu Asp Gly Lys Glu Ser Arg Ile Ser
                260                 265                 270

Val Gln Glu Arg Gln
        275

<210> SEQ ID NO 7
<211> LENGTH: 849
<212> TYPE: DNA
<213> ORGANISM: Macaca fascicularis
<220> FEATURE:
<221> NAME/KEY: CDS
<222> LOCATION: (1)..(849)

<400> SEQUENCE: 7 atg gtt cgt ctg cct ctg cag tgc gtc ctc tgg ggc tgc ttg ctg acc    48
Met Val Arg Leu Pro Leu Gln Cys Val Leu Trp Gly Cys Leu Leu Thr
1               5                   10                  15 gct gtc tat cca gaa cca ccc act gca tgc aga gaa aaa cag tac cta    96
Ala Val Tyr Pro Glu Pro Pro Thr Ala Cys Arg Glu Lys Gln Tyr Leu
            20                  25                  30 ata aac agt cag tgc tgt tct ttg tgc cag cca gga cag aaa ctg gtg    144
Ile Asn Ser Gln Cys Cys Ser Leu Cys Gln Pro Gly Gln Lys Leu Val
            35                  40                  45 agt gac tgc aca gag ttc acc gaa aca gaa tgc ctt cct tgc ggt gaa    192
Ser Asp Cys Thr Glu Phe Thr Glu Thr Glu Cys Leu Pro Cys Gly Glu
```

```
                       50                  55                  60
agc gaa ttc cta gac acc tgg aat aga gag aca cgc tgc cac cag cac       240
Ser Glu Phe Leu Asp Thr Trp Asn Arg Glu Thr Arg Cys His Gln His
 65                  70                  75                  80 aaa tac tgc gac ccc aac cta ggg ctt cgg gtc cag cag aag ggc acc       288
Lys Tyr Cys Asp Pro Asn Leu Gly Leu Arg Val Gln Gln Lys Gly Thr
                 85                  90                  95 tca gaa aca gac acc atc tgc acc tgt gaa gaa ggc ctg cac tgt acg       336
Ser Glu Thr Asp Thr Ile Cys Thr Cys Glu Glu Gly Leu His Cys Thr
            100                 105                 110 agt gag tcc tgt gag agc tgt gtc ccg cac cgc tca tgc ttg cct ggc       384
Ser Glu Ser Cys Glu Ser Cys Val Pro His Arg Ser Cys Leu Pro Gly
        115                 120                 125 ttt ggg gtc aag cag att gct aca ggg gtt tct gat acc atc tgt gag       432
Phe Gly Val Lys Gln Ile Ala Thr Gly Val Ser Asp Thr Ile Cys Glu
    130                 135                 140 ccc tgc ccg gtc ggc ttc ttc tcc aat gtg tca tct gct ttt gaa aag       480
Pro Cys Pro Val Gly Phe Phe Ser Asn Val Ser Ser Ala Phe Glu Lys
145                 150                 155                 160 tgt cgc cct tgg aca agc tgt gag acc aaa gac ctg gtt gtg caa cag       528
Cys Arg Pro Trp Thr Ser Cys Glu Thr Lys Asp Leu Val Val Gln Gln
                165                 170                 175 gca ggc aca aac aag act gat gtt gtc tgt ggt ccc cag gat cgg cag       576
Ala Gly Thr Asn Lys Thr Asp Val Val Cys Gly Pro Gln Asp Arg Gln
            180                 185                 190 aga gcc ctg gtg gtg atc ccc atc tgc ttg ggg atc ctg ttt gtc atc       624
Arg Ala Leu Val Val Ile Pro Ile Cys Leu Gly Ile Leu Phe Val Ile
        195                 200                 205 ctc ctc ttg gtg ctg gtc ttt atc agt gag tcc tca gaa aag gtg gcc       672
Leu Leu Leu Val Leu Val Phe Ile Ser Glu Ser Ser Glu Lys Val Ala
    210                 215                 220 aag aag cca aac gat aag gcc ccc cac ccc aag cag gaa ccc cag gag       720
Lys Lys Pro Asn Asp Lys Ala Pro His Pro Lys Gln Glu Pro Gln Glu
225                 230                 235                 240 atc aat ttt ctg gac gat ctt cct ggc tcc aac cct gcc gct cca gtg       768
Ile Asn Phe Leu Asp Asp Leu Pro Gly Ser Asn Pro Ala Ala Pro Val
                245                 250                 255 cag gag act tta cat gga tgc caa ccg gtc acc cag gag gat ggc aaa       816
Gln Glu Thr Leu His Gly Cys Gln Pro Val Thr Gln Glu Asp Gly Lys
            260                 265                 270 gag agt cgc atc tca gtg cag gag aga cag tga                          849
Glu Ser Arg Ile Ser Val Gln Glu Arg Gln
        275                 280

<210> SEQ ID NO 8
<211> LENGTH: 282
<212> TYPE: PRT
<213> ORGANISM: Macaca fascicularis

<400> SEQUENCE: 8

Met Val Arg Leu Pro Leu Gln Cys Val Leu Trp Gly Cys Leu Leu Thr
 1               5                  10                  15

Ala Val Tyr Pro Glu Pro Pro Thr Ala Cys Arg Glu Lys Gln Tyr Leu
            20                  25                  30

Ile Asn Ser Gln Cys Cys Ser Leu Cys Gln Pro Gly Gln Lys Leu Val
        35                  40                  45

Ser Asp Cys Thr Glu Phe Thr Glu Thr Glu Cys Leu Pro Cys Gly Glu
    50                  55                  60

Ser Glu Phe Leu Asp Thr Trp Asn Arg Glu Thr Arg Cys His Gln His
```

```
                65                  70                  75                  80
Lys Tyr Cys Asp Pro Asn Leu Gly Leu Arg Val Gln Gln Lys Gly Thr
                    85                  90                  95

Ser Glu Thr Asp Thr Ile Cys Thr Cys Glu Glu Gly Leu His Cys Thr
                100                 105                 110

Ser Glu Ser Cys Glu Ser Cys Val Pro His Arg Ser Cys Leu Pro Gly
                115                 120                 125

Phe Gly Val Lys Gln Ile Ala Thr Gly Val Ser Asp Thr Ile Cys Glu
            130                 135                 140

Pro Cys Pro Val Gly Phe Phe Ser Asn Val Ser Ser Ala Phe Glu Lys
145                 150                 155                 160

Cys Arg Pro Trp Thr Ser Cys Glu Thr Lys Asp Leu Val Val Gln Gln
                165                 170                 175

Ala Gly Thr Asn Lys Thr Asp Val Val Cys Gly Pro Gln Asp Arg Gln
                180                 185                 190

Arg Ala Leu Val Val Ile Pro Ile Cys Leu Gly Ile Leu Phe Val Ile
                195                 200                 205

Leu Leu Leu Val Leu Val Phe Ile Ser Glu Ser Ser Glu Lys Val Ala
            210                 215                 220

Lys Lys Pro Asn Asp Lys Ala Pro His Pro Lys Gln Glu Pro Gln Glu
225                 230                 235                 240

Ile Asn Phe Leu Asp Asp Leu Pro Gly Ser Asn Pro Ala Ala Pro Val
                245                 250                 255

Gln Glu Thr Leu His Gly Cys Gln Pro Val Thr Gln Glu Asp Gly Lys
                260                 265                 270

Glu Ser Arg Ile Ser Val Gln Glu Arg Gln
                275                 280

<210> SEQ ID NO 9
<211> LENGTH: 732
<212> TYPE: DNA
<213> ORGANISM: Homo sapiens
<220> FEATURE:
<221> NAME/KEY: CDS
<222> LOCATION: (1)..(732)

<400> SEQUENCE: 9 gca gct cag gaa gaa tgt gtc tgt gaa aac tac aag ctg gcc gta aac      48
Ala Ala Gln Glu Glu Cys Val Cys Glu Asn Tyr Lys Leu Ala Val Asn
1               5                   10                  15 tgc ttt gtg aat aat aat cgt caa tgc cag tgt act tca gtt ggt gca      96
Cys Phe Val Asn Asn Asn Arg Gln Cys Gln Cys Thr Ser Val Gly Ala
                20                  25                  30 caa aat act gtc att tgc tca aag ctg gct gcc aaa tgt ttg gtg atg     144
Gln Asn Thr Val Ile Cys Ser Lys Leu Ala Ala Lys Cys Leu Val Met
            35                  40                  45 aag gca gaa atg aat ggc tca aaa ctt ggg aga aga gca aaa cct gaa     192
Lys Ala Glu Met Asn Gly Ser Lys Leu Gly Arg Arg Ala Lys Pro Glu
        50                  55                  60 ggg gcc ctc cag aac aat gat ggg ctt tat gat cct gac tgc gat gag     240
Gly Ala Leu Gln Asn Asn Asp Gly Leu Tyr Asp Pro Asp Cys Asp Glu
65                  70                  75                  80 agc ggg ctc ttt aag gcc aag cag tgc aac ggc acc tcc acg tgc tgg     288
Ser Gly Leu Phe Lys Ala Lys Gln Cys Asn Gly Thr Ser Thr Cys Trp
                85                  90                  95 tgt gtg aac act gct ggg gtc aga aga aca gac aag gac act gaa ata     336
Cys Val Asn Thr Ala Gly Val Arg Arg Thr Asp Lys Asp Thr Glu Ile
                100                 105                 110
```

```
acc tgc tct gag cga gtg aga acc tac tgg atc atc att gaa cta aaa      384
Thr Cys Ser Glu Arg Val Arg Thr Tyr Trp Ile Ile Ile Glu Leu Lys
        115                 120                 125 cac aaa gca aga gaa aaa cct tat gat agt aaa agt ttg cgg act gca      432
His Lys Ala Arg Glu Lys Pro Tyr Asp Ser Lys Ser Leu Arg Thr Ala
130                 135                 140 ctt cag aag gag atc aca acg cgt tat caa ctg gat cca aaa ttt atc      480
Leu Gln Lys Glu Ile Thr Thr Arg Tyr Gln Leu Asp Pro Lys Phe Ile
145                 150                 155                 160 acg agt att ttg tat gag aat aat gtt atc act att gat ctg gtt caa      528
Thr Ser Ile Leu Tyr Glu Asn Asn Val Ile Thr Ile Asp Leu Val Gln
                165                 170                 175 aat tct tct caa aaa act cag aat gat gtg gac ata gct gat gtg gct      576
Asn Ser Ser Gln Lys Thr Gln Asn Asp Val Asp Ile Ala Asp Val Ala
            180                 185                 190 tat tat ttt gaa aaa gat gtt aaa ggt gaa tcc ttg ttt cat tct aag      624
Tyr Tyr Phe Glu Lys Asp Val Lys Gly Glu Ser Leu Phe His Ser Lys
            195                 200                 205 aaa atg gac ctg aca gta aat ggg gaa caa ctg gat ctg gat cct ggt      672
Lys Met Asp Leu Thr Val Asn Gly Glu Gln Leu Asp Leu Asp Pro Gly
210                 215                 220 caa act tta att tat tat gtt gat gaa aaa gca cct gaa ttc tca atg      720
Gln Thr Leu Ile Tyr Tyr Val Asp Glu Lys Ala Pro Glu Phe Ser Met
225                 230                 235                 240 cag ggt cta aaa                                                      732
Gln Gly Leu Lys <210> SEQ ID NO 10
<211> LENGTH: 244
<212> TYPE: PRT
<213> ORGANISM: Homo sapiens

<400> SEQUENCE: 10

Ala Ala Gln Glu Glu Cys Val Cys Glu Asn Tyr Lys Leu Ala Val Asn
1               5                   10                  15

Cys Phe Val Asn Asn Asn Arg Gln Cys Gln Cys Thr Ser Val Gly Ala
            20                  25                  30

Gln Asn Thr Val Ile Cys Ser Lys Leu Ala Ala Lys Cys Leu Val Met
        35                  40                  45

Lys Ala Glu Met Asn Gly Ser Lys Leu Gly Arg Arg Ala Lys Pro Glu
    50                  55                  60

Gly Ala Leu Gln Asn Asn Asp Gly Leu Tyr Asp Pro Asp Cys Asp Glu
65                  70                  75                  80

Ser Gly Leu Phe Lys Ala Lys Gln Cys Asn Gly Thr Ser Thr Cys Trp
                85                  90                  95

Cys Val Asn Thr Ala Gly Val Arg Arg Thr Asp Lys Asp Thr Glu Ile
            100                 105                 110

Thr Cys Ser Glu Arg Val Arg Thr Tyr Trp Ile Ile Ile Glu Leu Lys
        115                 120                 125

His Lys Ala Arg Glu Lys Pro Tyr Asp Ser Lys Ser Leu Arg Thr Ala
    130                 135                 140

Leu Gln Lys Glu Ile Thr Thr Arg Tyr Gln Leu Asp Pro Lys Phe Ile
145                 150                 155                 160

Thr Ser Ile Leu Tyr Glu Asn Asn Val Ile Thr Ile Asp Leu Val Gln
                165                 170                 175

Asn Ser Ser Gln Lys Thr Gln Asn Asp Val Asp Ile Ala Asp Val Ala
            180                 185                 190
```

```
Tyr Tyr Phe Glu Lys Asp Val Lys Gly Glu Ser Leu Phe His Ser Lys
        195                 200                 205

Lys Met Asp Leu Thr Val Asn Gly Glu Gln Leu Asp Leu Asp Pro Gly
    210                 215                 220

Gln Thr Leu Ile Tyr Tyr Val Asp Glu Lys Ala Pro Glu Phe Ser Met
225                 230                 235                 240

Gln Gly Leu Lys

<210> SEQ ID NO 11
<211> LENGTH: 732
<212> TYPE: DNA
<213> ORGANISM: Macaca fascicularis
<220> FEATURE:
<221> NAME/KEY: CDS
<222> LOCATION: (1)..(732)

<400> SEQUENCE: 11 gca gct cag aaa gaa tgt gtc tgt gaa aac tac aag ctg gcc gta aac     48
Ala Ala Gln Lys Glu Cys Val Cys Glu Asn Tyr Lys Leu Ala Val Asn
1               5                   10                  15 tgc ttt ttg aat gac aat ggt caa tgc cag tgt act tcg att ggt gca    96
Cys Phe Leu Asn Asp Asn Gly Gln Cys Gln Cys Thr Ser Ile Gly Ala
            20                  25                  30 caa aat act gtc ctt tgc tca aag ctg gct gcc aaa tgt ttg gtg atg   144
Gln Asn Thr Val Leu Cys Ser Lys Leu Ala Ala Lys Cys Leu Val Met
        35                  40                  45 aag gca gaa atg aac ggc tca aaa ctt ggg aga aga gcg aaa cct gaa   192
Lys Ala Glu Met Asn Gly Ser Lys Leu Gly Arg Arg Ala Lys Pro Glu
    50                  55                  60 ggg gct ctc cag aac aat gat ggc ctt tac gat cct gac tgc gat gag   240
Gly Ala Leu Gln Asn Asn Asp Gly Leu Tyr Asp Pro Asp Cys Asp Glu
65                  70                  75                  80 agc ggg ctc ttt aag gcc aag cag tgc aac ggc acc tcc acg tgc tgg   288
Ser Gly Leu Phe Lys Ala Lys Gln Cys Asn Gly Thr Ser Thr Cys Trp
                85                  90                  95 tgt gtg aac act gct ggg gtc aga aga act gac aag gac act gaa ata   336
Cys Val Asn Thr Ala Gly Val Arg Arg Thr Asp Lys Asp Thr Glu Ile
            100                 105                 110 acc tgc tct gag cga gtg aga acc tac tgg atc atc att gaa tta aaa   384
Thr Cys Ser Glu Arg Val Arg Thr Tyr Trp Ile Ile Ile Glu Leu Lys
        115                 120                 125 cac aaa gca aga gaa aaa cct tat gat gtt caa agt ttg cgg act gca   432
His Lys Ala Arg Glu Lys Pro Tyr Asp Val Gln Ser Leu Arg Thr Ala
    130                 135                 140 ctt gag gag gcg atc aaa acg cgt tat caa ctg gat cca aaa ttt atc   480
Leu Glu Glu Ala Ile Lys Thr Arg Tyr Gln Leu Asp Pro Lys Phe Ile
145                 150                 155                 160 aca aat att ttg tat gag gat aat gtt atc act att gat ctg gtt caa   528
Thr Asn Ile Leu Tyr Glu Asp Asn Val Ile Thr Ile Asp Leu Val Gln
                165                 170                 175 aat tct tct cag aaa act cag aat gat gtg gac ata gct gat gtg gct   576
Asn Ser Ser Gln Lys Thr Gln Asn Asp Val Asp Ile Ala Asp Val Ala
            180                 185                 190 tat tat ttt gaa aaa gat gtt aaa ggt gaa tcc ttg ttt cat tct aag   624
Tyr Tyr Phe Glu Lys Asp Val Lys Gly Glu Ser Leu Phe His Ser Lys
        195                 200                 205 aaa atg gac ctg aga gta aat ggg gaa caa ctg gat ctg gat cct ggt   672
Lys Met Asp Leu Arg Val Asn Gly Glu Gln Leu Asp Leu Asp Pro Gly
    210                 215                 220
```

```
caa act tta att tat tat gtc gat gaa aaa gca cct gaa ttc tca atg      720
Gln Thr Leu Ile Tyr Tyr Val Asp Glu Lys Ala Pro Glu Phe Ser Met
225             230                 235                 240 cag ggt cta aaa                                                      732
Gln Gly Leu Lys
```

<210> SEQ ID NO 12
<211> LENGTH: 244
<212> TYPE: PRT
<213> ORGANISM: Macaca fascicularis

<400> SEQUENCE: 12

```
Ala Ala Gln Lys Glu Cys Val Cys Glu Asn Tyr Lys Leu Ala Val Asn
1               5                   10                  15

Cys Phe Leu Asn Asp Asn Gly Gln Cys Gln Cys Thr Ser Ile Gly Ala
                20                  25                  30

Gln Asn Thr Val Leu Cys Ser Lys Leu Ala Ala Lys Cys Leu Val Met
            35                  40                  45

Lys Ala Glu Met Asn Gly Ser Lys Leu Gly Arg Arg Ala Lys Pro Glu
        50                  55                  60

Gly Ala Leu Gln Asn Asn Asp Gly Leu Tyr Asp Pro Asp Cys Asp Glu
65                  70                  75                  80

Ser Gly Leu Phe Lys Ala Lys Gln Cys Asn Gly Thr Ser Thr Cys Trp
                85                  90                  95

Cys Val Asn Thr Ala Gly Val Arg Arg Thr Asp Lys Asp Thr Glu Ile
                100                 105                 110

Thr Cys Ser Glu Arg Val Arg Thr Tyr Trp Ile Ile Ile Glu Leu Lys
            115                 120                 125

His Lys Ala Arg Glu Lys Pro Tyr Asp Val Gln Ser Leu Arg Thr Ala
130                 135                 140

Leu Glu Glu Ala Ile Lys Thr Arg Tyr Gln Leu Asp Pro Lys Phe Ile
145                 150                 155                 160

Thr Asn Ile Leu Tyr Glu Asp Asn Val Ile Thr Ile Asp Leu Val Gln
                165                 170                 175

Asn Ser Ser Gln Lys Thr Gln Asn Asp Val Asp Ile Ala Asp Val Ala
            180                 185                 190

Tyr Tyr Phe Glu Lys Asp Val Lys Gly Glu Ser Leu Phe His Ser Lys
        195                 200                 205

Lys Met Asp Leu Arg Val Asn Gly Glu Gln Leu Asp Leu Asp Pro Gly
    210                 215                 220

Gln Thr Leu Ile Tyr Tyr Val Asp Glu Lys Ala Pro Glu Phe Ser Met
225                 230                 235                 240

Gln Gly Leu Lys
```

<210> SEQ ID NO 13
<211> LENGTH: 735
<212> TYPE: DNA
<213> ORGANISM: Mus musculus
<220> FEATURE:
<221> NAME/KEY: CDS
<222> LOCATION: (1)..(735)

<400> SEQUENCE: 13

```
gcg gct cag aga gac tgt gtc tgt gac aac tac aag ctg gca aca agt       48
Ala Ala Gln Arg Asp Cys Val Cys Asp Asn Tyr Lys Leu Ala Thr Ser
1               5                   10                  15 tgc tct ctg aat gaa tat ggt gaa tgc cag tgt act tcc tat ggt aca       96
Cys Ser Leu Asn Glu Tyr Gly Glu Cys Gln Cys Thr Ser Tyr Gly Thr
```

```
                   20                  25                  30
cag aat act gtc att tgc tcc aaa ctg gcg tct aaa tgc ttg gcg atg        144
Gln Asn Thr Val Ile Cys Ser Lys Leu Ala Ser Lys Cys Leu Ala Met
         35                  40                  45 aaa gca gaa atg act cac agc aag tct ggg agg agg ata aag ccc gaa        192
Lys Ala Glu Met Thr His Ser Lys Ser Gly Arg Arg Ile Lys Pro Glu
 50                  55                  60 ggg gcg atc cag aac aac gat ggg ctg tac gac ccc gac tgc gac gag        240
Gly Ala Ile Gln Asn Asn Asp Gly Leu Tyr Asp Pro Asp Cys Asp Glu
 65                  70                  75                  80 cag ggg ctc ttc aaa gcc aag cag tgc aac ggc acc gcc acg tgc tgg        288
Gln Gly Leu Phe Lys Ala Lys Gln Cys Asn Gly Thr Ala Thr Cys Trp
                 85                  90                  95 tgt gtc aac acc gcc gga gtc cga aga acc gac aag gac acg gag atc        336
Cys Val Asn Thr Ala Gly Val Arg Arg Thr Asp Lys Asp Thr Glu Ile
            100                 105                 110 acg tgc tcc gag cgc gtg agg acc tac tgg atc atc att gaa cta aaa        384
Thr Cys Ser Glu Arg Val Arg Thr Tyr Trp Ile Ile Ile Glu Leu Lys
        115                 120                 125 cac aaa gaa aga gaa agc ccc tac gac cat cag agc ttg cag act gcg        432
His Lys Glu Arg Glu Ser Pro Tyr Asp His Gln Ser Leu Gln Thr Ala
    130                 135                 140 ctt caa gag gcg ttc aca tct cga tat aag ctg aat cag aaa ttt atc        480
Leu Gln Glu Ala Phe Thr Ser Arg Tyr Lys Leu Asn Gln Lys Phe Ile
145                 150                 155                 160 aaa aac att atg tat gag aat aat gtt atc acc att gat ctg atg caa        528
Lys Asn Ile Met Tyr Glu Asn Asn Val Ile Thr Ile Asp Leu Met Gln
                165                 170                 175 aac tct tct cag aaa aca caa gac gac gtg gac ata gct gat gtg gct        576
Asn Ser Ser Gln Lys Thr Gln Asp Asp Val Asp Ile Ala Asp Val Ala
            180                 185                 190 tac tat ttt gaa aaa gat gtg aag ggg gag tcc ctg ttc cat tct tct        624
Tyr Tyr Phe Glu Lys Asp Val Lys Gly Glu Ser Leu Phe His Ser Ser
        195                 200                 205 aag agc atg gac ctg aga gtg aac gga gag ccg ctc gat ctg gac ccc        672
Lys Ser Met Asp Leu Arg Val Asn Gly Glu Pro Leu Asp Leu Asp Pro
    210                 215                 220 ggg cag act ctg att tac tac gtt gat gaa aag gca ccc gag ttc tcc        720
Gly Gln Thr Leu Ile Tyr Tyr Val Asp Glu Lys Ala Pro Glu Phe Ser
225                 230                 235                 240 atg cag ggc ctc acg                                                    735
Met Gln Gly Leu Thr
                245

<210> SEQ ID NO 14
<211> LENGTH: 245
<212> TYPE: PRT
<213> ORGANISM: Mus musculus

<400> SEQUENCE: 14

Ala Ala Gln Arg Asp Cys Val Cys Asp Asn Tyr Lys Leu Ala Thr Ser
 1               5                  10                  15

Cys Ser Leu Asn Glu Tyr Gly Glu Cys Gln Cys Thr Ser Tyr Gly Thr
             20                  25                  30

Gln Asn Thr Val Ile Cys Ser Lys Leu Ala Ser Lys Cys Leu Ala Met
         35                  40                  45

Lys Ala Glu Met Thr His Ser Lys Ser Gly Arg Arg Ile Lys Pro Glu
 50                  55                  60

Gly Ala Ile Gln Asn Asn Asp Gly Leu Tyr Asp Pro Asp Cys Asp Glu
```

```
                65                  70                  75                  80
Gln Gly Leu Phe Lys Ala Lys Gln Cys Asn Gly Thr Ala Thr Cys Trp
                85                  90                  95

Cys Val Asn Thr Ala Gly Val Arg Arg Thr Asp Lys Asp Thr Glu Ile
            100                 105                 110

Thr Cys Ser Glu Arg Val Arg Thr Tyr Trp Ile Ile Glu Leu Lys
        115                 120                 125

His Lys Glu Arg Glu Ser Pro Tyr Asp His Gln Ser Leu Gln Thr Ala
    130                 135                 140

Leu Gln Glu Ala Phe Thr Ser Arg Tyr Lys Leu Asn Gln Lys Phe Ile
145                 150                 155                 160

Lys Asn Ile Met Tyr Glu Asn Asn Val Ile Thr Ile Asp Leu Met Gln
                165                 170                 175

Asn Ser Ser Gln Lys Thr Gln Asp Asp Val Asp Ile Ala Asp Val Ala
            180                 185                 190

Tyr Tyr Phe Glu Lys Asp Val Lys Gly Glu Ser Leu Phe His Ser Ser
        195                 200                 205

Lys Ser Met Asp Leu Arg Val Asn Gly Glu Pro Leu Asp Leu Asp Pro
    210                 215                 220

Gly Gln Thr Leu Ile Tyr Tyr Val Asp Glu Lys Ala Pro Glu Phe Ser
225                 230                 235                 240

Met Gln Gly Leu Thr
                245

<210> SEQ ID NO 15
<211> LENGTH: 945
<212> TYPE: DNA
<213> ORGANISM: Homo sapiens
<220> FEATURE:
<221> NAME/KEY: CDS
<222> LOCATION: (1)..(945)

<400> SEQUENCE: 15 atg gcg ccc ccg cag gtc ctc gcg ttc ggg ctt ctg ctt gcc gcg gcg      48
Met Ala Pro Pro Gln Val Leu Ala Phe Gly Leu Leu Leu Ala Ala Ala
1               5                   10                  15 acg gcg act ttt gcc gca gct cag gaa gaa tgt gtc tgt gaa aac tac      96
Thr Ala Thr Phe Ala Ala Ala Gln Glu Glu Cys Val Cys Glu Asn Tyr
            20                  25                  30 aag ctg gcc gta aac tgc ttt gtg aat aat aat cgt caa tgc cag tgt     144
Lys Leu Ala Val Asn Cys Phe Val Asn Asn Asn Arg Gln Cys Gln Cys
        35                  40                  45 act tca gtt ggt gca caa aat act gtc att tgc tca aag ctg gct gcc     192
Thr Ser Val Gly Ala Gln Asn Thr Val Ile Cys Ser Lys Leu Ala Ala
    50                  55                  60 aaa tgt ttg gtg atg aag gca gaa atg aat ggc tca aaa ctt ggg aga     240
Lys Cys Leu Val Met Lys Ala Glu Met Asn Gly Ser Lys Leu Gly Arg
65                  70                  75                  80 aga gca aaa cct gaa ggg gcc ctc cag aac aat gat ggg ctt tat gat     288
Arg Ala Lys Pro Glu Gly Ala Leu Gln Asn Asn Asp Gly Leu Tyr Asp
                85                  90                  95 cct gac tgc gat gag agc ggg ctc ttt aag gcc aag cag tgc aac ggc     336
Pro Asp Cys Asp Glu Ser Gly Leu Phe Lys Ala Lys Gln Cys Asn Gly
            100                 105                 110 acc tcc acg tgc tgg tgt gtg aac act gct ggg gtc aga aga aca gac     384
Thr Ser Thr Cys Trp Cys Val Asn Thr Ala Gly Val Arg Arg Thr Asp
        115                 120                 125 aag gac act gaa ata acc tgc tct gag cga gtg aga acc tac tgg atc     432
```

```
Lys Asp Thr Glu Ile Thr Cys Ser Glu Arg Val Arg Thr Tyr Trp Ile
    130                 135                 140 atc att gaa cta aaa cac aaa gca aga gaa aaa cct tat gat agt aaa      480
Ile Ile Glu Leu Lys His Lys Ala Arg Glu Lys Pro Tyr Asp Ser Lys
145                 150                 155                 160 agt ttg cgg act gca ctt cag aag gag atc aca acg cgt tat caa ctg      528
Ser Leu Arg Thr Ala Leu Gln Lys Glu Ile Thr Thr Arg Tyr Gln Leu
                165                 170                 175 gat cca aaa ttt atc acg agt att ttg tat gag aat aat gtt atc act      576
Asp Pro Lys Phe Ile Thr Ser Ile Leu Tyr Glu Asn Asn Val Ile Thr
            180                 185                 190 att gat ctg gtt caa aat tct tct caa aaa act cag aat gat gtg gac      624
Ile Asp Leu Val Gln Asn Ser Ser Gln Lys Thr Gln Asn Asp Val Asp
        195                 200                 205 ata gct gat gtg gct tat tat ttt gaa aaa gat gtt aaa ggt gaa tcc      672
Ile Ala Asp Val Ala Tyr Tyr Phe Glu Lys Asp Val Lys Gly Glu Ser
    210                 215                 220 ttg ttt cat tct aag aaa atg gac ctg aca gta aat ggg gaa caa ctg      720
Leu Phe His Ser Lys Lys Met Asp Leu Thr Val Asn Gly Glu Gln Leu
225                 230                 235                 240 gat ctg gat cct ggt caa act tta att tat tat gtt gat gaa aaa gca      768
Asp Leu Asp Pro Gly Gln Thr Leu Ile Tyr Tyr Val Asp Glu Lys Ala
                245                 250                 255 cct gaa ttc tca atg cag ggt cta aaa gct ggt gtt att gct gtt att      816
Pro Glu Phe Ser Met Gln Gly Leu Lys Ala Gly Val Ile Ala Val Ile
            260                 265                 270 gtg gtt gtg gtg ata gca gtt gtt gct gga att gtt gtg ctg gtt att      864
Val Val Val Val Ile Ala Val Val Ala Gly Ile Val Val Leu Val Ile
        275                 280                 285 tcc aga aag aag aga atg gca aag tat gag aag gct gag ata aag gag      912
Ser Arg Lys Lys Arg Met Ala Lys Tyr Glu Lys Ala Glu Ile Lys Glu
    290                 295                 300 atg ggt gag atg cat agg gaa ctc aat gca taa                          945
Met Gly Glu Met His Arg Glu Leu Asn Ala
305                 310

<210> SEQ ID NO 16
<211> LENGTH: 314
<212> TYPE: PRT
<213> ORGANISM: Homo sapiens

<400> SEQUENCE: 16

Met Ala Pro Pro Gln Val Leu Ala Phe Gly Leu Leu Leu Ala Ala Ala
1               5                   10                  15

Thr Ala Thr Phe Ala Ala Ala Gln Glu Glu Cys Val Cys Glu Asn Tyr
                20                  25                  30

Lys Leu Ala Val Asn Cys Phe Val Asn Asn Arg Gln Cys Gln Cys
            35                  40                  45

Thr Ser Val Gly Ala Gln Asn Thr Val Ile Cys Ser Lys Leu Ala Ala
        50                  55                  60

Lys Cys Leu Val Met Lys Ala Glu Met Asn Gly Ser Lys Leu Gly Arg
65                  70                  75                  80

Arg Ala Lys Pro Glu Gly Ala Leu Gln Asn Asn Asp Gly Leu Tyr Asp
                85                  90                  95

Pro Asp Cys Asp Glu Ser Gly Leu Phe Lys Ala Lys Gln Cys Asn Gly
            100                 105                 110

Thr Ser Thr Cys Trp Cys Val Asn Thr Ala Gly Val Arg Arg Thr Asp
        115                 120                 125
```

```
Lys Asp Thr Glu Ile Thr Cys Ser Glu Arg Val Arg Thr Tyr Trp Ile
    130                 135                 140
Ile Ile Glu Leu Lys His Lys Ala Arg Glu Lys Pro Tyr Asp Ser Lys
145                 150                 155                 160
Ser Leu Arg Thr Ala Leu Gln Lys Glu Ile Thr Thr Arg Tyr Gln Leu
                165                 170                 175
Asp Pro Lys Phe Ile Thr Ser Ile Leu Tyr Glu Asn Asn Val Ile Thr
            180                 185                 190
Ile Asp Leu Val Gln Asn Ser Ser Gln Lys Thr Gln Asn Asp Val Asp
        195                 200                 205
Ile Ala Asp Val Ala Tyr Tyr Phe Glu Lys Asp Val Lys Gly Glu Ser
    210                 215                 220
Leu Phe His Ser Lys Lys Met Asp Leu Thr Val Asn Gly Glu Gln Leu
225                 230                 235                 240
Asp Leu Asp Pro Gly Gln Thr Leu Ile Tyr Tyr Val Asp Glu Lys Ala
                245                 250                 255
Pro Glu Phe Ser Met Gln Gly Leu Lys Ala Gly Val Ile Ala Val Ile
            260                 265                 270
Val Val Val Val Ile Ala Val Val Ala Gly Ile Val Val Leu Val Ile
        275                 280                 285
Ser Arg Lys Lys Arg Met Ala Lys Tyr Glu Lys Ala Glu Ile Lys Glu
    290                 295                 300
Met Gly Glu Met His Arg Glu Leu Asn Ala
305                 310

<210> SEQ ID NO 17
<211> LENGTH: 945
<212> TYPE: DNA
<213> ORGANISM: Macaca fascicularis
<220> FEATURE:
<221> NAME/KEY: CDS
<222> LOCATION: (1)..(945)

<400> SEQUENCE: 17 atg gcg ccc ccg cag gtc ctc gcg ttc ggg ctt ctg ctt gcg gcg gcg      48
Met Ala Pro Pro Gln Val Leu Ala Phe Gly Leu Leu Leu Ala Ala Ala
1               5                   10                  15 act gcg agt ttt gcc gca gct cag aaa gaa tgt gtc tgt gaa aac tac      96
Thr Ala Ser Phe Ala Ala Ala Gln Lys Glu Cys Val Cys Glu Asn Tyr
            20                  25                  30 aag ctg gcc gta aac tgc ttt ttg aat gac aat ggt caa tgc cag tgt     144
Lys Leu Ala Val Asn Cys Phe Leu Asn Asp Asn Gly Gln Cys Gln Cys
        35                  40                  45 act tcg att ggt gca caa aat act gtc ctt tgc tca aag ctg gct gcc     192
Thr Ser Ile Gly Ala Gln Asn Thr Val Leu Cys Ser Lys Leu Ala Ala
    50                  55                  60 aaa tgt ttg gtg atg aag gca gaa atg aac ggc tca aaa ctt ggg aga     240
Lys Cys Leu Val Met Lys Ala Glu Met Asn Gly Ser Lys Leu Gly Arg
65                  70                  75                  80 aga gcg aaa cct gaa ggg gct ctc cag aac aat gat ggc ctt tac gat     288
Arg Ala Lys Pro Glu Gly Ala Leu Gln Asn Asn Asp Gly Leu Tyr Asp
                85                  90                  95 cct gac tgc gat gag agc ggg ctc ttt aag gcc aag cag tgc aac ggc     336
Pro Asp Cys Asp Glu Ser Gly Leu Phe Lys Ala Lys Gln Cys Asn Gly
            100                 105                 110 acc tcc acg tgc tgg tgt gtg aac act gct ggg gtc aga aga act gac     384
Thr Ser Thr Cys Trp Cys Val Asn Thr Ala Gly Val Arg Arg Thr Asp
        115                 120                 125
```

| | | |
|---|---|---|
| aag gac act gaa ata acc tgc tct gag cga gtg aga acc tac tgg atc<br>Lys Asp Thr Glu Ile Thr Cys Ser Glu Arg Val Arg Thr Tyr Trp Ile<br>130 135 140 | | 432 |
| atc att gaa tta aaa cac aaa gca aga gaa aaa cct tat gat gtt caa<br>Ile Ile Glu Leu Lys His Lys Ala Arg Glu Lys Pro Tyr Asp Val Gln<br>145 150 155 160 | | 480 |
| agt ttg cgg act gca ctt gag gag gcg atc aaa acg cgt tat caa ctg<br>Ser Leu Arg Thr Ala Leu Glu Glu Ala Ile Lys Thr Arg Tyr Gln Leu<br>165 170 175 | | 528 |
| gat cca aaa ttt atc aca aat att ttg tat gag gat aat gtt atc act<br>Asp Pro Lys Phe Ile Thr Asn Ile Leu Tyr Glu Asp Asn Val Ile Thr<br>180 185 190 | | 576 |
| att gat ctg gtt caa aat tct tct cag aaa act cag aat gat gtg gac<br>Ile Asp Leu Val Gln Asn Ser Ser Gln Lys Thr Gln Asn Asp Val Asp<br>195 200 205 | | 624 |
| ata gct gat gtg gct tat tat ttt gaa aaa gat gtt aaa ggt gaa tcc<br>Ile Ala Asp Val Ala Tyr Tyr Phe Glu Lys Asp Val Lys Gly Glu Ser<br>210 215 220 | | 672 |
| ttg ttt cat tct aag aaa atg gac ctg aga gta aat ggg gaa caa ctg<br>Leu Phe His Ser Lys Lys Met Asp Leu Arg Val Asn Gly Glu Gln Leu<br>225 230 235 240 | | 720 |
| gat ctg gat cct ggt caa act tta att tat tat gtc gat gaa aaa gca<br>Asp Leu Asp Pro Gly Gln Thr Leu Ile Tyr Tyr Val Asp Glu Lys Ala<br>245 250 255 | | 768 |
| cct gaa ttc tca atg cag ggt cta aaa gct ggt gtt att gct gtt att<br>Pro Glu Phe Ser Met Gln Gly Leu Lys Ala Gly Val Ile Ala Val Ile<br>260 265 270 | | 816 |
| gtg gtt gtg gtg ata gca att gtt gct gga att gtt gtg ctg gtt att<br>Val Val Val Val Ile Ala Ile Val Ala Gly Ile Val Val Leu Val Ile<br>275 280 285 | | 864 |
| tcc aga aag aag aga atg gca aag tat gag aag gct gag ata aag gag<br>Ser Arg Lys Lys Arg Met Ala Lys Tyr Glu Lys Ala Glu Ile Lys Glu<br>290 295 300 | | 912 |
| atg ggt gag ata cat agg gaa ctc aat gcg taa<br>Met Gly Glu Ile His Arg Glu Leu Asn Ala<br>305 310 | | 945 |

<210> SEQ ID NO 18
<211> LENGTH: 314
<212> TYPE: PRT
<213> ORGANISM: Macaca fascicularis

<400> SEQUENCE: 18

Met Ala Pro Pro Gln Val Leu Ala Phe Gly Leu Leu Leu Ala Ala Ala
1               5                   10                  15

Thr Ala Ser Phe Ala Ala Ala Gln Lys Glu Cys Val Cys Glu Asn Tyr
                20                  25                  30

Lys Leu Ala Val Asn Cys Phe Leu Asn Asp Asn Gly Gln Cys Gln Cys
            35                  40                  45

Thr Ser Ile Gly Ala Gln Asn Thr Val Leu Cys Ser Lys Leu Ala Ala
        50                  55                  60

Lys Cys Leu Val Met Lys Ala Glu Met Asn Gly Ser Lys Leu Gly Arg
65                  70                  75                  80

Arg Ala Lys Pro Glu Gly Ala Leu Gln Asn Asn Asp Gly Leu Tyr Asp
                85                  90                  95

Pro Asp Cys Asp Glu Ser Gly Leu Phe Lys Ala Lys Gln Cys Asn Gly
            100                 105                 110

Thr Ser Thr Cys Trp Cys Val Asn Thr Ala Gly Val Arg Arg Thr Asp
        115                 120                 125

-continued

```
Lys Asp Thr Glu Ile Thr Cys Ser Glu Arg Val Arg Thr Tyr Trp Ile
        130                 135                 140

Ile Ile Glu Leu Lys His Lys Ala Arg Glu Lys Pro Tyr Asp Val Gln
145                 150                 155                 160

Ser Leu Arg Thr Ala Leu Glu Glu Ala Ile Lys Thr Arg Tyr Gln Leu
                165                 170                 175

Asp Pro Lys Phe Ile Thr Asn Ile Leu Tyr Glu Asp Asn Val Ile Thr
            180                 185                 190

Ile Asp Leu Val Gln Asn Ser Ser Gln Lys Thr Gln Asn Asp Val Asp
        195                 200                 205

Ile Ala Asp Val Ala Tyr Tyr Phe Glu Lys Asp Val Lys Gly Glu Ser
    210                 215                 220

Leu Phe His Ser Lys Lys Met Asp Leu Arg Val Asn Gly Glu Gln Leu
225                 230                 235                 240

Asp Leu Asp Pro Gly Gln Thr Leu Ile Tyr Tyr Val Asp Glu Lys Ala
                245                 250                 255

Pro Glu Phe Ser Met Gln Gly Leu Lys Ala Gly Val Ile Ala Val Ile
            260                 265                 270

Val Val Val Val Ile Ala Ile Val Ala Gly Ile Val Val Leu Val Ile
        275                 280                 285

Ser Arg Lys Lys Arg Met Ala Lys Tyr Glu Lys Ala Glu Ile Lys Glu
    290                 295                 300

Met Gly Glu Ile His Arg Glu Leu Asn Ala
305                 310
```

```
<210> SEQ ID NO 19
<211> LENGTH: 948
<212> TYPE: DNA
<213> ORGANISM: Mus musculus
<220> FEATURE:
<221> NAME/KEY: CDS
<222> LOCATION: (1)..(948)

<400> SEQUENCE: 19 atg gcg ggt ccc cag gcc ctc gcg ttc ggg ctc ctg ctc gcg gtg gtc     48
Met Ala Gly Pro Gln Ala Leu Ala Phe Gly Leu Leu Leu Ala Val Val
1               5                   10                  15 aca gcg acg ctg gcc gcg gct cag aga gac tgt gtc tgt gac aac tac     96
Thr Ala Thr Leu Ala Ala Ala Gln Arg Asp Cys Val Cys Asp Asn Tyr
                20                  25                  30 aag ctg gca aca agt tgc tct ctg aat gaa tat ggt gaa tgc cag tgt    144
Lys Leu Ala Thr Ser Cys Ser Leu Asn Glu Tyr Gly Glu Cys Gln Cys
            35                  40                  45 act tcc tat ggt aca cag aat act gtc att tgc tcc aaa ctg gcg tct    192
Thr Ser Tyr Gly Thr Gln Asn Thr Val Ile Cys Ser Lys Leu Ala Ser
    50                  55                  60 aaa tgc ttg gcg atg aaa gca gaa atg act cac agc aag tct ggg agg    240
Lys Cys Leu Ala Met Lys Ala Glu Met Thr His Ser Lys Ser Gly Arg
65                  70                  75                  80 agg ata aag ccc gaa ggg gcg atc cag aac aac gat ggg ctg tac gac    288
Arg Ile Lys Pro Glu Gly Ala Ile Gln Asn Asn Asp Gly Leu Tyr Asp
                85                  90                  95 ccc gac tgc gac gag cag ggg ctc ttc aaa gcc aag cag tgc aac ggc    336
Pro Asp Cys Asp Glu Gln Gly Leu Phe Lys Ala Lys Gln Cys Asn Gly
            100                 105                 110 acc gcc acg tgc tgg tgt gtc aac acc gcc gga gtc cga aga acc gac    384
Thr Ala Thr Cys Trp Cys Val Asn Thr Ala Gly Val Arg Arg Thr Asp
    115                 120                 125
```

```
aag gac acg gag atc acg tgc tcc gag cgc gtg agg acc tac tgg atc      432
Lys Asp Thr Glu Ile Thr Cys Ser Glu Arg Val Arg Thr Tyr Trp Ile
    130                 135                 140 atc att gaa cta aaa cac aaa gaa aga gaa agc ccc tac gac cat cag      480
Ile Ile Glu Leu Lys His Lys Glu Arg Glu Ser Pro Tyr Asp His Gln
145                 150                 155                 160 agc ttg cag act gcg ctt caa gag gcg ttc aca tct cga tat aag ctg      528
Ser Leu Gln Thr Ala Leu Gln Glu Ala Phe Thr Ser Arg Tyr Lys Leu
                165                 170                 175 aat cag aaa ttt atc aaa aac att atg tat gag aat aat gtt atc acc      576
Asn Gln Lys Phe Ile Lys Asn Ile Met Tyr Glu Asn Asn Val Ile Thr
            180                 185                 190 att gat ctg atg caa aac tct tct cag aaa aca caa gac gac gtg gac      624
Ile Asp Leu Met Gln Asn Ser Ser Gln Lys Thr Gln Asp Asp Val Asp
        195                 200                 205 ata gct gat gtg gct tac tat ttt gaa aaa gat gtg aag ggg gag tcc      672
Ile Ala Asp Val Ala Tyr Tyr Phe Glu Lys Asp Val Lys Gly Glu Ser
    210                 215                 220 ctg ttc cat tct tct aag agc atg gac ctg aga gtg aac gga gag ccg      720
Leu Phe His Ser Ser Lys Ser Met Asp Leu Arg Val Asn Gly Glu Pro
225                 230                 235                 240 ctc gat ctg gac ccc ggg cag act ctg att tac tac gtt gat gaa aag      768
Leu Asp Leu Asp Pro Gly Gln Thr Leu Ile Tyr Tyr Val Asp Glu Lys
                245                 250                 255 gca ccc gag ttc tcc atg cag ggc ctc acg gcc ggg atc atc gct gtc      816
Ala Pro Glu Phe Ser Met Gln Gly Leu Thr Ala Gly Ile Ile Ala Val
            260                 265                 270 att gtg gtg gtg tca tta gca gtc atc gcg ggg att gtt gtc ctg gtt      864
Ile Val Val Val Ser Leu Ala Val Ile Ala Gly Ile Val Val Leu Val
        275                 280                 285 ata tct aca agg aag aaa tca gca aaa tat gag aag gct gag ata aag      912
Ile Ser Thr Arg Lys Lys Ser Ala Lys Tyr Glu Lys Ala Glu Ile Lys
    290                 295                 300 gag atg ggt gag atc cac aga gag ctt aat gcc taa                      948
Glu Met Gly Glu Ile His Arg Glu Leu Asn Ala
305                 310                 315
```

<210> SEQ ID NO 20
<211> LENGTH: 315
<212> TYPE: PRT
<213> ORGANISM: Mus musculus

<400> SEQUENCE: 20

```
Met Ala Gly Pro Gln Ala Leu Ala Phe Gly Leu Leu Leu Ala Val Val
1               5                   10                  15

Thr Ala Thr Leu Ala Ala Ala Gln Arg Asp Cys Val Cys Asp Asn Tyr
            20                  25                  30

Lys Leu Ala Thr Ser Cys Ser Leu Asn Glu Tyr Gly Glu Cys Gln Cys
        35                  40                  45

Thr Ser Tyr Gly Thr Gln Asn Thr Val Ile Cys Ser Lys Leu Ala Ser
    50                  55                  60

Lys Cys Leu Ala Met Lys Ala Glu Met Thr His Ser Lys Ser Gly Arg
65                  70                  75                  80

Arg Ile Lys Pro Glu Gly Ala Ile Gln Asn Asn Asp Gly Leu Tyr Asp
                85                  90                  95

Pro Asp Cys Asp Glu Gln Gly Leu Phe Lys Ala Lys Gln Cys Asn Gly
            100                 105                 110

Thr Ala Thr Cys Trp Cys Val Asn Thr Ala Gly Val Arg Arg Thr Asp
```

```
                115                 120                 125
       Lys Asp Thr Glu Ile Thr Cys Ser Glu Arg Val Arg Thr Tyr Trp Ile
           130                 135                 140

Ile Ile Glu Leu Lys His Lys Glu Arg Glu Ser Pro Tyr Asp His Gln
       145                 150                 155                 160

Ser Leu Gln Thr Ala Leu Gln Glu Ala Phe Thr Ser Arg Tyr Lys Leu
                       165                 170                 175

Asn Gln Lys Phe Ile Lys Asn Ile Met Tyr Glu Asn Asn Val Ile Thr
                   180                 185                 190

Ile Asp Leu Met Gln Asn Ser Ser Gln Lys Thr Gln Asp Asp Val Asp
                       195                 200                 205

Ile Ala Asp Val Ala Tyr Tyr Phe Glu Lys Asp Val Lys Gly Glu Ser
       210                 215                 220

Leu Phe His Ser Ser Lys Ser Met Asp Leu Arg Val Asn Gly Glu Pro
       225                 230                 235                 240

Leu Asp Leu Asp Pro Gly Gln Thr Leu Ile Tyr Tyr Val Asp Glu Lys
                       245                 250                 255

Ala Pro Glu Phe Ser Met Gln Gly Leu Thr Ala Gly Ile Ile Ala Val
                   260                 265                 270

Ile Val Val Val Ser Leu Ala Val Ile Ala Gly Ile Val Leu Val
                   275                 280                 285

Ile Ser Thr Arg Lys Lys Ser Ala Lys Tyr Glu Lys Ala Glu Ile Lys
                   290                 295                 300

Glu Met Gly Glu Ile His Arg Glu Leu Asn Ala
       305                 310                 315

<210> SEQ ID NO 21
<211> LENGTH: 321
<212> TYPE: DNA
<213> ORGANISM: Artificial Sequence
<220> FEATURE:
<223> OTHER INFORMATION: L6 DNA
<220> FEATURE:
<221> NAME/KEY: CDS
<222> LOCATION: (1)..(321)

<400> SEQUENCE: 21 gaa ata gtg ttg acg cag tct cca gcc acc ctg tct ttg tct cca ggg    48
Glu Ile Val Leu Thr Gln Ser Pro Ala Thr Leu Ser Leu Ser Pro Gly
1               5                   10                  15 gaa aga gcc acc ctc tcc tgc agg gcc agt cag agt gtt agc agc tac    96
Glu Arg Ala Thr Leu Ser Cys Arg Ala Ser Gln Ser Val Ser Ser Tyr
            20                  25                  30 tta gcc tgg tac caa cag aaa cct ggc cag gct ccc agg ctc ctc atc   144
Leu Ala Trp Tyr Gln Gln Lys Pro Gly Gln Ala Pro Arg Leu Leu Ile
        35                  40                  45 tat gat gca tcc aac agg gcc act ggc atc cca gcc agg ttc agt ggc   192
Tyr Asp Ala Ser Asn Arg Ala Thr Gly Ile Pro Ala Arg Phe Ser Gly
    50                  55                  60 agt ggg tct ggg aca gac ttc act ctc acc atc agc agc cta gag cct   240
Ser Gly Ser Gly Thr Asp Phe Thr Leu Thr Ile Ser Ser Leu Glu Pro
65                  70                  75                  80 gaa gat ttt gca gtt tat tac tgt cag cag cgt agc aac tgg cct ccg   288
Glu Asp Phe Ala Val Tyr Tyr Cys Gln Gln Arg Ser Asn Trp Pro Pro
                85                  90                  95 acg ttc ggc caa ggg acc aag gtg gaa atc aaa                       321
Thr Phe Gly Gln Gly Thr Lys Val Glu Ile Lys
            100                 105
```

<210> SEQ ID NO 22
<211> LENGTH: 107
<212> TYPE: PRT
<213> ORGANISM: Artificial Sequence
<220> FEATURE:
<223> OTHER INFORMATION: Synthetic Construct

<400> SEQUENCE: 22

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Thr Phe Gly Gln Gly Thr Lys Val Glu Ile Lys
            100                 105

<210> SEQ ID NO 23
<211> LENGTH: 11
<212> TYPE: PRT
<213> ORGANISM: Artificial Sequence
<220> FEATURE:
<223> OTHER INFORMATION: L6 CDR1 amino acid

<400> SEQUENCE: 23

Arg Ala Ser Gln Ser Val Ser Ser Tyr Leu Ala
1               5                   10

<210> SEQ ID NO 24
<211> LENGTH: 7
<212> TYPE: PRT
<213> ORGANISM: Artificial Sequence
<220> FEATURE:
<223> OTHER INFORMATION: L6 LCDR2 amino acid

<400> SEQUENCE: 24

Asp Ala Ser Asn Arg Ala Thr
1               5

<210> SEQ ID NO 25
<211> LENGTH: 9
<212> TYPE: PRT
<213> ORGANISM: Artificial Sequence
<220> FEATURE:
<223> OTHER INFORMATION: L6 LCDR3 amino acid

<400> SEQUENCE: 25

Gln Gln Arg Ser Asn Trp Pro Pro Thr
1               5

<210> SEQ ID NO 26
<211> LENGTH: 381
<212> TYPE: DNA
<213> ORGANISM: Homo sapiens
<220> FEATURE:
<221> NAME/KEY: CDS
<222> LOCATION: (1)..(381)

<400> SEQUENCE: 26

```
cag gtg cag cta cag cag tgg ggc gca gga ctg ttg aag cct tcg gag      48
Gln Val Gln Leu Gln Gln Trp Gly Ala Gly Leu Leu Lys Pro Ser Glu
1               5                   10                  15 acc ctg tcc ctc acc tgc gct gtc tat ggt ggg tcc ttc agt ggt tac      96
Thr Leu Ser Leu Thr Cys Ala Val Tyr Gly Gly Ser Phe Ser Gly Tyr
            20                  25                  30 tac tgg agc tgg atc cgc cag ccc ccc ggg aag ggg ctg gag tgg att     144
Tyr Trp Ser Trp Ile Arg Gln Pro Pro Gly Lys Gly Leu Glu Trp Ile
        35                  40                  45 ggg gaa atc aat cat ggt gga atc acc cac tac aat ccg tcc ctc aag     192
Gly Glu Ile Asn His Gly Gly Ile Thr His Tyr Asn Pro Ser Leu Lys
    50                  55                  60 agt cga gtc acc ata tca gta gac acg tcc aag aac cag ttc tcc ctg     240
Ser Arg Val Thr Ile Ser Val Asp Thr Ser Lys Asn Gln Phe Ser Leu
65                  70                  75                  80 aag ctg agt tct gtg acc gcc gcg gac acg gct gtg tat tac tgt gcg     288
Lys Leu Ser Ser Val Thr Ala Ala Asp Thr Ala Val Tyr Tyr Cys Ala
                85                  90                  95 aga gat aac tac tat ggt tcg ggg agt tat tat aag tac gac tac tac     336
Arg Asp Asn Tyr Tyr Gly Ser Gly Ser Tyr Tyr Lys Tyr Asp Tyr Tyr
            100                 105                 110 ggt atg gac gtc tgg ggc caa ggg acc acg gtc acc gtt tcc tca         381
Gly Met Asp Val Trp Gly Gln Gly Thr Thr Val Thr Val Ser Ser
        115                 120                 125
```

<210> SEQ ID NO 27
<211> LENGTH: 127
<212> TYPE: PRT
<213> ORGANISM: Homo sapiens

<400> SEQUENCE: 27

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Gly Gly Ile Thr His Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Asn Tyr Tyr Gly Ser Gly Ser Tyr Tyr Lys Tyr Asp Tyr Tyr
            100                 105                 110

Gly Met Asp Val Trp Gly Gln Gly Thr Thr Val Thr Val Ser Ser
        115                 120                 125
```

<210> SEQ ID NO 28
<211> LENGTH: 5
<212> TYPE: PRT
<213> ORGANISM: Artificial Sequence
<220> FEATURE:
<223> OTHER INFORMATION: R1066 HCDR1 amino acid

<400> SEQUENCE: 28

```
Gly Tyr Tyr Trp Ser
1               5
```

<210> SEQ ID NO 29
<211> LENGTH: 16
<212> TYPE: PRT
<213> ORGANISM: Artificial Sequence
<220> FEATURE:
<223> OTHER INFORMATION: R1066 HCDR2 amino acid

<400> SEQUENCE: 29

Glu Ile Asn His Gly Gly Ile Thr His Tyr Asn Pro Ser Leu Lys Ser
1               5                   10                  15

<210> SEQ ID NO 30
<211> LENGTH: 19
<212> TYPE: PRT
<213> ORGANISM: Artificial Sequence
<220> FEATURE:
<223> OTHER INFORMATION: R1066 HCDR3 amino acid

<400> SEQUENCE: 30

Asp Asn Tyr Tyr Gly Ser Gly Ser Tyr Tyr Lys Tyr Asp Tyr Tyr Gly
1               5                   10                  15

Met Asp Val

<210> SEQ ID NO 31
<211> LENGTH: 354
<212> TYPE: DNA
<213> ORGANISM: Homo sapiens
<220> FEATURE:
<221> NAME/KEY: CDS
<222> LOCATION: (1)..(354)

<400> SEQUENCE: 31 gaa gtg cag ctt gtg cag tcc ggg gct gaa gtg aag aag ccc ggg gaa      48
Glu Val Gln Leu Val Gln Ser Gly Ala Glu Val Lys Lys Pro Gly Glu
1               5                   10                  15 tcc ctg aag atc tcc tgt aag ggc tcc ggc tac tcc ttc atc atc tac      96
Ser Leu Lys Ile Ser Cys Lys Gly Ser Gly Tyr Ser Phe Ile Ile Tyr
                20                  25                  30 tgg atc ggc tgg gtt cgc cag atg cct ggg aag ggg ctg gag tgg atg     144
Trp Ile Gly Trp Val Arg Gln Met Pro Gly Lys Gly Leu Glu Trp Met
            35                  40                  45 ggg atc atc tat ccc aat gat gcc gat act cgc tac tcc ccc tcc ttc     192
Gly Ile Ile Tyr Pro Asn Asp Ala Asp Thr Arg Tyr Ser Pro Ser Phe
        50                  55                  60 cag ggg cag gtg act atc tcc gcc gac aag tcc atc tcc act gcc tat     240
Gln Gly Gln Val Thr Ile Ser Ala Asp Lys Ser Ile Ser Thr Ala Tyr
65                  70                  75                  80 ctg cag tgg tcc tcc ctg aag gcc tcc gat act gcc atg tac tac tgc     288
Leu Gln Trp Ser Ser Leu Lys Ala Ser Asp Thr Ala Met Tyr Tyr Cys
                85                  90                  95 gtg cgc ctg ggg act cgc gat tgg ttc gat cct tgg ggg cag ggg act     336
Val Arg Leu Gly Thr Arg Asp Trp Phe Asp Pro Trp Gly Gln Gly Thr
                100                 105                 110 ctt gtg act gtg tcc tcc                                             354
Leu Val Thr Val Ser Ser
        115

<210> SEQ ID NO 32
<211> LENGTH: 118
<212> TYPE: PRT
<213> ORGANISM: Homo sapiens

<400> SEQUENCE: 32

```
Glu Val Gln Leu Val Gln Ser Gly Ala Glu Val Lys Lys Pro Gly Glu
1               5                   10                  15

Ser Leu Lys Ile Ser Cys Lys Ser Gly Tyr Ser Phe Ile Ile Tyr
            20                  25                  30

Trp Ile Gly Trp Val Arg Gln Met Pro Gly Lys Gly Leu Glu Trp Met
            35                  40                  45

Gly Ile Ile Tyr Pro Asn Asp Ala Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Val Arg Leu Gly Thr Arg Asp Trp Phe Asp Pro Trp Gly Gln Gly Thr
            100                 105                 110

Leu Val Thr Val Ser Ser
            115

<210> SEQ ID NO 33
<211> LENGTH: 5
<212> TYPE: PRT
<213> ORGANISM: Artificial Sequence
<220> FEATURE:
<223> OTHER INFORMATION: R1090S55A HCDR1 amino acid

<400> SEQUENCE: 33

Ile Tyr Trp Ile Gly
1               5

<210> SEQ ID NO 34
<211> LENGTH: 17
<212> TYPE: PRT
<213> ORGANISM: Artificial Sequence
<220> FEATURE:
<223> OTHER INFORMATION: R1090S55A HCDR2 amino acid

<400> SEQUENCE: 34

Ile Ile Tyr Pro Asn Asp Ala Asp Thr Arg Tyr Ser Pro Ser Phe Gln
1               5                   10                  15

Gly

<210> SEQ ID NO 35
<211> LENGTH: 9
<212> TYPE: PRT
<213> ORGANISM: Artificial Sequence
<220> FEATURE:
<223> OTHER INFORMATION: R1090S55A HCDR3 amino acid

<400> SEQUENCE: 35

Leu Gly Thr Arg Asp Trp Phe Asp Pro
1               5

<210> SEQ ID NO 36
<211> LENGTH: 360
<212> TYPE: DNA
<213> ORGANISM: Homo sapiens
<220> FEATURE:
<221> NAME/KEY: CDS
<222> LOCATION: (1)..(360)

<400> SEQUENCE: 36 gag gtc cag ctg gta cag tct ggg gct gag gtg aag aag cct ggg gcc     48
Glu Val Gln Leu Val Gln Ser Gly Ala Glu Val Lys Lys Pro Gly Ala
1               5                   10                  15
```

```
tca gtg aag gtt tcc tgc aag gct tct gga tac tcc ttc act cgc tat    96
Ser Val Lys Val Ser Cys Lys Ala Ser Gly Tyr Ser Phe Thr Arg Tyr
        20                  25                  30 att atg cat tgg gtg cgc cag gcc ccc gga caa agg ctt gag tgg atg   144
Ile Met His Trp Val Arg Gln Ala Pro Gly Gln Arg Leu Glu Trp Met
            35                  40                  45 gga tgg atc aac gct ggc aat ggt aac aca aaa tat tca cag aag ttc   192
Gly Trp Ile Asn Ala Gly Asn Gly Asn Thr Lys Tyr Ser Gln Lys Phe
50                  55                  60 cag ggc aga gtc acc att acc agg gac aca tcc gcg aac aca gcc tac   240
Gln Gly Arg Val Thr Ile Thr Arg Asp Thr Ser Ala Asn Thr Ala Tyr
65                  70                  75                  80 atg gag ctg agc agc ctg aga tct gaa gac acg gct gta tac tac tgt   288
Met Glu Leu Ser Ser Leu Arg Ser Glu Asp Thr Ala Val Tyr Tyr Cys
                85                  90                  95 gcg aga gat gaa cca gtg gct ggt tct ttc ttt gac tac tgg ggc cag   336
Ala Arg Asp Glu Pro Val Ala Gly Ser Phe Phe Asp Tyr Trp Gly Gln
            100                 105                 110 gga acc ctg gtc acc gtc tcc tca                                   360
Gly Thr Leu Val Thr Val Ser Ser
        115                 120

<210> SEQ ID NO 37
<211> LENGTH: 120
<212> TYPE: PRT
<213> ORGANISM: Homo sapiens

<400> SEQUENCE: 37

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Arg Tyr
            20                  25                  30

Ile Met His Trp Val Arg Gln Ala Pro Gly Gln Arg Leu Glu Trp Met
        35                  40                  45

Gly Trp Ile Asn Ala Gly Asn Gly Asn Thr Lys Tyr Ser Gln Lys Phe
    50                  55                  60

Gln Gly Arg Val Thr Ile Thr Arg Asp Thr Ser Ala Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Glu Pro Val Ala Gly Ser Phe Phe Asp Tyr Trp Gly Gln
            100                 105                 110

Gly Thr Leu Val Thr Val Ser Ser
        115                 120

<210> SEQ ID NO 38
<211> LENGTH: 5
<212> TYPE: PRT
<213> ORGANISM: Artificial Sequence
<220> FEATURE:
<223> OTHER INFORMATION: R2089 HCDR1 amino acid

<400> SEQUENCE: 38

Arg Tyr Ile Met His
1               5

<210> SEQ ID NO 39
<211> LENGTH: 17
<212> TYPE: PRT
<213> ORGANISM: Artificial Sequence
```

<220> FEATURE:
<223> OTHER INFORMATION: R2089 HCDR2 amino acid

<400> SEQUENCE: 39

Trp Ile Asn Ala Gly Asn Gly Asn Thr Lys Tyr Ser Gln Lys Phe Gln
1               5                   10                  15
Gly

<210> SEQ ID NO 40
<211> LENGTH: 11
<212> TYPE: PRT
<213> ORGANISM: Artificial Sequence
<220> FEATURE:
<223> OTHER INFORMATION: R2089 HCDR3 amino acid

<400> SEQUENCE: 40

Asp Glu Pro Val Ala Gly Ser Phe Phe Asp Tyr
1               5                   10

<210> SEQ ID NO 41
<211> LENGTH: 384
<212> TYPE: DNA
<213> ORGANISM: Homo sapiens
<220> FEATURE:
<221> NAME/KEY: CDS
<222> LOCATION: (1)..(384)

<400> SEQUENCE: 41 cag gtg cag cta cag cag tgg ggc gca gga ctg ttg aag cct tcg gag      48
Gln Val Gln Leu Gln Gln Trp Gly Ala Gly Leu Leu Lys Pro Ser Glu
1               5                   10                  15 acc ctg tcc ctc acc tgc gct gtc tat ggt ggg tcc ttc agt ggt tac      96
Thr Leu Ser Leu Thr Cys Ala Val Tyr Gly Gly Ser Phe Ser Gly Tyr
                20                  25                  30 tac tgg agc tgg atc cgc cag tcc cca ggg aag gga ctg gag tgg att     144
Tyr Trp Ser Trp Ile Arg Gln Ser Pro Gly Lys Gly Leu Glu Trp Ile
            35                  40                  45 ggg gaa atc aat cat ggt gga atc acc aac tac aat ccg tcc ctc aag     192
Gly Glu Ile Asn His Gly Gly Ile Thr Asn Tyr Asn Pro Ser Leu Lys
        50                  55                  60 agt cga gtc acc ata tca gta gac acg tcc aag aac cag ttc tcc ctg     240
Ser Arg Val Thr Ile Ser Val Asp Thr Ser Lys Asn Gln Phe Ser Leu
65                  70                  75                  80 aag ctg ggc tct gtg acc gcc gcg gac acg gct gtg tat tac tgt gcg     288
Lys Leu Gly Ser Val Thr Ala Ala Asp Thr Ala Val Tyr Tyr Cys Ala
                85                  90                  95 aga gat aat tac tat ggt tcg ggg agt aat gat ggg gtc tac cag tac     336
Arg Asp Asn Tyr Tyr Gly Ser Gly Ser Asn Asp Gly Val Tyr Gln Tyr
            100                 105                 110 tac ggt ata gac gtc tgg ggc caa ggg acc acg gtc acc gtc tcc tca     384
Tyr Gly Ile Asp Val Trp Gly Gln Gly Thr Thr Val Thr Val Ser Ser
        115                 120                 125

<210> SEQ ID NO 42
<211> LENGTH: 128
<212> TYPE: PRT
<213> ORGANISM: Homo sapiens

<400> SEQUENCE: 42

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
                20                  25                  30

```
Tyr Trp Ser Trp Ile Arg Gln Ser Pro Gly Lys Gly Leu Glu Trp Ile
            35                  40                  45
Gly Glu Ile Asn His Gly Gly Ile Thr Asn Tyr Asn Pro Ser Leu Lys
        50                  55                  60
Ser Arg Val Thr Ile Ser Val Asp Thr Ser Lys Asn Gln Phe Ser Leu
 65                  70                  75                  80
Lys Leu Gly Ser Val Thr Ala Ala Asp Thr Ala Val Tyr Tyr Cys Ala
                85                  90                  95
Arg Asp Asn Tyr Tyr Gly Ser Gly Ser Asn Asp Gly Val Tyr Gln Tyr
                100                 105                 110
Tyr Gly Ile Asp Val Trp Gly Gln Gly Thr Thr Val Thr Val Ser Ser
            115                 120                 125

<210> SEQ ID NO 43
<211> LENGTH: 5
<212> TYPE: PRT
<213> ORGANISM: Artificial Sequence
<220> FEATURE:
<223> OTHER INFORMATION: R2178 HCDR1 amino acid

<400> SEQUENCE: 43

Gly Tyr Tyr Trp Ser
1               5

<210> SEQ ID NO 44
<211> LENGTH: 16
<212> TYPE: PRT
<213> ORGANISM: Artificial Sequence
<220> FEATURE:
<223> OTHER INFORMATION: R2178 HCDR2 amino acid

<400> SEQUENCE: 44

Glu Ile Asn His Gly Gly Ile Thr Asn Tyr Asn Pro Ser Leu Lys Ser
1               5                   10                  15

<210> SEQ ID NO 45
<211> LENGTH: 20
<212> TYPE: PRT
<213> ORGANISM: Artificial Sequence
<220> FEATURE:
<223> OTHER INFORMATION: R2178 HCDR3 amino acid

<400> SEQUENCE: 45

Asp Asn Tyr Tyr Gly Ser Gly Ser Asn Asp Gly Val Tyr Gln Tyr Tyr
1               5                   10                  15
Gly Ile Asp Val
            20

<210> SEQ ID NO 46
<211> LENGTH: 378
<212> TYPE: DNA
<213> ORGANISM: Homo sapiens
<220> FEATURE:
<221> NAME/KEY: CDS
<222> LOCATION: (1)..(378)

<400> SEQUENCE: 46 cag gtg cag ctg gtg cag tct ggg gct gag gtg aag aag cct ggg gcc      48
Gln Val Gln Leu Val Gln Ser Gly Ala Glu Val Lys Lys Pro Gly Ala
1               5                   10                  15 tca gtg aag gtc tcc tgc aag gct tct gga tac acc ttc acc ggc tac      96
Ser Val Lys Val Ser Cys Lys Ala Ser Gly Tyr Thr Phe Thr Gly Tyr
            20                  25                  30
```

```
tat atg cac tgg gtg cga cag gcc cct gga caa ggg ctt gag tgg atg      144
Tyr Met His Trp Val Arg Gln Ala Pro Gly Gln Gly Leu Glu Trp Met
         35                  40                  45 gga tgg atc aac cct gac agt ggt ggc aca aac tat gca cag aag ttt      192
Gly Trp Ile Asn Pro Asp Ser Gly Gly Thr Asn Tyr Ala Gln Lys Phe
 50                  55                  60 cag ggc agg gtc acc atg acc agg gac acg tcc atc agc aca gcc tac      240
Gln Gly Arg Val Thr Met Thr Arg Asp Thr Ser Ile Ser Thr Ala Tyr
 65                  70                  75                  80 atg gag ctg aac agg ctg aga tct gac gac acg gcc gtg tat tac tgt      288
Met Glu Leu Asn Arg Leu Arg Ser Asp Asp Thr Ala Val Tyr Tyr Cys
                 85                  90                  95 gcg aga gat cag ccc cta gga tat tgt act aat ggt gta tgc tcc tac      336
Ala Arg Asp Gln Pro Leu Gly Tyr Cys Thr Asn Gly Val Cys Ser Tyr
             100                 105                 110 ttt gac tac tgg ggc cag gga acc ctg gtc acc gtc tcc tca              378
Phe Asp Tyr Trp Gly Gln Gly Thr Leu Val Thr Val Ser Ser
         115                 120                 125

<210> SEQ ID NO 47
<211> LENGTH: 126
<212> TYPE: PRT
<213> ORGANISM: Homo sapiens

<400> SEQUENCE: 47

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Gly Tyr
                 20                  25                  30

Tyr Met His Trp Val Arg Gln Ala Pro Gly Gln Gly Leu Glu Trp Met
             35                  40                  45

Gly Trp Ile Asn Pro Asp Ser Gly Gly Thr Asn Tyr Ala Gln Lys Phe
 50                  55                  60

Gln Gly Arg Val Thr Met Thr Arg Asp Thr Ser Ile Ser Thr Ala Tyr
 65                  70                  75                  80

Met Glu Leu Asn Arg Leu Arg Ser Asp Asp Thr Ala Val Tyr Tyr Cys
                 85                  90                  95

Ala Arg Asp Gln Pro Leu Gly Tyr Cys Thr Asn Gly Val Cys Ser Tyr
             100                 105                 110

Phe Asp Tyr Trp Gly Gln Gly Thr Leu Val Thr Val Ser Ser
         115                 120                 125

<210> SEQ ID NO 48
<211> LENGTH: 321
<212> TYPE: DNA
<213> ORGANISM: Homo sapiens
<220> FEATURE:
<221> NAME/KEY: CDS
<222> LOCATION: (1)..(321)

<400> SEQUENCE: 48 gac atc cag atg acc cag tct cca tct tcc gtg tct gca tct gta gga       48
Asp Ile Gln Met Thr Gln Ser Pro Ser Ser Val Ser Ala Ser Val Gly
  1               5                  10                  15 gac aga gtc acc atc act tgt cgg gcg agt cag ggt att tac agc tgg       96
Asp Arg Val Thr Ile Thr Cys Arg Ala Ser Gln Gly Ile Tyr Ser Trp
                 20                  25                  30 tta gcc tgg tat cag cag aaa cca ggg aaa gcc cct aac ctc ctg atc      144
Leu Ala Trp Tyr Gln Gln Lys Pro Gly Lys Ala Pro Asn Leu Leu Ile
             35                  40                  45
```

```
tat act gca tcc act tta caa agt ggg gtc cca tca agg ttc agc ggc    192
Tyr Thr Ala Ser Thr Leu Gln Ser Gly Val Pro Ser Arg Phe Ser Gly
         50                  55                  60 agt gga tct ggg aca gat ttc act ctc acc atc agc agc ctg caa cct    240
Ser Gly Ser Gly Thr Asp Phe Thr Leu Thr Ile Ser Ser Leu Gln Pro
 65                  70                  75                  80 gaa gat ttt gca act tac tat tgt caa cag gct aac att ttc ccg ctc    288
Glu Asp Phe Ala Thr Tyr Tyr Cys Gln Gln Ala Asn Ile Phe Pro Leu
                 85                  90                  95 act ttc ggc gga ggg acc aag gtc cag atc aaa                        321
Thr Phe Gly Gly Gly Thr Lys Val Gln Ile Lys
            100                 105

<210> SEQ ID NO 49
<211> LENGTH: 107
<212> TYPE: PRT
<213> ORGANISM: Homo sapiens

<400> SEQUENCE: 49

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Tyr Ser Trp
            20                  25                  30

Leu Ala Trp Tyr Gln Gln Lys Pro Gly Lys Ala Pro Asn Leu Leu Ile
        35                  40                  45

Tyr Thr Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ile Phe Pro Leu
                85                  90                  95

Thr Phe Gly Gly Gly Thr Lys Val Gln Ile Lys
            100                 105

<210> SEQ ID NO 50
<211> LENGTH: 354
<212> TYPE: DNA
<213> ORGANISM: Homo sapiens
<220> FEATURE:
<221> NAME/KEY: CDS
<222> LOCATION: (1)..(354)

<400> SEQUENCE: 50 cag gtg cag ctg gtg cag tct ggg gct gag gtg aaa aag cct ggg gcc    48
Gln Val Gln Leu Val Gln Ser Gly Ala Glu Val Lys Lys Pro Gly Ala
1               5                   10                  15 tca gtg aag gtt tcc tgc aag gca tct gga tac acc ttc acc aac tac    96
Ser Val Lys Val Ser Cys Lys Ala Ser Gly Tyr Thr Phe Thr Asn Tyr
            20                  25                  30 tat atg cac tgg gtg cga cag gcc cct gga caa ggg ctt gag tgg atg    144
Tyr Met His Trp Val Arg Gln Ala Pro Gly Gln Gly Leu Glu Trp Met
        35                  40                  45 gga ata atc aac cct aat agt ggt agc aca ggc tac gca cag aag ttc    192
Gly Ile Ile Asn Pro Asn Ser Gly Ser Thr Gly Tyr Ala Gln Lys Phe
    50                  55                  60 cag ggc aga gtc acc atg acc agg gac acg tcc acg agc aca gtc tac    240
Gln Gly Arg Val Thr Met Thr Arg Asp Thr Ser Thr Ser Thr Val Tyr
65                  70                  75                  80 atg gag ctg agc agc ctg aga tct gag gac acg gcc gtg tat tac tgt    288
Met Glu Leu Ser Ser Leu Arg Ser Glu Asp Thr Ala Val Tyr Tyr Cys
```

```
            85                  90                  95
gcg aga tgg ggt tcg ggg agg ccc atg gac gtc tgg ggc caa ggg acc      336
Ala Arg Trp Gly Ser Gly Arg Pro Met Asp Val Trp Gly Gln Gly Thr
        100                 105                 110 acg gtc acc gtc tcc tca                                              354
Thr Val Thr Val Ser Ser
        115
```

<210> SEQ ID NO 51
<211> LENGTH: 118
<212> TYPE: PRT
<213> ORGANISM: Homo sapiens

<400> SEQUENCE: 51

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met His Trp Val Arg Gln Ala Pro Gly Gln Gly Leu Glu Trp Met
        35                  40                  45

Gly Ile Ile Asn Pro Asn Ser Gly Ser Thr Gly Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Trp Gly Ser Gly Arg Pro Met Asp Val Trp Gly Gln Gly Thr
            100                 105                 110

Thr Val Thr Val Ser Ser
        115
```

<210> SEQ ID NO 52
<211> LENGTH: 5
<212> TYPE: PRT
<213> ORGANISM: Artificial Sequence
<220> FEATURE:
<223> OTHER INFORMATION: Ep59 HCDR1 amino acid

<400> SEQUENCE: 52

```
Asn Tyr Tyr Met His
1               5
```

<210> SEQ ID NO 53
<211> LENGTH: 17
<212> TYPE: PRT
<213> ORGANISM: Artificial Sequence
<220> FEATURE:
<223> OTHER INFORMATION: Ep59 HCDR2 amino acid

<400> SEQUENCE: 53

```
Ile Ile Asn Pro Asn Ser Gly Ser Thr Gly Tyr Ala Gln Lys Phe Gln
1               5                   10                  15

Gly
```

<210> SEQ ID NO 54
<211> LENGTH: 9
<212> TYPE: PRT
<213> ORGANISM: Artificial Sequence
<220> FEATURE:
<223> OTHER INFORMATION: Ep59 HCDR3 amino acid

<400> SEQUENCE: 54

```
Trp Gly Ser Gly Arg Pro Met Asp Val
1               5
```

```
<210> SEQ ID NO 55
<211> LENGTH: 360
<212> TYPE: DNA
<213> ORGANISM: Homo sapiens
<220> FEATURE:
<221> NAME/KEY: CDS
<222> LOCATION: (1)..(360)

<400> SEQUENCE: 55 gag gtg cag ctg gtg cag tct ggc gct gag gtg aag aag cct ggg gcc        48
Glu Val Gln Leu Val Gln Ser Gly Ala Glu Val Lys Lys Pro Gly Ala
1               5                   10                  15 tca gtg aag gtt tcc tgc aag gca tct gga ttc acc ttc agc agt tac        96
Ser Val Lys Val Ser Cys Lys Ala Ser Gly Phe Thr Phe Ser Ser Tyr
            20                  25                  30 tat atg cac tgg gtg cga cag gcc cct gga caa ggt ctt gaa tgg atg       144
Tyr Met His Trp Val Arg Gln Ala Pro Gly Gln Gly Leu Glu Trp Met
        35                  40                  45 gga ata gtc aac cct act ggt ggt gcc aca agc tac gca cag aag ttc       192
Gly Ile Val Asn Pro Thr Gly Gly Ala Thr Ser Tyr Ala Gln Lys Phe
    50                  55                  60 cag ggg aga gtc acc atg acc agg gac acg tcc acg agc aca gtc tac       240
Gln Gly Arg Val Thr Met Thr Arg Asp Thr Ser Thr Ser Thr Val Tyr
65                  70                  75                  80 atg gag ctg agc agt ctg aga tct gag gac acg gcc gtg tat tac tgt       288
Met Glu Leu Ser Ser Leu Arg Ser Glu Asp Thr Ala Val Tyr Tyr Cys
                85                  90                  95 gcg aaa cat ggc tac ggt gcc tcg acc ctt ttt gac tcc tgg ggc cag       336
Ala Lys His Gly Tyr Gly Ala Ser Thr Leu Phe Asp Ser Trp Gly Gln
            100                 105                 110 gga acc ctg gtc acc gtc tcc tca                                        360
Gly Thr Leu Val Thr Val Ser Ser
        115                 120

<210> SEQ ID NO 56
<211> LENGTH: 120
<212> TYPE: PRT
<213> ORGANISM: Homo sapiens

<400> SEQUENCE: 56

Glu Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Ser Ser Tyr
            20                  25                  30

Tyr Met His Trp Val Arg Gln Ala Pro Gly Gln Gly Leu Glu Trp Met
        35                  40                  45

Gly Ile Val Asn Pro Thr Gly Gly Ala Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Lys His Gly Tyr Gly Ala Ser Thr Leu Phe Asp Ser Trp Gly Gln
            100                 105                 110

Gly Thr Leu Val Thr Val Ser Ser
        115                 120
```

<210> SEQ ID NO 57
<211> LENGTH: 5
<212> TYPE: PRT
<213> ORGANISM: Artificial Sequence
<220> FEATURE:
<223> OTHER INFORMATION: Ep203 HCDR1 amino acid

<400> SEQUENCE: 57

Ser Tyr Tyr Met His
1               5

<210> SEQ ID NO 58
<211> LENGTH: 17
<212> TYPE: PRT
<213> ORGANISM: Artificial Sequence
<220> FEATURE:
<223> OTHER INFORMATION: Ep203 HCDR2 amino acid

<400> SEQUENCE: 58

Ile Val Asn Pro Thr Gly Gly Ala Thr Ser Tyr Ala Gln Lys Phe Gln
1               5                   10                  15

Gly

<210> SEQ ID NO 59
<211> LENGTH: 11
<212> TYPE: PRT
<213> ORGANISM: Artificial Sequence
<220> FEATURE:
<223> OTHER INFORMATION: Ep203 HCDR3 amino acid

<400> SEQUENCE: 59

His Gly Tyr Gly Ala Ser Thr Leu Phe Asp Ser
1               5                   10

<210> SEQ ID NO 60
<211> LENGTH: 360
<212> TYPE: DNA
<213> ORGANISM: Homo sapiens
<220> FEATURE:
<221> NAME/KEY: CDS
<222> LOCATION: (1)..(360)

<400> SEQUENCE: 60 gaa gtg cag ctg gtg cag tcc ggg gct gag gtg aag aag cct ggg gcc    48
Glu Val Gln Leu Val Gln Ser Gly Ala Glu Val Lys Lys Pro Gly Ala
1               5                   10                  15 tca gtg aag gtg tcc tgc aag gca tct gga tac acc ttc acc agc aac    96
Ser Val Lys Val Ser Cys Lys Ala Ser Gly Tyr Thr Phe Thr Ser Asn
            20                  25                  30 tat atg cac tgg gtg cgc cag gcc cct gga caa ggg ctt gag tgg atg   144
Tyr Met His Trp Val Arg Gln Ala Pro Gly Gln Gly Leu Glu Trp Met
        35                  40                  45 gga ata atc aac cct agt ggt ggt gcc aca agc tac gca cag aag ttc   192
Gly Ile Ile Asn Pro Ser Gly Gly Ala Thr Ser Tyr Ala Gln Lys Phe
    50                  55                  60 cag ggc aga gtc acc atg acc agg gac acg tcc acg agc aca gtc tac   240
Gln Gly Arg Val Thr Met Thr Arg Asp Thr Ser Thr Ser Thr Val Tyr
65                  70                  75                  80 atg gag ctg agc agc ctg aga tct gag gac acg gcc gtg tat tac tgt   288
Met Glu Leu Ser Ser Leu Arg Ser Glu Asp Thr Ala Val Tyr Tyr Cys
                85                  90                  95 gcg agc ggt gga tac tat ggt tcg gtg att atg gac gtc tgg ggc caa   336
Ala Ser Gly Gly Tyr Tyr Gly Ser Val Ile Met Asp Val Trp Gly Gln
            100                 105                 110

```
            ggg acc ctg gtc acc gtc tcc tca                           360
            Gly Thr Leu Val Thr Val Ser Ser
                    115                 120
```

<210> SEQ ID NO 61
<211> LENGTH: 120
<212> TYPE: PRT
<213> ORGANISM: Homo sapiens

<400> SEQUENCE: 61

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Asn
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ala Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Ser Gly Gly Tyr Tyr Gly Ser Val Ile Met Asp Val Trp Gly Gln
            100                 105                 110

Gly Thr Leu Val Thr Val Ser Ser
        115                 120

<210> SEQ ID NO 62
<211> LENGTH: 5
<212> TYPE: PRT
<213> ORGANISM: Artificial Sequence
<220> FEATURE:
<223> OTHER INFORMATION: Epc051 HCDR1 amino acid

<400> SEQUENCE: 62

Ser Asn Tyr Met His
1               5

<210> SEQ ID NO 63
<211> LENGTH: 17
<212> TYPE: PRT
<213> ORGANISM: Artificial Sequence
<220> FEATURE:
<223> OTHER INFORMATION: Epc051 HCDR2 amino acid

<400> SEQUENCE: 63

Ile Ile Asn Pro Ser Gly Gly Ala Thr Ser Tyr Ala Gln Lys Phe Gln
1               5                   10                  15

Gly

<210> SEQ ID NO 64
<211> LENGTH: 11
<212> TYPE: PRT
<213> ORGANISM: Artificial Sequence
<220> FEATURE:
<223> OTHER INFORMATION: Epc051 HCDR3 amino acid

<400> SEQUENCE: 64

Gly Gly Tyr Tyr Gly Ser Val Ile Met Asp Val
1               5                   10

-continued

```
<210> SEQ ID NO 65
<211> LENGTH: 354
<212> TYPE: DNA
<213> ORGANISM: Homo sapiens
<220> FEATURE:
<221> NAME/KEY: CDS
<222> LOCATION: (1)..(354)

<400> SEQUENCE: 65 gaa gtg cag ctg gtg cag tcc ggg act gag gtg aaa aag cct ggg gcc      48
Glu Val Gln Leu Val Gln Ser Gly Thr Glu Val Lys Lys Pro Gly Ala
1               5                   10                  15 tca gtg aag gtt tcc tgc agg gca tct gga aac acc ttc acc aac tac      96
Ser Val Lys Val Ser Cys Arg Ala Ser Gly Asn Thr Phe Thr Asn Tyr
            20                  25                  30 tat ata cac tgg gtg cga cag gcc cct gga caa ggg ctt gag tgg atg     144
Tyr Ile His Trp Val Arg Gln Ala Pro Gly Gln Gly Leu Glu Trp Met
        35                  40                  45 gga ata atc aac cct agt ggt ggt gcc aca aac tac gca cag att ctc     192
Gly Ile Ile Asn Pro Ser Gly Gly Ala Thr Asn Tyr Ala Gln Ile Leu
    50                  55                  60 cag ggc aga gtc acc atg acc agg gac acg tcc acg agc acc gtc tac     240
Gln Gly Arg Val Thr Met Thr Arg Asp Thr Ser Thr Ser Thr Val Tyr
65                  70                  75                  80 atg gag ctg agc agc ctg aga tct gag gac acg gcc gtg tat tac tgt     288
Met Glu Leu Ser Ser Leu Arg Ser Glu Asp Thr Ala Val Tyr Tyr Cys
                85                  90                  95 gcg ggg ggg gga tca gca gcc acc ttt gcc tac tgg ggc cag gga acc     336
Ala Gly Gly Gly Ser Ala Ala Thr Phe Ala Tyr Trp Gly Gln Gly Thr
            100                 105                 110 ctg gtc acc gtc tcc tca                                             354
Leu Val Thr Val Ser Ser
        115

<210> SEQ ID NO 66
<211> LENGTH: 118
<212> TYPE: PRT
<213> ORGANISM: Homo sapiens

<400> SEQUENCE: 66

Glu Val Gln Leu Val Gln Ser Gly Thr Glu Val Lys Lys Pro Gly Ala
1               5                   10                  15

Ser Val Lys Val Ser Cys Arg Ala Ser Gly Asn Thr Phe Thr Asn Tyr
            20                  25                  30

Tyr Ile His Trp Val Arg Gln Ala Pro Gly Gln Gly Leu Glu Trp Met
        35                  40                  45

Gly Ile Ile Asn Pro Ser Gly Gly Ala Thr Asn Tyr Ala Gln Ile Leu
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Gly Gly Gly Ser Ala Ala Thr Phe Ala Tyr Trp Gly Gln Gly Thr
            100                 105                 110

Leu Val Thr Val Ser Ser
        115

<210> SEQ ID NO 67
<211> LENGTH: 5
<212> TYPE: PRT
<213> ORGANISM: Artificial Sequence
```

```
<220> FEATURE:
<223> OTHER INFORMATION: Epc112 HCDR1 amino acid

<400> SEQUENCE: 67

Asn Tyr Tyr Ile His
1               5

<210> SEQ ID NO 68
<211> LENGTH: 17
<212> TYPE: PRT
<213> ORGANISM: Artificial Sequence
<220> FEATURE:
<223> OTHER INFORMATION: Epc112 HCDR2 amino acid

<400> SEQUENCE: 68

Ile Ile Asn Pro Ser Gly Gly Ala Thr Asn Tyr Ala Gln Ile Leu Gln
1               5                   10                  15
Gly

<210> SEQ ID NO 69
<211> LENGTH: 9
<212> TYPE: PRT
<213> ORGANISM: Artificial Sequence
<220> FEATURE:
<223> OTHER INFORMATION: Epc112 HCDR3 amino acid

<400> SEQUENCE: 69

Gly Gly Ser Ala Ala Thr Phe Ala Tyr
1               5

<210> SEQ ID NO 70
<211> LENGTH: 348
<212> TYPE: DNA
<213> ORGANISM: Artificial Sequence
<220> FEATURE:
<223> OTHER INFORMATION: 3622W94 VH DNA
<220> FEATURE:
<221> NAME/KEY: CDS
<222> LOCATION: (1)..(348)

<400> SEQUENCE: 70 cag gta cag cta gtg caa tca ggg cct gaa gtg aag aag cct ggg gcc       48
Gln Val Gln Leu Val Gln Ser Gly Pro Glu Val Lys Lys Pro Gly Ala
1               5                   10                  15 tca gtg aaa gtt tcc tgc aag gct tct ggc tac acc ttc acc aac tat       96
Ser Val Lys Val Ser Cys Lys Ala Ser Gly Tyr Thr Phe Thr Asn Tyr
            20                  25                  30 gga atg aac tgg gta agg cag gcg cct gga cag ggg ctt gag tgg atg      144
Gly Met Asn Trp Val Arg Gln Ala Pro Gly Gln Gly Leu Glu Trp Met
        35                  40                  45 ggg tgg ata aac acc tac act gga gag cca aca tat ggt gaa gat ttc      192
Gly Trp Ile Asn Thr Tyr Thr Gly Glu Pro Thr Tyr Gly Glu Asp Phe
    50                  55                  60 aag gga cgg ttt gca ttc tct cta gac aca tcc gcc agc aca gcc tat      240
Lys Gly Arg Phe Ala Phe Ser Leu Asp Thr Ser Ala Ser Thr Ala Tyr
65                  70                  75                  80 atg gag ctc agc tcg ctg aga tcc gag gac act gca gtc tat ttc tgt      288
Met Glu Leu Ser Ser Leu Arg Ser Glu Asp Thr Ala Val Tyr Phe Cys
                85                  90                  95 gcg aga ttt ggt aac tac gta gac tac tgg ggt caa gga tca cta gtc      336
Ala Arg Phe Gly Asn Tyr Val Asp Tyr Trp Gly Gln Gly Ser Leu Val
            100                 105                 110 act gtc tcc tca                                                      348
Thr Val Ser Ser
```

<210> SEQ ID NO 71
<211> LENGTH: 116
<212> TYPE: PRT
<213> ORGANISM: Artificial Sequence
<220> FEATURE:
<223> OTHER INFORMATION: Synthetic Construct

<400> SEQUENCE: 71

```
Gln Val Gln Leu Val Gln Ser Gly Pro Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Pro Thr Tyr Gly Glu Asp Phe
    50                  55                  60

Lys Gly Arg Phe Ala Phe Ser Leu Asp Thr Ser Ala Ser Thr Ala Tyr
65                  70                  75                  80

Met Glu Leu Ser Ser Leu Arg Ser Glu Asp Thr Ala Val Tyr Phe Cys
                85                  90                  95

Ala Arg Phe Gly Asn Tyr Val Asp Tyr Trp Gly Gln Gly Ser Leu Val
            100                 105                 110

Thr Val Ser Ser
        115
```

<210> SEQ ID NO 72
<211> LENGTH: 336
<212> TYPE: DNA
<213> ORGANISM: Artificial Sequence
<220> FEATURE:
<223> OTHER INFORMATION: 3622W94 VL DNA
<220> FEATURE:
<221> NAME/KEY: CDS
<222> LOCATION: (1)..(336)

<400> SEQUENCE: 72

```
gat att gtg atg act cag tct cca ctc tcc ctg ccc gtc acc cct gga      48
Asp Ile Val Met Thr Gln Ser Pro Leu Ser Leu Pro Val Thr Pro Gly
1               5                   10                  15 gag ccg gcc tcc atc tcc tgt agg tct agt aag aat ctc ctg cat agt      96
Glu Pro Ala Ser Ile Ser Cys Arg Ser Ser Lys Asn Leu Leu His Ser
            20                  25                  30 aat ggc atc act tat ttg tat tgg tac ctg cag aag cca ggg cag tct     144
Asn Gly Ile Thr Tyr Leu Tyr Trp Tyr Leu Gln Lys Pro Gly Gln Ser
        35                  40                  45 cca cag ctc ctg atc tat cag atg tcc aac ctt gcc tca ggg gtc cct     192
Pro Gln Leu Leu Ile Tyr Gln Met Ser Asn Leu Ala Ser Gly Val Pro
    50                  55                  60 gac agg ttc agt agc agt gga tca ggc aca gat ttt aca ctg aaa atc     240
Asp Arg Phe Ser Ser Ser Gly Ser Gly Thr Asp Phe Thr Leu Lys Ile
65                  70                  75                  80 agc aga gtg gag gct gag gat gtt ggg gtt tat tac tgt gct caa aat     288
Ser Arg Val Glu Ala Glu Asp Val Gly Val Tyr Tyr Cys Ala Gln Asn
                85                  90                  95 cta gag att cct cgg acg ttc ggc caa ggg acc aag gtg gag atc aaa     336
Leu Glu Ile Pro Arg Thr Phe Gly Gln Gly Thr Lys Val Glu Ile Lys
            100                 105                 110
```

<210> SEQ ID NO 73

```
<211> LENGTH: 112
<212> TYPE: PRT
<213> ORGANISM: Artificial Sequence
<220> FEATURE:
<223> OTHER INFORMATION: Synthetic Construct

<400> SEQUENCE: 73

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Asn Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Ala Ser Gly Val Pro
    50                  55                  60

Asp Arg Phe Ser Ser Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Ile Pro Arg Thr Phe Gly Gln Gly Thr Lys Val Glu Ile Lys
            100                 105                 110

<210> SEQ ID NO 74
<211> LENGTH: 294
<212> TYPE: DNA
<213> ORGANISM: Artificial Sequence
<220> FEATURE:
<223> OTHER INFORMATION: IgG4 CH1 DNA
<220> FEATURE:
<221> NAME/KEY: CDS
<222> LOCATION: (1)..(294)

<400> SEQUENCE: 74 gct agc acc aaa gga cct tct gta ttt cct ctt gcg cca tgc tct cgc      48
Ala Ser Thr Lys Gly Pro Ser Val Phe Pro Leu Ala Pro Cys Ser Arg
1               5                   10                  15 tct acg tca gaa tca act gcc gct ctg ggg tgc ctg gtt aaa gac tac      96
Ser Thr Ser Glu Ser Thr Ala Ala Leu Gly Cys Leu Val Lys Asp Tyr
            20                  25                  30 ttc ccg gag cct gtg aca gtg agt tgg aac tcc ggc gcc ctg aca tca     144
Phe Pro Glu Pro Val Thr Val Ser Trp Asn Ser Gly Ala Leu Thr Ser
        35                  40                  45 gga gtg cat aca ttt ccc gcc gtg ctt cag agc agc gga ctt tat agc     192
Gly Val His Thr Phe Pro Ala Val Leu Gln Ser Ser Gly Leu Tyr Ser
    50                  55                  60 ctc agc agt gtg gtg acc gtg cca tct tcc agc ctg ggg acc aag acc     240
Leu Ser Ser Val Val Thr Val Pro Ser Ser Ser Leu Gly Thr Lys Thr
65                  70                  75                  80 tac acc tgt aac gtg gac cac aaa ccc agc aac acc aag gtt gat aag     288
Tyr Thr Cys Asn Val Asp His Lys Pro Ser Asn Thr Lys Val Asp Lys
                85                  90                  95 agg gtc                                                             294
Arg Val

<210> SEQ ID NO 75
<211> LENGTH: 98
<212> TYPE: PRT
<213> ORGANISM: Artificial Sequence
<220> FEATURE:
<223> OTHER INFORMATION: Synthetic Construct

<400> SEQUENCE: 75
```

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val

<210> SEQ ID NO 76
<211> LENGTH: 981
<212> TYPE: DNA
<213> ORGANISM: Artificial Sequence
<220> FEATURE:
<223> OTHER INFORMATION: IgG4PE R409K DNA
<220> FEATURE:
<221> NAME/KEY: CDS
<222> LOCATION: (1)..(981)

<400> SEQUENCE: 76 gct agc acc aag ggg cca tcc gtc ttc ccc ctg gcg ccc tgc tcc agg       48
Ala Ser Thr Lys Gly Pro Ser Val Phe Pro Leu Ala Pro Cys Ser Arg
1               5                   10                  15 agc acc tcc gag agc aca gcc gcc ctg ggc tgc ctg gtc aag gac tac       96
Ser Thr Ser Glu Ser Thr Ala Ala Leu Gly Cys Leu Val Lys Asp Tyr
                20                  25                  30 ttc ccc gaa ccg gtg acg gtg tcg tgg aac tca ggc gcc ctg acc agc      144
Phe Pro Glu Pro Val Thr Val Ser Trp Asn Ser Gly Ala Leu Thr Ser
            35                  40                  45 ggc gtg cac acc ttc ccg gct gtc cta cag tcc tca gga ctc tac tcc      192
Gly Val His Thr Phe Pro Ala Val Leu Gln Ser Ser Gly Leu Tyr Ser
        50                  55                  60 ctc agc agc gtg gtg acc gtg ccc tcc agc agc ttg ggc acg aag acc      240
Leu Ser Ser Val Val Thr Val Pro Ser Ser Leu Gly Thr Lys Thr
65                  70                  75                  80 tac acc tgc aac gta gat cac aag ccc agc aac acc aag gtg gac aag      288
Tyr Thr Cys Asn Val Asp His Lys Pro Ser Asn Thr Lys Val Asp Lys
                85                  90                  95 aga gtt gag tcc aaa tat ggt ccc cca tgc cca cca tgc cca gca cct      336
Arg Val Glu Ser Lys Tyr Gly Pro Pro Cys Pro Pro Cys Pro Ala Pro
                100                 105                 110 gag ttc gag ggg gga cca tca gtc ttc ctg ttc ccc cca aaa ccc aag      384
Glu Phe Glu Gly Gly Pro Ser Val Phe Leu Phe Pro Pro Lys Pro Lys
            115                 120                 125 gac act ctc atg atc tcc cgg acc cct gag gtc acg tgc gtg gtg gtg      432
Asp Thr Leu Met Ile Ser Arg Thr Pro Glu Val Thr Cys Val Val Val
        130                 135                 140 gac gtg agc cag gaa gac ccc gag gtc cag ttc aac tgg tac gtg gat      480
Asp Val Ser Gln Glu Asp Pro Glu Val Gln Phe Asn Trp Tyr Val Asp
145                 150                 155                 160 ggc gtg gag gtg cat aat gcc aag aca aag ccg cgg gag gag cag ttc      528
Gly Val Glu Val His Asn Ala Lys Thr Lys Pro Arg Glu Glu Gln Phe
                165                 170                 175 aac agc acg tac cgt gtg gtc agc gtc ctc acc gtc ctg cac cag gac      576
Asn Ser Thr Tyr Arg Val Val Ser Val Leu Thr Val Leu His Gln Asp
```

```
tgg ctg aac ggc aag gag tac aag tgc aag gtc tcc aac aaa ggc ctc    624
Trp Leu Asn Gly Lys Glu Tyr Lys Cys Lys Val Ser Asn Lys Gly Leu
        195                 200                 205 ccg tcc tcc atc gag aaa acc atc tcc aaa gcc aaa ggg cag ccc cga    672
Pro Ser Ser Ile Glu Lys Thr Ile Ser Lys Ala Lys Gly Gln Pro Arg
210                 215                 220 gag cca cag gtg tac acc ctg ccc cca tcc cag gag gag atg acc aag    720
Glu Pro Gln Val Tyr Thr Leu Pro Pro Ser Gln Glu Glu Met Thr Lys
225                 230                 235                 240 aac cag gtc agc ctg acc tgc ctg gtc aaa ggc ttc tac ccc agc gac    768
Asn Gln Val Ser Leu Thr Cys Leu Val Lys Gly Phe Tyr Pro Ser Asp
            245                 250                 255 atc gcc gtg gag tgg gag agc aat ggg cag ccg gag aac aac tac aag    816
Ile Ala Val Glu Trp Glu Ser Asn Gly Gln Pro Glu Asn Asn Tyr Lys
            260                 265                 270 acc acg cct ccc gtg ctg gac tcc gac ggc tcc ttc ttc ctc tac agc    864
Thr Thr Pro Pro Val Leu Asp Ser Asp Gly Ser Phe Phe Leu Tyr Ser
        275                 280                 285 aag cta acc gtg gac aag agc agg tgg cag gag ggg aat gtc ttc tca    912
Lys Leu Thr Val Asp Lys Ser Arg Trp Gln Glu Gly Asn Val Phe Ser
        290                 295                 300 tgc tcc gtg atg cat gag gct ctg cac aac cac tac aca cag aag agc    960
Cys Ser Val Met His Glu Ala Leu His Asn His Tyr Thr Gln Lys Ser
305                 310                 315                 320 ctc tcc ctg tct ctg ggt aaa                                        981
Leu Ser Leu Ser Leu Gly Lys
                325
```

<210> SEQ ID NO 77
<211> LENGTH: 327
<212> TYPE: PRT
<213> ORGANISM: Artificial Sequence
<220> FEATURE:
<223> OTHER INFORMATION: Synthetic Construct

<400> SEQUENCE: 77

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Glu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
```

```
                    165                 170                 175
Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
        210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Lys Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 78
<211> LENGTH: 297
<212> TYPE: DNA
<213> ORGANISM: Artificial Sequence
<220> FEATURE:
<223> OTHER INFORMATION: IgG4PE R409K DNA including stop codon

<400> SEQUENCE: 78
gctagcacca aggaccttc tgtatttcct cttgcgccat gctctcgctc tacgtcagaa        60
tcaactgccg ctctggggtg cctggttaaa gactacttcc cggagcctgt gacagtgagt       120
tggaactccg gcgccctgac atcaggagtg catacatttc ccgccgtgct tcagagcagc      180
ggactttata gcctcagcag tgtggtgacc gtgccatctt ccagcctggg gaccaagacc      240
tacacctgta acgtggacca caaacccagc aacaccaagg ttgataagag ggtctga         297

<210> SEQ ID NO 79
<211> LENGTH: 993
<212> TYPE: DNA
<213> ORGANISM: Artificial Sequence
<220> FEATURE:
<223> OTHER INFORMATION: Hetero IgG BsAbCHa
<220> FEATURE:
<221> NAME/KEY: CDS
<222> LOCATION: (1)..(993)

<400> SEQUENCE: 79 gct agc acc aag ggc cca tcg gtc ttc ccc ctg gca ccc tcc tcc aag        48
Ala Ser Thr Lys Gly Pro Ser Val Phe Pro Leu Ala Pro Ser Ser Lys
1               5                   10                  15 agc acc tct ggg ggc aca gcg gcc ctg ggc tgc ctg gtc aag gac tac        96
Ser Thr Ser Gly Gly Thr Ala Ala Leu Gly Cys Leu Val Lys Asp Tyr
            20                  25                  30 ttc ccc gaa ccg gtg acg gtg tcg tgg aac tca ggc gcc ctg acc agc       144
Phe Pro Glu Pro Val Thr Val Ser Trp Asn Ser Gly Ala Leu Thr Ser
        35                  40                  45 ggc gtg cac acc ttc ccg gct gtc cta cag tcc tca gga ctc tac tcc       192
Gly Val His Thr Phe Pro Ala Val Leu Gln Ser Ser Gly Leu Tyr Ser
```

```
ctc agc agc gtg gtg acc gtg ccc tcc agc agc ttg ggc acc cag acc       240
Leu Ser Ser Val Val Thr Val Pro Ser Ser Ser Leu Gly Thr Gln Thr
 65                  70                  75                  80 tac atc tgc aac gtg aat cac aag ccc agc aac acc aag gtg gac aag       288
Tyr Ile Cys Asn Val Asn His Lys Pro Ser Asn Thr Lys Val Asp Lys
                 85                  90                  95 aaa gtt gag ccc aaa tct tgt gac aaa act cac aca tgc cca ccg tgc       336
Lys Val Glu Pro Lys Ser Cys Asp Lys Thr His Thr Cys Pro Pro Cys
            100                 105                 110 cca gca cct gaa gcc gcg ggg gga ccg tca gtc ttc ctc ttc ccc cca       384
Pro Ala Pro Glu Ala Ala Gly Gly Pro Ser Val Phe Leu Phe Pro Pro
        115                 120                 125 aaa ccc aag gac acc ctc atg atc tcc cgg acc cct gag gtc aca tgc       432
Lys Pro Lys Asp Thr Leu Met Ile Ser Arg Thr Pro Glu Val Thr Cys
    130                 135                 140 gtg gtg gtg gac gtg agc cac gaa gac cct gag gtc aag ttc aac tgg       480
Val Val Val Asp Val Ser His Glu Asp Pro Glu Val Lys Phe Asn Trp
145                 150                 155                 160 tac gtg gac ggc gtg gag gtg cat aat gcc aag aca aag ccg cgg gag       528
Tyr Val Asp Gly Val Glu Val His Asn Ala Lys Thr Lys Pro Arg Glu
                165                 170                 175 gag cag tac aac agc acg tac cgt gtg gtc agc gtc ctc acc gtc ctg       576
Glu Gln Tyr Asn Ser Thr Tyr Arg Val Val Ser Val Leu Thr Val Leu
            180                 185                 190 cac cag gac tgg ctg aat ggc aag gag tac aag tgc aag gtc tcc aac       624
His Gln Asp Trp Leu Asn Gly Lys Glu Tyr Lys Cys Lys Val Ser Asn
        195                 200                 205 aaa gcc ctc cca gcc ccc atc gag aaa acc atc tcc aaa gcc aaa gga       672
Lys Ala Leu Pro Ala Pro Ile Glu Lys Thr Ile Ser Lys Ala Lys Gly
    210                 215                 220 cag cca cga gaa cca gaa gta gca acc ttc cca cct agt cgt gat gaa       720
Gln Pro Arg Glu Pro Glu Val Ala Thr Phe Pro Pro Ser Arg Asp Glu
225                 230                 235                 240 ttg acc aaa aac caa gtt acc ctg gta tgt ctt gtg aca gga ttc tac       768
Leu Thr Lys Asn Gln Val Thr Leu Val Cys Leu Val Thr Gly Phe Tyr
                245                 250                 255 ccc tca gat att gca gtt gaa tgg gag agc aat ggt caa cct gaa aac       816
Pro Ser Asp Ile Ala Val Glu Trp Glu Ser Asn Gly Gln Pro Glu Asn
            260                 265                 270 aac tac aaa act gat cct cct ctc ttg gaa tca gac ggg agt ttc gca       864
Asn Tyr Lys Thr Asp Pro Pro Leu Leu Glu Ser Asp Gly Ser Phe Ala
        275                 280                 285 ctt agt agc cgt ctg cgc gta gac aaa tcc cgg tgg caa cag ggg aac       912
Leu Ser Ser Arg Leu Arg Val Asp Lys Ser Arg Trp Gln Gln Gly Asn
    290                 295                 300 gta ttc tcc tgc tcc gtt atg cac gag gct ctt cac aat cat tat aca       960
Val Phe Ser Cys Ser Val Met His Glu Ala Leu His Asn His Tyr Thr
305                 310                 315                 320 cag aag tca ctt tct ctt tcc cct ggg aaa tga                           993
Gln Lys Ser Leu Ser Leu Ser Pro Gly Lys
                325                 330
```

<210> SEQ ID NO 80
<211> LENGTH: 330
<212> TYPE: PRT
<213> ORGANISM: Artificial Sequence
<220> FEATURE:
<223> OTHER INFORMATION: Synthetic Construct

<400> SEQUENCE: 80

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Glu Val Ala Thr Phe Pro Pro Ser Arg Asp Glu
225                 230                 235                 240

Leu Thr Lys Asn Gln Val Thr Leu Val Cys Leu Val Thr Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Asp Pro Pro Leu Leu Glu Ser Asp Gly Ser Phe Ala
        275                 280                 285

Leu Ser Ser Arg Leu Arg Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 81
<211> LENGTH: 993
<212> TYPE: DNA
<213> ORGANISM: Artificial Sequence
<220> FEATURE:
<223> OTHER INFORMATION: Hetero IgG BsAb CHb
<220> FEATURE:
<221> NAME/KEY: CDS
<222> LOCATION: (1)..(993)

<400> SEQUENCE: 81

```
gct agc acc aag ggc cca tcg gtc ttc ccc ctg gca ccc tcc tcc aag      48
Ala Ser Thr Lys Gly Pro Ser Val Phe Pro Leu Ala Pro Ser Ser Lys
```

```
1               5                   10                  15
agc acc tct ggg ggc aca gcg gcc ctg ggc tgc ctg gtc aag gac tac      96
Ser Thr Ser Gly Gly Thr Ala Ala Leu Gly Cys Leu Val Lys Asp Tyr
            20                  25                  30 ttc ccc gaa ccg gtg acg gtg tcg tgg aac tca ggc gcc ctg acc agc      144
Phe Pro Glu Pro Val Thr Val Ser Trp Asn Ser Gly Ala Leu Thr Ser
        35                  40                  45 ggc gtg cac acc ttc ccg gct gtc cta cag tcc tca gga ctc tac tcc      192
Gly Val His Thr Phe Pro Ala Val Leu Gln Ser Ser Gly Leu Tyr Ser
    50                  55                  60 ctc agc agc gtg gtg acc gtg ccc tcc agc agc ttg ggc acc cag acc      240
Leu Ser Ser Val Val Thr Val Pro Ser Ser Ser Leu Gly Thr Gln Thr
65                  70                  75                  80 tac atc tgc aac gtg aat cac aag ccc agc aac acc aag gtg gac aag      288
Tyr Ile Cys Asn Val Asn His Lys Pro Ser Asn Thr Lys Val Asp Lys
                85                  90                  95 aaa gtt gag ccc aaa tct tgt gac aaa act cac aca tgc cca ccg tgc      336
Lys Val Glu Pro Lys Ser Cys Asp Lys Thr His Thr Cys Pro Pro Cys
            100                 105                 110 cca gcc cct gaa gca gcc gga gga cct agc gta ttc ctt ttc ccc cca      384
Pro Ala Pro Glu Ala Ala Gly Gly Pro Ser Val Phe Leu Phe Pro Pro
        115                 120                 125 aaa cca aag gac aca ttg atg ata agc cgt acc cct gaa gtt act tgc      432
Lys Pro Lys Asp Thr Leu Met Ile Ser Arg Thr Pro Glu Val Thr Cys
    130                 135                 140 gtt gtg gta gat gta tcc cac gaa gat ccc gag gta cag ttc aaa tgg      480
Val Val Val Asp Val Ser His Glu Asp Pro Glu Val Gln Phe Lys Trp
145                 150                 155                 160 tac gtt gac ggt gta gag gtt cat aat gct aag act aag cca cgc gag      528
Tyr Val Asp Gly Val Glu Val His Asn Ala Lys Thr Lys Pro Arg Glu
                165                 170                 175 gaa caa tat aat tcc acc ttc agg gtt gtc tcc gtc ttg act gtc ctc      576
Glu Gln Tyr Asn Ser Thr Phe Arg Val Val Ser Val Leu Thr Val Leu
            180                 185                 190 cac cag gac tgg ctg aac gga aag gag tac aag tgc aag gtg agc aat      624
His Gln Asp Trp Leu Asn Gly Lys Glu Tyr Lys Cys Lys Val Ser Asn
        195                 200                 205 aaa gca ctc cca gct cct att gaa aag acc atc tcc aag acc aag gga      672
Lys Ala Leu Pro Ala Pro Ile Glu Lys Thr Ile Ser Lys Thr Lys Gly
    210                 215                 220 cag ccc cga gag cca gct gtc tat acc ctt cca cca agt cgt gaa gaa      720
Gln Pro Arg Glu Pro Ala Val Tyr Thr Leu Pro Pro Ser Arg Glu Glu
225                 230                 235                 240 atg acc aag aac cag gta aag ctc gtg tgt ttg gtg acc ggg ttt tac      768
Met Thr Lys Asn Gln Val Lys Leu Val Cys Leu Val Thr Gly Phe Tyr
                245                 250                 255 cct agt gat ata gca gtg gaa tgg gaa tct agc ggg caa cct gag aat      816
Pro Ser Asp Ile Ala Val Glu Trp Glu Ser Ser Gly Gln Pro Glu Asn
            260                 265                 270 aac tat tat aca act cca ccc atg ttg gac tca gac ggt tct ttt agc      864
Asn Tyr Tyr Thr Thr Pro Pro Met Leu Asp Ser Asp Gly Ser Phe Ser
        275                 280                 285 ctt gtc tcc tgg ctt aat gta gat aag agt cgc tgg cag caa ggg aat      912
Leu Val Ser Trp Leu Asn Val Asp Lys Ser Arg Trp Gln Gln Gly Asn
    290                 295                 300 att ttc tca tgc agt gtc atg cac gag gct ctg cac aac agg ttt aca      960
Ile Phe Ser Cys Ser Val Met His Glu Ala Leu His Asn Arg Phe Thr
305                 310                 315                 320 caa aaa agc ctg tcc ctg agt ccc ggc aag tga                          993
Gln Lys Ser Leu Ser Leu Ser Pro Gly Lys
```

```
Gln Lys Ser Leu Ser Leu Ser Pro Gly Lys
            325                 330

<210> SEQ ID NO 82
<211> LENGTH: 330
<212> TYPE: PRT
<213> ORGANISM: Artificial Sequence
<220> FEATURE:
<223> OTHER INFORMATION: Synthetic Construct

<400> SEQUENCE: 82

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Gln Phe Lys Trp
145                 150                 155                 160

Tyr Val Asp Gly Val Glu Val His Asn Ala Lys Thr Lys Pro Arg Glu
                165                 170                 175

Glu Gln Tyr Asn Ser Thr Phe Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Thr Lys Gly
    210                 215                 220

Gln Pro Arg Glu Pro Ala Val Tyr Thr Leu Pro Pro Ser Arg Glu Glu
225                 230                 235                 240

Met Thr Lys Asn Gln Val Lys Leu Val Cys Leu Val Thr Gly Phe Tyr
                245                 250                 255

Pro Ser Asp Ile Ala Val Glu Trp Glu Ser Ser Gly Gln Pro Glu Asn
            260                 265                 270

Asn Tyr Tyr Thr Thr Pro Pro Met Leu Asp Ser Asp Gly Ser Phe Ser
        275                 280                 285

Leu Val Ser Trp Leu Asn Val Asp Lys Ser Arg Trp Gln Gln Gly Asn
    290                 295                 300

Ile Phe Ser Cys Ser Val Met His Glu Ala Leu His Asn Arg Phe Thr
305                 310                 315                 320

Gln Lys Ser Leu Ser Leu Ser Pro Gly Lys
            325                 330

<210> SEQ ID NO 83
<211> LENGTH: 324
```

<212> TYPE: DNA
<213> ORGANISM: Artificial Sequence
<220> FEATURE:
<223> OTHER INFORMATION: Fab BsAb CH1-tag
<220> FEATURE:
<221> NAME/KEY: CDS
<222> LOCATION: (1)..(324)

<400> SEQUENCE: 83

```
gct agc acc aag ggg cca tcc gtc ttc ccc ctg gcg ccc tgc tcc agg      48
Ala Ser Thr Lys Gly Pro Ser Val Phe Pro Leu Ala Pro Cys Ser Arg
1               5                   10                  15 agc acc tcc gag agc aca gcc gcc ctg ggc tgc ctg gtc aag gac tac      96
Ser Thr Ser Glu Ser Thr Ala Ala Leu Gly Cys Leu Val Lys Asp Tyr
                20                  25                  30 ttc ccc gaa ccg gtg acg gtg tcg tgg aac tca ggc gcc ctg acc agc     144
Phe Pro Glu Pro Val Thr Val Ser Trp Asn Ser Gly Ala Leu Thr Ser
            35                  40                  45 ggc gtg cac acc ttc ccg gct gtc cta cag tcc tca gga ctc tac tcc     192
Gly Val His Thr Phe Pro Ala Val Leu Gln Ser Ser Gly Leu Tyr Ser
        50                  55                  60 ctc agc agc gtg gtg acc gtg ccc tcc agc agc ttg ggc acg aag acc     240
Leu Ser Ser Val Val Thr Val Pro Ser Ser Ser Leu Gly Thr Lys Thr
65                  70                  75                  80 tac acc tgc aac gta gat cac aag ccc agc aac acc aag gtg gac aag     288
Tyr Thr Cys Asn Val Asp His Lys Pro Ser Asn Thr Lys Val Asp Lys
                85                  90                  95 aga gtt gag tcc tac aaa gac gac gac gac aaa tga                     324
Arg Val Glu Ser Tyr Lys Asp Asp Asp Asp Lys
                100                 105
```

<210> SEQ ID NO 84
<211> LENGTH: 107
<212> TYPE: PRT
<213> ORGANISM: Artificial Sequence
<220> FEATURE:
<223> OTHER INFORMATION: Synthetic Construct

<400> SEQUENCE: 84

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Tyr Lys Asp Asp Asp Asp Lys
                100                 105
```

<210> SEQ ID NO 85
<211> LENGTH: 354
<212> TYPE: DNA
<213> ORGANISM: Artificial Sequence
<220> FEATURE:
<223> OTHER INFORMATION: F(ab')2 BsAb CH1-tag
<220> FEATURE:
<221> NAME/KEY: CDS
<222> LOCATION: (1)..(354)

```
<400> SEQUENCE: 85 gct agc acc aag ggg cca tcc gtc ttc ccc ctg gcg ccc tgc tcc agg      48
Ala Ser Thr Lys Gly Pro Ser Val Phe Pro Leu Ala Pro Cys Ser Arg
1               5                   10                  15 agc acc tcc gag agc aca gcc gcc ctg ggc tgc ctg gtc aag gac tac      96
Ser Thr Ser Glu Ser Thr Ala Ala Leu Gly Cys Leu Val Lys Asp Tyr
                20                  25                  30 ttc ccc gaa ccg gtg acg gtg tcg tgg aac tca ggc gcc ctg acc agc     144
Phe Pro Glu Pro Val Thr Val Ser Trp Asn Ser Gly Ala Leu Thr Ser
            35                  40                  45 ggc gtg cac acc ttc ccg gct gtc cta cag tcc tca gga ctc tac tcc     192
Gly Val His Thr Phe Pro Ala Val Leu Gln Ser Ser Gly Leu Tyr Ser
        50                  55                  60 ctc agc agc gtg gtg acc gtg ccc tcc agc agc ttg ggc acg aag acc     240
Leu Ser Ser Val Val Thr Val Pro Ser Ser Ser Leu Gly Thr Lys Thr
65                  70                  75                  80 tac acc tgc aac gta gat cac aag ccc agc aac acc aag gtg gac aag     288
Tyr Thr Cys Asn Val Asp His Lys Pro Ser Asn Thr Lys Val Asp Lys
                    85                  90                  95 aga gtt gag tcc aaa tat ggt ccc cca tgc cca cca tgc ccc tac aaa     336
Arg Val Glu Ser Lys Tyr Gly Pro Pro Cys Pro Pro Cys Pro Tyr Lys
                100                 105                 110 gac gac gac gac aaa tga                                             354
Asp Asp Asp Asp Lys
            115

<210> SEQ ID NO 86
<211> LENGTH: 117
<212> TYPE: PRT
<213> ORGANISM: Artificial Sequence
<220> FEATURE:
<223> OTHER INFORMATION: Synthetic Construct

<400> SEQUENCE: 86

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                    85                  90                  95

Arg Val Glu Ser Lys Tyr Gly Pro Pro Cys Pro Pro Cys Pro Tyr Lys
                100                 105                 110

Asp Asp Asp Asp Lys
            115
```